(12) United States Patent
Wehn et al.

(10) Patent No.: US 10,155,726 B2
(45) Date of Patent: Dec. 18, 2018

(54) SUBSTITUTED PYRIDINES AND USES THEREOF

(71) Applicant: PELOTON THERAPEUTICS, INC., Dallas, TX (US)

(72) Inventors: Paul Wehn, Dallas, TX (US); Rui Xu, Dallas, TX (US); Hanbiao Yang, Coppell, TX (US)

(73) Assignee: PELOTON THERAPEUTICS, INC., Dallas, TX (US)

( * ) Notice: Subject to any disclaimer, the term of this patent is extended or adjusted under 35 U.S.C. 154(b) by 0 days.

(21) Appl. No.: 15/553,570

(22) PCT Filed: Mar. 4, 2016

(86) PCT No.: PCT/US2016/021061
§ 371 (c)(1),
(2) Date: Aug. 24, 2017

(87) PCT Pub. No.: WO2016/144826
PCT Pub. Date: Sep. 15, 2016

(65) Prior Publication Data
US 2018/0148413 A1    May 31, 2018

Related U.S. Application Data

(60) Provisional application No. 62/131,789, filed on Mar. 11, 2015, provisional application No. 62/219,044, filed on Sep. 15, 2015.

(51) Int. Cl.
| | | |
|---|---|---|
| *C07D 221/18* | (2006.01) |
| *A61K 45/06* | (2006.01) |
| *A61K 31/438* | (2006.01) |
| *C07D 401/12* | (2006.01) |
| *C07D 237/26* | (2006.01) |
| *A61P 43/00* | (2006.01) |
| *A61P 35/00* | (2006.01) |

(52) U.S. Cl.
CPC .......... *C07D 221/18* (2013.01); *A61K 31/438* (2013.01); *A61K 45/06* (2013.01); *A61P 35/00* (2018.01); *A61P 43/00* (2018.01); *C07D 237/26* (2013.01); *C07D 401/12* (2013.01)

(58) Field of Classification Search
CPC .... A61K 45/06; A61K 31/438; C07D 401/12; C07D 221/18; C07D 237/26
USPC .......................................................... 514/248
See application file for complete search history.

(56) References Cited

U.S. PATENT DOCUMENTS

| | | | |
|---|---|---|---|
| 4,214,103 A | 7/1980 | Garman et al. |
| 4,364,875 A | 12/1982 | Sehring et al. |
| 4,426,385 A | 1/1984 | Cain |
| 4,505,929 A | 3/1985 | Markley et al. |
| 4,665,097 A | 5/1987 | Cain |
| 4,705,955 A | 11/1987 | Mileikowsky |
| 5,059,609 A | 10/1991 | Eggler et al. |
| 5,644,024 A | 7/1997 | Abrecht et al. |
| 8,003,656 B2 | 8/2011 | Bakthavatchalam et al. |
| 9,796,697 B2 | 10/2017 | Wehn et al. |
| 9,884,843 B2 | 2/2018 | Dixon et al. |
| 2005/0070474 A1 | 3/2005 | Krissansen et al. |
| 2005/0085541 A1 | 4/2005 | Shiohara et al. |
| 2006/0058361 A1 | 3/2006 | Fliri et al. |
| 2006/0128790 A1 | 6/2006 | Chu et al. |
| 2007/0088053 A1 | 4/2007 | Mirzadegan et al. |
| 2007/0155726 A1 | 7/2007 | Arnaiz et al. |
| 2007/0244071 A1 | 10/2007 | Dennis et al. |
| 2007/0265332 A1 | 11/2007 | Ge et al. |
| 2008/0070928 A1 | 3/2008 | Nonoshita et al. |
| 2008/0312313 A1 | 12/2008 | Carballido Herrera et al. |
| 2009/0286812 A1 | 11/2009 | Erickson et al. |
| 2009/0325961 A1 | 12/2009 | Duan et al. |
| 2010/0029694 A1 | 2/2010 | Herold et al. |
| 2010/0048537 A1 | 2/2010 | Matsuoka et al. |
| 2010/0168110 A1 | 7/2010 | Chhipa et al. |
| 2011/0054173 A1 | 3/2011 | Brewster et al. |
| 2012/0295937 A1 | 11/2012 | Linehan et al. |
| 2013/0116275 A1 | 5/2013 | Van Meir et al. |
| 2013/0137746 A1 | 5/2013 | Govek et al. |
| 2014/0057914 A1 | 2/2014 | Jones et al. |
| 2014/0073634 A1 | 3/2014 | Jones et al. |
| 2014/0128365 A1 | 5/2014 | Robl et al. |
| 2014/0148462 A1 | 5/2014 | Eckhardt et al. |
| 2014/0163025 A1 | 6/2014 | Eckhardt et al. |
| 2014/0200218 A1 | 7/2014 | Bellingham et al. |
| 2014/0371319 A1 | 12/2014 | Kazuta et al. |
| 2016/0250216 A1 | 9/2016 | Bruick et al. |
| 2016/0251307 A1 | 9/2016 | Dixon et al. |
| 2016/0368893 A1 | 12/2016 | Dixon et al. |
| 2017/0217891 A1 | 8/2017 | Dixon et al. |
| 2017/0217892 A1 | 8/2017 | Dixon et al. |
| 2018/0140569 A1 | 5/2018 | Josey et al. |
| 2018/0155279 A1 | 6/2018 | Dixon et al. |
| 2018/0162807 A1 | 6/2018 | Dixon et al. |
| 2018/0177754 A1 | 6/2018 | Josey et al. |

FOREIGN PATENT DOCUMENTS

| | | |
|---|---|---|
| CA | 1264763 A | 1/1990 |
| CN | 101058535 A | 10/2007 |
| DE | 705530 C | 4/1941 |
| DE | 2423972 A1 | 1/1975 |
| DE | 3239449 A1 | 5/1983 |
| DE | 3209878 A1 | 9/1983 |
| EP | 0027555 A1 | 4/1981 |
| EP | 2599774 A1 | 6/2013 |
| FR | 1574139 A | 7/1969 |
| GB | 2017087 A | 10/1979 |

(Continued)

OTHER PUBLICATIONS

Prelog et al. Helvetica Chimica Acta (1946), 29, 1163-9.*

(Continued)

*Primary Examiner* — Kahsay Habte
(74) *Attorney, Agent, or Firm* — Wilson Sonsini Goodrich & Rosati

(57) ABSTRACT

Substituted pyridines that modulate HIF-2a activity, pharmaceutical compositions containing the substituted pyridines, and methods of using these chemical entities for treating proliferative diseases and conditions associated with HIF-2a activity are described herein.

24 Claims, 4 Drawing Sheets

(56) References Cited

FOREIGN PATENT DOCUMENTS

| | | |
|---|---|---|
| JP | S4872169 A | 9/1973 |
| JP | S57169449 A | 10/1982 |
| JP | S58124758 A | 7/1983 |
| JP | S6351363 A | 3/1988 |
| WO | WO-9324434 A1 | 12/1993 |
| WO | WO-9842671 A1 | 10/1998 |
| WO | WO-0116097 A1 | 3/2001 |
| WO | WO-2004113303 A1 | 12/2004 |
| WO | WO-2006027684 A1 | 3/2006 |
| WO | WO-2006083781 A1 | 8/2006 |
| WO | WO-2006125972 A1 | 11/2006 |
| WO | WO-2007071441 A1 | 6/2007 |
| WO | WO-2007099423 A1 | 9/2007 |
| WO | WO-2008157273 A1 | 12/2008 |
| WO | WO-2009093133 A1 | 7/2009 |
| WO | WO-2010058032 A2 | 5/2010 |
| WO | WO-2010068794 A2 | 6/2010 |
| WO | WO-2010079443 A1 | 7/2010 |
| WO | WO-2010103438 A1 | 9/2010 |
| WO | WO-2010137620 A1 | 12/2010 |
| WO | WO-2010141956 A2 | 12/2010 |
| WO | WO-2011105603 A1 | 9/2011 |
| WO | WO-2011121366 A1 | 10/2011 |
| WO | WO-2011124930 A1 | 10/2011 |
| WO | WO-2012123129 A1 | 9/2012 |
| WO | WO-2012170442 A1 | 12/2012 |
| WO | WO-2013011033 A1 | 1/2013 |
| WO | WO-2013040863 A1 | 3/2013 |
| WO | WO-2013057101 A1 | 4/2013 |
| WO | WO-2013064984 A1 | 5/2013 |
| WO | WO-2013110433 A1 | 8/2013 |
| WO | WO-2013133325 A1 | 9/2013 |
| WO | WO-2014078479 A2 | 5/2014 |
| WO | WO-2015035223 A1 | 3/2015 |
| WO | WO-2015095048 A1 | 6/2015 |
| WO | WO-2016144825 A1 | 9/2016 |
| WO | WO-2016144826 A1 | 9/2016 |
| WO | WO-2016145032 A1 | 9/2016 |
| WO | WO-2016145045 A1 | 9/2016 |
| WO | WO-2016145236 A1 | 9/2016 |
| WO | WO-2016168510 A1 | 10/2016 |

OTHER PUBLICATIONS

Akincioglu, et al. Novel sulfamides as potential carbonic anhydrase isoenzymes inhibitors. Bioorg Med Chem. Mar. 15, 2013;21(6):1379-85. doi: 10.1016/j.bmc.2013.01.019. Epub Jan. 22, 2013.

Bertout, et al. HIF2alpha inhibition promotes p53 pathway activity, tumor cell death, and radiation responses. Proc Natl Acad Sci U S A. Aug. 25, 2009;106(34):14391-6. doi: 10.1073/pnas.0907357106. Epub Aug. 12, 2009.

Bhatt, et al. Hypoxia-inducible factor-2alpha: effect on radiation sensitivity and differential regulation by an mTOR inhibitor. BJU Int. Aug. 2008;102(3):358-63. doi: 10.1111/j.1464-410X.2008.07558. x. Epub Apr. 3, 2008.

Cardoso, et al. Identification of Cys255 in HIF-1α as a novel site for development of covalent inhibitors of HIF-1α/ARNT PasB domain protein-protein interaction. Protein Sci. Dec. 2012;21(12):1885-96. doi: 10.1002/pro.2172. Epub Nov. 9, 2012.

Carew, et al. ELR510444 inhibits tumor growth and angiogenesis by abrogating HIF activity and disrupting microtubules in renal cell carcinoma. PLoS One. 2012;7(1):e31120. doi: 10.1371/journal.pone. 0031120. Epub Jan. 25, 2012.

CAS Registry No. 1050878-94-8 (Sep. 2008).
CAS Registry No. 1062399-04-05 (Oct. 2008).
CAS Registry No. 1090604-08-2 (Dec. 2008).
CAS Registry No. 1119387-77-7 (Mar. 2009).
CAS Registry No. 1147778-06-0 (May 2009).
CAS Registry No. 1386280-55-2 (Aug. 2012).
CAS Registry No. 81614-92-8. (Nov. 1984).
CAS Registry No. 879353-79-4 (Apr. 2006).
CAS Registry No. 903274-78-2 (Aug. 2006).
CAS Registry No. 950051-37-3 (Oct. 2007).
CAS Registry No. 21081-71-0, Database Registry, Chemical Abstracts Services, [retrieved on Mar. 23, 2017], Published 1968.
Co-pending U.S. Appl. No. 15/556,153, filed Sep. 6, 2017.
Co-pending U.S. Appl. No. 15/556,248, filed Sep. 6, 2017.
Co-pending U.S. Appl. No. 15/556,607, filed Sep. 7, 2017.
Co-pending U.S. Appl. No. 15/556,609, filed Sep. 7, 2017.
Co-pending U.S. Appl. No. 15/564,348, filed Oct. 4, 2017.
Co-pending U.S. Appl. No. 15/805,390, filed Nov. 7, 2017.
European Search Report dated Mar. 29, 2017 for EP Application No. 14871152.6.
European Search Report dated Mar. 8, 2017 for EP Application No. 14842085.4.
Giatromanolaki, et al. Relation of hypoxia inducible factor 1 alpha and 2 alpha in operable non-small cell lung cancer to angiogenic/molecular profile of tumours and survival. Br J Cancer. Sep. 14, 2001;85(6):881-90.

Gordan, et al. HIF-2alpha promotes hypoxic cell proliferation by enhancing c-myc transcriptional activity. Cancer Cell. Apr. 2007;11(4):335-47.

He, et al. Downregulating hypoxia-inducible factor-2α improves the efficacy of doxorubicin in the treatment of hepatocellular carcinoma. Cancer Sci. Mar. 2012;103(3):528-34. doi: 10.1111/j.1349-7006.2011.02177.x. Epub Jan. 13, 2012.

Holmquist-Mengelbier, et al. Recruitment of HIF-1alpha and HIF-2alpha to common target genes is differentially regulated in neuroblastoma: HIF-2alpha promotes an aggressive phenotype. Cancer Cell. Nov. 2006;10(5):413-23.

Hu, et al. Differential roles of hypoxia-inducible factor lalpha (HIF-1alpha) and HIF-2alpha in hypoxic gene regulation. Mol Cell Biol. Dec. 2003;23(24):9361-74.

Karoor, et al. Alveolar hypoxia promotes murine lung tumor growth through a VEGFR-2/EGFR-dependent mechanism. Cancer Prey Res (Phila). Aug. 2012;5(8):1061-71. doi: 10.1158/1940-6207.CAPR-12-0069-T. Epub Jun. 14, 2012.

Keith, et al. HIF1α and HIF2α: sibling rivalry in hypoxic tumour growth and progression. Nat Rev Cancer. Dec. 15, 2011;12(1):9-22. doi: 10.1038/nrc3183.

Key, et al. Principles of ligand binding within a completely buried cavity in HIF2alpha PAS-B. J Am Chem Soc. Dec. 9, 2009;131(48):17647-54. doi: 10.1021/ja9073062.

Kim, et al. HIF2alpha cooperates with RAS to promote lung tumorigenesis in mice. J Clin Invest. Aug. 2009;119(8):2160-70.

King, F.D., Biososteres, Conformational restriction, and pro-drugs-case history: An example of a conformational restriction approach. Med. Chem., Principle and Practice (1994), pp. 206-208.

Kondo, et a. Inhibition of HIF2alpha is sufficient to suppress pVHL-defective tumor growth. PLoS Biol. Dec. 2003;1(3):E83, 439-444. Epub Dec. 22, 2003.

Kondo, et al. Inhibition of HIF is necessary for tumor suppression by the von Hippel-Lindau protein. Cancer Cell. Apr. 2002;1(3):237-46.

Koshiji, et al. HIF-1alpha induces cell cycle arrest by functionally counteracting Myc. EMBO J. May 5, 2004;23(9):1949-56. Epub Apr. 8, 2004.

Lee, et al. Acriflavine inhibits HIF-1 dimerization, tumor growth, and vascularization. Proc Natl Acad Sci U S A. Oct. 20, 2009;106(42):17910-5. doi: 10.1073/pnas.0909353106. Epub Oct. 1, 2009.

Li et al. Hypoxia-inducible factors regulate tumorigenic capacity of glioma stem cells. Cancer Cell 15(6):501-513 (2009).

Lin, et al., Efficient in silico assay of inhibitors of hepatitis c virus RNA-dependent RNA polymerase by structure-based virtual screening and in vitro evaluation. Assay and drug development technologies. 9(3): Jun. 2011; pp. 290-298. XP55350132.

Maher, et al. von Hippel-Lindau disease: a clinical and scientific review. Eur J Hum Genet. Jun. 2011;19(6):617-23. doi: 10.1038/ejhg.2010.175. Epub Mar. 9, 2011.

Mandriota, et al. HIF activation identifies early lesions in VHL kidneys: evidence for site-specific tumor suppressor function in the nephron. Cancer Cell. Jun. 2002;1(5):459-68.

(56) References Cited

OTHER PUBLICATIONS

Maranchie, et al. The contribution of VHL substrate binding and HIF1-alpha to the phenotype of VHL loss in renal cell carcinoma. Cancer Cell. Apr. 2002;1(3):247-55.
Mazumdar, et al. HIF-2alpha deletion promotes Kras-driven lung tumor development. Proc Natl Acad Sci U S A. Aug. 10, 2010;107(32):14182-7. doi: 10.1073/pnas.1001296107. Epub Jul. 21, 2010.
Miranda, et al. A cyclic peptide inhibitor of HIF-1 heterodimerization that inhibits hypoxia signaling in cancer cells. J Am Chem Soc. Jul. 17, 2013;135(28):10418-25. doi: 10.1021/ja402993u. Epub Jul. 9, 2013.
Morrison and Boyd, Isotope Effects. Org. Chem., 3rd ed., (1974), pp. 353-356.
Nguyen, et al. Epigenetic regulation of hypoxia inducible factor in diseases and therapeutics. Arch Pharm Res. Mar. 2013;36(3):252-63. doi: 10.1007/s12272-013-0058-x. Epub Feb. 26, 2013.
Notice of Allowance dated Oct. 6, 2017 for U.S. Appl. No. 15/439,494.
Notice of Allowance dated Oct. 11, 2017 for U.S. Appl. No. 15/439,308.
Notice of Allowance dated Oct. 19, 2017 for U.S. Appl. No. 14/905,776.
Notice of Allowance dated Nov. 9, 2017 for U.S. Appl. No. 15/037,047.
Office Action dated Mar. 24, 2017 for U.S. Appl. No. 15/037,047.
Office Action dated Apr. 28, 2017 for U.S. Appl. No. 14/905,776.
Office Action dated Aug. 16, 2017 for U.S. Appl. No. 15/037,047.
Office Action dated Sep. 8, 2017 for U.S. Appl. No. 14/905,776.
Office Action dated Nov. 21, 2016 for U.S. Appl. No. 15/037,047.
Office Action dated Dec. 16, 2016 for U.S. Appl. No. 14/905,776.
Owens, et al. Smooth muscle cell hypertrophy versus hyperplasia in hypertension. Proc Natl Acad Sci U S A. Dec. 1981;78(12):7759-63.
Percy, et al. A gain-of-function mutation in the HIF2A gene in familial erythrocytosis. N Engl J Med. Jan. 10, 2008;358(2):162-8. doi: 10.1056/NEJMoa073123.
Percy, et al. Two new mutations in the HIF2A gene associated with erythrocytosis. Am J Hematol. Apr. 2012;87(4):439-42. doi: 10.1002/ajh.23123. Epub Feb. 24, 2012.
PubChem. Compound Summary for CID 21110550. 1-10. Create Date: Dec. 5, 2007. [retrieved on Jan. 20, 2015]. Retrieved from the Internet.<URL:http://pubchem.ncbi.nlm.nih.gov/compound/21110550>. entire document.
PubChem. Compound Summary for CID 825455. 1-11. Create Date: Jul. 9, 2005. [retrieved on Jan. 20, 2015]. Retrieved from the Internet.<URL:http://pubchem.ncbi.nlm.nih.gov/compound/825455>. entire document.
Raval, et al. Contrasting properties of hypoxia-inducible factor 1 (HIF-1) and HIF-2 in von Hippel-Lindau-associated renal cell carcinoma. Mol Cell Biol. Jul. 2005;25(13):5675-86.
Rogers, et al. Development of inhibitors of the PAS-B domain of the HIF-2α transcription factor. J Med Chem. Feb. 28, 2013;56(4):1739-47. doi: 10.1021/jm301847z. Epub Feb. 18, 2013.
Sakairi, et al. Synthesis and SAR studies of bicyclic amine series GPR119 agonists. Bioorganic & Medicinal Chemistry Letters. 2012; 22:5123-5128.
Scheuermann, et al. Allosteric inhibition of hypoxia inducible factor-2 with small molecules. Nat Chem Biol. Apr. 2013;9(4):271-6. doi: 10.1038/nchembio.1185. Epub Feb. 24, 2013.
Scheuermann, et al. Artificial ligand binding within the HIF2alpha PAS-B domain of the HIF2 transcription factor. Proc Natl Acad Sci U S A. Jan. 13, 2009;106(2):450-5. doi: 10.1073/pnas.0808092106. Epub Jan. 7, 2009.
Semenza. Hypoxia-inducible factors: mediators of cancer progression and targets for cancer therapy. Trends Pharmacol Sci. Apr. 2012;33(4):207-14. doi: 10.1016/j.tips.2012.01.005. Epub Mar. 6, 2012.
Shen, et al. The VHL/HIF axis in clear cell renal carcinoma. Semin Cancer Biol. Feb. 2013;23(1):18-25. doi: 10.1016/j.semcancer.2012.06.001. Epub Jun. 13, 2012.
Song et al., Synthesis and Biochemical Evaluation of Thiochromanone Thiosemicarbazone Analogues as Inhibitors of Cathepsin L ACS Med. Chem. Lett.. (2012), vol. 3(6), pp. 450-453.
Svensson, et al., Bromination of bicyclic phenols with SO2 heterocyclic annelated rings, ACTA Pharmaceutica Suecica, Royal Pharmaceutical Institute, Sweden, vol. 12, No. 5-6, Jan. 1, 1975: pp. 401-406.
Talks, et al. The expression and distribution of the hypoxia-inducible factors HIF-1alpha and HIF-2alpha in normal human tissues, cancers, and tumor-associated macrophages. Am J Pathol. Aug. 2000;157(2):411-21.
Tan, et al. Identification of a novel small-molecule inhibitor of the hypoxia-inducible factor 1 pathway. Cancer Res. Jan. 15, 2005;65(2):605-12.
Vanharanta, et al. Epigenetic expansion of VHL-HIF signal output drives multiorgan metastasis in renal cancer. Nat Med. Jan. 2013;19(1):50-6. doi: 10.1038/nm.3029. Epub Dec. 9, 2012.
Xue, et al. Hypoxia-inducible factor-2α activation promotes colorectal cancer progression by dysregulating iron homeostasis. Cancer Res. May 1, 2012;72(9):2285-93. doi: 10.1158/0008-5472.CAN-11-3836. Epub Mar. 14, 2012.
Xue, et al. Hypoxia-inducible factor-2α is essential in activating the COX2/mPGES-1/PGE2 signaling axis in colon cancer. Carcinogenesis. Jan. 2013;34(1):163-9. doi: 10.1093/carcin/bgs313. Epub Oct. 5, 2012.
Zhuang, et al. Somatic HIF2A gain-of-function mutations in paraganglioma with polycythemia. N Engl J Med. Sep. 6, 2012;367(10):922-30. doi: 10.1056/NEJMoa1205119.
Zimmer, et al. Inhibition of hypoxia-inducible factor is sufficient for growth suppression of VHL−/− tumors. Mol Cancer Res. Feb. 2004;2(2):89-95.
Zimmer, et al. Small-molecule inhibitors of HIF-2a translation link its 5'UTR iron-responsive element to oxygen sensing. Mol Cell. Dec. 26, 2008;32(6):838-48. doi: 10.1016/j.molcel.2008.12.004.
Small, W. and Donnelly, E.D. Leibel and Phillips textbook of Radiation oncology. JAMA. 2012; 307(1):93.
U.S. Appl. No. 15/805,390 Office Action dated Apr. 3, 2018.
Al-Kaabi, et al. Studies on fused 2(1H)-pyridinethiones: new routes for the synthesis of fused 1H-pyrazolo[3,4-b]pyridines and fused thieno[2,3-b]pyridines. Restrived from SN. Database accession No. 1992:633914.
Anonymous: "A Phase 1, Dose-Escalation Trial of PT2385 Tablets In Patients With Advanced Clear Cell Renal Cell Carcinoma—Full Tex View—Clinical Trials.gov", Nov. 19, 2014 (Nov. 19, 2014), XP55486644.
Banker et al. Modern Pharmaceutics. 3rd ed. Marcel Dekker, New York.p. 596 (1996).
Biellmann, et al. Synthesis and reactions of [1,4-dihydropyridinecarboxylic acids]. Tetrahedron (1970), 26(20), 4799-808.
Bundgaard, Design of Prodrugs, chapter 1, p. 1. (Year: 1985).
Catozzi, et al. Synthesis of the Louisianin Alkaloid Family via a 1,2,4-Triazine Inverse-Electron-Demand Diels-Alder Approach. Journal of Organic Chemistry. vol. 74, No. 21, Nov. 6, 2009, pp. 8343-8354.
Dittmar, et al. (4+2)-Cycloadditionen Der 1.2.4-Triazine-Ein Neuer Weg Zu 4-H-Acepinen. Tetrahedron Letters. El Sevier. Amsterdamn, NL, No. 59, Jan. 1, 1969, pp. 5171-5174.
European search report with written opinion dated Jul. 16, 2018 for EP application No. 16762264.
Freeman. Reaction of Cyanoacetamide and Some 2-Acylcyclanones. Jan. 1, 1969. pp. 3670-3672.
Gewald, et al. Reaktion von methylenaktiven Nitrilen und Cyanamid mit acylierten Enaminen//Reaction of Methylene Active Nitriles and Cyanamide with Acylated Enamines. Journal Fur Praktische Chemie: Practical Applications and Applied Chemistry: Covering All Aspects of Applied Chemistry, Wiley, DE, vol. 324, No. 6, Jan. 1, 1982, pp. 933-941.
Kozhevnikov, et al. Synthesis of Cyclometallated Platinum Complexes with Substituted Thienylpyridines and Detailed Characterization of Their Luminescence Properties. Inorganic Chemistry, vol. 48, No. 9, Apr. 1, 2009, pp. 4179-4189.

(56) References Cited

OTHER PUBLICATIONS

Lone, et al. A Substrate-Free Activity-Based Protein Profiling Screen for the Discovery of Selective PREPL Inhibitors. Journal of the American Chemical Society. vol. 133, No. 30, Aug. 3, 2011 (Aug. 3, 2011), pp. 11665-11674, XP55486936.
Luke, et al. PD-1 pathway inhibitors: The next generation of immunotherapy for advanced melanoma. Oncotarget. Feb. 2015; 6(6): 3479-3492.
McLean, et al. The "inverse electron-demand" Diels-Alder reaction in polymer synthesis. Part 3. Model Diels-Alder reactions of some bis(1,2,4-triazines) with dienophiles and some bis-dienophiles with heterocyclic dienes. XP002782445, retrieved from STN, Database accession No. 1996:608859.
Navarro, et al. American Association for Cancer Research (AACR)—106th Annual Meeting. Philadelphia, Pennsylvania, USA—Apr. 18-22, 2015. Drugs of the Future. vol. 40, No. 5, May 205, p. 341, XP55272384.
Neunhoeffer, et al. Cycloaddition reactions with azabenzenes. XVIII. Synthesis of [2]pyrindines. Heterocycles (1993), 35(2), 1089-101.
Notice of Allowance dated Aug. 13, 2018 for U.S. Appl. No. 15/805,390.
Office action dated Jul. 3, 2018 for U.S. Appl. No. 15/556,607.
Office action dated Aug. 16, 2018 for U.S. Appl. No. 15/564,348.
Office action dated Sep. 17, 2018 for U.S. Appl. No. 15/556,609.
Platonov, et al. Thermolytic reactions of polyfluoroorganic compounds. XXI. Thermolytic reations of hexafluorobenzene and pentafluoropyridine with potassium fluoride and poly(tetrafluoroethylene). XP002782444. Chemical Abstracts Service, Columbus, Ohio, US. Retrieved from STN. Database accession No. 1979:6196.
Schroder, et al. Non-steroidal anti-inflammatory agents. 6. Anti-inflammatory methanesulfonamides I. European Journal of Medicinal Chemistry, 1982, vol. 17, No. 1, p. 35-42.
Seki, et al. 6,7-Dihydro-5H-2-pyrindines. Retrieved from STN. Database accession No. 1974:3400.
Silverman et al. Chapter 8: Prodrugs and drug delivery systems. In: The Organic Chemistry of Drug Design and Drug Action. San Diego: Academic Press, Inc. p. 352-401 (1992).
Vanneman, et al. Combining immunotherapy and targeted therapies in cancer treatment. Nat Rev Cancer. Mar. 22, 2012;12(4):237-51. doi: 10.1038/nrc3237.
Winter, et al. The Vinylogous Mannich Reaction: An Efficient Access to Substituted Nicotinonitriles. SYNLETT, No. 13, Jan. 1, 2003, pp. 1959-1964.
"Wolff, (ed.), Burger's Medicinal Chemistry and Drug Discovery, Fifth Edition, vol. 1: Principles and Practice, San Diego, California, John Wiley & Sons, 1994, pp. 975-977. (4 pages)".

\* cited by examiner

SUBSTITUTED PYRIDINES AND USES THEREOF

CROSS REFERENCE TO RELATED APPLICATIONS

This application is a National Stage Entry of PCT/US2016/021061, filed Mar. 4, 2016, which claims the benefit of U.S. Provisional Application No. 62/131,789, filed on Mar. 11, 2015, and U.S. Provisional Application No. 62/219,044, filed on Sep. 15, 2015, each incorporated herein by reference in its entirety.

BACKGROUND OF THE INVENTION

This invention was in part funded by a grant from Cancer Prevention Research Institute of Texas (Grant number R1009).

An adequate supply of oxygen to tissues is essential in maintaining mammalian cell function and physiology. A deficiency in oxygen supply to tissues is a characteristic of a number of pathophysiologic conditions in which there is insufficient blood flow to provide adequate oxygenation, for example, ischemic disorders, cancer, and atherosclerosis. The hypoxic (low oxygen) environment of tissues activates a signaling cascade that drives the induction or repression of the transcription of a multitude of genes implicated in events such as angiogenesis (neo-vascularization), glucose metabolism, and cell survival/death. A key to this hypoxic transcriptional response lies in the transcription factor, the hypoxia-inducible factors (HIF). HIFs are overexpressed in a vast array of cancers through hypoxia-dependent and independent mechanisms and expression is associated with poor patient prognosis.

HIFs consist of an oxygen-sensitive HIFα subunit and constitutively expressed HIFβ subunit. When HIFs are activated, the HIFα and HIFβ subunits assemble a functional heterodimer (the a subunit heterodimerizes with the β subunit). Both HIFα and HIFβ have two identical structural characteristics, a basic helix-loop-helix (bHLH) and PAS domains (PAS is an acronym referring to the first proteins, PER, ARNT, SIM, in which this motif was identified). There are three human HIFα subunits (HIF-1α, HIF-2α, and HIF-3α) that are oxygen sensitive. Among the three subunits, HIF-1α is the most ubiquitously expressed and induced by low oxygen concentrations in many cell types. HIF-2a is highly similar to HIF-1α in both structure and function, but exhibits more restricted tissue-specific expression, and might also be differentially regulated by nuclear translocation. HIF-3a also exhibits conservation with HIF-1α and HIF-2α in the HLH and PAS domains. HIFβ (also referred to as ARNT—Aryl Hydrocarbon Receptor Nuclear Translocator), the dimerization partner of the HIFα subunits, is constitutively expressed in all cell types and is not regulated by oxygen concentration.

SUMMARY OF THE INVENTION

The present invention addresses a need in the art by providing HIF-2α inhibitors as described herein.

In one aspect, the present invention provides a compound of Formula I:

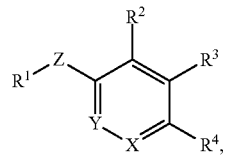

Formula I or a pharmaceutically acceptable salt or prodrug thereof, wherein:
X is $CR^5$ or N;
Y is $CR^6$ or N, wherein at least one of X and Y is N;
Z is O, S, $CHR^7$, $NR^8$ or absent;
$R^1$ is alkyl, heteroalkyl, cycloalkyl, heterocycloalkyl, aryl, heteroaryl, acyl or cyano;
$R^2$ is nitro, carboxaldehyde, carboxyl, ester, amido, cyano, halo, sulfonyl, alkyl, alkenyl, alkynyl or heteroalkyl;
$R^3$ is hydrogen, halo, cyano, alkyl, heteroalkyl, alkenyl, alkynyl, amino, carboxaldehyde, carboxylic acid, oxime, ester, amido or acyl; or $R^2$ and $R^3$ taken together form a cyclic moiety;
$R^4$ is nitro, halo, cyano, alkyl, cycloalkyl, heteroaryl, carboxyl, sulfinyl, sulfonamidyl, sulfonyl, sulfoximinyl or fluoroalkylsulfonyl; and
$R^5$, $R^6$, $R^7$ and $R^8$ are independently hydrogen, halo, hydroxy, cyano, alkyl or alkoxy.

In another aspect, the invention provides a compound of Formula I-A:

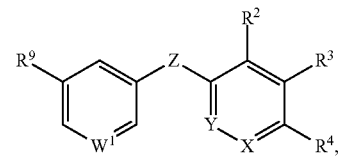

or a pharmaceutically acceptable salt or prodrug thereof, wherein:
X is $CR^5$ or N;
Y is $CR^6$ or N, wherein at least one of X and Y is N;
Z is O, S, $CHR^7$, $NR^8$ or absent;
$R^2$ is nitro, carboxaldehyde, carboxylic acid, ester, amido, cyano, halo, sulfonyl or alkyl;
$R^3$ is hydrogen, halo, cyano, alkyl, heteroalkyl, alkenyl, alkynyl, amino, oxime or acyl; or $R^2$ and $R^3$ taken together form a cyclic moiety;
$R^4$ is nitro, halo, cyano, alkyl, sulfinyl, sulfonamidyl, sulfonyl or sulfoximinyl;
$R^5$, $R^6$, $R^7$ and $R^8$ are independently hydrogen, halo, hydroxy, cyano, alkyl or alkoxy;
$W^1$ is N or $CR^{10}$;
$R^9$ is cyano, halo, alkyl or alkoxy; and
$R^{10}$ is hydrogen, cyano, halo, alkyl or alkoxy.

In another aspect, the invention provides a compound of Formula I-B:

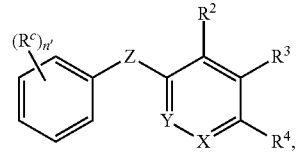

or a pharmaceutically acceptable salt or prodrug thereof, wherein:
X is $CR^5$ or N;
Y is $CR^6$ or N, wherein at least one of X and Y is N;
Z is O, S, $CHR^7$, $NR^8$ or absent;

$R^2$ is nitro, carboxaldehyde, carboxylic acid, ester, amido, cyano, halo, sulfonyl or alkyl;

$R^3$ is hydrogen, halo, cyano, alkyl, heteroalkyl, alkenyl, alkynyl, amino, oxime or acyl; or $R^2$ and $R^3$ taken together form a cyclic moiety;

$R^4$ is nitro, halo, cyano, alkyl, sulfinyl, sulfonamidyl, sulfonyl or sulfoximinyl;

$R^5$, $R^6$, $R^7$ and $R^8$ are independently hydrogen, halo, hydroxy, cyano, alkyl or alkoxy;

$R^c$ is hydrogen, cyano, halo, alkyl or alkoxy; and n' is 0, 1, 2, 3 or 4.

In yet another aspect, the invention provides a compound of Formula I-C:

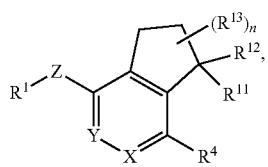

or a pharmaceutically acceptable salt or prodrug thereof, wherein:

X is $CR^5$ or N;

Y is $CR^6$ or N, wherein at least one of X and Y is N;

Z is O, S, $CHR^7$, $NR^8$ or absent;

$R^1$ is alkyl, heteroalkyl, cycloalkyl, heterocycloalkyl, aryl or heteroaryl;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^5$, $R^6$, $R^7$ and $R^8$ are independently hydrogen, halo, hydroxy, cyano, alkyl or alkoxy;

$R^{11}$ is hydrogen, hydroxy, alkoxy or amino;

$R^{12}$ is hydrogen, alkyl, alkenyl or alkynyl; or $R^{11}$ and $R^{12}$ in combination form oxo or oxime;

each of $R^{13}$ is independently selected from the group consisting of hydrogen, fluoro, chloro, hydroxy, alkyl and heteroalkyl; or two $R^{13}$s and the carbon atom(s) to which they are attached form a 3- to 8-membered cycloalkyl or heterocycloalkyl moiety; and n is 0, 1, 2, 3 or 4.

In some other embodiments of compounds of Formula I-C, $R^1$ is phenyl, monocyclic heteroaryl or bicyclic heteroaryl. In some embodiments, $R^1$ is phenyl or pyridyl. In yet other embodiments, $R^1$ is cycloalkyl or heterocycloalkyl. Compounds of Formula I-C are also provided wherein $R^1$ is substituted with at least one substituent selected from the group consisting of halo, $C_1$-$C_4$ alkyl, $C_1$-$C_4$ alkoxy and cyano.

In still other embodiments of compounds of Formula I-C, $R^4$ is cyano, fluoroalkyl, sulfinyl, sulfonamidyl, sulfonyl or sulfoximinyl. In other embodiments, $R^4$ is fluoroalkyl or fluoroalkylsulfonyl. In some other embodiments, $R^{11}$ is hydroxy or amino. In further embodiments, $R^{11}$ is hydroxy. In yet other embodiments, $R^{12}$ is hydrogen. In yet another embodiment, $R^{13}$ is fluoro and n is 1, 2 or 3.

In some embodiments of compounds of Formula I-C, $R^4$ is cyano, fluoroalkyl, sulfinyl, sulfonamidyl, sulfonyl or sulfoximinyl; $R^{11}$ is hydroxy or amino; and $R^{12}$ is hydrogen. In still another embodiment, $R^{13}$ is fluoro. In yet another embodiment, Z is O. In some embodiments, Z is S. In still other embodiments, Z is $NR^8$. In another embodiment, Z is $CHR^7$. In some embodiments, Z is absent.

In some other embodiments of compounds of Formula I-C, $R^4$ is fluoroalkyl; n is 0, 1, 2 or 3; Z is O; $R^{11}$ is hydroxy; and $R^{12}$ is hydrogen. In still other embodiments, $R^4$ is sulfonyl; n is 0, 1, 2 or 3; Z is O; $R^{11}$ is hydroxy; and $R^{12}$ is hydrogen. In yet other embodiments, $R^1$ is phenyl, pyridyl, cycloalkyl or heterocycloalkyl. In some embodiments, X is N and Y is $CR^6$. In another embodiment, X is $CR^5$ and Y is N. In yet another embodiment, X is N and Y is N.

In still another aspect, the invention provides a compound of Formula I-D, I-E, I-F or I-G:

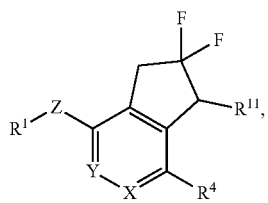

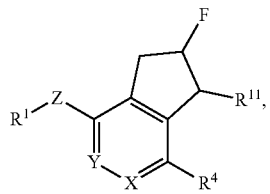

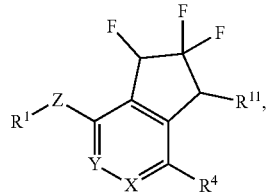

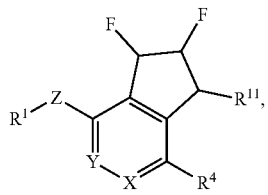

or a pharmaceutically acceptable salt or prodrug thereof, wherein:

X is $CR^5$ or N;

Y is $CR^6$ or N, wherein at least one of X and Y is N;

Z is O, S, $CHR^7$, $NR^8$ or absent;

$R^1$ is alkyl, heteroalkyl, cycloalkyl, heterocycloalkyl, aryl or heteroaryl;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^5$, $R^6$, $R^7$ and $R^8$ are independently hydrogen, halo, hydroxy, cyano, alkyl or alkoxy; and $R^{11}$ is hydrogen, hydroxy, alkoxy or amino.

In a further aspect, the invention provides a compound of Formula I-H, I-I, I-J or I-K:

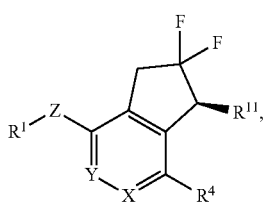

I-H

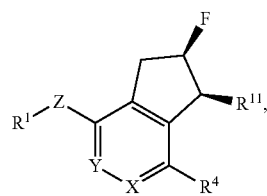

I-I

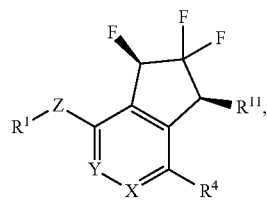

I-J

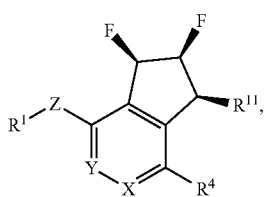

I-K or a pharmaceutically acceptable salt or prodrug thereof, wherein:

X is $CR^5$ or N;

Y is $CR^6$ or N, wherein at least one of X and Y is N;

Z is O, S, $CHR^7$, $NR^8$ or absent;

$R^1$ is alkyl, heteroalkyl, cycloalkyl, heterocycloalkyl, aryl or heteroaryl;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^5$, $R^6$, $R^7$ and $R^8$ are independently hydrogen, halo, hydroxy, cyano, alkyl or alkoxy; and $R^{11}$ is hydroxy or amino.

In one aspect, the present invention provides a compound of Formula I:

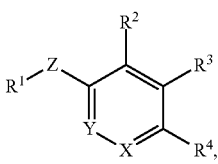

Formula I or a pharmaceutically acceptable salt or prodrug thereof, wherein:

X is $CR^5$ or N;

Y is $CR^6$ or N, wherein at least one of X and Y is N;

Z is —O—, —S—, —S(O)—, —S(O)$_2$—, —C(O)—, —C($HR^7$)—, —N($R^8$)—, $C_1$-$C_3$ alkylene, $C_1$-$C_3$ heteroalkylene, $C_1$-$C_3$ alkenylene or absent;

$R^1$ is alkyl, heteroalkyl, cycloalkyl, heterocycloalkyl, aryl, heteroaryl, acyl or cyano;

$R^2$ is nitro, carboxaldehyde, carboxyl, ester, amido, cyano, halo, sulfonyl, alkyl, alkenyl, alkynyl or heteroalkyl;

$R^3$ is hydrogen, halo, cyano, alkyl, heteroalkyl, alkenyl, alkynyl, amino, carboxaldehyde, carboxylic acid, oxime, ester, amido or acyl; or $R^2$ and $R^3$ taken together form a cyclic moiety;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl; and $R^5$, $R^6$, $R^7$ and $R^8$ are independently hydrogen, halo, hydroxy, cyano, alkyl or alkoxy.

In another aspect, the invention provides a compound of Formula I-A:

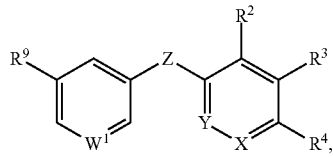

or a pharmaceutically acceptable salt or prodrug thereof, wherein:

X is $CR^5$ or N;

Y is $CR^6$ or N, wherein at least one of X and Y is N;

Z is —O—, —S—, —S(O)—, —S(O)$_2$—, —C(O)—, —C($HR^7$)—, —N($R^8$)—, $C_1$-$C_3$ alkylene, $C_1$-$C_3$ heteroalkylene, $C_1$-$C_3$ alkenylene or absent;

$R^2$ is nitro, carboxaldehyde, carboxylic acid, ester, amido, cyano, halo, sulfonyl or alkyl;

$R^3$ is hydrogen, halo, cyano, alkyl, heteroalkyl, alkenyl, alkynyl, amino, oxime or acyl; or $R^2$ and $R^3$ taken together form a cyclic moiety;

$R^4$ is nitro, halo, cyano, alkyl, sulfinyl, sulfonamidyl, sulfonyl or sulfoximinyl;

$R^5$, $R^6$, $R^7$ and $R^8$ are independently hydrogen, halo, hydroxy, cyano, alkyl or alkoxy;

$W^1$ is N or $CR^{10}$;

$R^9$ is cyano, halo, alkyl or alkoxy; and $R^{10}$ is hydrogen, cyano, halo, alkyl or alkoxy.

In another aspect, the invention provides a compound of Formula I-B:

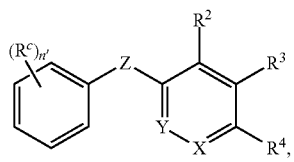

or a pharmaceutically acceptable salt or prodrug thereof, wherein:

X is $CR^5$ or N;

Y is $CR^6$ or N, wherein at least one of X and Y is N;

Z is —O—, —S—, —S(O)—, —S(O)$_2$—, —C(O)—, —C($HR^7$)—, —N($R^8$)—, $C_1$-$C_3$ alkylene, $C_1$-$C_3$ heteroalkylene, $C_1$-$C_3$ alkenylene or absent;

$R^2$ is nitro, carboxaldehyde, carboxylic acid, ester, amido, cyano, halo, sulfonyl or alkyl;

$R^3$ is hydrogen, halo, cyano, alkyl, heteroalkyl, alkenyl, alkynyl, amino, oxime or acyl; or $R^2$ and $R^3$ taken together form a cyclic moiety;

$R^4$ is nitro, halo, cyano, alkyl, sulfinyl, sulfonamidyl, sulfonyl or sulfoximinyl;

$R^5$, $R^6$, $R^7$ and $R^8$ are independently hydrogen, halo, hydroxy, cyano, alkyl or alkoxy;

$R^c$ is hydrogen, cyano, halo, alkyl or alkoxy; and n' is 0, 1, 2, 3 or 4.

In yet another aspect, the invention provides a compound of Formula I-C:

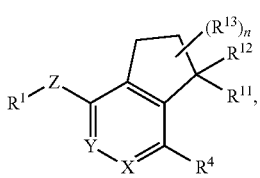

or a pharmaceutically acceptable salt or prodrug thereof, wherein:

X is $CR^5$ or N;

Y is $CR^6$ or N, wherein at least one of X and Y is N;

Z is —O—, —S—, —S(O)—, —S(O)$_2$—, —C(O)—, —C($HR^7$)—, —N($R^8$)—, $C_1$-$C_3$ alkylene, $C_1$-$C_3$ heteroalkylene, $C_1$-$C_3$ alkenylene or absent;

$R^1$ is alkyl, heteroalkyl, cycloalkyl, heterocycloalkyl, aryl or heteroaryl;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^5$, $R^6$, $R^7$ and $R^8$ are independently hydrogen, halo, hydroxy, cyano, alkyl or alkoxy;

$R^{11}$ is hydrogen, halo, hydroxy, alkoxy or amino;

$R^{12}$ is hydrogen, alkyl, alkenyl or alkynyl; or $R^{11}$ and $R^{12}$ in combination form =O, =CH$_2$ or =N(OH);

each of $R^{13}$ is independently selected from the group consisting of hydrogen, fluoro, chloro, hydroxy, alkyl and heteroalkyl; and two $R^{13}$s and the carbon atom(s) to which they are attached may form a 3- to 8-membered cycloalkyl or heterocycloalkyl moiety; and n is 0, 1, 2, 3 or 4.

In some embodiments of compounds of Formula I-C, $R^{12}$ is hydrogen. In further embodiments, $R^{13}$ is fluoro and n is 1, 2 or 3. In some embodiments, $R^{12}$ is hydrogen, alkyl, alkenyl or alkynyl; or $R^{11}$ and $R^{12}$ in combination form =O or =N(OH).

In certain embodiments of compounds of Formula I-C, $R^4$ is fluoroalkyl; n is 0, 1, 2 or 3; Z is —O—; $R^{11}$ is hydroxy; and $R^{12}$ is hydrogen. In still other embodiments, $R^4$ is sulfonyl; n is 0, 1, 2 or 3; Z is —O—; $R^{11}$ is hydroxy; and $R^{12}$ is hydrogen.

In still another aspect, the invention provides a compound of Formula I-D, I-E, I-F or I-G:

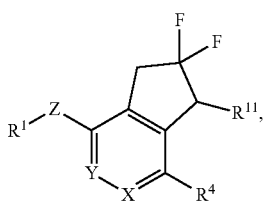

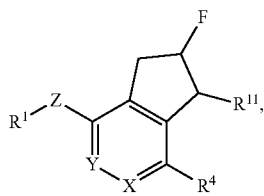

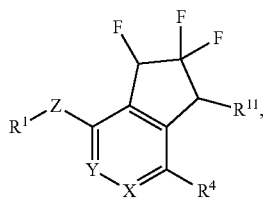

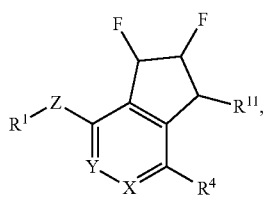

or a pharmaceutically acceptable salt or prodrug thereof, wherein:

X is $CR^5$ or N;

Y is $CR^6$ or N, wherein at least one of X and Y is N;

Z is —O—, —S—, —S(O)—, —S(O)$_2$—, —C(O)—, —C($HR^7$)—, —N($R^8$)—, $C_1$-$C_3$ alkylene, $C_1$-$C_3$ heteroalkylene, $C_1$-$C_3$ alkenylene or absent;

$R^1$ is alkyl, heteroalkyl, cycloalkyl, heterocycloalkyl, aryl or heteroaryl;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^5$, $R^6$, $R^7$ and $R^8$ are independently hydrogen, halo, hydroxy, cyano, alkyl or alkoxy; and $R^{11}$ is hydrogen, halo, hydroxy, alkoxy or amino.

In a further aspect, the invention provides a compound of Formula I-H, I-I, I-J or I-K:

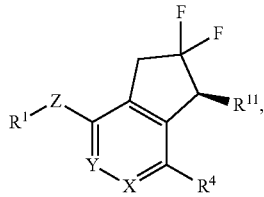

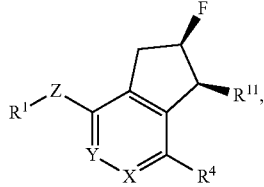

-continued

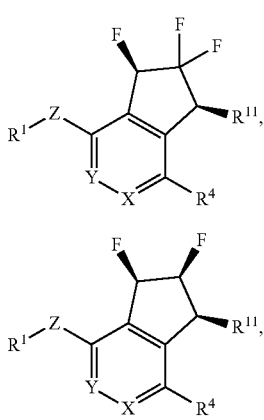

I-J

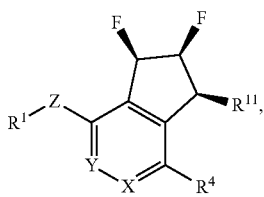

I-K or a pharmaceutically acceptable salt or prodrug thereof, wherein:

X is $CR^5$ or N;

Y is $CR^6$ or N, wherein at least one of X and Y is N;

Z is —O—, —S—, —S(O)—, —S(O)$_2$—, —C(O)—, —C(HR$^7$)—, —N(R$^8$)—, $C_1$-$C_3$ alkylene, $C_1$-$C_3$ heteroalkylene, $C_1$-$C_3$ alkenylene or absent;

$R^1$ is alkyl, heteroalkyl, cycloalkyl, heterocycloalkyl, aryl or heteroaryl;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^5$, $R^6$, $R^7$ and $R^8$ are independently hydrogen, halo, hydroxy, cyano, alkyl or alkoxy; and $R^{11}$ is hydroxy or amino.

In some embodiments of compounds of Formula I-C, I-H, I-I, I-J, or I-K, $R^1$ is phenyl, monocyclic heteroaryl or bicyclic heteroaryl. In some embodiments, $R^1$ is phenyl or pyridyl. In yet other embodiments, $R^1$ is cycloalkyl or heterocycloalkyl. In yet another embodiment, $R^1$ is cyclobutyl. Compounds of Formula I-C, I-H, I-I, I-J, or I-K are also provided wherein $R^1$ is substituted with at least one substituent selected from the group consisting of halo, hydroxy, $C_1$-$C_4$ alkyl, $C_1$-$C_4$ alkoxy and cyano. In some embodiments, $R^1$ is substituted with one to six fluorines. In certain embodiments, $R^1$ is selected from

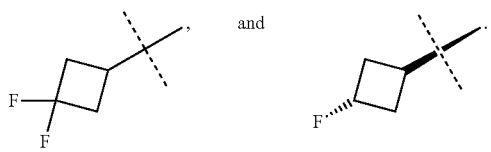

In certain embodiments of compounds of Formula I-C, I-H, I-I, I-J, or I-K, $R^4$ is cyano, fluoroalkyl, sulfinyl, sulfonamidyl, sulfonyl, sulfoximinyl, or fluroalkylsulfonyl. In other embodiments, $R^4$ is fluoroalkyl or fluoroalkylsulfonyl. In some other embodiments, $R^{11}$ is hydroxy or amino. In further embodiments, $R^{11}$ is hydroxy. In yet other embodiments, $R^{12}$ is hydrogen. In yet another embodiment, $R^{13}$ is fluoro and n is 1, 2 or 3.

In some embodiments of compounds of Formula I-C, I-H, I-I, I-J, or I-K, $R^4$ is cyano, fluoroalkyl, sulfinyl, sulfonamidyl, sulfonyl or sulfoximinyl; $R^{11}$ is hydroxy or amino; and $R^{12}$ is hydrogen. In still another embodiment, $R^{13}$ is fluoro. In yet another embodiment, Z is —O—. In some embodiments, Z is —S—. In still other embodiments, Z is —N(R$^8$)—. In another embodiment, Z is —C(HR$^7$)—. In some embodiments, Z is absent.

In some other embodiments of compounds of Formula I-C, I-H, I-I, I-J, or I-K, $R^4$ is fluoroalkyl; Z is —O—; and $R^{11}$ is hydroxy. In still other embodiments, $R^4$ is sulfonyl; Z is —O—; and $R^{11}$ is hydroxy. In yet other embodiments, $R^1$ is phenyl, pyridyl, cycloalkyl or heterocycloalkyl. In some embodiments, $R^1$ is cyclobutyl. In some embodiments, $R^1$ is substituted with at least one substituent selected from the group consisting of halo, hydroxy, $C_1$-$C_4$ alkyl, $C_1$-$C_4$ alkoxy and cyano. In some embodiments, X is N and Y is $CR^6$. In another embodiment, X is $CR^5$ and Y is N. In yet another embodiment, X is N and Y is N.

In yet another aspect, the present invention provides a pharmaceutical composition comprising a compound disclosed herein and a pharmaceutically acceptable carrier.

In still yet another aspect, the present invention provides a method for inhibiting HIF-2α signaling output, comprising contacting HIF-2α with an effective amount of a compound disclosed herein.

In another aspect, the present invention provides a method for inhibiting HIF-2α, comprising contacting HIF-2α with an effective amount of a compound disclosed herein, wherein inhibition of HIF-2α is evidenced by a reduction of one or more biological effects selected from the group consisting of heterodimerization of HIF-2α to ARNT, HIF-2α target gene expression, VEGF gene expression, VEGF protein secretion, and the mRNA level of a HIF-2α-regulated gene.

In yet another aspect, the present invention provides a method for inhibiting HIF-2α, comprising contacting HIF-2α with an effective amount of a compound disclosed herein, thereby reducing the heterodimerization of HIF-2α to ARNT but not heterodimerization of HIF-1α to ARNT.

In practicing any of the methods described herein, the contacting may further comprise contacting a cell that expresses HIF-2α. In some other embodiments, the method further comprises administering a second therapeutic agent to the cell. In other embodiments, the contacting step of the method may take place in vivo. In another embodiment, the contacting step of the method may take place in vitro.

In some other aspects, the present invention provides a method for treating a condition associated with HIF-2α, comprising administering to a subject in need thereof an effective amount of a compound disclosed herein. In some embodiments, the present invention provides a method for treating a neoplastic condition in a subject, comprising administering to said subject a therapeutically effective amount of a pharmaceutical composition of a compound disclosed herein. In some embodiments, a method for treating renal cell carcinoma (RCC) in a subject, comprising administering to said subject a therapeutically effective amount of a pharmaceutical composition of a compound disclosed herein, is provided. In a further embodiment, said subject may be a human. In yet another embodiment, said renal cell carcinoma may be clear cell renal cell carcinoma (ccRCC).

In certain aspects, the present invention provides a method of treating von Hippel-Lindau (VHL) disease, comprising administering to a subject in need thereof an effective amount of a compound described herein.

In still another aspect, the present invention provides a kit comprising a pharmaceutical composition of a compound disclosed herein and instructions for using the composition to treat a subject suffering from renal cell carcinoma.

INCORPORATION BY REFERENCE

All publications, patents and patent applications mentioned in this specification are herein incorporated by reference to the same extent as if each individual publication, patent or patent application was specifically and individually indicated to be incorporated by reference.

DETAILED DESCRIPTION OF THE INVENTION

Figure 1:
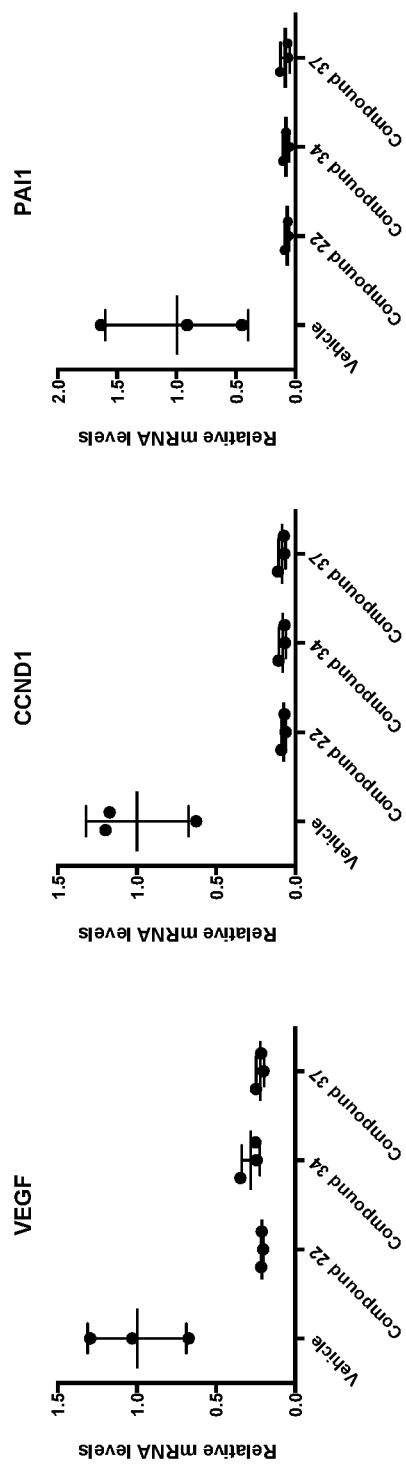
FIG. 1 shows decreased mRNA levels of HIF-2α target genes in 786-0 xenografts following treatment with compounds 22, 34, or 37.

While preferred embodiments of the present invention have been shown and described herein, it will be obvious to those skilled in the art that such embodiments are provided by way of example only. Numerous variations, changes and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

As used herein, "agent" or "biologically active agent" refers to a biological, pharmaceutical, or chemical compound or other moiety. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oliopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor, or an undesired immune response as manifested in autoimmune disease.

The term "cell proliferation" refers to a phenomenon by which the cell number has changed as a result of division. This term also encompasses cell growth by which the cell morphology has changed (e.g., increased in size) consistent with a proliferative signal.

The terms "co-administration," "administered in combination with," and their grammatical equivalents, encompass administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, the terms "treatment", "treating", "palliating" and "ameliorating" are used interchangeably. These terms refer to an approach for obtaining beneficial or desired results including, but are not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compositions may be administered to a patient at risk of developing a particular disease, or to a patient reporting one or more of the physiological symptoms of a disease, even though a diagnosis of this disease may not have been made.

A "therapeutic effect," as used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable" means that a chemical entity, such as a compound, a carrier, an additive or a salt, is acceptable for being administered to a subject.

The term "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

The term "selective inhibition" or "selectively inhibit" as applied to a biologically active agent refers to the agent's ability to selectively reduce the target signaling activity as compared to off-target signaling activity, via direct or indirect interaction with the target.

The term "subject" includes, but is not limited to, humans of any age group, e.g., a pediatric subject (e.g., infant, child or adolescent) or adult subject (e.g., young adult, middle-aged adult or senior adult)) and/or other primates (e.g., cynomolgus monkeys or rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. The methods described herein can be useful in both human therapeutics and veterinary applications. In some embodiments, the patient is a mammal, and in some embodiments, the patient is human.

"Radiation therapy" or "radiation treatment" means exposing a patient, using routine methods and compositions known to the practitioner, to radiation emitters such as alpha-particle emitting radionucleotides (e.g., actinium and thorium radionuclides), low linear energy transfer (LET) radiation emitters (e.g., beta emitters), conversion electron emitters (e.g., strontium-89 and samarium-153-EDTMP), or high-energy radiation, including without limitation x-rays, gamma rays, and neutrons.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

The term "in vivo" refers to an event that takes place in a subject's body.

The term "in vitro" refers to an event that takes place outside of a subject's body. For example, an in vitro assay encompasses any assay run outside of a subject's body. In vitro assays encompass cell-based assays in which cells alive or dead are employed. In vitro assays also encompass a cell-free assay in which no intact cells are employed.

The term "HIF-2α" refers to a monomeric protein that contains several conserved structured domains: basic helix-loop-helix (bHLH), and two Per-ARNT-Sim (PAS) domains designated PAS-A and PAS-B, in addition to C-terminal regulatory regions. "HIF-2α" is also alternatively known by several other names in the scientific literature, including Endothelial PAS Domain Protein 1 (EPAS1), HIF-2A, PASD2, HIF-2-Alpha, HIF-2-Alpha, HLF, Hypoxia-Inducible Factor 2-Alpha, HIF-1alpha-Like Factor, and MOP2. As a member of the bHLH/PAS family of transcription factors, "HIF-2α" forms an active heterodimeric transcription factor complex by binding to the ARNT (also known as HIF-1β) protein through non-covalent interactions. In some embodiments, "HIF-2α" may refer to a fragment of the native protein. In some further embodiments, the fragment may include residues 239 to 348 of the native protein sequence.

The term "scintillation proximity assay" (SPA) refers to a homogeneous assay in which light is emitted when a radio-labeled ligand is brought into close proximity to a radio-sensitive bead. The assay typically contains a target protein that contains a tag (e.g., His Tag, Glutathione S-transferase Tag). The tag on the protein is used to bind the target protein to the scintillation bead. Radio-labeled ligand (e.g., labeled with tritium) that binds to the protein is now in close proximity to the bead, and when the radio-label (e.g., tritium) decays, the high energy particle hits the bead resulting in the emission of light that is detected by a detector, such as photomultiplier tube or CCD camera. When unlabeled ligands or compounds that bind to the protein are used in the assay, they displace the radio-labeled ligand, resulting in loss of signal. For a general reference describing the assay, see Park, et al. *Analytical Biochemistry* 269: 94-104, 1999.

"HIF-2α activity" as used herein has its ordinary meaning in the art. HIF-2α activity, for example, includes activation of gene transcription mediated by HIF-2α.

The term "inhibiting HIF-2α activity", as used herein, refers to slowing, reducing, altering, as well as completely eliminating and/or preventing HIF-2α activity.

The term "alkyl" refers to a straight or branched hydrocarbon chain radical comprising carbon and hydrogen atoms, containing no unsaturation, and having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, n-propyl, isopropyl, n-butyl, isobutyl, sec-butyl, tert-butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl, (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "fluoroalkyl" refers to an alkyl group substituted with one or more fluorine atoms. In some embodiments, it is a $C_1$-$C_4$ alkyl group substituted with one or more fluorine atoms. Typical fluoroalkyl groups include, but are in no way limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

The term "alkenyl" refers to a straight or branched hydrocarbon chain radical group comprising carbon and hydrogen atoms, containing at least one double bond, and having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group may contain 2 carbon atoms, 3 carbon atoms, etc., up to and including 10 carbon atoms. In certain embodiments, an alkenyl comprises two to eight carbon atoms (i.e., $C_2$-$C_8$ alkenyl). In other embodiments, an alkenyl comprises two to five carbon atoms (i.e., $C_2$-$C_5$ alkenyl). The alkenyl is attached to the rest of the molecule by a single bond, for example, ethenyl (i.e., vinyl), prop-1-enyl, but-1-enyl, pent-1-enyl, penta-1,4-dienyl, and the like. Unless stated otherwise specifically in the specification, an alkenyl group is optionally substituted by one or more of the following substituents: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "alkynyl" refers to a straight or branched hydrocarbon chain radical group comprising carbon and hydrogen atoms, containing at least one triple bond, and having from two to ten carbon atoms (i.e., $C_2$-$C_{10}$ alkynyl). In some embodiments, an alkynyl group may contain one or more double bonds. Whenever it appears herein, a numerical range such as "2 to 10" refers to each integer in the given range; e.g., "2 to 10 carbon atoms" means that the alkynyl group may contain 2 carbon atoms, 3 carbon atoms, etc., up to and including 10 carbon atoms. In certain embodiments, an alkynyl comprises two to eight carbon atoms (i.e., $C_2$-$C_8$ alkynyl). In other embodiments, an alkynyl has two to five carbon atoms (i.e., $C_2$-$C_5$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "aromatic" or "aryl" refers to an aromatic radical with six to ten ring atoms (i.e., $C_6$-$C_{10}$ aromatic or $C_6$-$C_{10}$ aryl) which has at least one ring having a conjugated pi electron system which is carbocyclic (e.g., phenyl, fluorenyl, and naphthyl). Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

"Aralkyl" or "arylalkyl" refers to an (aryl)alkyl- radical wherein the arylalkyl moiety is attached via the alkyl portion of the moiety. Aryl and alkyl are as disclosed herein and are optionally substituted by one or more of the substituents described as suitable substituents for aryl and alkyl, respectively.

The term "heteroaryl" or, alternatively, "heteroaromatic" refers to a 5- to 18-membered aromatic radical (i.e., C$_5$-C$_{18}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical, e.g., nitrogen or sulfur, is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzofurazanyl, benzothiazolyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteroaryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl. Examples of monocylic heteroaryls include, but are not limited to, imidazolyl, pyridinyl, pyrrolyl, pyrazinyl, pyrimidinyl, thiazolyl, furanyl and thienyl.

Substituted heteroaryl also includes ring systems substituted with one or more oxide substituents, such as pyridinyl N-oxides.

"Heteroarylalkyl" refers to a moiety having a heteroaryl moiety, as described herein, connected to an alkyl moiety, as described herein, wherein the connection to the remainder of the molecule is through the alkyl group. Heteroaryl and alkyl are as disclosed herein and are optionally substituted by one or more of the substituents described as suitable substituents for heteroaryl and alkyl, respectively.

The term "acyl" refers to a —C(=O)R radical, wherein R is alkyl, cycloalkyl, aryl, heteroaryl, heteroalkyl, or heterocycloalkyl, which are as described herein. The R group is attached to the parent structure through the carbonyl functionality. In some embodiments, it is a C$_1$-C$_{10}$ acyl radical which refers to the total number of chain or ring atoms of the alkyl, cycloalkyl, aryl, heteroalkyl, heteroaryl or heterocycloalkyl portion of the acyl group plus the carbonyl carbon of acyl, i.e. ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "halo", "halide", or alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" refer to haloalkyl and haloalkoxy groups, respectively, in which the halo is fluoro. Examples of fluoroalkyl include, but are not limited to, —$CH_2F$, —$CHF_2$, —$CF_3$, —$CF_2CH_3$, —$CH_2CF_3$, and —$CF_2CF_3$. The alkyl part of the haloalkyl radical may be optionally substituted as defined above for an alkyl group.

The term "cyano" refers to a —CN radical.

The term "alkoxy" refers to an —O-alkyl radical, including from wherein alkyl is as described herein and contains 1 to 10 carbon atoms (i.e., $C_1$-$C_{10}$ alkoxy) of a straight, branched, or cyclic configuration and combinations thereof attached to the parent structure through an oxygen. Examples include methoxy, ethoxy, propoxy, isopropoxy, cyclopropyloxy, cyclohexyloxy and the like. Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms. In some embodiments, it is a $C_1$-$C_4$ alkoxy group. Unless stated otherwise specifically in the specification, an alkoxy moiety may be substituted by one or more of the substituents described as suitable substituents for an alkyl radical.

The term "sp$^3$ hybridized carbon" refers to a carbon atom that is bonded to four other atoms. sp$^3$ hybridization results from the combination of the s orbital and all three p orbitals in the second energy level of carbon. It results in four equivalent orbitals and the geometric arrangement of those four orbitals is tetrahedral.

The term "sulfonyl" refers to a —$S(=O)_2R^a$ radical, wherein $R^a$ is selected from the group consisting of alkyl, amino, cycloalkyl, aryl, heteroalkyl, heteroaryl (bonded through a ring carbon) and heterocycloalkyl (bonded through a ring carbon). Unless stated otherwise specifically in the specification, the $R^a$ group may be substituted by one or more of the substituents described as suitable substituents for an alkyl, an aryl or a heteroaryl radical.

The term "sulfoximinyl" refers to a —$S(=O)(=NR^a)R^b$ radical, wherein $R^a$ is selected from the group consisting of hydrogen, alkyl, cycloalkyl, aryl, cyano, carbamoyl, acyl, heteroaryl (bonded through a ring carbon) and heterocycloalkyl (bonded through a ring carbon) and $R^b$ is independently selected from the group consisting of alkyl, cycloalkyl, aryl, heteroalkyl, heteroaryl (bonded through a ring carbon) and heterocycloalkyl (bonded through a ring carbon). Unless stated otherwise specifically in the specification, the $R^a$ and $R^b$ groups may be substituted by one or more of the substituents described as suitable substituents for an alkyl, an aryl or a heteroaryl radical.

"Sulfonamide," "sulfonamidyl" or "sulfonamido" refers to a —$S(=O)_2N(R^a)_2$ radical, wherein each $R^a$ is selected independently from the group consisting of hydrogen, alkyl, heteroalkyl, cycloalkyl, aryl, heteroaryl and heterocycloalkyl. The $R^a$ groups in —$N(R^a)_2$ of the —$S(=O)_2$—N$(R^a)_2$ radical may be taken together with the nitrogen to which it is attached to form a 4-, 5-, 6-, or 7-membered ring. In some embodiments, it is a $C_1$-$C_{10}$ sulfonamido, wherein each $R^a$ in sulfonamido contains 1 carbon, 2 carbons, 3 carbons or 4 carbons total. A sulfonamido group is optionally substituted by one or more of the substituents described for alkyl, cycloalkyl, aryl and heteroaryl, respectively.

The term "fluoroalkylsulfonyl" refers to a —$S(=O)_2R^a$ radical, wherein $R^a$ is fluoroalkyl. In some embodiments, $R^a$ is $C_1$-$C_4$ alkyl, substituted with one or more fluorines.

The term "cycloalkyl" refers to a monocyclic or polycyclic non-aromatic radical that contains carbon and hydrogen, and may be saturated, or partially unsaturated. Cycloalkyl groups include groups having from 3 to 10 ring atoms (e.g., $C_3$-$C_{10}$ cycloalkyl). Whenever it appears herein, a numerical range such as "3 to 10" refers to each integer in the given range; e.g., "3 to 10 carbon atoms" means that the cycloalkyl group may consist of 3 carbon ring atoms, 4 carbon ring atoms, 5 carbon ring atoms, etc., up to and including 10 carbon ring atoms. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —$OR^a$, —$SR^a$, —OC$(=O)R^a$, —$OC(=O)OR^a$, —$OC(=O)N(R^a)_2$, —$N(R^a)_2$, —$C(=O)OR^a$, —$C(=O)R^a$, —$C(=O)N(R^a)_2$, —$N(R^a)C(=O)OR^a$, —$N(R^a)C(=O)N(R^a)_2$, —$N(R^a)C(NR^a)N(R^a)_2$, —$N(R^a)C(=O)R^a$, —$N(R^a)S(=O)_tR^a$ (where t is 1 or 2), —$N(R^a)S(=O)_tN(R^a)_2$ (where t is 1 or 2), —$S(=O)_tR^a$ (where t is 1 or 2), —$S(=O)N(R^a)_2$ (where t is 1 or 2), —$PO_3(R^a)_2$, —$OPO_3WY$ (where W and Y are independently hydrogen, methyl, ethyl, alkyl, lithium, sodium or potassium) or —$OPO_3Z$ (where Z is calcium, magnesium or iron), wherein each $R^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "heterocyclyl" or "heterocycloalkyl" refers to a stable 3- to 18-membered nonaromatic ring (e.g., $C_3$-$C_{18}$ heterocycloalkyl) radical that comprises two to twelve ring carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, etc., up to and including 18 ring atoms. In some embodiments, it is a $C_5$-$C_{10}$ heterocycloalkyl. In some embodiments, it is a $C_4$-$C_{10}$ heterocycloalkyl. In some embodiments, it is a $C_3$-$C_{10}$ heterocycloalkyl. Unless stated otherwise specifically in the specification, the heterocycloalkyl radical may be a monocyclic, bicyclic, tricyclic or tetracyclic ring system, which may include fused or bridged ring systems. The heteroatoms in the heterocycloalkyl radical may be optionally oxidized. One or more nitrogen atoms, if present, may optionally be quaternized. The heterocycloalkyl radical may be partially or fully saturated. The heterocycloalkyl may be attached to the rest of the molecule through any atom of the ring(s). Examples of such heterocycloalkyl radicals include, but are not limited to, 6,7-dihydro-5H-cyclopenta[b]pyridine, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiomorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur and nitrogen, as well as combinations comprising at least one of the foregoing heteroatoms; the other ring, usually with 3 to 7 ring atoms, optionally contains 1-3 heteroatoms independently selected form oxygen, sulfur and nitrogen and is not aromatic.

The terms "heteroalkyl", "heteroalkenyl" and "heteroalkynyl" include optionally substituted alkyl, alkenyl and alkynyl radicals, which respectively have one or more skeletal chain atoms selected from an atom other than carbon, e.g., oxygen, nitrogen, sulfur, phosphorus or combinations thereof. A numerical range, which refers to the chain length in total, may be given. For example, $C_3$-$C_4$ heteroalkyl has a chain length of 3-4 atoms. For example, a —CH$_2$OCH$_2$CH$_3$ radical is referred to as a "$C_4$ heteroalkyl", which includes the heteroatom in the atom chain length description. Connection to the rest of the molecule may be through either a heteroatom or a carbon in the heteroalkyl chain. A heteroalkyl may be a substituted alkyl. The same definition applies to heteroalkenyl or heteroalkynyl. Unless otherwise stated in the specification, a heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "amino" or "amine" refers to a —N(R$^a$)$_2$ radical group, where each R$^a$ is independently hydrogen, alkyl, heteroalkyl, fluoroalkyl, cycloalkyl, aryl, aralkyl, heterocloalkyl, heterocycloalkylalkyl, heteroaryl or heteroarylalkyl, unless stated otherwise specifically in the specification. When a —N(R$^a$)$_2$ group has two R$^a$ other than hydrogen, they can be combined with the nitrogen atom to form a 3-, 4-, 5-, 6-, 7- or 8-membered ring. For example, —N(R$^a$)$_2$ is meant to include, but not be limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "substituted amino" also refers to N-oxides of N(R$^a$)$_2$ as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

The term "acyloxy" refers to a RC(=O)O— radical wherein R is alkyl, cycloalkyl, aryl, heteroalkyl, heteroaryl or heterocycloalkyl, which are as described herein. In some embodiments, it is a $C_1$-$C_4$ acyloxy radical, which refers to the total number of chain or ring atoms of the alkyl, cycloalkyl, aryl, heteroalkyl, heteroaryl or heterocycloalkyl portion of the acyloxy group plus the carbonyl carbon of acyl, i.e., the other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more of the following substituents: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

The term "amide" or "amido" refers to a chemical moiety with formula —C(=O)N(R$^a$)$_2$ or —NR$^a$C(=O)R$^a$, wherein each of R$^a$ is independently selected from the group consisting of hydrogen, alkyl, cycloalkyl, aryl, heteroaryl (bonded through a ring carbon) and heterocycloalkyl. Two R$^a$s may optionally be taken together with the nitrogen to which it is attached to form a 4-10 membered ring. In some embodiments, it is a $C_1$-$C_4$ amido or amide radical, which includes the amide carbonyl in the total number of carbons in the radical. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound having an amine or a carboxylic acid moiety, thereby forming a prodrug. Any amine, hydroxy or carboxyl side chain on the compounds described herein can be amidified. The procedures and specific groups to make such amides are known to those of skilled in the art and can readily be found in reference sources such as Wuts, *Greene's Protective Groups in Organic Synthesis*, 5$^{th}$ Ed., Wiley, New York, N.Y., 2014, which is incorporated herein by reference in its entirety.

"Carboxaldehyde" refers to a —C(=O)H radical.

"Carboxyl" refers to a —C(=O)OH radical.

"Ester" refers to a chemical radical of formula —C(=O)OR, where R is selected from the group consisting of alkyl, cycloalkyl, aryl, heteroaryl (bonded through a ring carbon) and heterocycloalkyl (bonded through a ring carbon). Any amine, hydroxy, or carboxyl side chain on the compounds described herein can be esterified. The procedures and specific groups to make such esters are known to those skilled in the art and can readily be found in reference sources such as Wuts, *Greene's Protective Groups in Organic Synthesis*, 5$^{th}$ Ed., Wiley, New York, N.Y., 2014, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(NR$^a$)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —PO$_3$(R$^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

"Imino" refers to a =N—R$^a$ radical, wherein R$^a$ is hydrogen, alkyl, heteroalkyl, cycloalkyl, cyano, aryl, heterocycloalkyl or heteroaryl.

"Isocyanato" refers to a —NCO radical.

"Isothiocyanato" refers to a —NCS radical.

"Mercaptyl" refers to an —S(alkyl) or —SH radical.

"Methylene" refers to a =CH$_2$ radical.

"Hydroxy" refers to a —OH radical.

"Oxa" refers to a —O— radical.

"Oxo" refers to a =O radical.

"Nitro" refers to a —NO$_2$ radical.

"Oxime" refers to a =N(—OR) radical, where R is hydrogen or alkyl.

"Sulfinyl" refers to a —S(=O)R radical, where R is selected from the group consisting of alkyl, cycloalkyl, aryl, heteroalkyl, heteroaryl (bonded through a ring carbon) and heterocycloalkyl (bonded through a ring carbon). In some embodiments, R is fluoroalkyl.

"Sulfoxyl" refers to a —S(=O)$_2$OH radical.

"Sulfonate" refers to a —S(=O)$_2$OR radical, where R is selected from the group consisting of alkyl, cycloalkyl, aryl, heteroalkyl, heteroaryl (bonded through a ring carbon) and heteroalkyl (bonded through a ring carbon). The R group is optionally substituted by one or more of the substituents described for alkyl, heteroalkyl, cycloalkyl, heterocycloalkyl, aryl, and heteroaryl, respectively.

"Thiocyanato" refers to a —CNS radical.

"Thioxo" refers to a =S radical.

"Moiety" refers to a specific segment or functional group of a molecule. Chemical moieties are often recognized chemical entities embedded in or appended to a molecule.

"Substituted" means that the referenced group may be substituted with one or more additional group(s) individually and independently selected from acyl, alkyl, alkylaryl, heteroalkyl, cycloalkyl, aralkl, heterocycloalkyl, aryl, carbohydrate, carbonate, heteroaryl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamide, sulfoxyl, sulfonate, urea, and amino, including mono- and di-substituted amino groups and the protected derivatives thereof. The substituents themselves may be substituted, for example, a cycloalkyl substituent may have a halide substituted at one or more ring carbons, and the like. The protecting groups that may form the protective derivatives of the above substituents are known to those of skill in the art and may be found in references such as Wuts, *Greene's Protective Groups in Organic Synthesis*, 5$^{th}$ Ed., Wiley, New York, N.Y., 2014.

The term "optional" or "optionally" means that the subsequently described event or circumstance may or may not occur, and includes instances where the event or circumstance occurs and instances in which it does not. For example, "alkyl optionally substituted with" encompasses both "alkyl" and "alkyl" substituted with groups as defined herein. It will be understood by those skilled in the art, with respect to any group containing one or more substituents, that such groups are not intended to introduce any substitution or substitution patterns which would be deemed unacceptable by one of ordinary skill in the art.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present invention, whether radioactive or not, are encompassed within the scope of the present invention. For example, hydrogen has three naturally occurring isotopes, denoted $^1$H (protium), $^2$H (deuterium), and $^3$H (tritium). Protium is the most abundant isotope in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art or by processes analogous to those described in the Schemes and Examples herein using appropriate isotopically-enriched reagents and/or intermediates. See Pleiss and Voger, *Synthesis and Applications of Isotopically Labeled Compounds*, Vol. 7, Wiley, ISBN-10: 0471495018, published on Mar. 14, 2001.

"Isomers" are different compounds that have the same molecular formula. "Stereoisomers" are isomers that differ only in the way the atoms are arranged in space. "Enantiomers" are a pair of stereoisomers that are non superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms, mixtures of diastereomers and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, chemical entities described herein are intended to include all Z-, E- and tautomeric forms as well.

The term "enantiomeric excess," as used herein, is the percent excess of one enantiomer compared to that of the other enantiomer in a mixture, and can be calculated using the following equation: enantiomeric excess=$((R-S)/(R+S))\times 100=\%(R^*)-\%(S^*)$, wherein R and S are the number of moles of each enantiomer in the mixture, and $R^*$ and $S^*$ are the respective mole fractions of the enantiomers in the mixture. For example, for a mixture with 87% R enantiomer and 13% S enantiomer, the enantiomeric excess is 74%.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

"Protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in Wuts, *Greene's Protective Groups in Organic Synthesis*, 5$^{th}$ Ed., Wiley, New York, N.Y., 2014. For example, a hydroxy protected form is where at least one of the hydroxy groups present in a compound is protected with a hydroxy protecting group. Likewise, amines and other reactive groups may similarly be protected.

"Solvate" refers to a compound in physical association with one or more molecules of a pharmaceutically acceptable solvent. It will be understood that the present chemical entities encompass the present chemical entities and solvates of the compound, as well as mixtures thereof.

"Solvent," "organic solvent," and "inert solvent" each means a solvent inert under the conditions of the reaction being described in conjunction therewith, including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R)- and (S)-isomers of the compounds of the present invention, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Pharmaceutically acceptable forms of the compounds recited herein include pharmaceutically acceptable salts, chelates, non-covalent complexes, prodrugs, and mixtures thereof. In certain embodiments, the compounds described herein are in the form of pharmaceutically acceptable salts. In addition, if the compound described herein is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range.

Abbreviations used herein have their conventional meaning within the chemical and biological arts.

The following abbreviations and terms have the indicated meanings throughout:
DAST=Diethylaminosulfur trifluoride
DCM=Dichloromethane
MTBE=Methyl t-butyl ether
HATU=O-(7-azabenzotriazol-1-yl)-N,N,N',N'-tetramethyluronium hexafluorophosphate
NBS=N-Bromosuccinimide
NMP=N-Methyl-2-pyrrolidone
e.e. or ee=Enantiomeric excess
PPTS=Pyridinium p-toluenesulfonate
TLC=Thin Layer Chromatography
DMAP=4-Dimethylaminopyridine
DMF=N,N-Dimethylformamide When stereochemistry is not specified, certain small molecules described herein include, but are not limited to, when possible, their isomers, such as enantiomers and diastereomers, mixtures of enantiomers, including racemates, mixtures of diastereomers, and other mixtures thereof, to the extent they can be made by one of ordinary skill in the art by routine experimentation. In those situations, the single enantiomers or diastereomers, i.e., optically active forms, can be obtained by asymmetric synthesis or by resolution of the racemates or mixtures of diastereomers. Resolution of the racemates or mixtures of diastereomers, if possible, can be accomplished, for example, by conventional methods such as crystallization in the presence of a resolving agent, or chromatography, using, for example, a chiral high-pressure liquid chromatography (HPLC) column. Furthermore, a mixture of two enantiomers enriched in one of the two can be purified to provide further optically enriched form of the major enantiomer by recrystallization and/or trituration. In addition, such certain small molecules include Z- and E-forms (or cis- and trans-forms) of certain small molecules with carbon-carbon double bonds or carbon-nitrogen double bonds. Where certain small molecules described herein exist in various tautomeric forms, the term "certain small molecule" is intended to include all tautomeric forms of the certain small molecule.

When "\" is drawn across a bond, it denotes where a bond disconnection or attachment occurs. For example, in the chemical structure shown below,

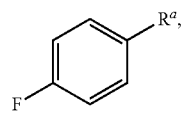

$R^a$ is attached to the para position of a fluorophenyl ring through a single bond. When $R^a$ is phenyl, it can also be drawn as

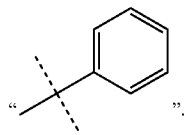

The waved line "∿" means a bond with undefined stereochemistry. For example,

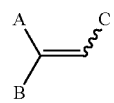

represents a mixture of

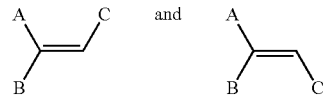

When a bond is drawn across a ring, it means substitution at a non-specific ring atom or position. For example, in the structure shown below,

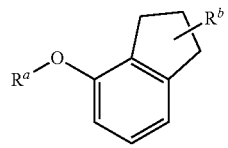

$R^b$ may be attached to any one of the —$CH_2$— in the five-membered ring.

When a bold bond "╱" appears two or more times in the same chemical structure, a mixture of the two cis isomers of the compound is described. For example,

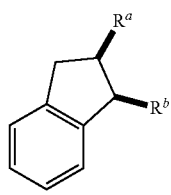

represents a mixture of the two isomers

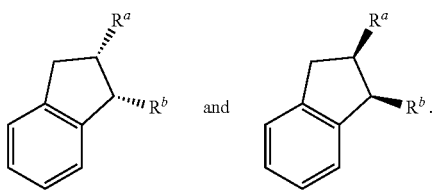

In one aspect, the present invention provides a compound of Formula I:

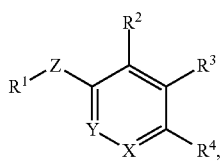

Formula I or a pharmaceutically acceptable salt or prodrug thereof, wherein:
X is $CR^5$ or N;
Y is $CR^6$ or N, wherein at least one of X and Y is N;
Z is O, S, $CHR^7$, $NR^8$ or absent;
$R^1$ is alkyl, heteroalkyl, cycloalkyl, heterocycloalkyl, aryl, heteroaryl, acyl or cyano;
$R^2$ is nitro, carboxaldehyde, carboxyl, ester, amido, cyano, halo, sulfonyl, alkyl, alkenyl, alkynyl or heteroalkyl;
$R^3$ is hydrogen, halo, cyano, alkyl, heteroalkyl, alkenyl, alkynyl, amino, carboxaldehyde, carboxylic acid, oxime, ester, amido or acyl; or $R^2$ and $R^3$ taken together form a cyclic moiety;
$R^4$ is nitro, halo, cyano, alkyl, cycloalkyl, heteroaryl, carboxyl, sulfinyl, sulfonamidyl, sulfonyl, sulfoximinyl or fluoroalkylsulfonyl; and
$R^5$, $R^6$, $R^7$ and $R^8$ are independently hydrogen, halo, hydroxy, cyano, alkyl or alkoxy.

In one aspect, the present invention provides a compound of Formula I:

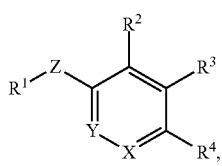

Formula I or a pharmaceutically acceptable salt or prodrug thereof, wherein:
X is $CR^5$ or N;
Y is $CR^6$ or N, wherein at least one of X and Y is N;
Z is —O—, —S—, —S(O)—, —S(O)$_2$—, —C(O)—, —C($HR^7$)—, —N($R^8$)—, $C_1$-$C_3$ alkylene, $C_1$-$C_3$ heteroalkylene, $C_1$-$C_3$ alkenylene or absent;
$R^1$ is alkyl, heteroalkyl, cycloalkyl, heterocycloalkyl, aryl, heteroaryl, acyl or cyano;
$R^2$ is nitro, carboxaldehyde, carboxyl, ester, amido, cyano, halo, sulfonyl, alkyl, alkenyl, alkynyl or heteroalkyl;
$R^3$ is hydrogen, halo, cyano, alkyl, heteroalkyl, alkenyl, alkynyl, amino, carboxaldehyde, carboxylic acid, oxime, ester, amido or acyl; or $R^2$ and $R^3$ taken together form a cyclic moiety;
$R^4$ is nitro, halo, cyano, alkyl, cycloalkyl, heteroaryl, carboxyl, sulfinyl, sulfonamidyl, sulfonyl, sulfoximinyl or fluoroalkylsulfonyl; and
$R^5$, $R^6$, $R^7$ and $R^8$ are independently hydrogen, halo, hydroxy, cyano, alkyl or alkoxy.

In some embodiments, for a compound of Formula I, $R^1$ is further selected from alkyl, heteroalkyl, cycloalkyl, cycloalkenyl, heterocycloalkyl, aryl, heteroaryl, acyl or cyano.

In some embodiments, $R^1$ is phenyl or monocyclic heteroaryl. In some further embodiments, $R^1$ is phenyl or pyridyl, optionally substituted with one or more substituents selected from the group consisting of halo, alkyl, alkoxy and cyano. In a further embodiment, the substituent(s) is selected from the group consisting of halo, $C_1$-$C_4$ alkyl, $C_1$-$C_4$ alkoxy and cyano.

In some embodiments, $R^1$ is bicyclic heteroaryl. In a further embodiment, the bicyclic heteroaryl is substituted with one or more substituents selected from the group consisting of halo, $C_1$-$C_4$ alkyl, $C_1$-$C_4$ alkoxy and cyano.

In some embodiments, $R^1$ is pyridyl N-oxide. In a further embodiment, the pyridyl N-oxide is substituted with one or more substituents selected from the group consisting of halo, $C_1$-$C_4$ alkyl, $C_1$-$C_4$ alkoxy and cyano.

In some embodiments, $R^1$ is

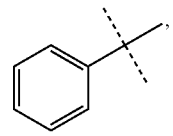

wherein the aryl ring may optionally be substituted with one or more substituents selected from the group consisting of cyano, halo, alkyl and alkoxy. In a further embodiment, the substituent(s) is selected from the group consisting of halo, $C_1$-$C_4$ alkyl, $C_1$-$C_4$ alkoxy and cyano.

In some embodiments, $R^1$ is

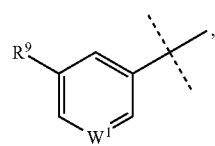

wherein $W^1$ is N or $CR^{10}$, $R^9$ is cyano, halo, alkyl or alkoxy, and $R^{10}$ is hydrogen, cyano, halo, alkyl or alkoxy. In a further embodiment, $R^9$ is cyano, halo, $C_1$-$C_4$ alkyl or $C_1$-$C_4$ alkoxy, and $R^{10}$ is hydrogen, cyano, halo, $C_1$-$C_4$ alkyl or $C_1$-$C_4$ alkoxy.

In some embodiments, $R^1$ is selected from the group consisting of:

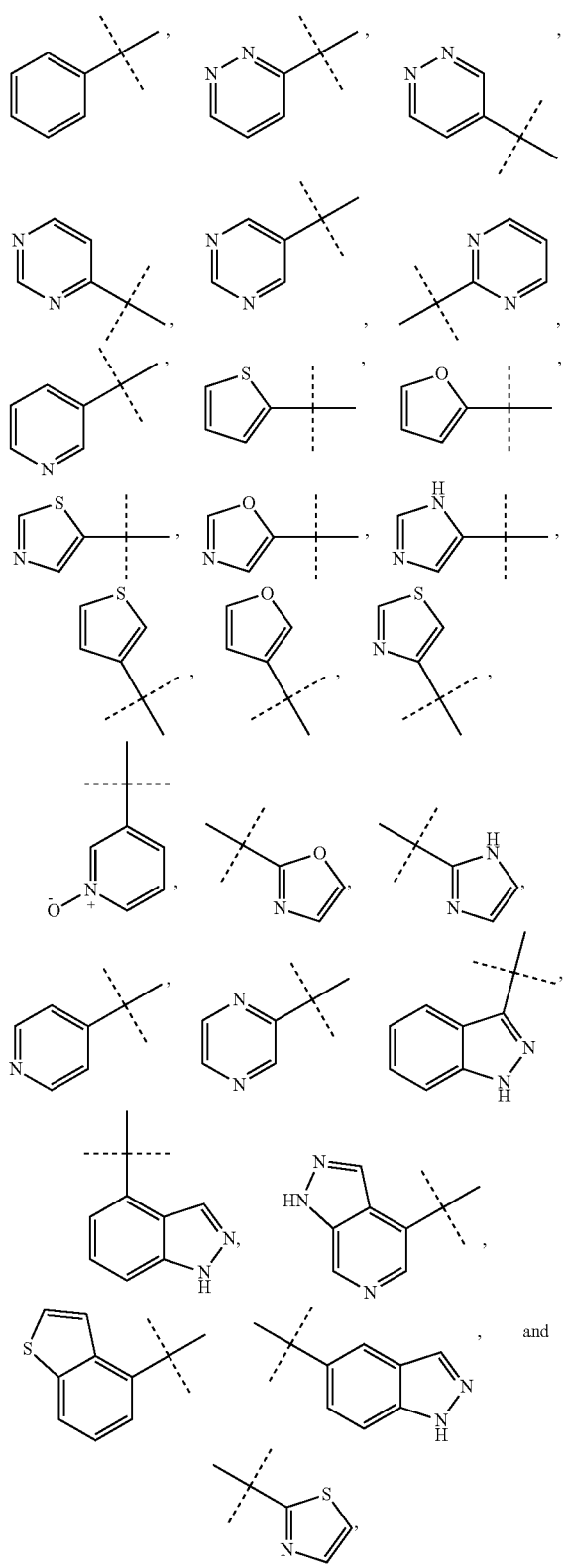

and the rings specified for $R^1$ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is selected from the group consisting of:

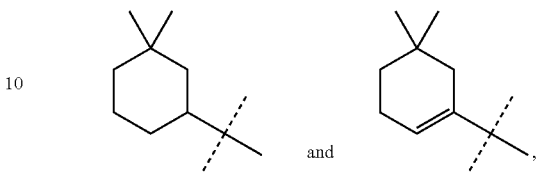

and the rings specified for $R^1$ may optionally be substituted with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

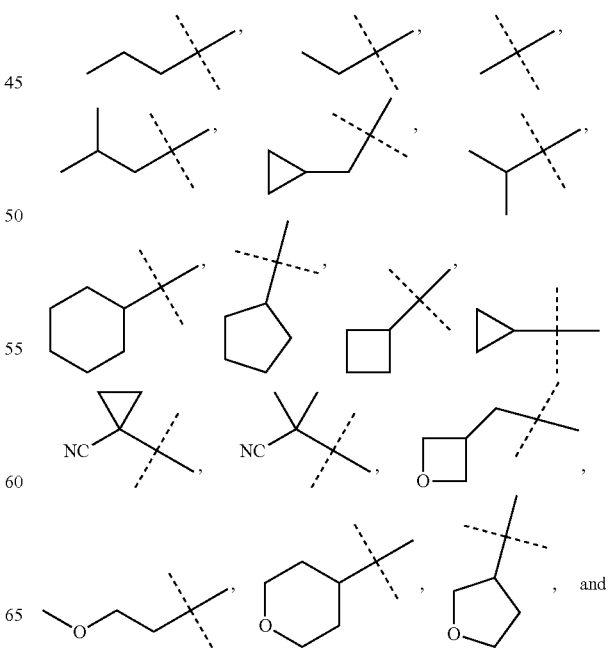

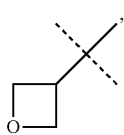

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^2$ is cyano, halo or alkyl. In some embodiments, $R^2$ is halo or alkyl. In some embodiments, $R^2$ is fluoro, chloro, bromo or iodo. In some embodiments, $R^2$ is fluoroalkyl. In some further embodiments, $R^2$ is —$CH_2F$, —$CHF_2$ or —$CF_3$. In another embodiment, $R^2$ is hydrogen. In some other embodiments, $R^2$ is heteroalkyl, alkenyl or alkynyl.

In some embodiments, $R^3$ is hydrogen, halo, cyano, alkyl, alkenyl, heteroalkyl or acyl; or $R^2$ and $R^3$ taken together form a cyclic moiety. In a further embodiment, $R^3$ is halo, cyano or alkyl. In yet a further embodiment, $R^3$ is —$(CH_2)_n$OH, wherein n is 1, 2 or 3. In still a further embodiment, $R^3$ is —$CH_2OH$.

In some embodiments, $R^2$ and $R^3$ taken together with the atoms to which they are attached form a 5- or 6-membered carbocycle with at least one $sp^3$ hybridized carbon. Representative compounds with the carbocycle include, but are not limited to, the following:

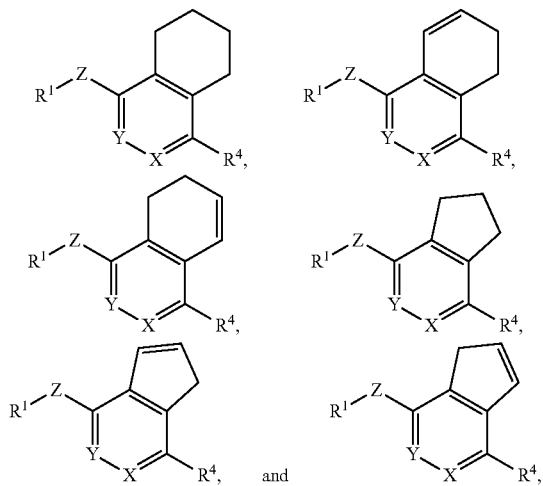

wherein the carbocycle formed by linking $R^2$ and $R^3$ may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano. In yet other embodiments, the substituent(s) is cycloalkyl or heterocycloalkyl and shares one or more ring atoms with the carbocycle formed by linking $R^2$ and $R^3$. In some embodiments, the substituent(s) is $C_3$-$C_5$ cycloalkyl or $C_3$-$C_5$ heterocycloalkyl. In other embodiments, the substituent is oxo.

In some embodiments, $R^2$ and $R^3$ taken together with the atoms to which they are attached form a 5- or 6-membered heterocycle, including, but not limited to, a lactone or lactol, wherein said heterocycle may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano.

In some embodiments, $R^4$ is halo, cyano, fluoroalkyl, sulfinyl, sulfonamidyl, sulfonyl, sulfoximinyl or fluoroalkylsulfonyl. In some embodiments, $R^4$ is cyano, fluoroalkyl, sulfonamidyl, sulfinyl, sulfonyl or sulfoximinyl. In some embodiments, $R^4$ is fluoroalkyl, sulfonamidyl, sulfonyl, sulfoximinyl or fluoroalkylsulfonyl. In a further embodiment, $R^4$ is fluoroalkyl. In yet another embodiment, $R^4$ is sulfonyl. In still another embodiment, $R^4$ is fluoroalkylsulfonyl.

In some embodiments, $R^4$ is —$S(=O)_2R^a$, wherein $R^a$ is alkyl or cycloalkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —$CH_2F$, —$CHF_2$, —$CF_3$, —$CH_2CF_3$, —$CH_2CHF_2$, —$CH_2CH_2F$, —$CHFCH_3$ and —$CF_2CH_3$. In still a further embodiment, $R^a$ is methyl, optionally substituted with one or more fluorines.

In some embodiments, $R^4$ is —$S(=O)(=NR^b)R^a$, wherein $R^a$ is alkyl or cycloalkyl and $R^b$ is hydrogen, cyano or alkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —$CH_2F$, —$CHF_2$, —$CF_3$, —$CH_2CF_3$, —$CH_2CHF_2$, —$CH_2CH_2F$, —$CHFCH_3$ and —$CF_2CH_3$.

In some embodiments, $R^4$ is —$S(=O)_2N(R^a)_2$, wherein each $R^a$ is independently hydrogen, alkyl, heteroalkyl, cycloalkyl or heterocycloalkyl, and at least one $R^a$ is hydrogen. In a further embodiment, both $R^a$s are hydrogen. In another further embodiment, one $R^a$ is hydrogen and the other $R^a$ is $C_1$-$C_4$ alkyl.

In some embodiments, $R^4$ is selected from the group consisting of —CN, —$CF_3$, —$S(=O)CH_3$, —$S(=O)_2CH_3$, —$S(=O)_2CH_2F$, —$S(=O)_2CHF_2$, —$S(=O)_2CF_3$, —$S(=O)_2NH_2$, —$S(=O)_2NHCH_3$, —$S(=O)(=NH)CH_3$, —$S(=O)(=NH)CH_2F$, —$S(=O)(=NH)CHF_2$, —$S(=O)(=NH)CF_3$, —$S(=O)(=N—CN)CH_3$, —$S(=O)(=N—CN)CH_2F$, —$S(=O)(=N—CN)CHF_2$ and —$S(=O)(=N—CN)CF_3$.

In some embodiments, $R^5$ is hydrogen. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen. In some other embodiments, $R^8$ is $C_1$-$C_4$ alkyl or $C_1$-$C_4$ alkoxy. In a further embodiment, $R^8$ is methyl.

In some embodiments, $R^3$ is hydrogen, $R^4$ is —$S(=O)_2R^a$ or —$S(=O)(=NR^b)R^c$, wherein $R^a$ is fluoroalkyl, $R^b$ is hydrogen, cyano or alkyl and $R^c$ is alkyl. In a further embodiment, $R^1$ is selected from the group consisting of

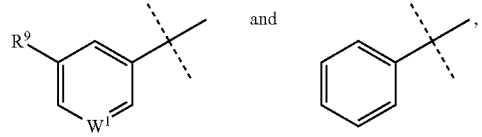

wherein $W^1$ is N or $CR^{10}$, $R^9$ is cyano, halo, alkyl or alkoxy, and $R^{10}$ is hydrogen, cyano, halo, alkyl or alkoxy; and

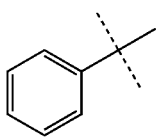

may optionally be substituted with one or more substituents selected from the group consisting of cyano, halo, alkyl and alkoxy. In a further embodiment, the alkyl is $C_1$-$C_4$ alkyl. In another further embodiment, the alkoxy is $C_1$-$C_4$ alkoxy.

In some embodiments, each of $R^2$ and $R^3$ is independently alkyl and $R^4$ is cyano, fluoroalkyl, sulfonamidyl, sulfinyl, sulfonyl, sulfoximinyl or fluoroalkylsulfonyl.

In some embodiments, $R^3$ is —$CH_2OH$. In a further embodiment, $R^4$ is cyano, fluoroalkyl, sulfonamidyl, sulfinyl, sulfonyl, sulfoximinyl or fluoroalkylsulfonyl and $R^5$ is hydrogen. In still a further embodiment, $R^2$ is cyano, halo or alkyl.

In some embodiments, $R^1$ is phenyl or monocyclic heteroaryl; $R^2$ is nitro, halo, cyano or alkyl; $R^3$ is halo, cyano or alkyl; $R^4$ is cyano, fluoroalkyl, sulfonamidyl, sulfinyl, sulfonyl, sulfoximinyl or fluoroalkylsulfonyl. In a further embodiment, $R^4$ is selected from the group consisting of —CN, —$CF_3$, —S(=O)$CH_3$, —S(=O)$_2CH_3$, —S(=O)$_2$$CH_2F$, —S(=O)$_2CHF_2$, —S(=O)$_2CF_3$, —S(=O)$_2NH_2$, —S(=O)$_2NHCH_3$, —S(=O)(=NH)$CH_3$, —S(=O)(=NH)$CH_2F$, —S(=O)(=NH)$CHF_2$, —S(=O)(=NH)$CF_3$, —S(=O)(=N—CN)$CH_3$, —S(=O)(=N—CN)$CH_2F$, —S(=O)(=N—CN)$CHF_2$ and —S(=O)(=N—CN)$CF_3$. In still a further embodiment, $R^5$ is hydrogen.

In some embodiments, $R^1$ is bicyclic heteroaryl; $R^2$ is nitro, halo, cyano or alkyl; $R^3$ is halo, cyano or alkyl; $R^4$ is cyano, fluoroalkyl, sulfonamidyl, sulfinyl, sulfonyl, sulfoximinyl or fluoroalkylsulfonyl; and $R^5$ is hydrogen.

In some embodiments, $R^1$ is phenyl, monocyclic heteroaryl or bicyclic heteroaryl; $R^2$ is halo, cyano or alkyl; $R^3$ is halo, cyano or alkyl; $R^4$ is cyano, fluoroalkyl, sulfonamidyl, sulfinyl, sulfonyl, sulfoximinyl or fluoroalkylsulfonyl; and $R^5$ is hydrogen.

In some embodiments, $R^2$ and $R^3$ together with the atoms to which they are attached form a 5- or 6-membered carbocycle with at least one $sp^3$ hybridized carbon; $R^4$ is cyano, fluoroalkyl, sulfonamidyl, sulfinyl, sulfonyl, sulfoximinyl or fluoroalkylsulfonyl; and $R^5$ is hydrogen. In a further embodiment, $R^1$ is phenyl or monocyclic heteroaryl. In another further embodiment, $R^1$ is bicyclic heteroaryl.

In some embodiments, X is N and Y is $CR^6$. In other embodiments, X is $CR^5$ and Y is N. In still other embodiments, X is N and Y is N.

In some embodiments, Z is O. In other embodiments, Z is S. In further embodiments, Z is $CHR^7$. In yet other embodiments, Z is $NR^8$. In some embodiments, Z is absent.

In some embodiments, Z is —O—, —S—, —S(O)—, —S(O)$_2$—, —S(O$_2$)N($R^8$)—, —C(O)—, —C(O)O—, —C($HR^7$)—, —N($R^8$)—, —C(O)N($R^8$)—, alkylene, alkenylene, alkynylene, heteroalkylene, or absent. In some embodiments, Z is —O—, —S—, —S(O)—, —S(O)$_2$—, —C(O)—, —C($HR^7$)—, —N($R^8$)—, $C_1$-$C_3$ alkylene, $C_1$-$C_3$ heteroalkylene, $C_1$-$C_3$ alkenylene or absent. In some embodiments, Z is —O—. In other embodiments, Z is —S—. In further embodiments, Z is —C($HR^7$)—. In yet other embodiments, Z is —N($R^8$). In some embodiments, Z is absent.

In another aspect, the invention provides a compound of Formula I-A:

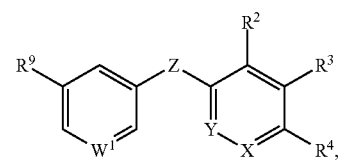

or a pharmaceutically acceptable salt or prodrug thereof, wherein:
X is $CR^5$ or N;
Y is $CR^6$ or N, wherein at least one of X and Y is N;
Z is O, S, $CHR^7$, $NR^8$ or absent;
$R^2$ is nitro, carboxaldehyde, carboxylic acid, ester, amido, cyano, halo, sulfonyl or alkyl;
$R^3$ is hydrogen, halo, cyano, alkyl, heteroalkyl, alkenyl, alkynyl, amino, oxime or acyl; or $R^2$ and $R^3$ taken together form a cyclic moiety;
$R^4$ is nitro, halo, cyano, alkyl, sulfinyl, sulfonamidyl, sulfonyl or sulfoximinyl;
$R^5$, $R^6$, $R^7$ and $R^8$ are independently hydrogen, halo, hydroxy, cyano, alkyl or alkoxy;
$W^1$ is N or $CR^{10}$;
$R^9$ is cyano, halo, alkyl or alkoxy; and
$R^{10}$ is hydrogen, cyano, halo, alkyl or alkoxy.

In another aspect, the invention provides a compound of Formula I-A:

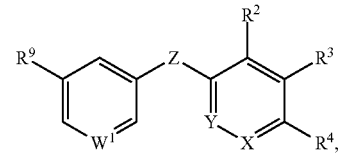

or a pharmaceutically acceptable salt or prodrug thereof, wherein:
X is $CR^5$ or N;
Y is $CR^6$ or N, wherein at least one of X and Y is N;
Z is —O—, —S—, —S(O)—, —S(O)$_2$—, —C(O)—, —C($HR^7$)—, —N($R^8$)—, $C_1$-$C_3$ alkylene, $C_1$-$C_3$ heteroalkylene, $C_1$-$C_3$ alkenylene or absent;
$R^2$ is nitro, carboxaldehyde, carboxylic acid, ester, amido, cyano, halo, sulfonyl or alkyl;
$R^3$ is hydrogen, halo, cyano, alkyl, heteroalkyl, alkenyl, alkynyl, amino, oxime or acyl; or $R^2$ and $R^3$ taken together form a cyclic moiety;
$R^4$ is nitro, halo, cyano, alkyl, sulfinyl, sulfonamidyl, sulfonyl or sulfoximinyl;
$R^5$, $R^6$, $R^7$ and $R^8$ are independently hydrogen, halo, hydroxy, cyano, alkyl or alkoxy;
$W^1$ is N or $CR^{10}$;
$R^9$ is cyano, halo, alkyl or alkoxy; and
$R^{10}$ is hydrogen, cyano, halo, alkyl or alkoxy.

In some embodiments, $R^2$ is cyano, halo or alkyl. In some embodiments, $R^2$ is halo or alkyl. In some embodiments, $R^2$ is fluoro, chloro, bromo or iodo. In some embodiments, $R^2$ is fluoroalkyl. In some further embodiments, $R^2$ is —$CH_2F$, —$CHF_2$ or —$CF_3$.

In some embodiments, $R^3$ is hydrogen, halo, cyano, alkyl, alkenyl, heteroalkyl or acyl; or $R^2$ and $R^3$ taken together form a cyclic moiety. In a further embodiment, $R^3$ is halo, cyano or alkyl. In yet a further embodiment, $R^3$ is —($CH_2$)$_n$OH, wherein n is 1, 2 or 3. In still a further embodiment, $R^3$ is —$CH_2OH$.

In some embodiments, $R^2$ and $R^3$ taken together with the atoms to which they are attached form a 5- or 6-membered carbocycle with at least one sp$^3$ hybridized carbon. Representative compounds with the carbocycle include, but are not limited to, the following

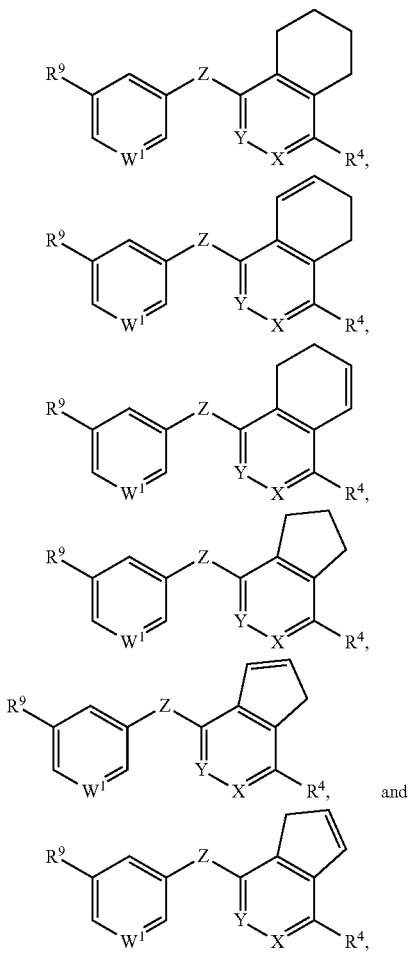

wherein the carbocycle formed by linking $R^2$ and $R^3$ may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano. In yet other embodiments, the substituent(s) is cycloalkyl or heterocycloalkyl and shares one or more ring atoms with the carbocycle formed by linking $R^2$ and $R^3$. In some embodiments, the substituent(s) is $C_3$-$C_5$ cycloalkyl or $C_3$-$C_5$ heterocycloalkyl. In other embodiments, the substituent is oxo.

In some embodiments, $R^2$ and $R^3$ taken together with the atoms to which they are attached form a 5- or 6-membered heterocycle, including, but not limited to, a lactone or lactol, wherein said heterocycle may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano.

In some embodiments, $R^4$ is halo, cyano, fluoroalkyl, sulfinyl, sulfonamidyl, sulfonyl, sulfoximinyl or fluoroalkylsulfonyl. In some embodiments, $R^4$ is cyano, fluoroalkyl, sulfonamidyl, sulfinyl, sulfonyl or sulfoximinyl. In some embodiments, $R^4$ is fluoroalkyl, sulfonamidyl, sulfonyl or sulfoximinyl. In a further embodiment, $R^4$ is fluoroalkyl. In yet another embodiment, $R^4$ is sulfonyl. In still another embodiment, $R^4$ is fluoroalkylsulfonyl.

In some embodiments, $R^4$ is —S(═O)$_2$R$^a$, wherein R$^a$ is alkyl or cycloalkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$. In still a further embodiment, R$^a$ is methyl, optionally substituted with one or more fluorines.

In some embodiments, $R^4$ is —S(═O)(═NR$^b$)R$^a$, wherein R$^a$ is alkyl or cycloalkyl and R$^b$ is hydrogen, cyano or alkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(═O)$_2$N(R$^a$)$_2$, wherein each R$^a$ is independently hydrogen, alkyl, heteroalkyl, cycloalkyl or heterocycloalkyl, and at least one R$^a$ is hydrogen. In a further embodiment, both R$^a$s are hydrogen. In another further embodiment, one R$^a$ is hydrogen and the other R$^a$ is $C_1$-$C_4$ alkyl.

In some embodiments, $R^4$ is selected from the group consisting of —CN, —CF$_3$, —S(═O)CH$_3$, —S(═O)$_2$CH$_3$, —S(═O)$_2$CH$_2$F, —S(═O)$_2$CHF$_2$, —S(═O)$_2$CF$_3$, —S(═O)$_2$NH$_2$, —S(═O)$_2$NHCH$_3$, —S(═O)(═NH)CH$_3$, —S(═O)(═NH)CH$_2$F, —S(═O)(═NH)CHF$_2$, —S(═O)(═NH)CF$_3$, —S(═O)(═N—CN)CH$_3$, —S(═O)(═N—CN)CH$_2$F, —S(═O)(═N—CN)CHF$_2$ and —S(═O)(═N—CN)CF$_3$.

In some embodiments, $R^5$ is hydrogen. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen. In some other embodiments, $R^8$ is $C_1$-$C_4$ alkyl or $C_1$-$C_4$ alkoxy. In a further embodiment, $R^8$ is methyl.

In some embodiments, $R^9$ is cyano, halo, $C_1$-$C_4$ alkyl or $C_1$-$C_4$ alkoxy.

In some embodiments, $R^{10}$ is hydrogen, cyano, halo, $C_1$-$C_4$ alkyl or $C_1$-$C_4$ alkoxy.

In some embodiments, $R^2$ and $R^3$ taken together with the atoms to which they are attached form a 5- or 6-membered carbocycle with at least one sp$^3$ hybridized carbon and $R^4$ is cyano, fluoroalkyl, sulfonamidyl, sulfinyl, sulfonyl, sulfoximinyl or fluoroalkylsulfonyl.

In some embodiments, $R^3$ is —CH$_2$OH and $R^4$ is cyano, fluoroalkyl, sulfonamidyl, sulfonyl or sulfoximinyl. In a further embodiment, $R^5$ is hydrogen. In still a further embodiment, $R^2$ is cyano, halo or alkyl.

In some embodiments, $R^2$ is halo, cyano or alkyl; $R^3$ is CH$_2$OH; $R^4$ is cyano, fluoroalkyl, sulfonamidyl, sulfonyl or sulfoximinyl. In a further embodiment, $R^4$ is selected from the group consisting of —CN, —CF$_3$, —S(═O)CH$_3$, —S(═O)$_2$CH$_3$, —S(═O)$_2$CH$_2$F, —S(═O)$_2$CHF$_2$, —S(═O)$_2$CF$_3$, —S(═O)$_2$NH$_2$, —S(═O)$_2$NHCH$_3$, —S(═O)(═NH)CH$_3$, —S(═O)(═NH)CH$_2$F, —S(═O)(═NH)CHF$_2$, —S(═O)(═NH)CF$_3$, —S(═O)(═N—CN)CH$_3$, —S(═O)(═N—CN)CH$_2$F, —S(═O)(═N—CN)CHF$_2$ and —S(═O)(═N—CN)CF$_3$.

In some embodiments, X is N and Y is $CR^6$. In other embodiments, X is $CR^5$ and Y is N. In still other embodiments, X is N and Y is N.

In some embodiments, Z is O. In other embodiments, Z is S. In further embodiments, Z is $CHR^7$. In yet other embodiments, Z is $NR^8$. In some embodiments, Z is absent.

In some embodiments, Z is —O—, —S—, —S(O)—, —S(O)$_2$—, —S(O$_2$)N(R$^8$)—, —C(O)—, —C(O)O—, —C(HR$^7$)—, —N(R$^8$)—, —C(O)N(R$^8$)—, alkylene, alkenylene, alkynylene, heteroalkylene, or absent. In some embodiments, Z is —O—, —S—, —S(O)—, —S(O)$_2$—, —C(O)—, —C(HR$^7$)—, —N(R$^8$)—, $C_1$-$C_3$ alkylene, $C_1$-$C_3$ heteroalkylene, $C_1$-$C_3$ alkenylene or absent. In some embodiments, Z is —O—. In other embodiments, Z is —S—. In further embodiments, Z is —C(HR$^7$)—. In yet other embodiments, Z is —N(R$^8$). In some embodiments, Z is absent.

In another aspect, the invention provides a compound of Formula I-B:

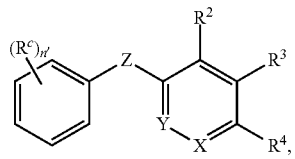

or a pharmaceutically acceptable salt or prodrug thereof, wherein:

X is $CR^5$ or N;
Y is $CR^6$ or N, wherein at least one of X and Y is N;
Z is O, S, $CHR^7$, $NR^8$ or absent;
$R^2$ is nitro, carboxaldehyde, carboxylic acid, ester, amido, cyano, halo, sulfonyl or alkyl;
$R^3$ is hydrogen, halo, cyano, alkyl, heteroalkyl, alkenyl, alkynyl, amino, oxime or acyl; or $R^2$ and $R^3$ taken together form a cyclic moiety;
$R^4$ is nitro, halo, cyano, alkyl, sulfinyl, sulfonamidyl, sulfonyl or sulfoximinyl;
$R^5$, $R^6$, $R^7$ and $R^8$ are independently hydrogen, halo, hydroxy, cyano, alkyl or alkoxy;
$R^c$ is hydrogen, cyano, halo, alkyl or alkoxy; and
n' is 0, 1, 2, 3 or 4.

In another aspect, the invention provides a compound of Formula I-B:

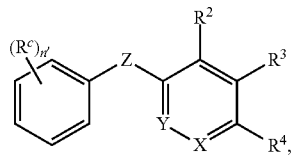

or a pharmaceutically acceptable salt or prodrug thereof, wherein:

X is $CR^5$ or N;
Y is $CR^6$ or N, wherein at least one of X and Y is N;
Z is —O—, —S—, —S(O)—, —S(O)$_2$—, —C(O)—, —C(HR$^7$)—, —N(R$^8$)—, $C_1$-$C_3$ alkylene, $C_1$-$C_3$ heteroalkylene, $C_1$-$C_3$ alkenylene or absent;
$R^2$ is nitro, carboxaldehyde, carboxylic acid, ester, amido, cyano, halo, sulfonyl or alkyl;
$R^3$ is hydrogen, halo, cyano, alkyl, heteroalkyl, alkenyl, alkynyl, amino, oxime or acyl; or $R^2$ and $R^3$ taken together form a cyclic moiety;
$R^4$ is nitro, halo, cyano, alkyl, sulfinyl, sulfonamidyl, sulfonyl or sulfoximinyl;
$R^5$, $R^6$, $R^7$ and $R^8$ are independently hydrogen, halo, hydroxy, cyano, alkyl or alkoxy;
$R^c$ is hydrogen, cyano, halo, alkyl or alkoxy; and
n' is 0, 1, 2, 3 or 4.

In some embodiments, $R^2$ is cyano, halo or alkyl. In some embodiments, $R^2$ is halo or alkyl. In some embodiments, $R^2$ is fluoro, chloro, bromo or iodo. In some embodiments, $R^2$ is fluoroalkyl. In some further embodiments, $R^2$ is —CH$_2$F, —CHF$_2$ or —CF$_3$.

In some embodiments, $R^3$ is hydrogen, halo, cyano, alkyl, alkenyl, heteroalkyl or acyl; or $R^2$ and $R^3$ taken together form a cyclic moiety. In a further embodiment, $R^3$ is halo, cyano or alkyl. In yet a further embodiment, $R^3$ is —(CH$_2$)$_n$OH, wherein n is 1, 2 or 3.

In some embodiments, $R^2$ and $R^3$ taken together with the atoms to which they are attached form a 5- or 6-membered carbocycle with at least one sp$^3$ hybridized carbon. Representative compounds with the carbocycle include, but are not limited to, the following:

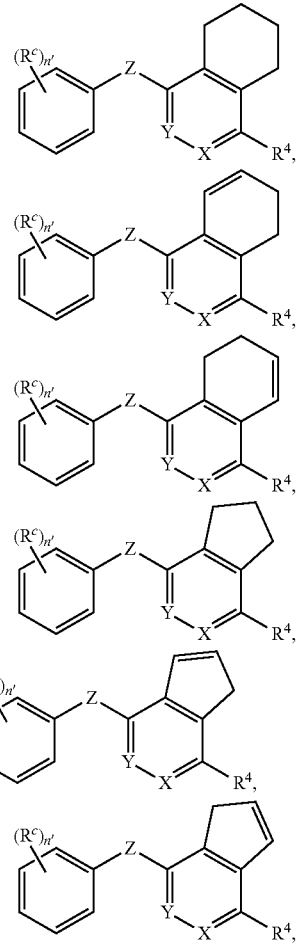

wherein the carbocycle formed by linking $R^2$ and $R^3$ may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano. In yet other embodiments, the substituent(s) is cycloalkyl or heterocycloalkyl and shares one or more ring atoms with the carbocycle formed by linking $R^2$ and $R^3$. In some embodiments, the substituent(s) is $C_3$-$C_5$ cycloalkyl or $C_3$-$C_5$ heterocycloalkyl. In other embodiments, the substituent is oxo.

In some embodiments, $R^2$ and $R^3$ taken together with the atoms to which they are attached form a 5- or 6-membered heterocycle, including, but not limited to, a lactone or lactol, wherein said heterocycle may be optionally substituted with fluoro, chloro, hydroxy, alkyl or heteroalkyl. In a further embodiment, the substituent(s) is selected from the group consisting of halo, $C_1$-$C_4$ alkyl, $C_1$-$C_4$ alkoxy and cyano.

In some embodiments, $R^3$ is hydrogen, $R^4$ is is —S(=O)$_2$ $R^a$ or —S(=O)(=NR$^b$)$R^d$, wherein $R^a$ is fluoroalkyl, $R^b$ is hydrogen, cyano or alkyl and $R^d$ is alkyl.

In some embodiments, $R^4$ is halo, cyano, fluoroalkyl, sulfinyl, sulfonamidyl, sulfonyl, sulfoximinyl or fluoroalkylsulfonyl. In some embodiments, $R^4$ is cyano, fluoroalkyl, sulfonamidyl, sulfinyl, sulfonyl or sulfoximinyl. In some embodiments, $R^4$ is fluoroalkyl, sulfonamidyl, sulfonyl or sulfoximinyl. In a further embodiment, $R^4$ is fluoroalkyl. In yet another embodiment, $R^4$ is sulfonyl. In still another embodiment, $R^4$ is fluoroalkylsulfonyl.

In some embodiments, $R^4$ is —S(=O)$_2$$R^a$, wherein $R^a$ is alkyl or cycloalkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$. In still a further embodiment, $R^a$ is methyl, optionally substituted with one or more fluorines.

In some embodiments, $R^4$ is —S(=O)(=NR$^b$)$R^a$, wherein $R^a$ is alkyl or cycloalkyl and $R^b$ is hydrogen, cyano or alkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(=O)$_2$—N(R$^a$)$_2$, wherein each $R^a$ is independently hydrogen, alkyl, heteroalkyl, cycloalkyl or heterocycloalkyl, and at least one $R^a$ is hydrogen. In a further embodiment, both $R^a$s are hydrogen. In another further embodiment, one $R^a$ is hydrogen and the other $R^a$ is $C_1$-$C_4$ alkyl.

In some embodiments, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^5$ is hydrogen. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen. In some other embodiments, $R^8$ is $C_1$-$C_4$ alkyl or $C_1$-$C_4$ alkoxy. In a further embodiment, $R^8$ is methyl.

In some embodiments, $R^2$ and $R^3$ taken together with the atoms to which they are attached form a 5- or 6-membered carbocycle with at least one sp$^3$ hybridized carbon and $R^4$ is cyano, fluoroalkyl, sulfonamidyl, sulfinyl, sulfonyl, sulfoximinyl or fluoroalkylsulfonyl. In a further embodiment, $R^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, $R^3$ is —CH$_2$OH and $R^4$ is fluoroalkyl, sulfonamidyl, sulfonyl, sulfinyl or sulfoximinyl. In a further embodiment, $R^5$ is hydrogen. In still a further embodiment, $R^2$ is cyano, halo or alkyl.

In some embodiments, $R^2$ is halo, cyano or alkyl; $R^3$ is CH$_2$OH; $R^4$ is fluoroalkyl, sulfonamidyl, sulfonyl, sulfinyl or sulfoximinyl. In a further embodiment, $R^4$ is selected from the group consisting of —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, X is N and Y is CR$^6$. In other embodiments, X is CR$^5$ and Y is N. In still other embodiments, X is N and Y is N.

In some embodiments, Z is O. In other embodiments, Z is S. In further embodiments, Z is CHR$^7$. In yet other embodiments, Z is NR$^8$. In some embodiments, Z is absent.

In some embodiments, Z is —O—, —S—, —S(O)—, —S(O)$_2$—, —S(O$_2$)N(R$^8$)—, —C(O)—, —C(O)O—, —C(HR$^7$)—, —N(R$^8$)—, —C(O)N(R$^8$)—, alkylene, alkenylene, alkynylene, heteroalkylene, or absent. In some embodiments, Z is —O—, —S—, —S(O)—, —S(O)$_2$—, —C(O)—, —C(HR$^7$)—, —N(R$^8$)—, $C_1$-$C_3$ alkylene, $C_1$-$C_3$ heteroalkylene, $C_1$-$C_3$ alkenylene or absent. In some embodiments, Z is —O—. In other embodiments, Z is —S—. In further embodiments, Z is —C(HR$^7$)—. In yet other embodiments, Z is —N(R$^8$). In some embodiments, Z is absent.

In some embodiments, $R^c$ is cyano, halo, $C_1$-$C_4$ alkyl or $C_1$-$C_4$ alkoxy.

In yet another aspect, the invention provides a compound of Formula I-C:

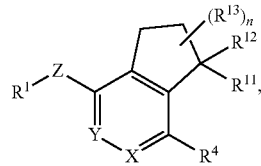

or a pharmaceutically acceptable salt or prodrug thereof, wherein:

X is CR$^5$ or N;

Y is CR$^6$ or N, wherein at least one of X and Y is N;

Z is O, S, CHR$^7$, NR$^8$ or absent;

$R^1$ is alkyl, heteroalkyl, cycloalkyl, heterocycloalkyl, aryl or heteroaryl;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^5$, $R^6$, $R^7$ and $R^8$ are independently hydrogen, halo, hydroxy, cyano, alkyl or alkoxy;

$R^{11}$ is hydrogen, hydroxy, alkoxy or amino;

$R^{12}$ is hydrogen, alkyl, alkenyl or alkynyl; or $R^{11}$ and $R^{12}$ in combination form oxo or oxime;

each of $R^{13}$ is independently selected from the group consisting of hydrogen, fluoro, chloro, hydroxy, alkyl and heteroalkyl; or two $R^{13}$s and the carbon atom(s) to which they are attached form a 3- to 8-membered cycloalkyl or heterocycloalkyl moiety; and n is 0, 1, 2, 3 or 4.

In yet another aspect, the invention provides a compound of Formula I-C:

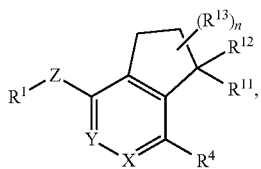

or a pharmaceutically acceptable salt or prodrug thereof, wherein:

X is $CR^5$ or N;

Y is $CR^6$ or N, wherein at least one of X and Y is N;

Z is —O—, —S—, —S(O)—, —S(O)$_2$—, —C(O)—, —C(HR$^7$)—, —N(R$^8$)—, $C_1$-$C_3$ alkylene, $C_1$-$C_3$ heteroalkylene, $C_1$-$C_3$ alkenylene or absent;

$R^1$ is alkyl, heteroalkyl, cycloalkyl, heterocycloalkyl, aryl or heteroaryl;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^5$, $R^6$, $R^7$ and $R^8$ are independently hydrogen, halo, hydroxy, cyano, alkyl or alkoxy;

$R^{11}$ is hydrogen, halo, hydroxy, alkoxy or amino;

$R^{12}$ is hydrogen, alkyl, alkenyl or alkynyl; or $R^{11}$ and $R^{12}$ in combination form =O, =CH$_2$ or =N(OH);

each of $R^{13}$ is independently selected from the group consisting of hydrogen, fluoro, chloro, hydroxy, alkyl and heteroalkyl; and two $R^{13}$s and the carbon atom(s) to which they are attached may form a 3- to 8-membered cycloalkyl or heterocycloalkyl moiety; and n is 0, 1, 2, 3 or 4.

In some embodiments, for a compound of Formula I-C, $R^1$ is further selected from alkyl, heteroalkyl, cycloalkyl, cycloalkenyl, heterocycloalkyl, aryl and heteroaryl.

In some embodiments, $R^1$ is phenyl or monocyclic heteroaryl. In some further embodiments, $R^1$ is phenyl or pyridyl, optionally substituted with one or more substituents selected from the group consisting of halo, alkyl, alkoxy and cyano. In a further embodiment, $R^1$ is

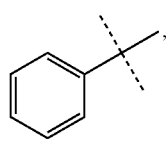

wherein the aryl ring is optionally substituted with one or more substituents selected from the group consisting of cyano, halo, alkyl and alkoxy. In another further embodiment, $R^1$ is

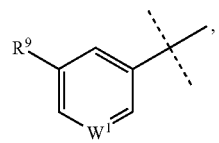

wherein $W^1$ is N or $CR^{10}$, $R^9$ is cyano, halo, alkyl or alkoxy, and $R^{10}$ is hydrogen, cyano, halo, alkyl or alkoxy.

In some embodiments, $R^1$ is bicyclic heteroaryl.

In some embodiments, $R^1$ is selected from the group consisting of:

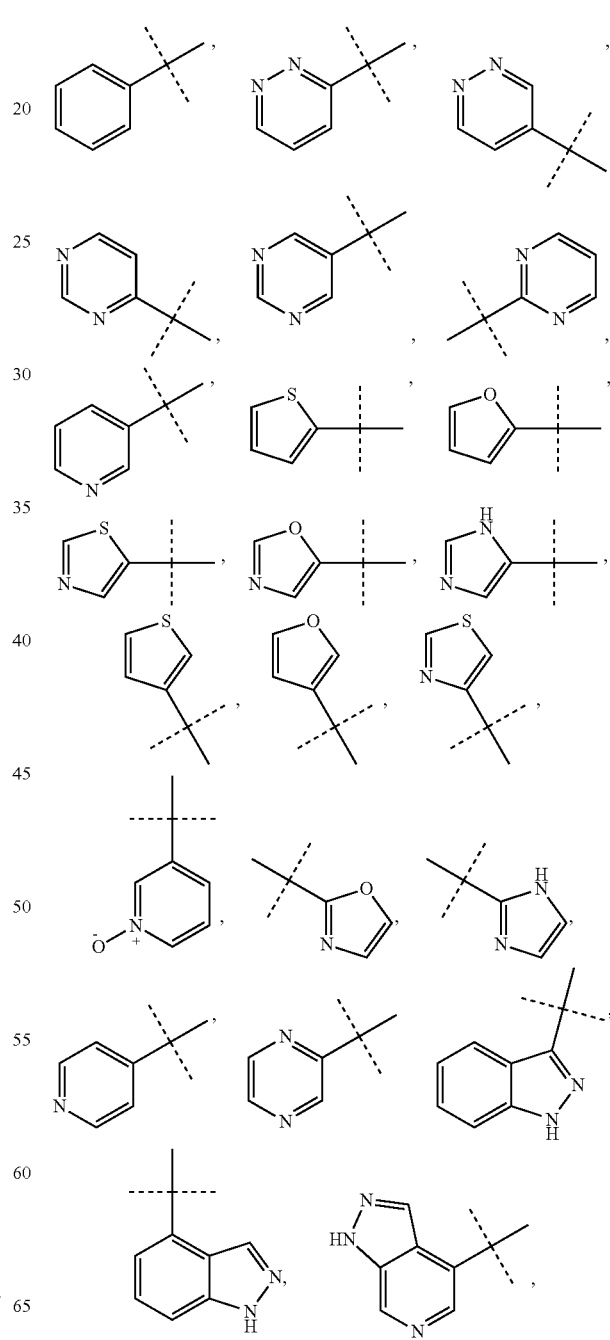

45

-continued

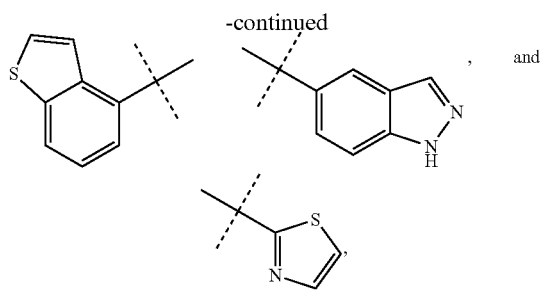

and the rings specified for R¹ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, R¹ is selected from the group consisting of:

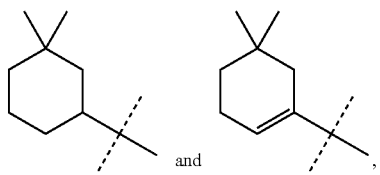

and the rings specified for R¹ may optionally be substituted with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiments, R¹ is cycloalkyl. In other embodiments, R¹ is heterocycloalkyl. In a further embodiment, R¹ is $C_3$-$C_6$ cycloalkyl or $C_3$-$C_6$ heterocycloalkyl. In yet a further embodiment, R¹ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, R¹ is cycloalkyl. In other embodiments, R¹ is heterocycloalkyl. In a further embodiment, R¹ is $C_3$-$C_6$ cycloalkyl or $C_3$-$C_6$ heterocycloalkyl. In yet a further embodiment, R¹ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, hydroxy, $C_1$-$C_4$ alkyl, $C_1$-$C_4$ alkoxy and cyano. In another further embodiment, the substituent(s) is at least one fluoro. In some embodiments, R¹ is substituted with one to six fluorines.

In some embodiments, R¹ is acyl or cyano. In a further embodiment, R¹ is acetyl.

In some embodiments, R¹ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, R¹ is heteroalkyl.

46

In some embodiments, R¹ is selected from the group consisting of:

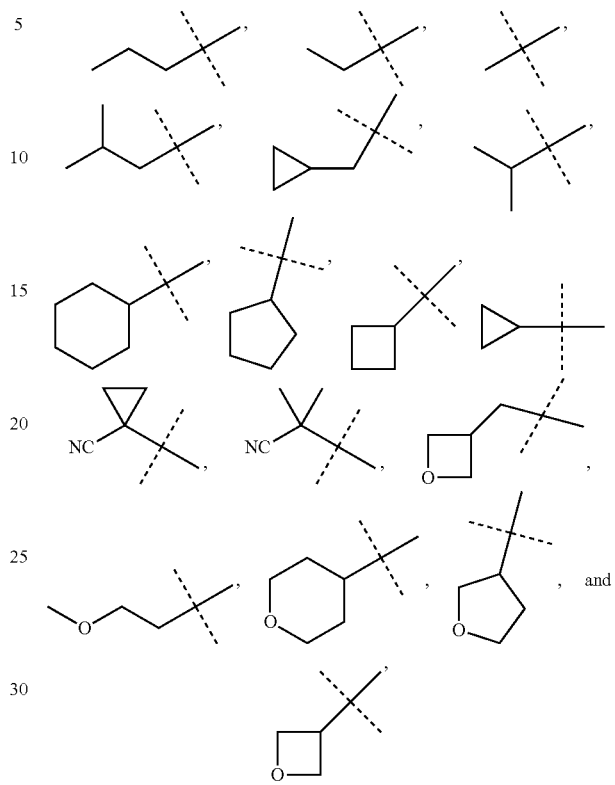

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, R¹ is selected from:

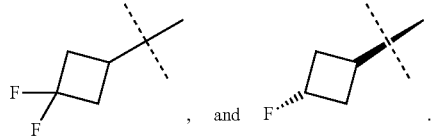

In some embodiments, R⁴ is cyano, fluoroalkyl, sulfinyl, sulfonamidyl, sulfonyl, sulfoximinyl, or fluoroalkylsulfonyl.

In some embodiments, R⁴ is cyano, fluoroalkyl, sulfinyl, sulfonamidyl, sulfonyl or sulfoximinyl. In some embodiments, R⁴ is fluoroalkyl, sulfonamidyl, sulfinyl, sulfonyl or sulfoximinyl. In a further embodiment, R⁴ is fluoroalkyl. In yet another embodiment, R⁴ is sulfonyl. In still another embodiment, R⁴ is fluoroalkylsulfonyl.

In some embodiments, R⁴ is —S(=O)₂Rᵃ, wherein Rᵃ is alkyl or cycloalkyl. In a further embodiment, Rᵃ is $C_1$-$C_4$ alkyl, optionally substituted with one or more fluorines. Suitable examples of fluorine-substituted $C_1$-$C_4$ alkyl include, but are not limited to, —CH₂F, —CHF₂, —CF₃, —CH₂CF₃, —CH₂CHF₂, —CH₂CH₂F, —CHFCH₃ and —CF₂CH₃. In still a further embodiment, Rᵃ is methyl, optionally substituted with one or more fluorines.

In some embodiments, R⁴ is —S(=O)(=NRᵇ)Rᵃ, wherein Rᵃ is alkyl or cycloalkyl and Rᵇ is hydrogen, cyano or alkyl. In a further embodiment, $R^a$ is $C_1$-$C_4$ alkyl, optionally substituted with one or more fluorines. Suitable examples of fluorine-substituted $C_1$-$C_4$ alkyl include, but are not limited to, —$CH_2F$, —$CHF_2$, —$CF_3$, —$CH_2CF_3$, —$CH_2CHF_2$, —$CH_2CH_2F$, —$CHFCH_3$ and —$CF_2CH_3$.

In some embodiments, $R^4$ is —S(=O)$_2$N($R^a$)$_2$, wherein each $R^a$ is independently hydrogen, alkyl, heteroalkyl, cycloalkyl or heterocycloalkyl, and at least one $R^a$ is hydrogen. In another further embodiment, one $R^a$ is hydrogen and the other $R^a$ is $C_1$-$C_4$ alkyl.

In some embodiments, $R^4$ is selected from the group consisting of —CN, —$CF_3$, —S(=O)$CH_3$, —S(=O)$_2CH_3$, —S(=O)$_2CH_2F$, —S(=O)$_2CHF_2$, —S(=O)$_2CF_3$, —S(=O)$_2NH_2$, —S(=O)$_2NHCH_3$, —S(=O)(=NH)$CH_3$, —S(=O)(=NH)$CH_2F$, —S(=O)(=NH)$CHF_2$, —S(=O)(=NH)$CF_3$, —S(=O)(=N—CN)$CH_3$, —S(=O)(=N—CN)$CH_2F$, —S(=O)(=N—CN)$CHF_2$ and —S(=O)(=N—CN)$CF_3$.

In some embodiments, $R^5$ is hydrogen or alkyl. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen or alkyl. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen or alkyl. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen or alkyl. In some other embodiments, $R^8$ is $C_1$-$C_4$ alkyl or $C_1$-$C_4$ alkoxy. In a further embodiment, $R^8$ is methyl.

In some embodiments, $R^{12}$ is hydrogen, alkyl, alkenyl or alkynyl; or $R^{11}$ and $R^{12}$ in combination form =O or =N(OH).

In some embodiments, $R^{11}$ is hydroxy or amino. In a further embodiment, $R^{11}$ is hydroxy. In another further embodiment, $R^{11}$ is amino.

In some embodiments, $R^{12}$ is hydrogen. In some other embodiments, $R^{12}$ is alkyl or alkenyl.

In some embodiments, $R^{13}$ is fluoro. In a further embodiment, n is 1, 2 or 3. In a further embodiment, two $R^{13}$s in combination form oxo, oxime or methylene. In still further embodiments, two $R^{13}$s and the carbon atom(s) to which they are attached form a 3- to 8-membered cycloalkyl or heterocycloalkyl moiety.

In some embodiments, $R^1$ is monocyclic aryl or monocyclic heteroaryl and $R^{11}$ is hydroxy or amino. In a further embodiment, $R^{13}$ is fluoro. In still a further embodiment, n is 1, 2 or 3.

In some embodiments, $R^1$ is phenyl or monocyclic heteroaryl, $R^{11}$ is hydroxy or amino, $R^{13}$ is fluoro, n is 1, 2 or 3, and $R^5$ is hydrogen.

In some embodiments, $R^1$ is bicyclic heteroaryl and $R^{11}$ is hydroxy or amino. In a further embodiment, $R^{13}$ is fluoro. In still a further embodiment, n is 1, 2 or 3.

In some embodiments, $R^1$ is bicyclic heteroaryl, $R^{11}$ is hydroxy or amino, $R^{13}$ is fluoro, n is 1, 2 or 3, and $R^5$ is hydrogen.

In some embodiments, $R^4$ is cyano, fluoroalkyl, sulfonamidyl, sulfinyl, sulfonyl, sulfoximinyl or fluoroalkylsulfonyl, and $R^{11}$ is hydroxy or amino. In a further embodiment, $R^{12}$ is hydrogen. In another further embodiment, $R^{13}$ is fluoro. In still a further embodiment, n is 1, 2 or 3.

In some embodiments, $R^4$ is cyano, fluoroalkyl, sulfonamidyl, sulfinyl, sulfonyl, sulfoximinyl or fluoroalkylsulfonyl; $R^{11}$ is hydroxy or amino; $R^{13}$ is fluoro; n is 1, 2 or 3; and $R^5$ is hydrogen. In a further embodiment, $R^{12}$ is hydrogen.

In some embodiments $R^{11}$ is hydroxy or amino and $R^{12}$ is hydrogen. In a further embodiment, $R^{13}$ is fluoro. In still a further embodiment, n is 1, 2 or 3.

In some embodiments $R^{11}$ is hydroxy or amino, $R^{12}$ is hydrogen, $R^{13}$ is fluoro, n is 1, 2 or 3, and $R^5$ is hydrogen. In a further embodiment, $R^4$ is selected from the group consisting of —CN, —$CF_3$, —S(=O)$CH_3$, —S(=O)$_2CH_3$, —S(=O)$_2CH_2F$, —S(=O)$_2CHF_2$, —S(=O)$_2CF_3$, —S(=O)$_2NH_2$, —S(=O)$_2NHCH_3$, —S(=O)(=NH)$CH_3$, —S(=O)(=NH)$CH_2F$, —S(=O)(=NH)$CHF_2$, —S(=O)(=NH)$CF_3$, —S(=O)(=N—CN)$CH_3$, —S(=O)(=N—CN)$CH_2F$, —S(=O)(=N—CN)$CHF_2$ and —S(=O)(=N—CN)$CF_3$.

In some embodiments, $R^4$ is fluoroalkyl; n is 0, 1, 2 or 3; Z is O; $R^{11}$ is hydroxy; and $R^{12}$ is hydrogen.

In some embodiments, $R^4$ is sulfonyl or fluoroalkylsulfonyl; n is 0, 1, 2 or 3; Z is O; $R^{11}$ is hydroxy; and $R^{12}$ is hydrogen.

In some embodiments, X is N and Y is $CR^6$. In other embodiments, X is $CR^5$ and Y is N. In still other embodiments, X is N and Y is N.

In some embodiments, Z is O. In other embodiments, Z is S. In further embodiments, Z is $CHR^7$. In yet other embodiments, Z is $NR^8$. In some embodiments, Z is absent.

In some embodiments, Z is —O—, —S—, —S(O)—, —S(O)$_2$—, —S(O$_2$)N($R^8$)—, —C(O)—, —C(O)O—, —C($HR^7$)—, —N(R)—, —C(O)N(R)—, alkylene, alkenylene, alkynylene, heteroalkylene, or absent. In some embodiments, Z is —O—, —S—, —S(O)—, —S(O)$_2$—, —C(O)—, —C($HR^7$)—, —N($R^8$)—, $C_1$-$C_3$ alkylene, $C_1$-$C_3$ heteroalkylene, $C_1$-$C_3$ alkenylene or absent. In some embodiments, Z is —O—. In other embodiments, Z is —S—. In further embodiments, Z is —C($HR^7$)—. In yet other embodiments, Z is —N($R^8$). In some embodiments, Z is absent.

In still another aspect, the invention provides a compound of Formula I-D, I-E, I—F or I-G:

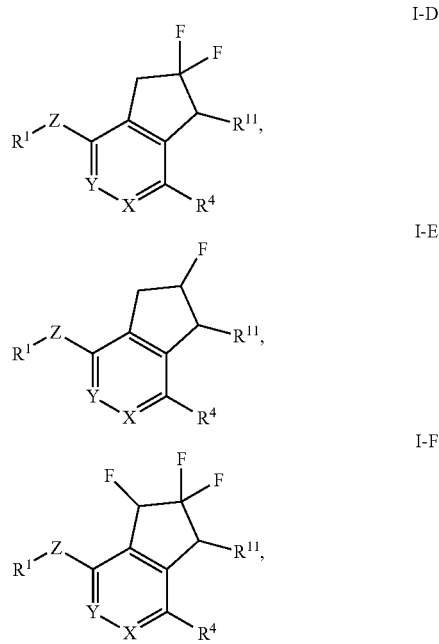

-continued

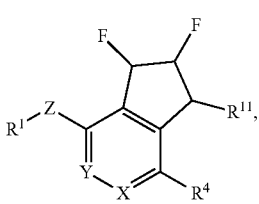
I-G or a pharmaceutically acceptable salt or prodrug thereof, wherein:
X is $CR^5$ or N;
Y is $CR^6$ or N, wherein at least one of X and Y is N;
Z is O, S, $CHR^7$, $NR^8$ or absent;
$R^1$ is alkyl, heteroalkyl, cycloalkyl, heterocycloalkyl, aryl or heteroaryl;
$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;
$R^5$, $R^6$, $R^7$ and $R^8$ are independently hydrogen, halo, hydroxy, cyano, alkyl or alkoxy; and
$R^{11}$ is hydrogen, hydroxy, alkoxy or amino.

In still another aspect, the invention provides a compound of Formula I-D, I-E, I-F or I-G:

I-D

I-E

I-F

I-G or a pharmaceutically acceptable salt or prodrug thereof, wherein:
X is $CR^5$ or N;
Y is $CR^6$ or N, wherein at least one of X and Y is N;
Z is —O—, —S—, —S(O)—, —S(O)$_2$—, —C(O)—, —C(HR$^7$)—, —N(R$^8$)—, $C_1$-$C_3$ alkylene, $C_1$-$C_3$ heteroalkylene, $C_1$-$C_3$ alkenylene or absent;
$R^1$ is alkyl, heteroalkyl, cycloalkyl, heterocycloalkyl, aryl or heteroaryl;
$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;
$R^5$, $R^6$, $R^7$ and $R^8$ are independently hydrogen, halo, hydroxy, cyano, alkyl or alkoxy; and
$R^{11}$ is hydrogen, halo, hydroxy, alkoxy or amino.

In some embodiments, for a compound of Formula I-D, I-E, I-F, or I-G, $R^1$ is further selected from alkyl, heteroalkyl, cycloalkyl, cycloalkenyl, heterocycloalkyl, aryl and heteroaryl.

In some embodiments, $R^1$ is monocyclic aryl or monocyclic heteroaryl. In some further embodiments, $R^1$ is phenyl or pyridyl, optionally substituted with one or more substituents selected from the group consisting of halo, alkyl, alkoxy and cyano. In a further embodiment, $R^1$ is

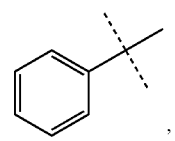

wherein the aryl ring is optionally substituted with one or more substituents selected from the group consisting of cyano, halo, alkyl and alkoxy. In another further embodiment, $R^1$ is

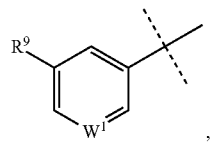

wherein $W^1$ is N or $CR^{10}$, $R^9$ is cyano, halo, alkyl or alkoxy, and $R^{10}$ is hydrogen, cyano, halo, alkyl or alkoxy.

In some embodiments, $R^1$ is bicyclic heteroaryl having at least one N atom.

In some embodiments, $R^1$ is selected from the group consisting of:

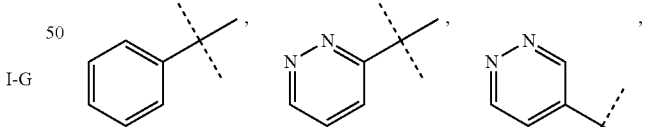

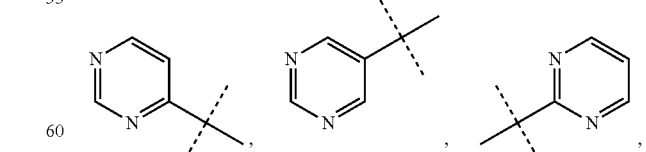

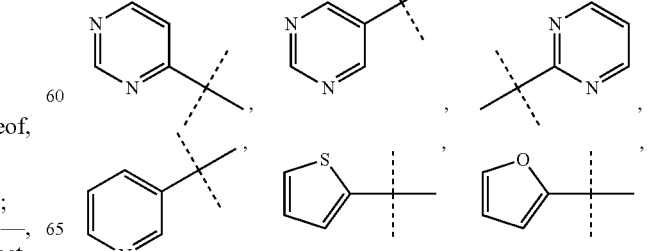

-continued

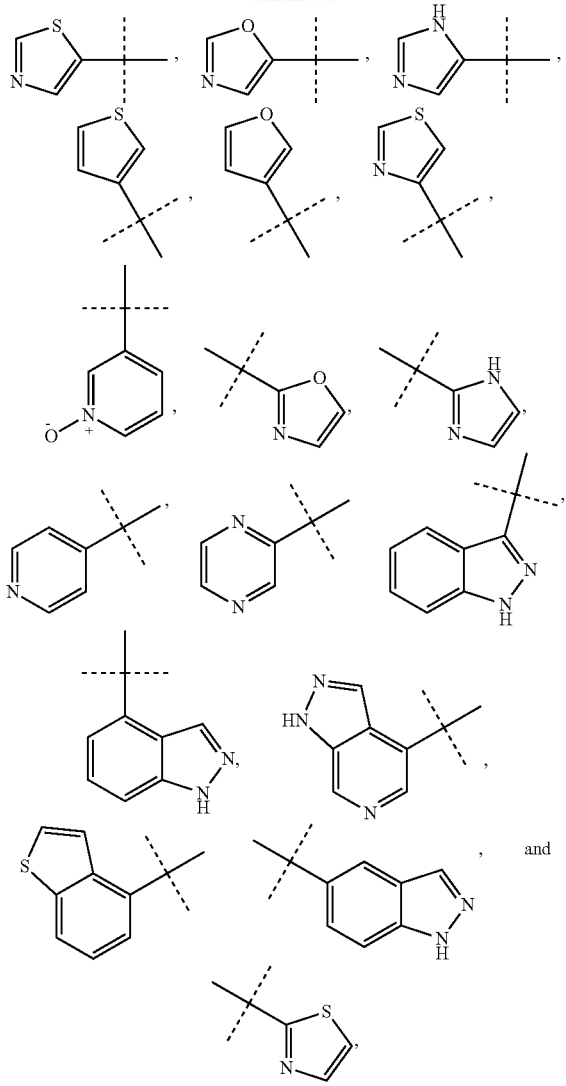

and the rings specified for R¹ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, R¹ is selected from the group consisting of:

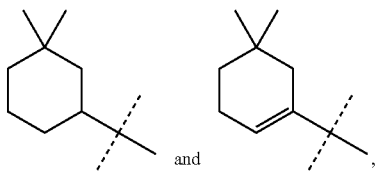

and the rings specified for R¹ may optionally be substituted with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiments, R¹ is cycloalkyl. In other embodiments, R¹ is heterocycloalkyl. In a further embodiment, R¹ is $C_3$-$C_6$ cycloalkyl or $C_3$-$C_6$ heterocycloalkyl. In yet a further embodiment, R¹ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, R¹ is acyl or cyano. In a further embodiment, R¹ is acetyl.

In some embodiments, R¹ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, R¹ is heteroalkyl.

In some embodiments, R¹ is selected from the group consisting of:

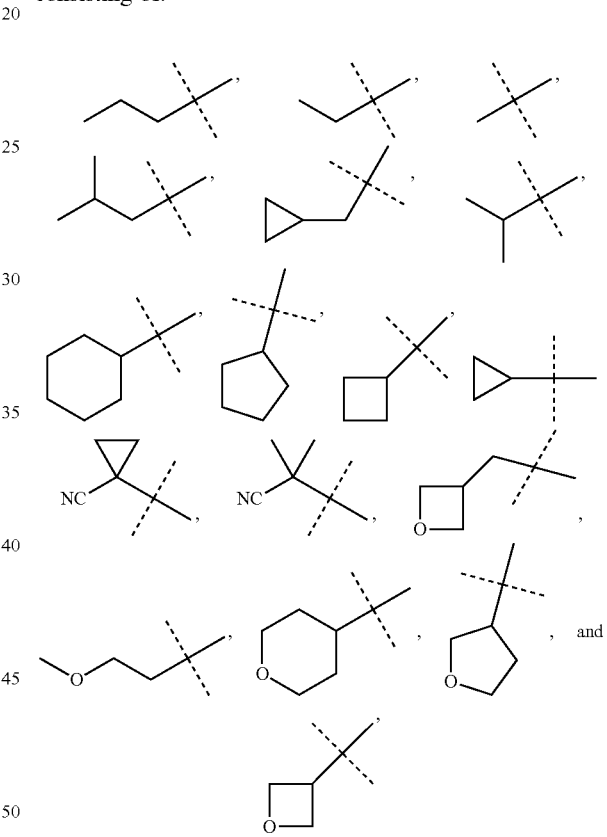

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, R⁴ is cyano, fluoroalkyl, sulfinyl, sulfonamidyl, sulfonyl or sulfoximinyl. In some embodiments, R⁴ is fluoroalkyl, sulfonamidyl, sulfinyl, sulfonyl or sulfoximinyl. In a further embodiment, R⁴ is fluoroalkyl. In yet another embodiment, R⁴ is sulfonyl. In still another embodiment, R⁴ is fluoroalkylsulfonyl.

In some embodiments, R⁴ is —S(=O)₂Rᵃ, wherein Rᵃ is alkyl or cycloalkyl. In a further embodiment, Rᵃ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, R$^4$ is —S(=O)(=NR$^b$)R$^a$, wherein R$^a$ is alkyl or cycloalkyl and R$^b$ is hydrogen, cyano or alkyl. In a further embodiment, R$^a$ is C$_1$-C$_4$ alkyl, optionally substituted with one or more fluorines. Suitable examples of fluorine-substituted C$_1$-C$_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, R$^4$ is —S(=O)$_2$N(R$^a$)$_2$, wherein each R$^a$ is independently hydrogen, alkyl, heteroalkyl, cycloalkyl or heterocycloalkyl, and at least one R$^a$ is hydrogen. In another further embodiment, both R$^a$s are hydrogen. In a further embodiment, one R$^a$ is hydrogen and the other R$^a$ is C$_1$-C$_4$ alkyl.

In some embodiments, R$^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, R$^5$ is hydrogen or alkyl. In some other embodiments, R$^5$ is C$_1$-C$_4$ alkyl or C$_1$-C$_4$ alkoxy. In a further embodiment, R$^5$ is methyl.

In some embodiments, R$^6$ is hydrogen or alkyl. In some other embodiments, R$^6$ is C$_1$-C$_4$ alkyl or C$_1$-C$_4$ alkoxy. In a further embodiment, R$^6$ is methyl.

In some embodiments, R$^7$ is hydrogen or alkyl. In some other embodiments, R$^7$ is C$_1$-C$_4$ alkyl or C$_1$-C$_4$ alkoxy. In a further embodiment, R$^7$ is methyl.

In some embodiments, R$^8$ is hydrogen or alkyl. In some other embodiments, R$^8$ is C$_1$-C$_4$ alkyl or C$_1$-C$_4$ alkoxy. In a further embodiment, R$^8$ is methyl.

In some embodiments, R$^{11}$ is hydroxy. In another further embodiment, R$^{11}$ is amino.

In some embodiments, R$^1$ is phenyl or monocyclic heteroaryl and R$^{11}$ is hydroxy or amino.

In some embodiments, R$^1$ is bicyclic heteroaryl and R$^{11}$ is hydroxy or amino. In a further embodiment, X is CR$^5$ and R$^5$ is hydrogen. In another further embodiment, R$^5$ is alkyl. In still a further embodiment, R$^5$ is C$_1$-C$_4$ alkyl.

In some embodiments R$^1$ is bicyclic heteroaryl and R$^4$ is cyano, fluoroalkyl, sulfinyl, sulfonamidyl, sulfonyl or sulfoximinyl. In a further embodiment, X is CR$^5$ and R$^5$ is hydrogen. In another further embodiment, R$^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments R$^1$ is bicyclic heteroaryl; R$^4$ is cyano, fluoroalkyl, sulfinyl, sulfonamidyl, sulfonyl or sulfoximinyl; R$^{11}$ is hydroxy or amino; and X is CR$^5$ or N; and R$^5$ is hydrogen. In a further embodiment, R$^{11}$ is hydroxy. In another further embodiment, R$^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments R$^1$ is phenyl or monocyclic heteroaryl and R$^4$ is cyano, fluoroalkyl, sulfinyl, sulfonamidyl, sulfonyl or sulfoximinyl. In a further embodiment, X is CR$^5$ and R$^5$ is hydrogen. In another further embodiment, R$^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments R$^1$ is phenyl or monocyclic heteroaryl; R$^4$ is cyano, fluoroalkyl, sulfinyl, sulfonamidyl, sulfonyl or sulfoximinyl; R$^{11}$ is hydroxy or amino; and X is CR$^5$ or N; and R$^5$ is hydrogen. In a further embodiment, R$^1$ is hydroxy. In another further embodiment, R$^4$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CF$_3$, —S(=O)(=N—CN)CH$_3$, —S(=O)(=N—CN)CH$_2$F, —S(=O)(=N—CN)CHF$_2$ and —S(=O)(=N—CN)CF$_3$.

In some embodiments, X is N and Y is CR$^6$. In other embodiments, X is CR$^5$ and Y is N. In still other embodiments, X is N and Y is N.

In some embodiments, Z is O. In other embodiments, Z is S. In further embodiments, Z is CHR$^7$. In yet other embodiments, Z is NR$^8$. In some embodiments, Z is absent.

In some embodiments, Z is —O—, —S—, —S(O)—, —S(O)$_2$—, —S(O$_2$)N(R)—, —C(O)—, —C(O)O—, —C(HR$^7$)—, —N(R$^8$)—, —C(O)N(R$^8$)—, alkylene, alkenylene, alkynylene, heteroalkylene, or absent. In some embodiments, Z is —O—, —S—, —S(O)—, —S(O)$_2$—, —C(O)—, —C(HR$^7$)—, —N(R$^8$)—, C$_1$-C$_3$ alkylene, C$_1$-C$_3$ heteroalkylene, C$_1$-C$_3$ alkenylene or absent. In some embodiments, Z is —O—. In other embodiments, Z is —S—. In further embodiments, Z is —C(HR$^7$)—. In yet other embodiments, Z is —N(R$^8$). In some embodiments, Z is absent.

In a further aspect, the invention provides a compound of Formula I-H, I-I, I-J or I-K:

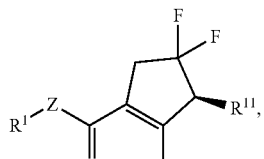

I-H

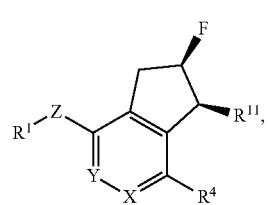

I-I

-continued

I-J

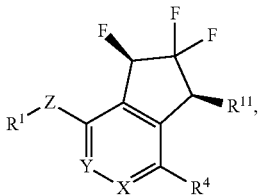

I-K

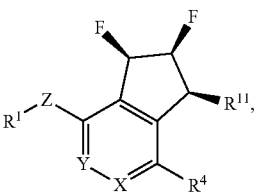

or a pharmaceutically acceptable salt or prodrug thereof, wherein:

X is $CR^5$ or N;

Y is $CR^6$ or N, wherein at least one of X and Y is N;

Z is O, S, $CHR^7$, $NR^8$ or absent;

$R^1$ is alkyl, heteroalkyl, cycloalkyl, heterocycloalkyl, aryl or heteroaryl;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^5$, $R^6$, $R^7$ and $R^8$ are independently hydrogen, halo, hydroxy, cyano, alkyl or alkoxy; and $R^{11}$ is hydroxy or amino.

In a further aspect, the invention provides a compound of Formula I-H, I-I, I-J or I-K:

I-H

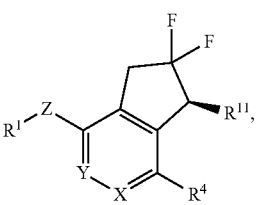

I-I

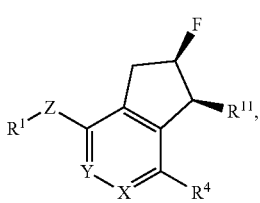

I-J

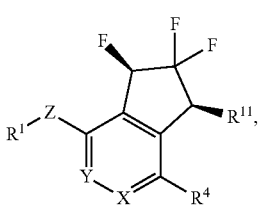

-continued

I-K

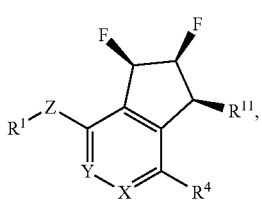

or a pharmaceutically acceptable salt or prodrug thereof, wherein:

X is $CR^5$ or N;

Y is $CR^6$ or N, wherein at least one of X and Y is N;

Z is —O—, —S—, —S(O)—, —S(O)$_2$—, —C(O)—, —C($HR^7$)—, —N($R^8$)—, $C_1$-$C_3$ alkylene, $C_1$-$C_3$ heteroalkylene, $C_1$-$C_3$ alkenylene or absent;

$R^1$ is alkyl, heteroalkyl, cycloalkyl, heterocycloalkyl, aryl or heteroaryl;

$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;

$R^5$, $R^6$, $R^7$ and $R^8$ are independently hydrogen, halo, hydroxy, cyano, alkyl or alkoxy; and $R^{11}$ is hydrogen, halo, hydroxy, alkoxy or amino.

In some embodiments, for a compound of Formula I-H, I-I, I-J, or I-K, $R^1$ is further selected from alkyl, heteroalkyl, cycloalkyl, cycloalkenyl, heterocycloalkyl, aryl and heteroaryl.

In some embodiments, $R^1$ is monocyclic aryl or monocyclic heteroaryl. In some further embodiments, $R^1$ is phenyl or pyridyl, optionally substituted with one or more substituents selected from the group consisting of halo, alkyl, alkoxy and cyano. In a further embodiment, $R^1$ is

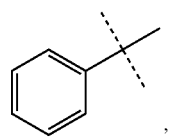

wherein the aryl ring is optionally substituted with one or more substituents selected from the group consisting of cyano, halo, alkyl and alkoxy. In another further embodiment, $R^1$ is

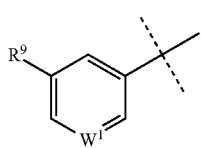

wherein $W^1$ is N or $CR^{10}$, $R^9$ is cyano, halo, alkyl or alkoxy, and $R^{10}$ is hydrogen, cyano, halo, alkyl or alkoxy.

In some embodiments, $R^1$ is bicyclic heteroaryl.

In some embodiments, $R^1$ is selected from the group consisting of:

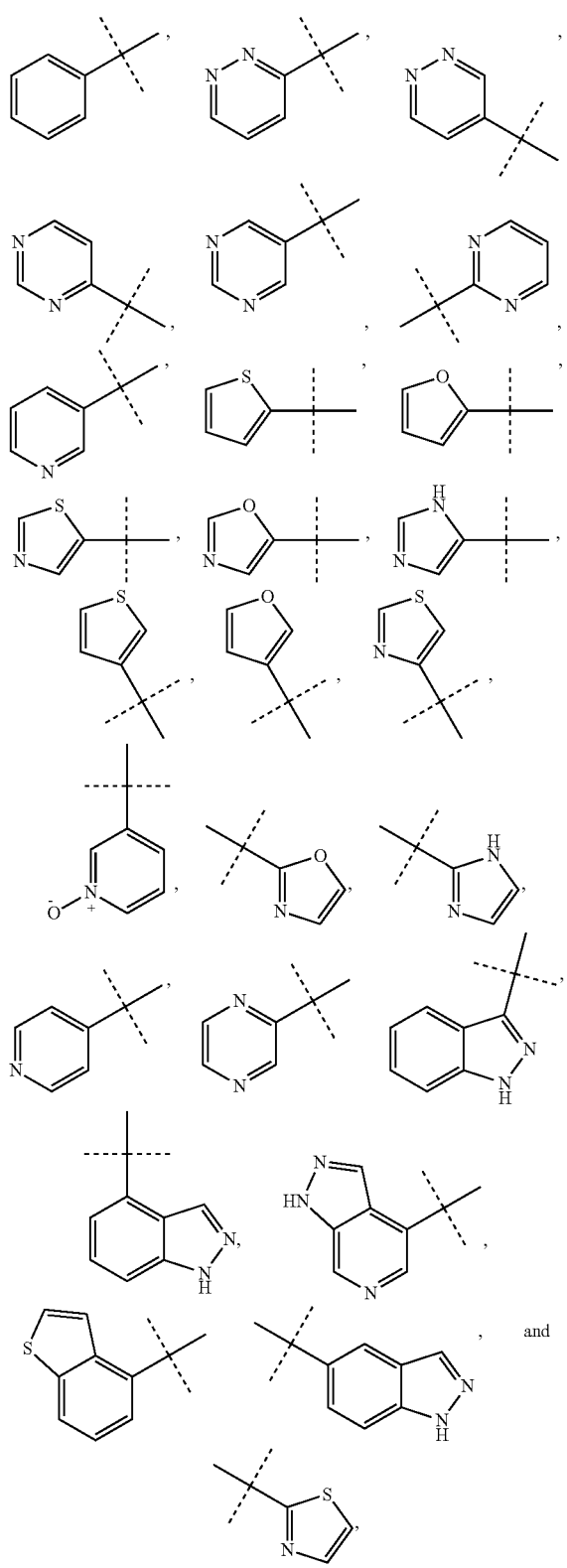

and the rings specified for $R^1$ may optionally be substituted with one or more substituents described for aryl and heteroaryl. In a further embodiment, the substituent(s) is selected from the group consisting of halo, $C_1$-$C_4$ alkyl, $C_1$-$C_4$ alkoxy and cyano.

In some embodiments, $R^1$ is selected from the group consisting of:

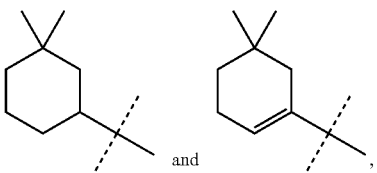

and the rings specified for $R^1$ may optionally be substituted with one or more substituents described for cycloalkyl. In a further embodiment, the substituent(s) is selected from the group consisting of halo, hydroxy, $C_1$-$C_4$ alkyl, $C_1$-$C_4$ alkoxy, cyano and oxo.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, $C_1$-$C_4$ alkyl, $C_1$-$C_4$ alkoxy and cyano. In another further embodiment, the substituent(s) is at least one fluoro.

In some embodiments, $R^1$ is cycloalkyl. In other embodiments, $R^1$ is heterocycloalkyl. In a further embodiment, $R^1$ is $C_3$-$C_6$ cycloalkyl or $C_3$-$C_6$ heterocycloalkyl. In yet a further embodiment, $R^1$ is cyclobutyl. In some embodiments, said cycloalkyl, cyclobutyl or heterocycloalkyl may optionally be substituted with one or more substituents described for cycloalkyl or heterocycloalkyl. In a further embodiment, the substituent(s) is selected from the group consisting of halo, hydroxy, $C_1$-$C_4$ alkyl, $C_1$-$C_4$ alkoxy and cyano. In another further embodiment, the substituent(s) is at least one fluoro. In some embodiments, $R^1$ is substituted with one to six fluorines.

In some embodiments, $R^1$ is acyl or cyano. In a further embodiment, $R^1$ is acetyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is alkyl. In a further embodiment, the alkyl is substituted with at least one substituent(s) selected from the group consisting of halo, $C_1$-$C_4$ alkyl, $C_1$-$C_4$ alkoxy and cyano. In another further embodiment, the alkyl is substituted with at least one fluoro. In some embodiments, $R^1$ is heteroalkyl.

In some embodiments, $R^1$ is selected from the group consisting of:

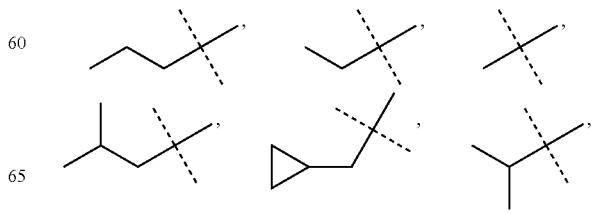

-continued

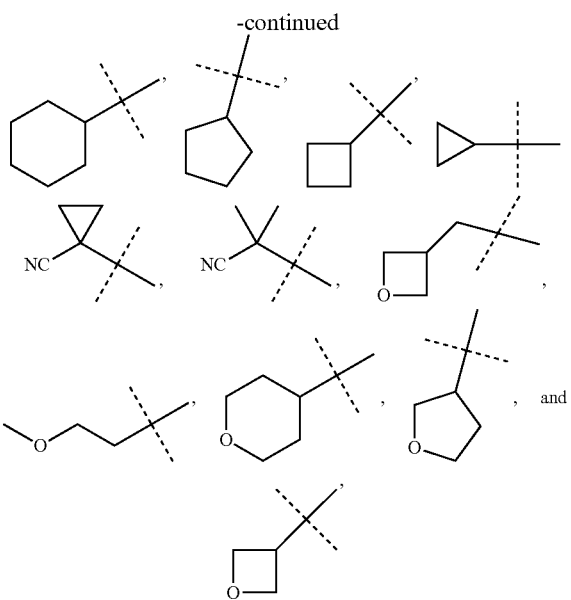

wherein each of the members may optionally be substituted with one or more substituents selected from the group consisting of cyano, halo, alkyl and alkoxy. In a further embodiment, the substituent(s) is selected from the group consisting of fluoro, $C_1$-$C_4$ alkyl, $C_1$-$C_4$ alkoxy and cyano.

In some embodiments, $R^1$ is selected from:

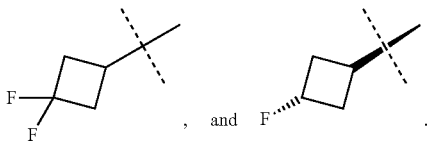

In some embodiments, $R^4$ is cyano, fluoroalkyl, sulfinyl, sulfonamidyl, sulfonyl, sulfoximinyl, or fluoroalkylsulfonyl.

In some embodiments, $R^4$ is cyano, fluoroalkyl, sulfinyl, sulfonamidyl, sulfonyl or sulfoximinyl. In a further embodiment, $R^4$ is fluoroalkyl. In yet another embodiment, $R^4$ is sulfonyl. In still another embodiment, $R^4$ is fluoroalkylsulfonyl.

In some embodiments, $R^4$ is —S(═O)$_2$R$^a$, wherein R$^a$ is alkyl or cycloalkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$. In still a further embodiment, R$^a$ is methyl, optionally substituted with one or more fluorines.

In some embodiments, $R^4$ is —S(═O)(═NR$^b$)R$^a$, wherein R$^a$ is alkyl or cycloalkyl and R$^b$ is hydrogen, cyano or alkyl. In a further embodiment, R$^a$ is $C_1$-$C_4$ alkyl, optionally substituted with one or more fluorines. Suitable examples of fluorine-substituted $C_1$-$C_4$ alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$ and —CF$_2$CH$_3$.

In some embodiments, $R^4$ is —S(═O)$_2$N(R$^a$)$_2$, wherein each R$^a$ is independently hydrogen, alkyl, heteroalkyl, cycloalkyl or heterocycloalkyl, and at least one R$^a$ is hydrogen. In another further embodiment, both R$^a$s are hydrogen. In a further embodiment, one R$^a$ is hydrogen and the other R$^a$ is $C_1$-$C_4$ alkyl.

In some embodiments, $R^4$ is selected from the group consisting of —CN, —CF$_3$, —S(═O)CH$_3$, —S(═O)$_2$CH$_3$, —S(═O)$_2$CH$_2$F, —S(═O)$_2$CHF$_2$, —S(═O)$_2$CF$_3$, —S(═O)$_2$NH$_2$, —S(═O)$_2$NHCH$_3$, —S(═O)(═NH)CH$_3$, —S(═O)(═NH)CH$_2$F, —S(═O)(═NH)CHF$_2$, —S(═O)(═NH)CF$_3$, —S(═O)(═N—CN)CH$_3$, —S(═O)(═N—CN)CH$_2$F, —S(═O)(═N—CN)CHF$_2$ and —S(═O)(═N—CN)CF$_3$.

In some embodiments, $R^5$ is hydrogen or alkyl. In some other embodiments, $R^5$ is $C_1$-$C_4$ alkyl or $C_1$-$C_4$ alkoxy. In a further embodiment, $R^5$ is methyl.

In some embodiments, $R^6$ is hydrogen or alkyl. In some other embodiments, $R^6$ is $C_1$-$C_4$ alkyl or $C_1$-$C_4$ alkoxy. In a further embodiment, $R^6$ is methyl.

In some embodiments, $R^7$ is hydrogen or alkyl. In some other embodiments, $R^7$ is $C_1$-$C_4$ alkyl or $C_1$-$C_4$ alkoxy. In a further embodiment, $R^7$ is methyl.

In some embodiments, $R^8$ is hydrogen or alkyl. In some other embodiments, $R^8$ is $C_1$-$C_4$ alkyl or $C_1$-$C_4$ alkoxy. In a further embodiment, $R^8$ is methyl.

In some embodiments, $R^{11}$ is hydroxy. In another further embodiment, $R^{11}$ is amino.

In some embodiments, $R^1$ is phenyl or monocyclic heteroaryl and $R^{11}$ is hydroxy or amino.

In some embodiments, $R^1$ is bicyclic heteroaryl and $R^{11}$ is hydroxy or amino. In a further embodiment, X is CR$^5$ and $R^5$ is hydrogen. In another further embodiment, $R^5$ is alkyl. In still a further embodiment, $R^5$ is $C_1$-$C_4$ alkyl.

In some embodiments $R^1$ is bicyclic heteroaryl and $R^4$ is cyano, fluoroalkyl, sulfinyl, sulfonamidyl, sulfonyl or sulfoximinyl. In a further embodiment, X is CR$^5$ and $R^5$ is hydrogen. In another further embodiment, $R^4$ is selected from the group consisting of —CN, —CF$_3$, —S(═O)CH$_3$, —S(═O)$_2$CH$_3$, —S(═O)$_2$CH$_2$F, —S(═O)$_2$CHF$_2$, —S(═O)$_2$CF$_3$, —S(═O)$_2$NH$_2$, —S(═O)$_2$NHCH$_3$, —S(═O)(═NH)CH$_3$, —S(═O)(═NH)CH$_2$F, —S(═O)(═NH)CHF$_2$, —S(═O)(═NH)CF$_3$, —S(═O)(═N—CN)CH$_3$, —S(═O)(═N—CN)CH$_2$F, —S(═O)(═N—CN)CHF$_2$ and —S(═O)(═N—CN)CF$_3$.

In some embodiments $R^1$ is bicyclic heteroaryl; $R^4$ is cyano, fluoroalkyl, sulfinyl, sulfonamidyl, sulfonyl or sulfoximinyl; $R^{11}$ is hydroxy or amino; and X is CR$^5$ or N; and $R^5$ is hydrogen. In a further embodiment, $R^{11}$ is hydroxy. In another further embodiment, $R^4$ is selected from the group consisting of —CN, —CF$_3$, —S(═O)CH$_3$, —S(═O)$_2$CH$_3$, —S(═O)$_2$CH$_2$F, —S(═O)$_2$CHF$_2$, —S(═O)$_2$CF$_3$, —S(═O)$_2$NH$_2$, —S(═O)$_2$NHCH$_3$, —S(═O)(═NH)CH$_3$, —S(═O)(═NH)CH$_2$F, —S(═O)(═NH)CHF$_2$, —S(═O)(═NH)CF$_3$, —S(═O)(═N—CN)CH$_3$, —S(═O)(═N—CN)CH$_2$F, —S(═O)(═N—CN)CHF$_2$ and —S(═O)(═N—CN)CF$_3$.

In some embodiments $R^1$ is phenyl or monocyclic heteroaryl and $R^4$ is cyano, fluoroalkyl, sulfinyl, sulfonamidyl, sulfonyl or sulfoximinyl. In a further embodiment, X is CR$^5$ and $R^5$ is hydrogen. In another further embodiment, $R^4$ is selected from the group consisting of —CN, —CF$_3$, —S(═O)CH$_3$, —S(═O)$_2$CH$_3$, —S(═O)$_2$CH$_2$F, —S(═O)$_2$CHF$_2$, —S(═O)$_2$CF$_3$, —S(═O)$_2$NH$_2$, —S(═O)$_2$NHCH$_3$, —S(═O)(═NH)CH$_3$, —S(═O)(═NH)CH$_2$F, —S(═O)(═NH)CHF$_2$, —S(═O)(═NH)CF$_3$, —S(═O)(═N—CN)CH$_3$, —S(═O)(═N—CN)CH$_2$F, —S(═O)(═N—CN)CHF$_2$ and —S(═O)(═N—CN)CF$_3$.

In some embodiments $R^1$ is phenyl or monocyclic heteroaryl; $R^4$ is cyano, fluoroalkyl, sulfinyl, sulfonamidyl, sulfonyl or sulfoximinyl; $R^{11}$ is hydroxy or amino; and X is CR$^5$ or N; and $R^5$ is hydrogen. In a further embodiment, $R^{11}$ is hydroxy. In another further embodiment, $R^4$ is selected from the group consisting of —CN, —CF₃, —S(═O)CH₃, —S(═O)₂CH₃, —S(═O)₂CH₂F, —S(═O)₂CHF₂, —S(═O)₂CF₃, —S(═O)₂NH₂, —S(═O)₂NHCH₃, —S(═O)₂NHCH₃, —S(═O)(═NH)CH₃, —S(═O)(═NH)CH₂F, —S(═O)(═NH)CHF₂, —S(═O)(═NH)CF₃, —S(═O)(═N—CN)CH₃, —S(═O)(═N—CN)CH₂F, —S(═O)(═N—CN)CHF₂ and —S(═O)(═N—CN)CF₃.

In some embodiments, R⁴ is fluoroalkyl; Z is —O—; and R¹¹ is hydroxy. In some embodiments, R⁴ is sulfonyl; Z is —O—; and R¹¹ is hydroxy. In some embodiments, R¹ is phenyl, pyridyl, cycloalkyl or heterocycloalkyl, substituted with at least one substituent selected from the group consisting of halo, hydroxy, C₁-C₄ alkyl, C₁-C₄ alkoxy and cyano.

In some embodiments, X is N and Y is CR⁶. In other embodiments, X is CR⁵ and Y is N. In still other embodiments, X is N and Y is N.

In some embodiments, Z is O. In other embodiments, Z is S. In further embodiments, Z is CHR⁷. In yet other embodiments, Z is NR⁸. In some embodiments, Z is absent.

In some embodiments, Z is —O—, —S—, —S(O)—, —S(O)₂—, —S(O₂)N(R⁸)—, —C(O)—, —C(O)O—, —C(HR⁷)—, —N(R⁸)—, —C(O)N(R⁸)—, alkylene, alkenylene, alkynylene, heteroalkylene, or absent. In some embodiments, Z is —O—, —S—, —S(O)—, —S(O)₂—, —C(O)—, —C(HR⁷)—, —N(R⁸)—, C₁-C₃ alkylene, C₁-C₃ heteroalkylene, C₁-C₃ alkenylene or absent. In some embodiments, Z is —O—. In other embodiments, Z is —S—. In further embodiments, Z is —C(HR⁷)—. In yet other embodiments, Z is —N(R⁸). In some embodiments, Z is absent.

In some embodiments, a compound of any one of Formulae I-H-I-K may have an enantiomeric excess of at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or even higher. In some embodiments, a compound of any one of Formulae I-H-I-K may have an enantiomeric excess of about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99%.

In some other embodiments, exemplary compounds may include, but are not limited to, a compound or pharmaceutically acceptable salt or prodrug thereof, selected from the following:

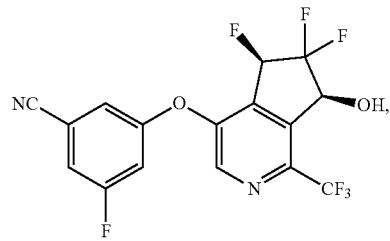

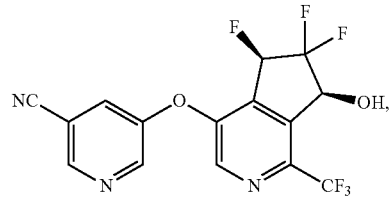

-continued

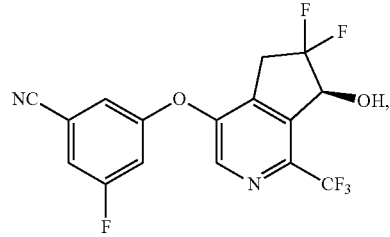

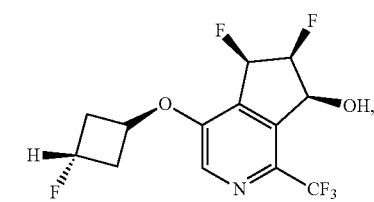

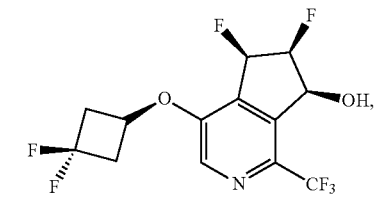

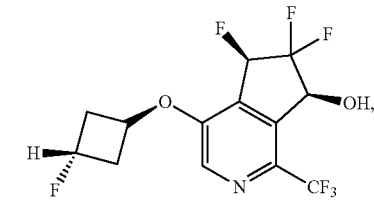

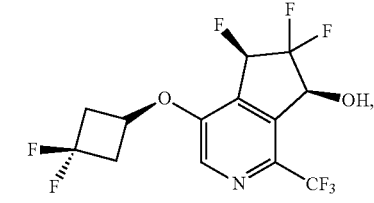

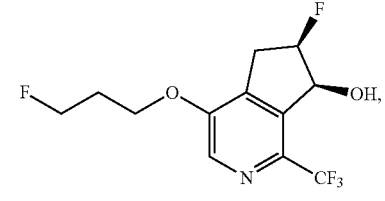

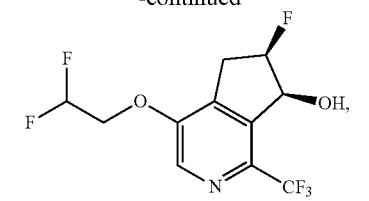
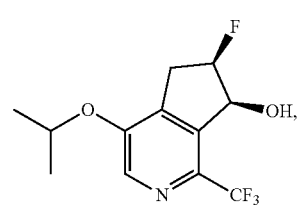
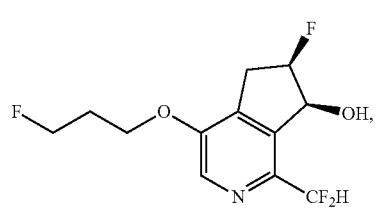
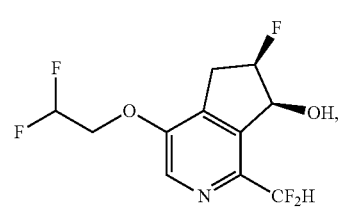
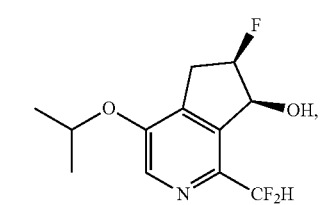
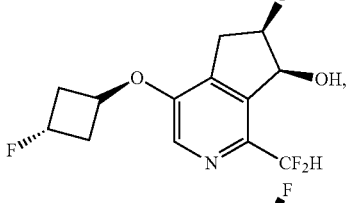
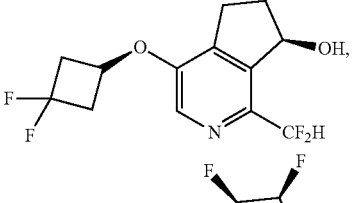
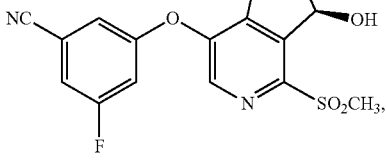
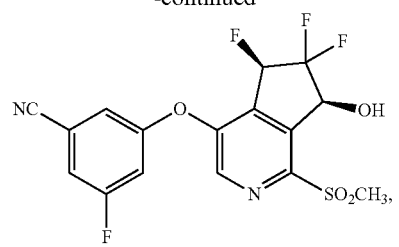
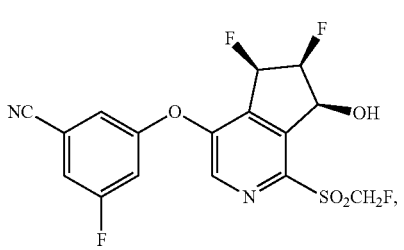
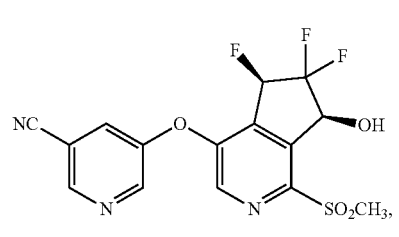
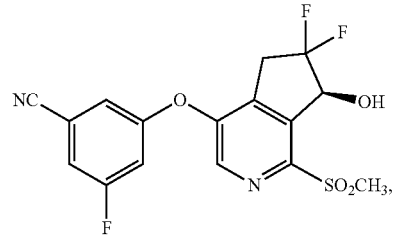
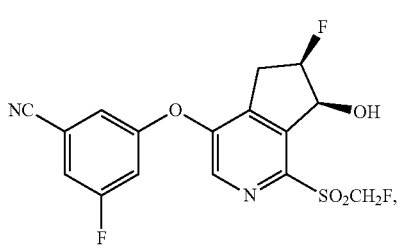
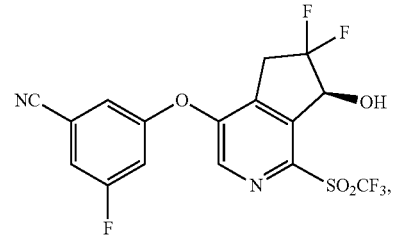
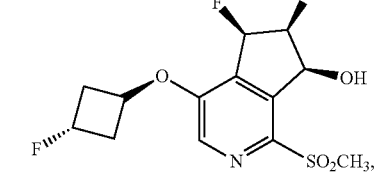

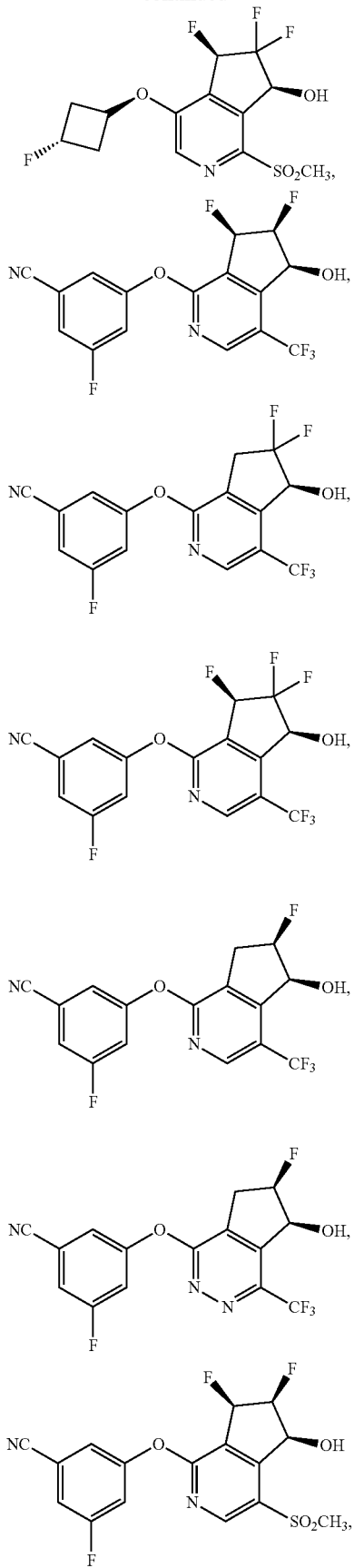
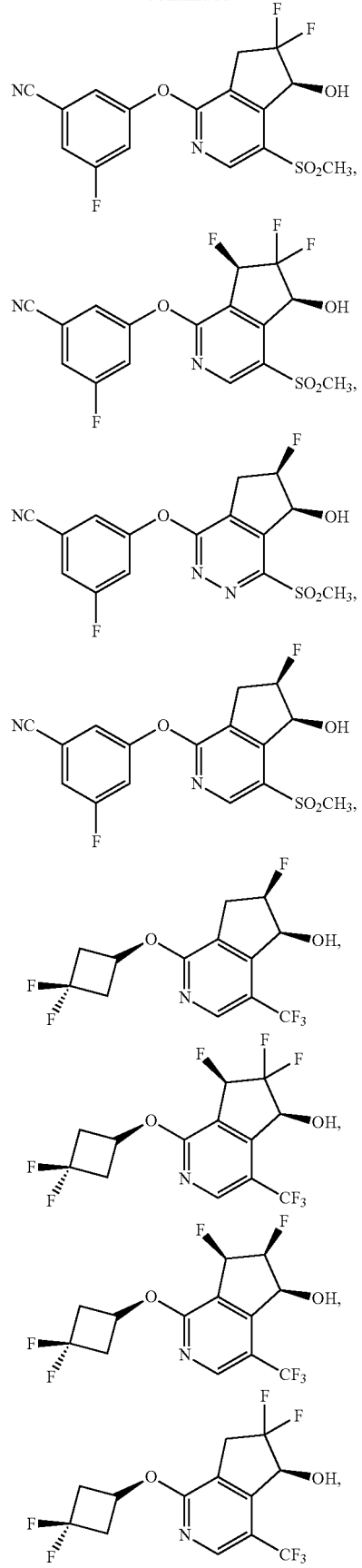

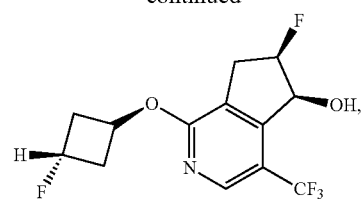
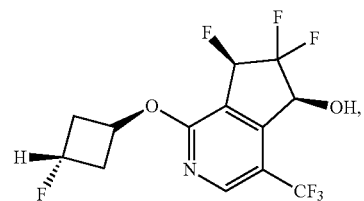
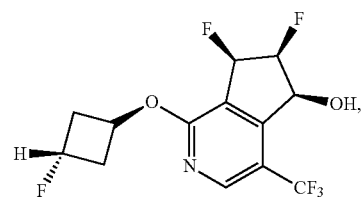
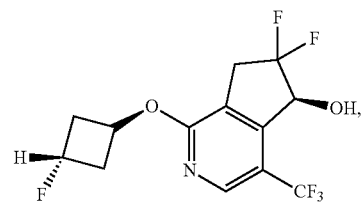
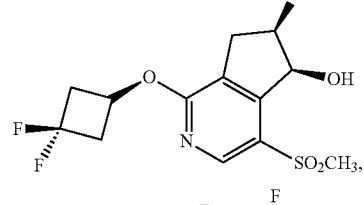
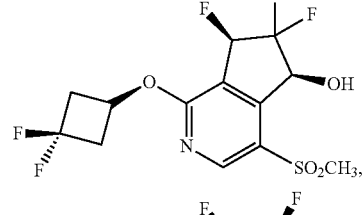
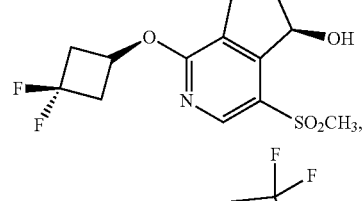
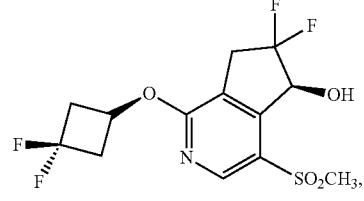
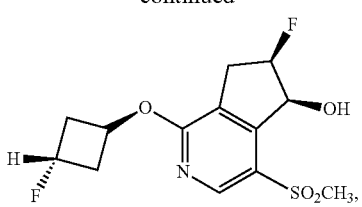
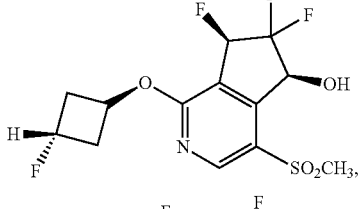
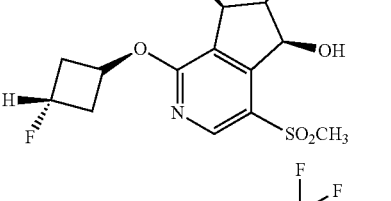
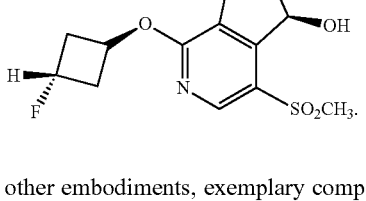
In some other embodiments, exemplary compounds may include, but are not limited to, a compound or pharmaceutically acceptable salt or prodrug thereof, selected from the following:
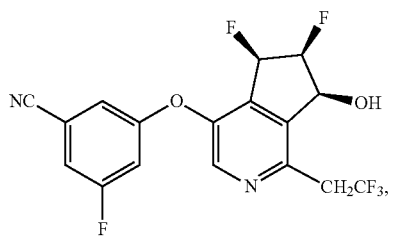
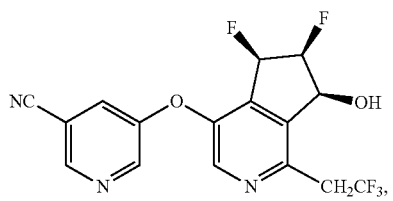
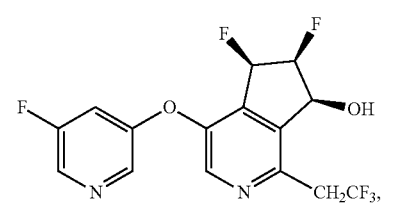

-continued
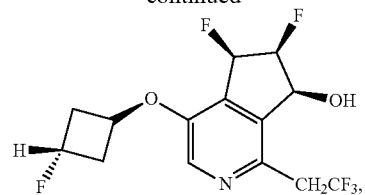
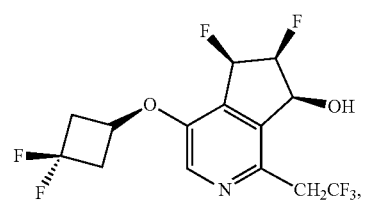
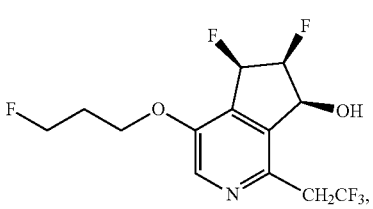
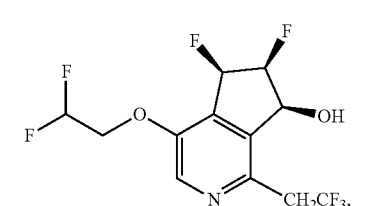
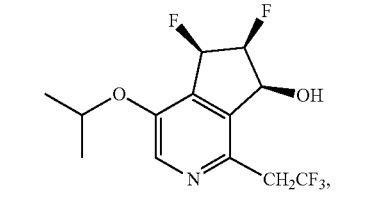
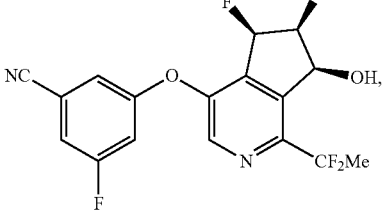
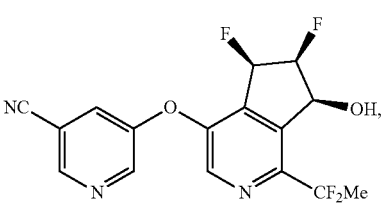
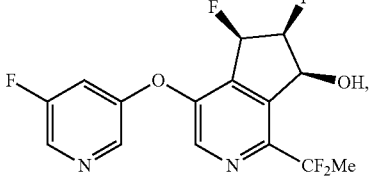
-continued
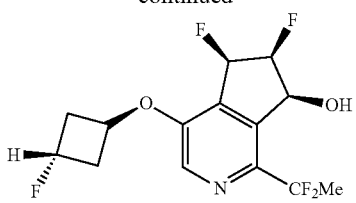
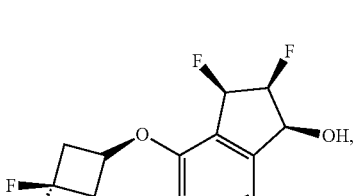
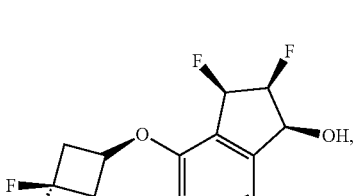
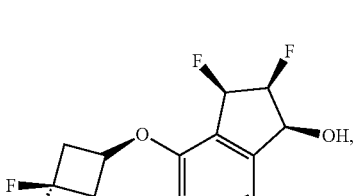
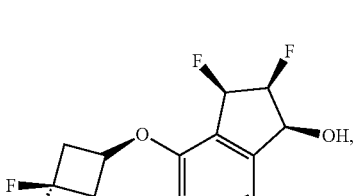
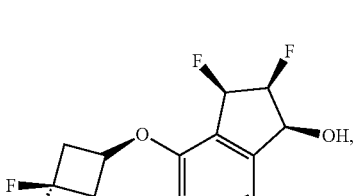
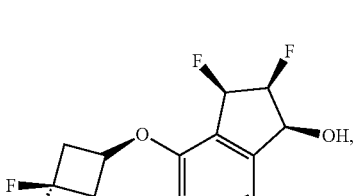
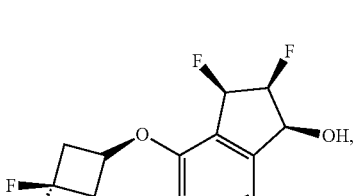

71
-continued
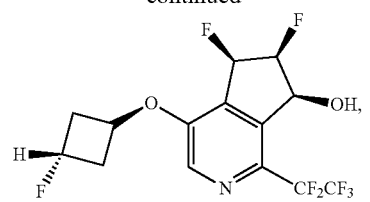
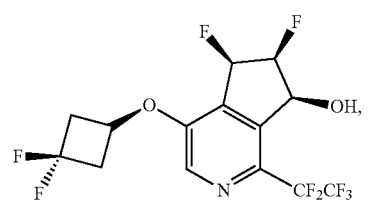
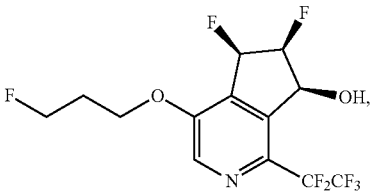
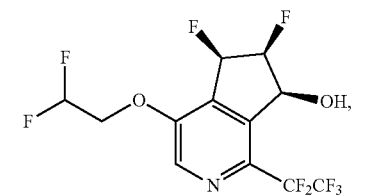
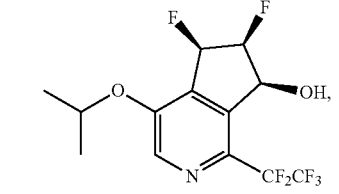
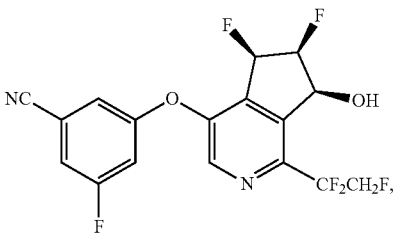
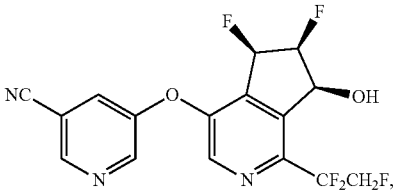
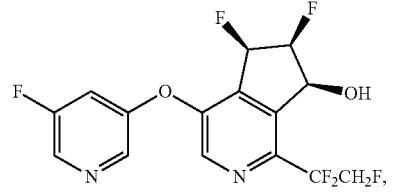
72
-continued
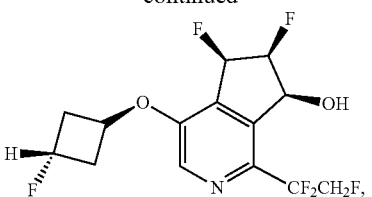
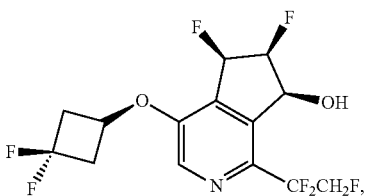
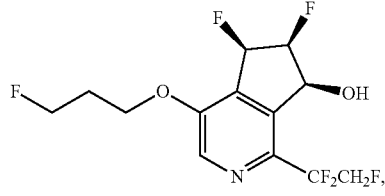
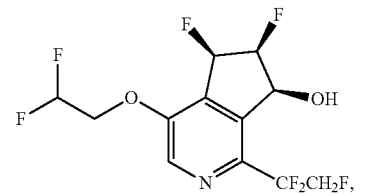
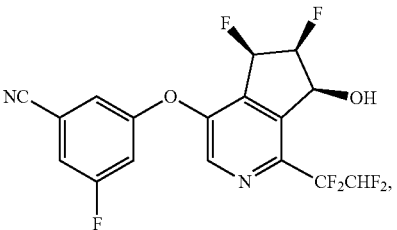
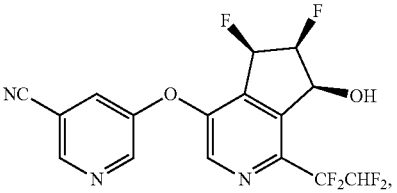
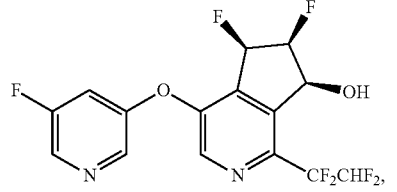

-continued

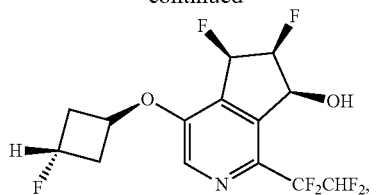

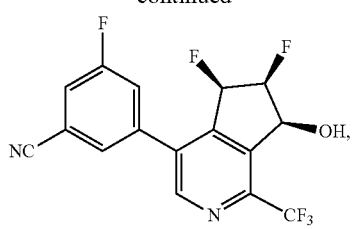

-continued

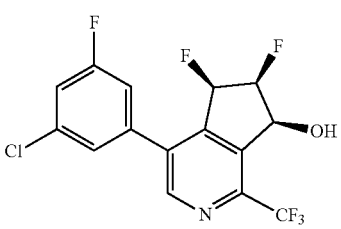

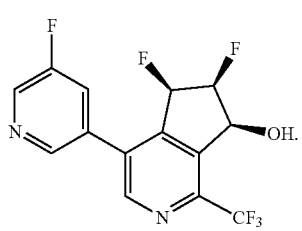

In another aspect, the present disclosure provides a compound or pharmaceutically acceptable salt or prodrug thereof, selected from the group consisting of the compounds given in Table 1.

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Schemes 1-5, the steps in some cases may be performed in a different order than the order shown in Schemes 1-5. Various modifications to these synthetic reaction schemes may be made and will be suggested to one skilled in the art having referred to the disclosure contained in this Application. Numberings or R groups in each scheme do not necessarily correspond to that of the claims or other schemes or tables herein.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

In general, compounds of the invention may be prepared by the following reaction schemes:

Scheme 1

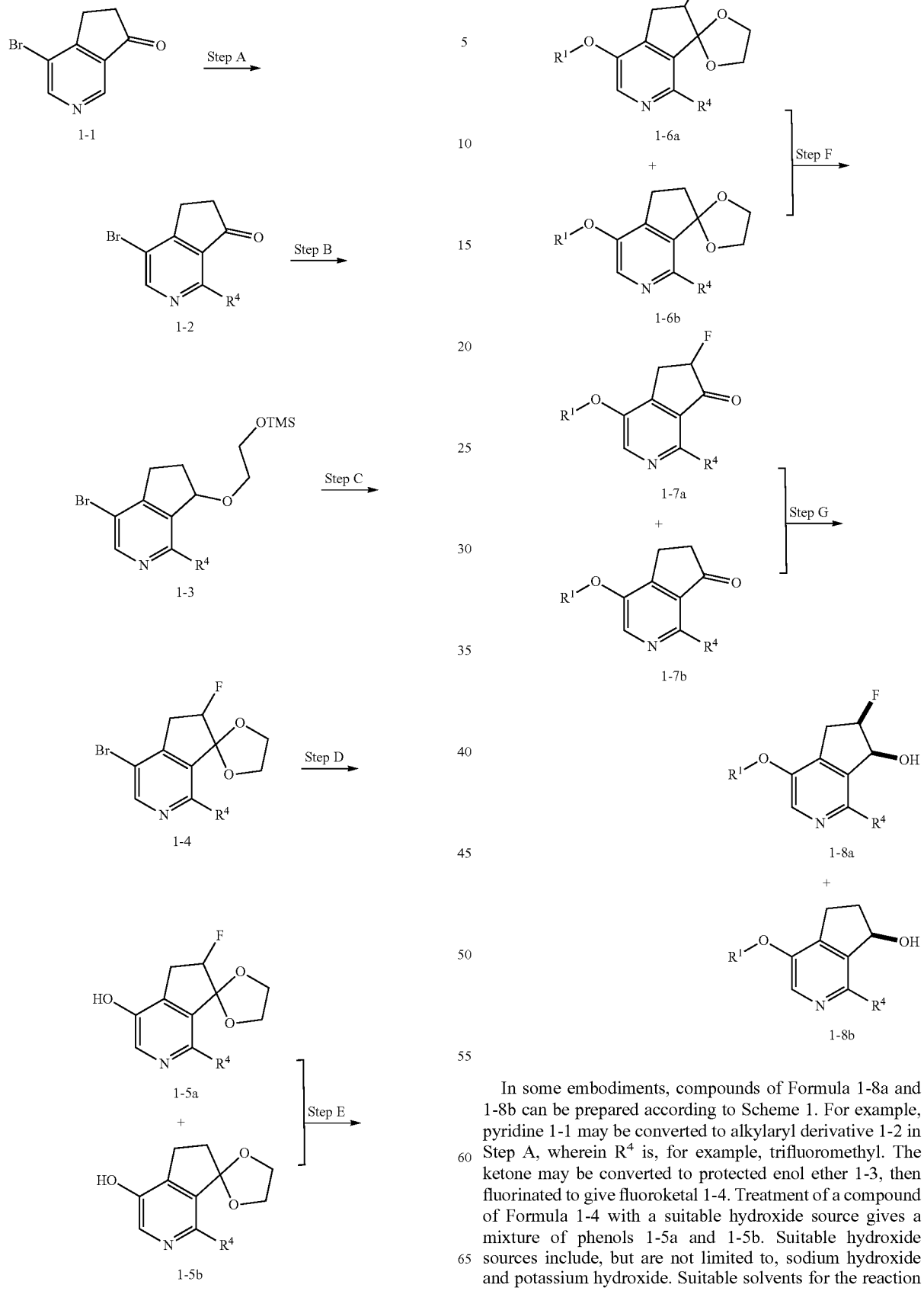

In some embodiments, compounds of Formula 1-8a and 1-8b can be prepared according to Scheme 1. For example, pyridine 1-1 may be converted to alkylaryl derivative 1-2 in Step A, wherein $R^4$ is, for example, trifluoromethyl. The ketone may be converted to protected enol ether 1-3, then fluorinated to give fluoroketal 1-4. Treatment of a compound of Formula 1-4 with a suitable hydroxide source gives a mixture of phenols 1-5a and 1-5b. Suitable hydroxide sources include, but are not limited to, sodium hydroxide and potassium hydroxide. Suitable solvents for the reaction include, but are not limited to, DMSO, DMA, DMF and EtOH. The phenols can undergo an SNAr reaction with a suitable halide to give aryl ethers of Formulae 1-6a and 1-6b, which may be deprotected to give the resultant ketones. In some embodiments, a compound of Formula 1-7 is reduced with a hydride source to give a racemic mixture. In other embodiments, an asymmetric reduction is carried out, affording alcohols 1-8a and 1-8b, separable by methods known to one skilled in the art, such as, for example, conventional column chromatography. For example, direct asymmetric reduction of ketones 1-7a and 1-7b may be accomplished chemically or enzymatically (Step G). For a recent review on enzymatic reduction of ketones, see Moore, et al. *Acc. Chem. Res.* 40: 1412-1419, 2007. Examples of chemical asymmetric reduction of ketones include, but are not limited to, Corey-Bakshi-Shibata (CBS) reduction, asymmetric hydrogenation and asymmetric transfer hydrogenation. In some embodiments, the asymmetric transfer hydrogenation is catalyzed by ruthenium. For examples of methods and catalysts for ruthenium catalyzed transfer hydrogenation, see U.S. Pat. Nos. 6,184,381 and 6,887,820. Exemplary catalysts for asymmetric transfer hydrogenation include, but are not limited to, the following (shown as the R, R configuration):

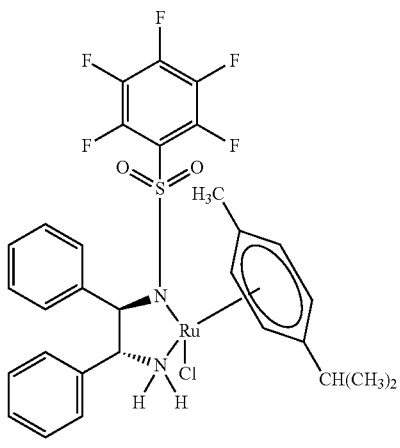

RuCl(FsDPEN)(p-cymene)

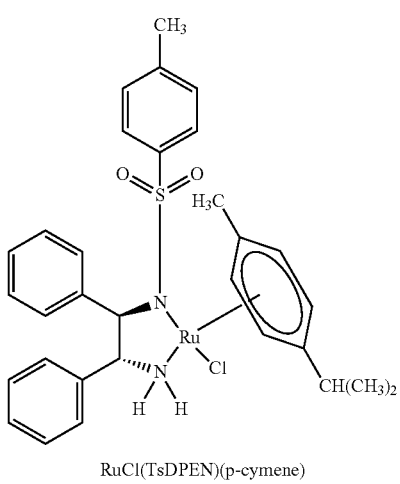

RuCl(TsDPEN)(p-cymene)

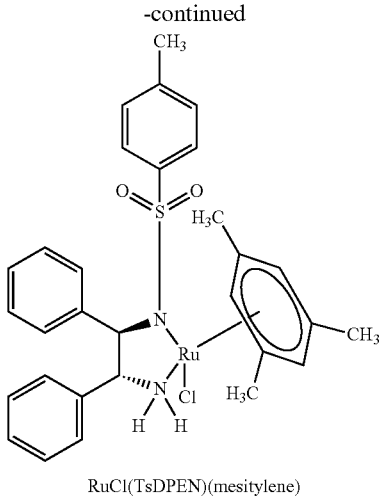

RuCl(TsDPEN)(mesitylene)

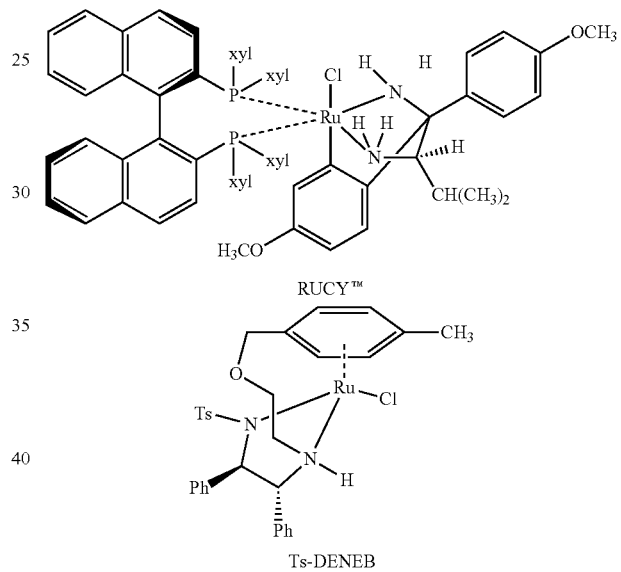

RUCY™

Ts-DENEB

The asymmetric transfer hydrogenation may be carried out at or below room temperature. In some embodiments, the asymmetric transfer hydrogenation is carried out at about 4° C. The alcohol product may have an enantiomeric excess of at least 90%, at least 91%, at least 92%, at least 93%, at least 94%, at least 95%, at least 96%, at least 97%, or even higher. It is well understood by one skilled in the art that changing the catalyst configuration will lead to a product with the opposite configuration.

Scheme 2

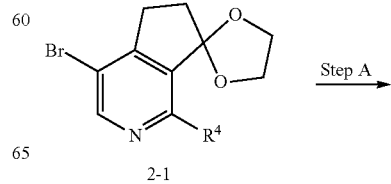

2-1

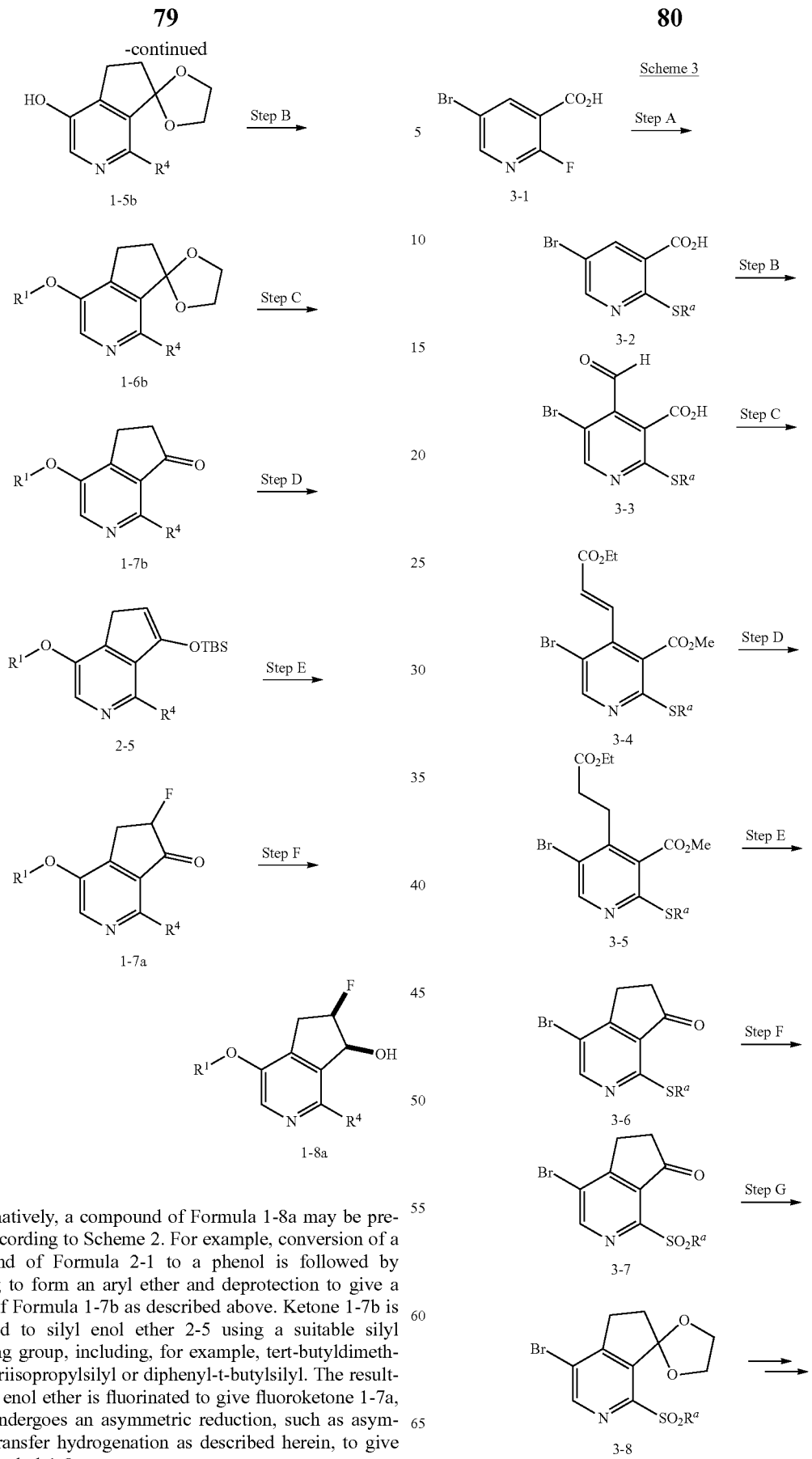

Alternatively, a compound of Formula 1-8a may be prepared according to Scheme 2. For example, conversion of a compound of Formula 2-1 to a phenol is followed by coupling to form an aryl ether and deprotection to give a ketone of Formula 1-7b as described above. Ketone 1-7b is converted to silyl enol ether 2-5 using a suitable silyl protecting group, including, for example, tert-butyldimethylsilyl, triisopropylsilyl or diphenyl-t-butylsilyl. The resulting silyl enol ether is fluorinated to give fluoroketone 1-7a, which undergoes an asymmetric reduction, such as asymmetric transfer hydrogenation as described herein, to give chiral alcohol 1-8a.

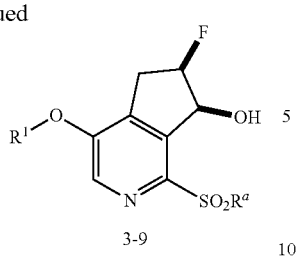

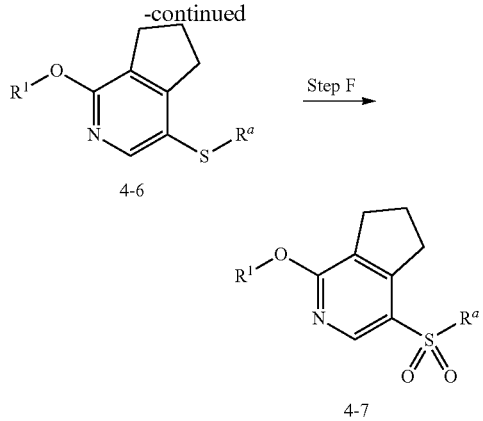

A compound of Formula 3-9 can be prepared following the general procedure outlined in Scheme 3, wherein the aryl fluoride of a compound of Formula 3-1 is displaced with an alkyl thiol to give 3-2. Formation of benzaldehyde 3-3 may be followed by, for example, a Wittig reaction, to give alkene 3-4, which is reduced to an alkane of Formula 3-5 under suitable conditions. In some embodiments, a Dieckmann condensation reaction is followed by a decarboxylation to give ketone 3-6. Oxidation of a compound of Formula 3-6 to give a compound of Formula 3-7 may be accomplished by a variety of methods known in the art, including, but not limited to, $RuCl_3$ catalyzed oxidation in the presence of $NaIO_4$, oxidation with m-chloroperoxybenzoic acid (mCPBA) and oxidation with Oxone®. Protection of the ketone, for example, as the cyclic ketal (3-8) is followed by the general procedures outlined in Scheme 2 to give a compound of Formula 3-9.

In some embodiments, a compound of Formula 4-7 can be prepared according to Scheme 4. Formation of a chloropyridine of Formula 4-2 may be followed by a nucleophilic aromatic substitution (SNAr) reaction with a suitable substrate of formula $R^1OH$ to give a compound of Formula 4-3. Temperatures for carrying out the SNAr reaction may depend on the reactivity of both $R^1OH$ and/or compound 4-2. The reaction may be carried out at a temperature range from about room temperature to 200° C. In some embodiments, the temperature range is from room temperature to 60° C. In some other embodiments, the temperature range is from 60° C. to 100° C. In some other embodiments, the temperature range is from 100 OC to 200° C. Aryl bromide 4-3 may undergo a transition-metal catalyzed coupling reaction with a thioate to give a compound of Formula 4-4. Hydrolysis, alkylation with a suitable alkyl halide and oxidation affords a compound of Formula 4-7.

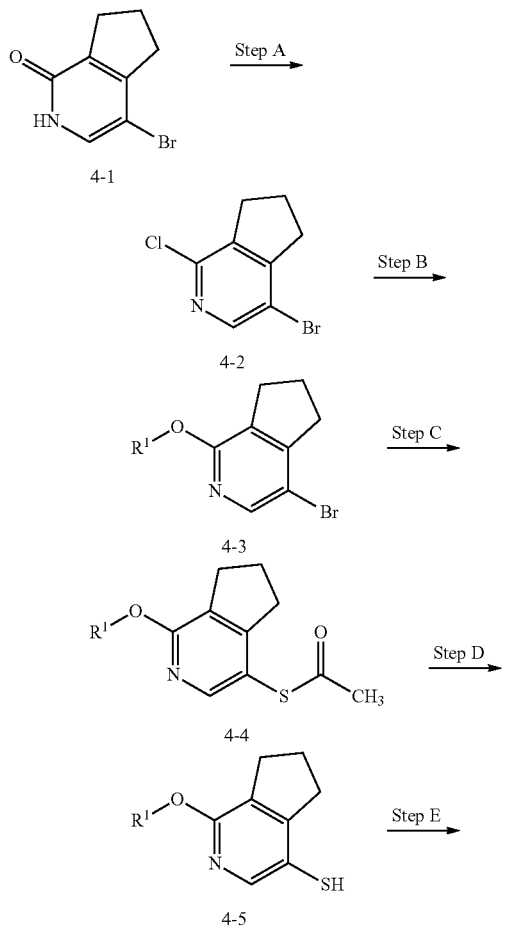

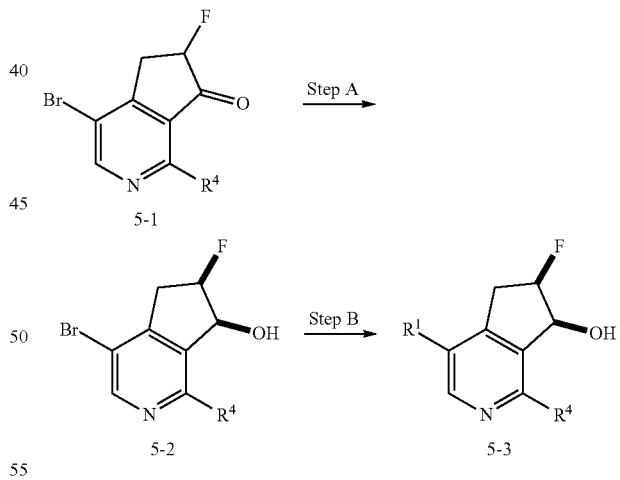

In some embodiments, a ketone of Formula 5-1 may be reduced to give 5-2, optionally with high enantioselectivity using asymmetric transfer hydrogenation or enzymatic reduction conditions as described herein. A compound of Formula 5-2 and a suitable coupling partner, including, but not limited to, a boronic acid of formula $R^1B(OH)_2$, may undergo a coupling reaction to give a compound of Formula 5-3.

In some other embodiments, a compound of a formula given in Table 1 is synthesized according to one of the general routes outlined in Schemes 1-5, Examples 1-5 or by methods generally known in the art.

TABLE 1

| No. | Structure | Mass Characterization | ¹H NMR Data |
|---|---|---|---|
| 1 | 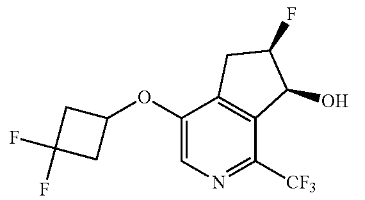 [SMILES: O[C@H]1c2c(C(F)(F)F)ncc(OC3CC(F)(F)C3)c2C[C@H]1F] | (M + H) 328 | (400 MHz, CDCl$_3$): δ 8.04 (s, 1H), 5.46-5.26 (m, 2H), 4.89-4.79 (m, 1H), 3.36-3.08 (m, 4H), 2.91-2.74 (m, 2H), 2.60 (dd, 1H) |
| 2 | 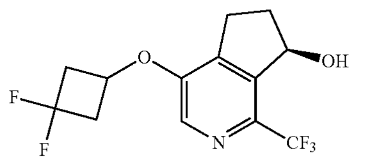 [SMILES: O[C@@H]1CCc2c(OC3CC(F)(F)C3)cnc(C(F)(F)F)c21] | (M + H) 310 | (400 MHz, CDCl$_3$): δ 7.98 (s, 1H), 5.59-5.54 (m, 1H), 4.88-4.79 (m, 1H), 3.24-3.07 (m, 3H), 2.89 (dd, 1H), 2.89-2.74 (m, 2H), 2.44-2.34 (m, 1H), 2.28-2.21 (m, 1H), 2.12-2.09 (m, 1H) |
| 3 | 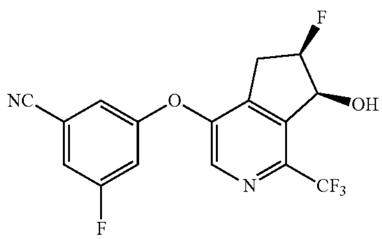 [SMILES: N#Cc1cc(F)cc(Oc2cnc(C(F)(F)F)c3c2C[C@@H](F)[C@H]3O)c1] | (M + H) 357 | (400 MHz, CDCl$_3$): δ 8.33 (s, 1H), 7.22 (ddd, 1H), 7.10-7.08 (m, 1H), 6.99 (dt, 1H), 5.54-5.46 (m, 1H), 5.46-5.28 (m, 1H), 3.26 (ddd, 1H), 3.11 (ddd, 1H), 2.67 (dd, 1H) |
| 4 | 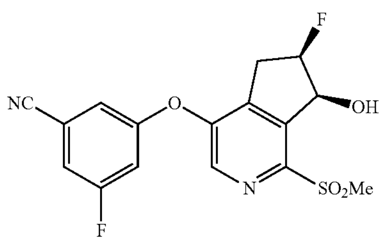 [SMILES: CS(=O)(=O)c1ncc(Oc2cc(F)cc(C#N)c2)c2c1[C@H](O)[C@H](F)C2] | (M + H) 367 | (400 MHz, CDCl$_3$): δ 8.27 (s, 1H), 7.25 (ddd, 1H), 7.14 (m, 1H), 7.03 (dt, 1H), 5.69 (dt, 1H), 5.53-5.36 (m, 1H), 4.24 (d, 1H), 3.34 (s, 3H), 3.31-3.24 (m, 1H), 3.09 (ddd, 1H) |
| 5 | 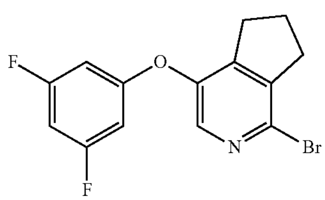 [SMILES: Fc1cc(F)cc(Oc2cnc(Br)c3c2CCC3)c1] | 326/328 (M + H) | |
| 6 | 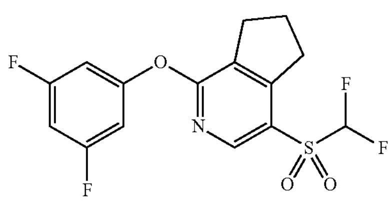 [SMILES: O=S(=O)(c1cnc(Oc2cc(F)cc(F)c2)c2c1CCC2)C(F)F] | 362 (M + H) | (400 MHz, CDCl$_3$): δ 7.49 (s, 1H), 6.80-6.71 (m, 3H), 6.19 (t, 1H), 3.36 (t, 2H), 3.06 (t, 2H), 2.31-2.23 (m, 2H) |
| 7 | 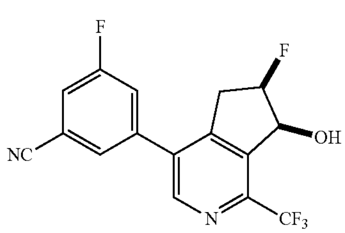 [SMILES: N#Cc1cc(F)cc(-c2cnc(C(F)(F)F)c3c2C[C@@H](F)[C@H]3O)c1] | (M + H) 341 | (400 MHz, CDCl$_3$): δ 8.65 (s, 1H), 7.53-7.48 (m, 2H), 7.40 (ddd, 1H), 5.56-5.48 (m, 1H), 5.35 (ddt, 1H), 3.41 (ddd, 1H), 3.21 (ddd, 1H), 2.65 (dd, 1H) |

TABLE 1-continued

| No. | Structure | Mass Characterization | ¹H NMR Data |
|---|---|---|---|
| 8 | 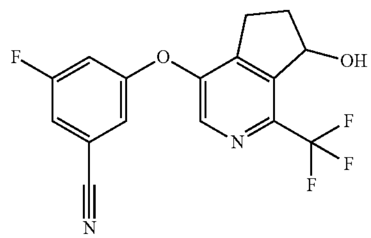 [SMILES: N#Cc1cc(F)cc(Oc2cnc(C(F)(F)F)c3c2CCC3O)c1] | 339 (M + H) | |
| 9 | 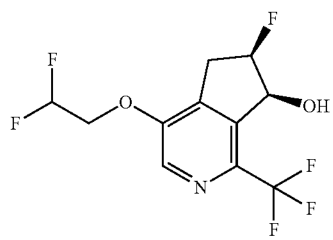 [SMILES: O[C@H]1c2c(C(F)(F)F)ncc(OCC(F)F)c2C[C@H]1F] | 302 (M + H) | |
| 10 | 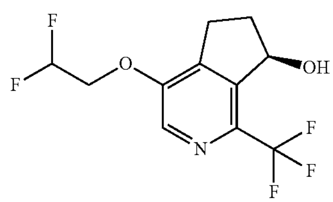 [SMILES: O[C@@H]1CCc2c(OCC(F)F)cnc(C(F)(F)F)c21] | 284 (M + H) | |
| 11 | 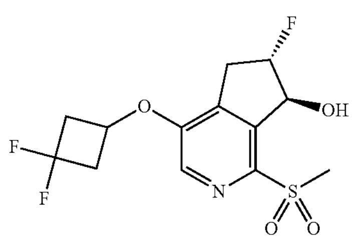 [SMILES: CS(=O)(=O)c1ncc(OC2CC(F)(F)C2)c2c1[C@H](O)[C@@H](F)C2] | 338 (M + H) | |
| 12 | 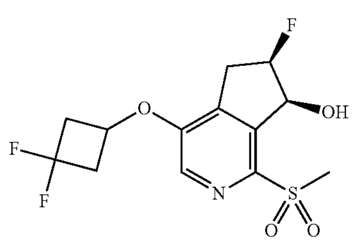 [SMILES: CS(=O)(=O)c1ncc(OC2CC(F)(F)C2)c2c1[C@H](O)[C@H](F)C2] | 338 (M + H) | |
| 13 | 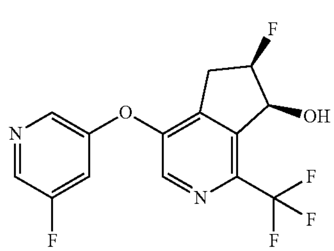 [SMILES: O[C@H]1c2c(C(F)(F)F)ncc(Oc3cncc(F)c3)c2C[C@H]1F] | 333 (M + H) | |

TABLE 1-continued

| No. | Structure | Mass Characterization | ¹H NMR Data |
|---|---|---|---|
| 14 | 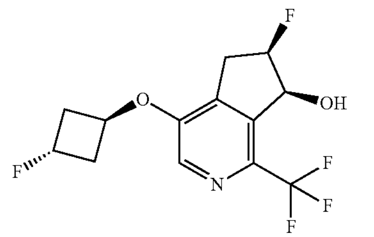 [SMILES: O[C@H]1c2c(C(F)(F)F)ncc(O[C@H]3C[C@H](F)C3)c2C[C@H]1F] | 310 (M + H) | |
| 15 | 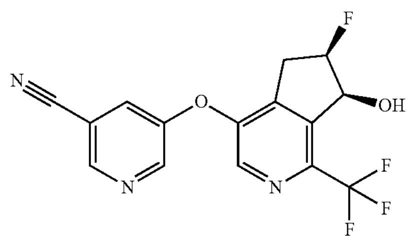 [SMILES: N#Cc1cncc(Oc2cnc(C(F)(F)F)c3c2C[C@@H](F)[C@H]3O)c1] | 340 (M + H) | |
| 16 | 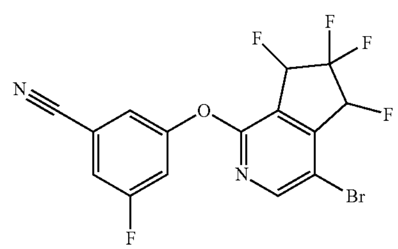 [SMILES: N#Cc1cc(F)cc(Oc2ncc(Br)c3c2C(F)C(F)(F)C3F)c1] | 405/407 (M + H) | (400 MHz, CDCl$_3$): δ 8.38 (d, 1H), 7.37-7.36 (m, 1H), 7.30 (ddd, 1H), 7.24 (dt, 1H), 6.09 (dddd, 1H), 6.00 (dddd, 1H) |
| 17 | 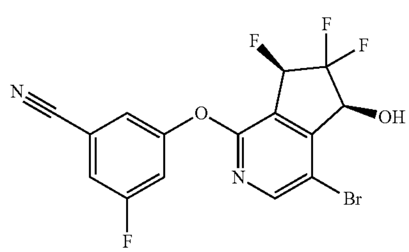 [SMILES: N#Cc1cc(F)cc(Oc2ncc(Br)c3c2[C@@H](F)C(F)(F)[C@H]3O)c1] | 403/405 (M + H) | (400 MHz, CDCl$_3$): δ 8.36 (d, 1H), 7.37-7.35 (m, 1H), 7.29 (ddd, 1H), 7.25 (dt, 1H), 5.86 (dd, 1H), 5.11 (ddd, 1H), 2.73 (d, 1H) |
| 18 | 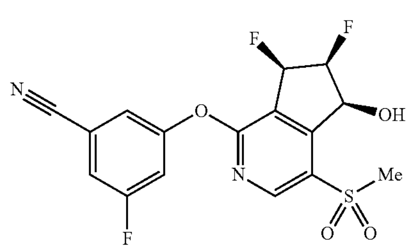 [SMILES: CS(=O)(=O)c1cnc(Oc2cc(F)cc(C#N)c2)c2c1[C@H](O)[C@H](F)[C@@H]2F] | 385 (M + H) | (400 MHz, CDCl$_3$): δ 8.75 (d, 1H), 7.39-7.37 (m, 1H), 7.34 (ddd, 1H), 7.29-7.25 (m, 1H), 6.25 (ddd, 1H), 5.94-5.87 (m, 1H), 5.44 (ddd, 1H), 3.66-3.58 (m,1H), 3.29 (s, 3H) |
| 19 | 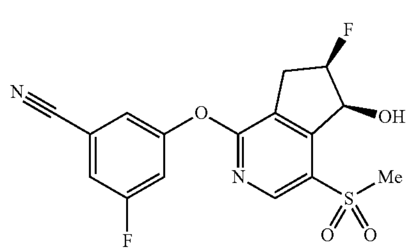 [SMILES: CS(=O)(=O)c1cnc(Oc2cc(F)cc(C#N)c2)c2c1[C@H](O)[C@H](F)C2] | 367 (M + H) | (400 MHz, CDCl$_3$): δ 8.60-8.59 (m, 1H), 7.35-7.33 (m, 1H), 7.31 (ddd, 1H), 7.24 (dt, 1H), 5.63 (ddd, 1H), 5.51 (dtd, 1H), 3.76 (dd, 1H), 3.47-3.35 (m, 1H), 3.31 (s, 3H), 3.29-3.15 (m, 1H) |

TABLE 1-continued

| No. | Structure | Mass Characterization | ¹H NMR Data |
|---|---|---|---|
| 20 | 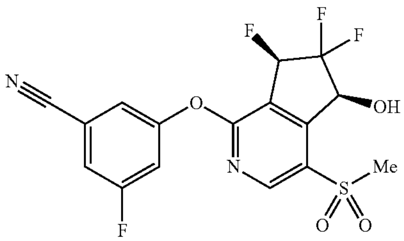 [SMILES: CS(=O)(=O)c1cnc(Oc2cc(F)cc(C#N)c2)c2c1[C@H](O)C(F)(F)[C@@H]2F] | 403 (M + H) | (400 MHz, CDCl₃): δ 8.80 (d, 1H), 7.40-7.38 (m, 1H), 7.36 (ddd, 1H), 7.28 (dt, 1H), 5.88 (dd, 1H), 5.66-5.60 (m, 1H), 3.52 (dd, 1H), 3.28 (s, 3H) |
| 21 | 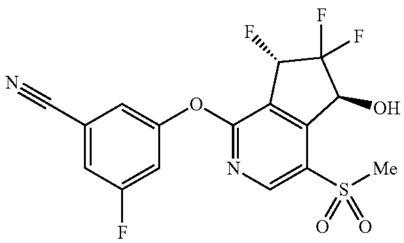 [SMILES: CS(=O)(=O)c1cnc(Oc2cc(F)cc(C#N)c2)c2c1[C@H](O)C(F)(F)[C@H]2F] | 403 (M + H) | (400 MHz, CDCl₃): δ 8.77 (d, 1H), 7.39-7.37 (m, 1H), 7.35 (ddd, 1H), 7.27 (dt, 1H), 6.00 (dd, 1H), 5.83 (tdd, 1H), 3.97 (d, 1H), 3.29 (s, 3H) |
| 22 | 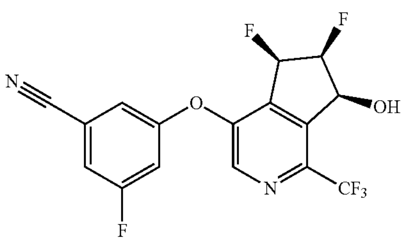 [SMILES: N#Cc1cc(F)cc(Oc2cnc(C(F)(F)F)c3c2[C@@H](F)[C@@H](F)[C@H]3O)c1] | 375 (M + H) | (400 MHz, CDCl₃): δ 8.42 (s, 1H), 7.28 (ddd, 1H), 7.20-7.18 (m, 1H), 7.09 (dt, 1H), 5.92 (dt, 1H), 5.53-5.46 (m, 1H), 5.19 (ddt, 1H), 2.66 (ddd, 1H) |
| 23 | 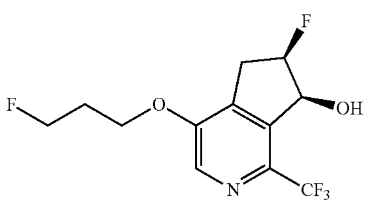 [SMILES: O[C@H]1c2c(C(F)(F)F)ncc(OCCCF)c2C[C@H]1F] | 298 (M + H) | |
| 24 | 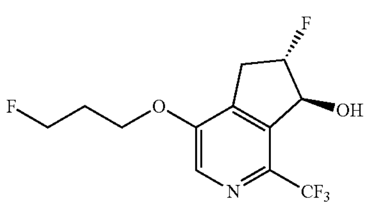 [SMILES: O[C@H]1c2c(C(F)(F)F)ncc(OCCCF)c2C[C@@H]1F] | 298 (M + H) | |
| 25 | 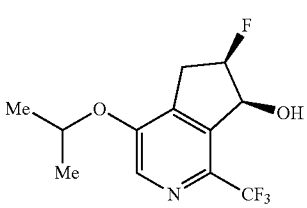 [SMILES: CC(C)Oc1cnc(C(F)(F)F)c2c1C[C@@H](F)[C@H]2O] | 280 (M + H) | |
| 26 | 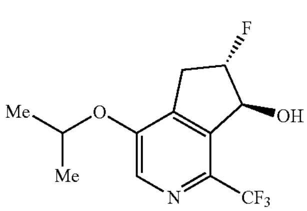 [SMILES: CC(C)Oc1cnc(C(F)(F)F)c2c1C[C@H](F)[C@H]2O] | 280 (M + H) | |

TABLE 1-continued

| No. | Structure | Mass Characterization | ¹H NMR Data |
|---|---|---|---|
| 27 | 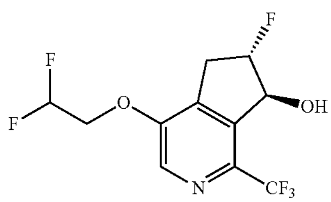 [SMILES: O[C@H]1c2c(C(F)(F)F)ncc(OCC(F)F)c2C[C@@H]1F] | 302 (M + H) | |
| 28 | 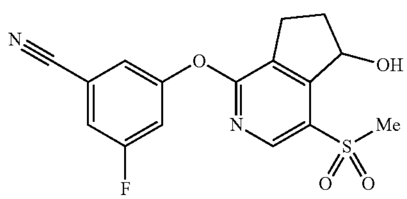 [SMILES: CS(=O)(=O)c1cnc(Oc2cc(F)cc(C#N)c2)c2c1C(O)CC2] | 349 (M + H) | (400 MHz, CDCl₃): δ 8.52-8.51 (m, 1H), 7.33 (ddd, 1H), 7.29 (ddd, 1H), 7.23 (dt, 1H), 5.71-5.66 (m, 1H), 3.64 (d, 1H), 3.26-3.17 (m, 1H), 3.22 (s, 3H), 2.99-2.90 (ddd, 1H), 2.66-2.56 (m, 1H), 2.32-2.22 (m, 1H) |
| 29 | 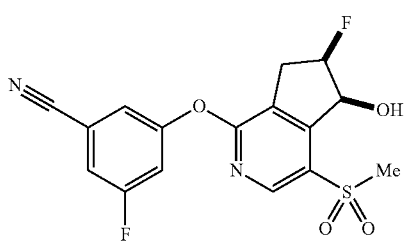 [SMILES: CS(=O)(=O)c1cnc(Oc2cc(F)cc(C#N)c2)c2c1[C@H](O)[C@H](F)C2] | 367 (M + H) | (400 MHz, CDCl₃): δ 8.60-8.59 (m, 1H), 7.35-7.33 (m, 1H), 7.31 (ddd, 1H), 7.24 (dt, 1H), 5.63 (ddd, 1H), 5.52 (dtd, 1H), 3.76 (dd, 1H), 3.47-3.35 (m, 1H), 3.31 (s, 3H), 3.29-3.15 (m, 1H) |
| 30 | 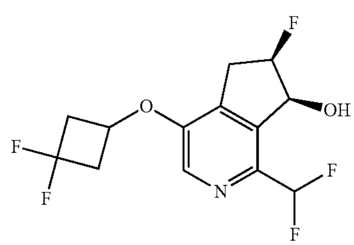 [SMILES: O[C@H]1c2c(C(F)F)ncc(OC3CC(F)(F)C3)c2C[C@H]1F] | 310 (M + H) | |
| 31 | 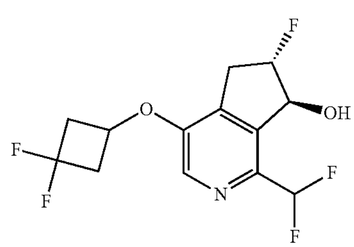 [SMILES: O[C@H]1c2c(C(F)F)ncc(OC3CC(F)(F)C3)c2C[C@@H]1F] | 310 (M + H) | |
| 32 | 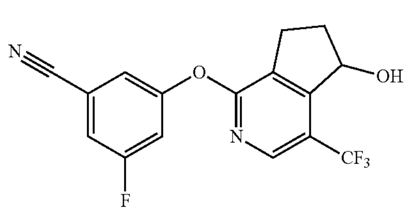 | 339 (M + H) | (400 MHz, CDCl₃): δ 8.29-8.27 (m, 1lH), 7.34-7.32 (m, 1H), 7.26 (ddd, 1H), 7.22 (dt, 1H), 5.57-5.10 (m, 1H), 3.22 (dt, 1H), 2.96 (ddd, 1H), 2.56-2.45 (m, 1H), 2.33-2.25 (m, 1H), 2.22-2.18 (m, 1H) |

TABLE 1-continued

| No. | Structure | Mass Characterization | ¹H NMR Data |
|---|---|---|---|
| 33 | 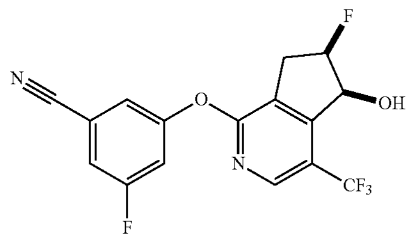 [SMILES: N#Cc1cc(F)cc(Oc2ncc(C(F)(F)F)c3c2C[C@@H](F)[C@H]3O)c1] | 357 (M + H) | (400 MHz, CDCl$_3$): δ 8.36-8.34 (m, 1H), 7.35-7.32 (m, 1H), 7.28 (ddd, 1H), 7.23 (dt, 1H), 5.53-5.35 (m, 2H), 3.40 (ddd, 1H), 3.22 (ddd, 1H), 2.73-2.68 (m, 1H) |
| 34 | 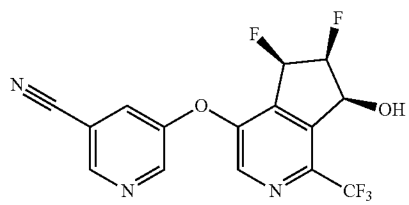 [SMILES: N#Cc1cncc(Oc2cnc(C(F)(F)F)c3c2[C@@H](F)[C@@H](F)[C@H]3O)c1] | 358 (M + H) | (400 MHz, CDCl$_3$): δ 8.79 (dd, 1H), 8.71 (d, 1H), 8.41 (s, 1H), 7.67 (dd, 1H), 5.94 (dt, 1H), 5.53-5.46 (m, 1H), 5.21 (ddt, 1H), 2.73 (ddd, 1H) |
| 35 | 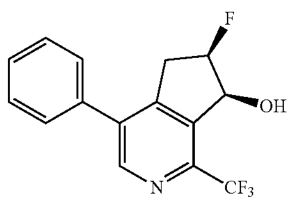 [SMILES: O[C@H]1c2c(C(F)(F)F)ncc(-c3ccccc3)c2C[C@H]1F] | 298 (M + H) | (400 MHz, CDCl$_3$): δ 8.68 (s, 1H), 7.55-7.45 (m, 3H), 7.44-7.40 (m, 2H), 5.54-5.46 (m, 1H), 5.31 (ddt, 1H), 3.46 (ddd, 1H), 3.24 (ddd, 1H), 2.61 (dd, 1H) |
| 36 | 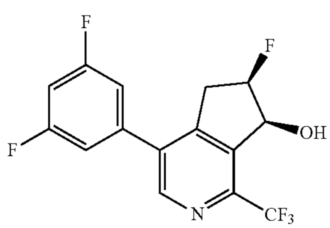 [SMILES: O[C@H]1c2c(C(F)(F)F)ncc(-c3cc(F)cc(F)c3)c2C[C@H]1F] | 334 (M + H) | (400 MHz, CDCl$_3$): δ 8.65 (s, 1H), 6.99-6.91 (m, 3H), 5.54-5.47 (m, 1H), 5.33 (ddt, 1H), 3.44 (ddd, 1H), 3.23 (ddd, 1H), 2.63 (dd, 1H) |
| 37 | 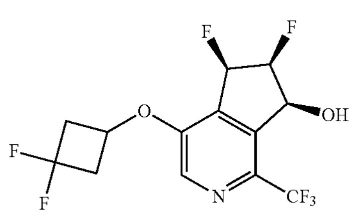 [SMILES: O[C@H]1c2c(C(F)(F)F)ncc(OC3CC(F)(F)C3)c2[C@@H](F)[C@H]1F] | 346 (M + H) | (400 MHz, CDCl$_3$): δ 8.24 (s, 1H), 5.95 (ddd, 1H), 5.47-5.41 (m, 1H), 5.07 (ddt, 1H), 4.97-4.88 (m, 1H), 3.30-3.15 (m, 2H), 2.99-2.79 (m, 2H), 2.54-2.49 (m, 1H) |
| 38 | 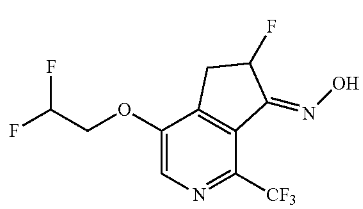 [SMILES: O/N=C1/c2c(C(F)(F)F)ncc(OCC(F)F)c2CC1F] | 315 (M + H) | (400 MHz, DMSO-d$_6$): δ 8.30 (s, 1H), 6.26 (tt, 1H), 6.15 (ddd, 1H), 4.55 (td, 2H), 3.46-3.32 (m, 1H), 3.13 (ddd, 1H) |
| 39 | 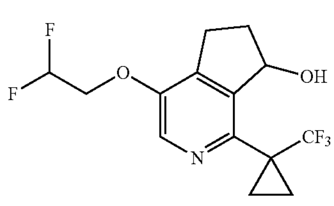 [SMILES: OC1CCc2c(OCC(F)F)cnc(C3(C(F)(F)F)CC3)c21] | 324 (M + H) | (400 MHz, CDCl$_3$): δ 8.14 (s, 1H), 6.10 (tt, 1H), 5.58-5.30 (m, 1H), 4.39-4.24 (m, 2H), 3.10 (dt, 1H), 2.87 (ddd, 1H), 2.37-2.27 (m, 1H), 2.20-2.12 (m, 1H), 1.90-1.86 (m, 1H), 1.47-1.39 (m, 2H), 1.27-1.21 (m, 2H) |

TABLE 1-continued

| No. | Structure | Mass Characterization | ¹H NMR Data |
|---|---|---|---|
| 40 | 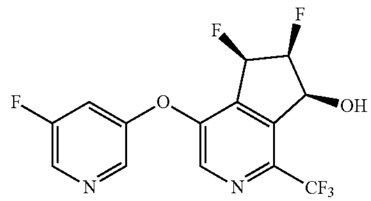 [SMILES: O[C@H]1c2c(C(F)(F)F)ncc(Oc3cncc(F)c3)c2[C@@H](F)[C@H]1F] | 351 (M + H) | |
| 41 | 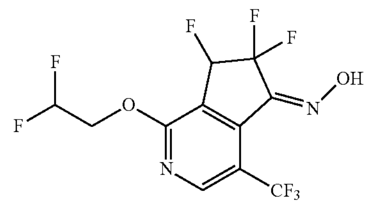 [SMILES: O/N=C1/c2c(C(F)(F)F)cnc(OCC(F)F)c2C(F)C1(F)F] | 351 (M + H) | (400 MHz, CDCl₃): δ 8.75 (d, 1H), 8.65-8.62 (m, 1H), 6.17 (tt, 1H), 5.83 (dd, 1H), 4.83-4.64 (m, 2H) |
| 42 | 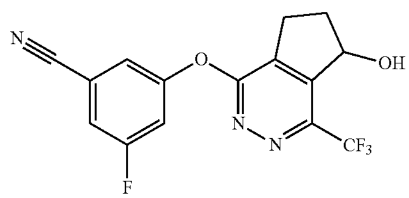 [SMILES: N#Cc1cc(F)cc(Oc2nnc(C(F)(F)F)c3c2CCC3O)c1] | 340 (M + H) | (400 MHz, CDCl₃): δ 7.43-7.41 (m, 1H), 7.33 (dt, 1H), 7.33-7.29 (m, 1H), 5.67-5.62 (m, 1H), 3.36-3.26 (m, 1H), 3.05 (ddd, 1H), 2.63-2.53 (m, 1H), 2.40-2.30 (m, 2H) |

Method of Use:

In one aspect, the present invention provides a method for treating a proliferative disorder in a subject in need thereof, comprising administering to said subject a HIF-2α inhibitor. In some embodiments, the proliferative disorder is a cancer condition. In some further embodiments, said cancer condition is a cancer selected from the group consisting of lung cancer, head and neck squamous cell carcinoma, pancreatic cancer, breast cancer, ovarian cancer, renal cell carcinoma, prostate cancer, neuroendocrine cancer, gastric cancer, bladder cancer and colon cancer. In another embodiment, the cancer condition is renal cell carcinoma.

In a further embodiment, the present invention provides a method of treating a cancer condition, wherein the HIF-2α inhibitor is effective in one or more of inhibiting proliferation of cancer cells, inhibiting metastasis of cancer cells, killing cancer cells and reducing severity or incidence of symptoms associated with the presence of cancer cells. In some other embodiments, said method comprises administering to the cancer cells a therapeutically effective amount of a HIF-2α inhibitor. In some embodiments, the administration takes place in vitro. In other embodiments, the administration takes place in vivo.

In some embodiments, the present invention provides a method of treating a von Hippel-Lindau (VHL) disease, comprising administering to a subject in need thereof an effective amount of a HIF-2α inhibitor described herein. VHL disease is an autosomal dominant syndrome that not only predisposes patients to kidney cancer (~70% lifetime risk), but also to hemangioblastomas, pheochromocytoma and pancreatic neuroendocrine tumors. VHL disease results in tumors with constitutively active HIF-α proteins with the majority of these dependent on HIF-2α activity (Maher, et al. *Eur. J. Hum. Genet.* 19: 617-623, 2011). HIF-2α has been linked to cancers of the retina, adrenal gland and pancreas through both VHL disease and activating mutations. Recently, gain-of-function HIF-2α mutations have been identified in erythrocytosis and paraganglioma with polycythemia (Zhuang, et al. *NEJM* 367: 922-930, 2012; Percy, et al. *NEJM* 358: 162-168, 2008; and Percy, et al. *Am. J. Hematol.* 87: 439-442, 2012). Notably, a number of known HIF-2α target gene products (e.g., VEGF, PDGF, and cyclin D1) have been shown to play pivotal roles in cancers derived from kidney, liver, colon, lung, and brain. In fact, therapies targeted against one of the key HIF-2α regulated gene products, VEGF, have been approved for the treatment of these cancers.

As used herein, a therapeutically effective amount of a HIF-2α inhibitor refers to an amount sufficient to effect the intended application, including but not limited to, disease treatment, as defined herein. Also contemplated in the subject methods is the use of a sub-therapeutic amount of a HIF-2α inhibitor for treating an intended disease condition.

The amount of the HIF-2α inhibitor administered may vary depending upon the intended application (in vitro or in vivo), or the subject and disease condition being treated, e.g., the weight and age of the subject, the severity of the disease condition, the manner of administration and the like, which can readily be determined by one of ordinary skill in the art.

Measuring inhibition of biological effects of HIF-2α can comprise performing an assay on a biological sample, such as a sample from a subject. Any of a variety of samples may be selected, depending on the assay. Examples of samples include, but are not limited to blood samples (e.g. blood plasma or serum), exhaled breath condensate samples, bronchoalveolar lavage fluid, sputum samples, urine samples, and tissue samples.

A subject being treated with a HIF-2α inhibitor may be monitored to determine the effectiveness of treatment, and the treatment regimen may be adjusted based on the subject's physiological response to treatment. For example, if inhibition of a biological effect of HIF-2α inhibition is above or below a threshold, the dosing amount or frequency may be decreased or increased, respectively. The methods can further comprise continuing the therapy if the therapy is determined to be efficacious. The methods can comprise maintaining, tapering, reducing, or stopping the administered amount of a compound in the therapy if the therapy is determined to be efficacious. The methods can comprise increasing the administered amount of a compound in the therapy if it is determined not to be efficacious. Alternatively, the methods can comprise stopping therapy if it is determined not to be efficacious. In some embodiments, treatment with a HIF-2α inhibitor is discontinued if inhibition of the biological effect is above or below a threshold, such as in a lack of response or an adverse reaction. The biological effect may be a change in any of a variety of physiological indicators.

In general, a HIF-2α inhibitor is a compound that inhibits one or more biological effects of HIF-2α. Examples of biological effects of HIF-2α include, but are not limited to, heterodimerization of HIF-2α to HIF-1β, HIF-2α target gene expression, VEGF gene expression, and VEGF protein secretion. In some embodiments, the HIF-2α inhibitor is selective for HIF-2α, such that the inhibitor inhibits heterodimerization of HIF-2α to HIF-1β but not heterodimerization of HIF-1α to HIF-1β. Such biological effects may be inhibited by about or more than about 10%, 20%, 30%, 40%, 50%, 60%, 70%, 80%, 90%, 95%, or more.

Hypoxia-inducible factors (HIFs), like HIF-2α, are transcription factors that respond to changes in available oxygen in the cellular environment (e.g. a decrease in oxygen, or hypoxia). The HIF signaling cascade mediates the effects of hypoxia, the state of low oxygen concentration, on the cell. Hypoxia often keeps cells from differentiating. However, hypoxia promotes the formation of blood vessels, and is important for the formation of a vascular system in embryos, and cancer tumors. The hypoxia in wounds also promotes the migration of keratinocytes and the restoration of the epithelium. A HIF-2α inhibitor of the present disclosure may be administered in an amount effective in reducing any one or more of such effects of HIF-2a activity.

HIF-2α activity can be inhibited by inhibiting heterodimerization of HIF-2α to HIF-1β (ARNT), such as with inhibitor compounds disclosed herein. A variety of methods for measuring HIF-2α dimerization are available. In some embodiments, the HIF-2α inhibitor binds the PAS-B domain cavity of HIF-2α.

Inhibition of heterodimerization of HIF-2α to HIF-1β (ARNT) may also be determined by a reduction in HIF-2α target gene mRNA expression. mRNA quantitation can be performed using real-time PCR technology. (Wong, et al, "Real-time PCR for mRNA quantitation", 2005. BioTechniques 39, 1: 1-1.). Yet another method for determining inhibition of heterodimerization of HIF-2α to HIF-1β (ARNT) is by co-immunoprecipitation.

As described herein, HIF-2α is a transcription factor that plays important roles in regulating expression of target genes. Non-limiting examples of HIF-2α target genes include HMOX1, SFTPA1, CXCR4, PAI1, BDNF, hTERT, ATP7A, and VEGF. For instance, HIF-2α is an activator of VEGF. Further non-limiting examples of HIF-2α target genes include HMOX1, EPO, CXCR4, PAI1, CCND1, CLUT1, IL6, and VEGF. A HIF-2α inhibitor of the present disclosure may be administered in an amount effective in reducing expression of any one or more of genes induced by HIF-2α activity. A variety of methods is available for the detection of gene expression levels, and includes the detection of gene transcription products (polynucleotides) and translation products (polypeptides). For example, gene expression can be detected and quantified at the DNA, RNA or mRNA level. Various methods that have been used to quantify mRNA include in situ hybridization techniques, fluorescent in situ hybridization techniques, reporter genes, RNase protection assays, Northern blotting, reverse transcription (RT)-PCR, SAGE, DNA microarray, tiling array, and RNA-seq. Examples of methods for the detection of polynucleotides include, but are not limited to selective colorimetric detection of polynucleotides based on the distance-dependent optical properties of gold nanoparticles, and solution phase detection of polynucleotides using interacting fluorescent labels and competitive hybridization. Examples for the detection of proteins include, but are not limited to microscopy and protein immunostaining, protein immunoprecipitation, immunoelectrophoresis, western blot, BCA assay, spectrophotometry, mass spectrophotometry and enzyme assay.

In some embodiments, inhibition of HIF-2α is characterized by a decrease in VEGF gene expression. The decrease may be measured by any of a variety of methods, such as those described herein. As a further example, the mRNA expression level of VEGF can be measured by quantitative PCR (QT-PCR), microarray, RNA-seq and nanostring. As another example, an ELISA assay can be used to measure the level VEGF protein secretion.

In some other embodiments, the subject methods are useful for treating a disease condition associated with HIF-2α. Any disease condition that results directly or indirectly from an abnormal activity or expression level of HIF-2α can be an intended disease condition. In some embodiments, the disease condition is a proliferative disorder, such as described herein, including but not limited to cancer. A role of HIF-2α in tumorigenesis and tumor progression has been implicated in many human cancers. Constitutively active HIF-2α may be the result of defective VHL or a low concentration of oxygen in a cancer cell. Rapidly growing tumors are normally hypoxic due to poor vascularization, a condition that activates HIF-2α in support of tumor cell survival and proliferation. Constitutive activation of HIF-2α is emerging as a common theme in diverse human cancers, consequently agents that target HIF-2α have therapeutic value.

The data presented in the Examples herein below demonstrate the anti-cancer effects of a HIF-2α inhibitor. As such, the subject method is particularly useful for treating a proliferative disorder, such as a neoplastic condition. Non-limiting examples of such conditions include but are not limited to acanthoma, acinic cell carcinoma, acoustic neuroma, acral lentiginous melanoma, acrospiroma, acute eosinophilic leukemia, acute lymphoblastic leukemia, acute megakaryoblastic leukemia, acute monocytic leukemia, acute myeloblastic leukemia with maturation, acute myeloid dendritic cell leukemia, acute myeloid leukemia, acute promyelocytic leukemia, adamantinoma, adenocarcinoma, adenoid cystic carcinoma, adenoma, adenomatoid odontogenic tumor, adrenocortical carcinoma, adult T-cell leukemia, aggressive NK-cell leukemia, AIDS-related cancers, AIDS-related lymphoma, alveolar soft part sarcoma, ameloblastic fibroma, anal cancer, anaplastic large cell lymphoma, anaplastic thyroid cancer, angioimmunoblastic T-cell lymphoma, angiomyolipoma, angiosarcoma, appendix cancer, astrocytoma, atypical teratoid rhabdoid tumor, basal cell carcinoma, basal-like carcinoma, B-cell leukemia, B-cell lymphoma, bellini duct carcinoma, biliary tract cancer, bladder cancer, blastoma, bone cancer, bone tumor, brain stem glioma, brain tumor, breast cancer, brenner tumor, bronchial tumor, bronchioloalveolar carcinoma, brown tumor, Burkitt's lymphoma, carcinoid tumor, carcinoma, carcinosarcoma, Castleman's disease, central nervous system embryonal tumor, cerebellar astrocytoma, cerebral astrocytoma, cervical cancer, cholangiocarcinoma, chondroma, chondrosarcoma, chordoma, choriocarcinoma, choroid plexus papilloma, chronic lymphocytic leukemia, chronic monocytic leukemia, chronic myelogenous leukemia, chronic myeloproliferative disorder, chronic neutrophilic leukemia, clear cell renal cell carcinoma, clear-cell tumor, colon cancer, colorectal cancer, craniopharyngioma, cutaneous T-cell lymphoma, dermatofibrosarcoma protuberans, dermoid cyst, desmoplastic small round cell tumor, diffuse large B cell lymphoma, dysembryoplastic neuroepithelial tumor, embryonal carcinoma, endodermal sinus tumor, endometrial cancer, endometrial uterine cancer, endometrioid tumor, enteropathy-associated T-cell lymphoma, ependymoblastoma, ependymoma, epithelioid sarcoma, erythroleukemia, esophageal cancer, esthesioneuroblastoma, Ewing's sarcoma, extracranial germ cell tumor, extragonadal germ cell tumor, extrahepatic bile duct cancer, extramammary Paget's disease, fallopian tube cancer, fibroma, fibrosarcoma, follicular lymphoma, follicular thyroid cancer, gallbladder cancer, ganglioglioma, ganglioneuroma, gastric cancer, gastric lymphoma, gastrointestinal cancer, gastrointestinal carcinoid tumor, gastrointestinal stromal tumor, germ cell tumor, germinoma, gestational choriocarcinoma, gestational trophoblastic tumor, giant cell tumor of bone, glioblastoma multiforme, glioma, gliomatosis cerebri, glomus tumor, glucagonoma, gonadoblastoma, granulosa cell tumor, hairy cell leukemia, head and neck cancer, heart cancer, hemangioblastoma, hemangiopericytoma, hemangiosarcoma, hematological malignancy, hepatocellular carcinoma, hepatosplenic T-cell lymphoma, Hodgkin lymphoma, hypopharyngeal cancer, hypothalamic glioma, inflammatory breast cancer, intraocular melanoma, islet cell carcinoma, juvenile myelomonocytic leukemia, Kaposi's sarcoma, kidney cancer, klatskin tumor, krukenberg tumor, laryngeal cancer, lentigo maligna melanoma, leukemia, lip and oral cavity cancer, liposarcoma, lung cancer, luteoma, lymphangioma, lymphangiosarcoma, lymphoepithelioma, lymphoid leukemia, lymphoma, macroglobulinemia, malignant fibrous histiocytoma, malignant glioma, malignant mesothelioma, malignant peripheral nerve sheath tumor, malignant rhabdoid tumor, malignant triton tumor, malt lymphoma, mantle cell lymphoma, mast cell leukemia, mediastinal germ cell tumor, mediastinal tumor, medullary thyroid cancer, medulloblastoma, medulloepithelioma, melanoma, meningioma, merkel cell carcinoma, mesothelioma, metastatic squamous neck cancer with occult primary, metastatic urothelial carcinoma, mixed mullerian tumor, monocytic leukemia, mouth cancer, mucinous tumor, multiple endocrine neoplasia syndrome, multiple myeloma, mycosis fungoides, myelodysplastic disease, myeloid leukemia, myeloid sarcoma, myeloproliferative disease, myxoma, nasal cavity cancer, nasopharyngeal cancer, neoplasm, neurinoma, neuroblastoma, neurofibroma, neuroma, nodular melanoma, non-Hodgkin lymphoma, non-melanoma skin cancer, non-small cell lung cancer, ocular oncology, oligoastrocytoma, oligodendroglioma, oncocytoma, optic nerve sheath meningioma, oral cancer, oropharyngeal cancer, osteosarcoma, ovarian cancer, ovarian epithelial cancer, ovarian germ cell tumor, ovarian low malignant potential tumor, pancoast tumor, pancreatic cancer, papillary thyroid cancer, papillomatosis, paraganglioma, paranasal sinus cancer, parathyroid cancer, penile cancer, perivascular epithelioid cell tumor, pharyngeal cancer, pheochromocytoma, pineal parenchymal tumor of intermediate differentiation, pineoblastoma, pituicytoma, pituitary adenoma, pituitary tumor, plasma cell neoplasm, pleuropulmonary blastoma, polyembryoma, precursor T-lymphoblastic lymphoma, primitive neuroectodermal tumor, prostate cancer, pseudomyxoma peritonei, rectal cancer, renal cell carcinoma, retinoblastoma, rhabdomyoma, rhabdomyosarcoma, Richter's transformation, sacrococcygeal teratoma, salivary gland cancer, sarcoma, schwannomatosis, sebaceous gland carcinoma, secondary neoplasm, seminoma, serous tumor, Sertoli-Leydig cell tumor, sex cord-stromal tumor, sezary syndrome, signet ring cell carcinoma, skin cancer, small blue round cell tumor, small cell carcinoma, small cell lung cancer, small cell lymphoma, small intestine cancer, soft tissue sarcoma, somatostatinoma, soot wart, spinal tumor, splenic marginal zone lymphoma, squamous cell carcinoma, stomach cancer, superficial spreading melanoma, supratentorial primitive neuroectodermal tumor, surface epithelial-stromal tumor, synovial sarcoma, T-cell acute lymphoblastic leukemia, T-cell large granular lymphocyte leukemia, T-cell leukemia, T-cell lymphoma, T-cell prolymphocytic leukemia, teratoma, terminal lymphatic cancer, testicular cancer, thecoma, throat cancer, thymic carcinoma, thymoma, thyroid cancer, transitional cell cancer of renal pelvis and ureter, transitional cell carcinoma, urachal cancer, urethral cancer, urogenital neoplasm, uterine sarcoma, uveal melanoma, vaginal cancer, verner morrison syndrome, verrucous carcinoma, visual pathway glioma, vulvar cancer, Waldenstrom's macroglobulinemia, Warthin's tumor, Wilms' tumor or any combination thereof.

In some embodiments, the methods of administering a HIF-2α inhibitor described herein are applied to the treatment of cancers of the adrenal glands, blood, bone marrow, brain, breast, cervix, colon, head and neck, kidney, liver, lung, ovary, pancreas, plasma cells, rectum, retina, skin, spine, throat or any combination thereof.

Certain embodiments contemplate a human subject such as a subject that has been diagnosed as having or being at risk for developing or acquiring a proliferative disorder condition. Certain other embodiments contemplate a non-human subject, for example a non-human primate such as a macaque, chimpanzee, gorilla, vervet, orangutan, baboon or other non-human primate, including such non-human subjects that can be known to the art as preclinical models. Certain other embodiments contemplate a non-human subject that is a mammal, for example, a mouse, rat, rabbit, pig, sheep, horse, bovine, goat, gerbil, hamster, guinea pig or other mammal. There are also contemplated other embodiments in which the subject or biological source can be a non-mammalian vertebrate, for example, another higher vertebrate, or an avian, amphibian or reptilian species, or another subject or biological source. In certain embodiments of the present invention, a transgenic animal is utilized. A transgenic animal is a non-human animal in which one or more of the cells of the animal includes a nucleic acid that is non-endogenous (i.e., heterologous) and is present as an extrachromosomal element in a portion of its cell or stably integrated into its germ line DNA (i.e., in the genomic sequence of most or all of its cells).

Therapeutic Efficacy:

In some embodiments, therapeutic efficacy is measured based on an effect of treating a proliferative disorder, such as cancer. In general, therapeutic efficacy of the methods and compositions of the invention, with regard to the treatment of a proliferative disorder (e.g. cancer, whether benign or malignant), may be measured by the degree to which the methods and compositions promote inhibition of tumor cell proliferation, the inhibition of tumor vascularization, the eradication of tumor cells, the reduction in the rate of growth of a tumor, and/or a reduction in the size of at least one tumor. Several parameters to be considered in the determination of therapeutic efficacy are discussed herein. The proper combination of parameters for a particular situation can be established by the clinician. The progress of the inventive method in treating cancer (e.g., reducing tumor size or eradicating cancerous cells) can be ascertained using any suitable method, such as those methods currently used in the clinic to track tumor size and cancer progress. The primary efficacy parameter used to evaluate the treatment of cancer by the inventive method and compositions preferably is a reduction in the size of a tumor. Tumor size can be figured using any suitable technique, such as measurement of dimensions, or estimation of tumor volume using available computer software, such as FreeFlight software developed at Wake Forest University that enables accurate estimation of tumor volume. Tumor size can be determined by tumor visualization using, for example, CT, ultrasound, SPECT, spiral CT, MRI, photographs, and the like. In embodiments where a tumor is surgically resected after completion of the therapeutic period, the presence of tumor tissue and tumor size can be determined by gross analysis of the tissue to be resected, and/or by pathological analysis of the resected tissue.

In some desirable embodiments, the growth of a tumor is stabilized (i.e., one or more tumors do not increase more than 1%, 5%, 10%, 15%, or 20% in size, and/or do not metastasize) as a result of the inventive method and compositions. In some embodiments, a tumor is stabilized for at least about 1, 2, 3, 4, 5, 6, 7, 8, 9, 10, 11, 12, or more weeks. In some embodiments, a tumor is stabilized for at least about 1, 2, 3, 4, 5, 6, 7, 8, 9, 10, 11, 12, or more months. In some embodiments, a tumor is stabilized for at least about 1, 2, 3, 4, 5, 6, 7, 8, 9, 10, or more years. Preferably, the inventive method reduces the size of a tumor at least about 5% (e.g., at least about 10%, 15%, 20%, or 25%). More preferably, tumor size is reduced at least about 30% (e.g., at least about 35%, 40%, 45%, 50%, 55%, 60%, or 65%). Even more preferably, tumor size is reduced at least about 70% (e.g., at least about 75%, 80%, 85%, 90%, or 95%). Most preferably, the tumor is completely eliminated, or reduced below a level of detection. In some embodiments, a subject remains tumor free (e.g. in remission) for at least about 1, 2, 3, 4, 5, 6, 7, 8, 9, 10, 11, 12, or more weeks following treatment. In some embodiments, a subject remains tumor free for at least about 1, 2, 3, 4, 5, 6, 7, 8, 9, 10, 11, 12, or more months following treatment. In some embodiments, a subject remains tumor free for at least about 1, 2, 3, 4, 5, 6, 7, 8, 9, 10, or more years after treatment.

In some embodiments, the efficacy of the inventive method in reducing tumor size can be determined by measuring the percentage of necrotic (i.e., dead) tissue of a surgically resected tumor following completion of the therapeutic period. In some further embodiments, a treatment is therapeutically effective if the necrosis percentage of the resected tissue is greater than about 20% (e.g., at least about 30%, 40%, 50%, 60%, 70%, 80%, 90%, or 100%), more preferably about 90% or greater (e.g., about 90%, 95%, or 100%). Most preferably, the necrosis percentage of the resected tissue is 100%, that is, no tumor tissue is present or detectable.

The efficacy of the inventive method can be determined by a number of secondary parameters. Examples of secondary parameters include, but are not limited to, detection of new tumors, detection of tumor antigens or markers (e.g., CEA, PSA, or CA-125), biopsy, surgical downstaging (i.e., conversion of the surgical stage of a tumor from unresectable to resectable), PET scans, survival, disease progression-free survival, time to disease progression, quality of life assessments such as the Clinical Benefit Response Assessment, and the like, all of which can point to the overall progression (or regression) of cancer in a human. Biopsy is particularly useful in detecting the eradication of cancerous cells within a tissue. Radioimmunodetection (RAID) is used to locate and stage tumors using serum levels of markers (antigens) produced by and/or associated with tumors ("tumor markers" or "tumor-associated antigens"), and can be useful as a pre-treatment diagnostic predicate, a post-treatment diagnostic indicator of recurrence, and a post-treatment indicator of therapeutic efficacy. Examples of tumor markers or tumor-associated antigens that can be evaluated as indicators of therapeutic efficacy include, but are not limited to, carcinembryonic antigen (CEA), prostate-specific antigen (PSA), CA-125, CA19-9, ganglioside molecules (e.g., GM2, GD2, and GD3), MART-1, heat shock proteins (e.g., gp96), sialyl Tn (STn), tyrosinase, MUC-1, HER-2/neu, c-erb-B2, KSA, PSMA, p53, RAS, EGF-R, VEGF, MAGE, and gp100. Other tumor-associated antigens are known in the art. RAID technology in combination with endoscopic detection systems also can efficiently distinguish small tumors from surrounding tissue (see, for example, U.S. Pat. No. 4,932,412).

In additional desirable embodiments, the treatment of cancer in a human patient in accordance with the inventive method is evidenced by one or more of the following results: (a) the complete disappearance of a tumor (i.e., a complete response), (b) about a 25% to about a 50% reduction in the size of a tumor for at least four weeks after completion of the therapeutic period as compared to the size of the tumor before treatment, (c) at least about a 50% reduction in the size of a tumor for at least four weeks after completion of the therapeutic period as compared to the size of the tumor before the therapeutic period, and (d) at least a 2% decrease (e.g., about a 5%, 10%, 20%, 30%, 40%, 50%, 60%, 70%, 80% or 90% decrease) in a specific tumor-associated antigen level at about 4-12 weeks after completion of the therapeutic period as compared to the tumor-associated antigen level before the therapeutic period. While at least a 2% decrease in a tumor-associated antigen level is preferred, any decrease in the tumor-associated antigen level is evidence of treatment of a cancer in a patient by the inventive method. For example, with respect to unresectable, locally advanced pancreatic cancer, treatment can be evidenced by at least a 10% decrease in the CA19-9 tumor-associated antigen level at 4-12 weeks after completion of the therapeutic period as compared to the CA19-9 level before the therapeutic period. Similarly, with respect to locally advanced rectal cancer, treatment can be evidenced by at least a 10% decrease in the CEA tumor-associated antigen level at 4-12 weeks after completion of the therapeutic period as compared to the CEA level before the therapeutic period.

With respect to quality of life assessments, such as the Clinical Benefit Response Criteria, the therapeutic benefit of the treatment in accordance with the invention can be evidenced in terms of pain intensity, analgesic consumption, and/or the Karnofsky Performance Scale score. The treatment of cancer in a human patient alternatively, or in addition, is evidenced by (a) at least a 50% decrease (e.g., at least a 60%, 70%, 80%, 90%, or 100% decrease) in pain intensity reported by a patient, such as for any consecutive four week period in the 12 weeks after completion of treatment, as compared to the pain intensity reported by the patient before treatment, (b) at least a 50% decrease (e.g., at least a 60%, 70%, 80%, 90%, or 100% decrease) in analgesic consumption reported by a patient, such as for any consecutive four week period in the 12 weeks after completion of treatment as compared to the analgesic consumption reported by the patient before treatment, and/or (c) at least a 20 point increase (e.g., at least a 30 point, 50 point, 70 point, or 90 point increase) in the Karnofsky Performance Scale score reported by a patient, such as for any consecutive four week period in the 12 weeks after completion of the therapeutic period as compared to the Karnofsky Performance Scale score reported by the patient before the therapeutic period.

The treatment of a proliferative disorder (e.g. cancer, whether benign or malignant) in a human patient desirably is evidenced by one or more (in any combination) of the foregoing results, although alternative or additional results of the referenced tests and/or other tests can evidence treatment efficacy.

In some embodiments, tumor size is reduced as a result of the inventive method preferably without significant adverse events in the subject. Adverse events are categorized or "graded" by the Cancer Therapy Evaluation Program (CTEP) of the National Cancer Institute (NCI), with Grade 0 representing minimal adverse side effects and Grade 4 representing the most severe adverse events. Desirably, the inventive method is associated with minimal adverse events, e.g. Grade 0, Grade 1, or Grade 2 adverse events, as graded by the CTEP/NCI. However, as discussed herein, reduction of tumor size, although preferred, is not required in that the actual size of tumor may not shrink despite the eradication of tumor cells. Eradication of cancerous cells is sufficient to realize a therapeutic effect. Likewise, any reduction in tumor size is sufficient to realize a therapeutic effect.

Detection, monitoring and rating of various cancers in a human are further described in Cancer Facts and Figures 2001, American Cancer Society, New York, N.Y., and International Patent Application WO 01/24684. Accordingly, a clinician can use standard tests to determine the efficacy of the various embodiments of the inventive method in treating cancer. However, in addition to tumor size and spread, the clinician also may consider quality of life and survival of the patient in evaluating efficacy of treatment.

In some embodiments, administration of a HIF-2α inhibitor provides improved therapeutic efficacy over treatment with either agent alone. Improved efficacy may be measured using any method known in the art, including but not limited to those described herein. In some embodiments, the improved therapeutic efficacy is an improvement of at least about 10%, 20%, 30%, 40%, 50%, 60%, 70%, 75%, 80%, 90%, 95%, 100%, 110%, 120%, 150%, 200%, 300%, 400%, 500%, 600%, 700%, 1000% or more, using an appropriate measure (e.g. tumor size reduction, duration of tumor size stability, duration of time free from metastatic events, duration of disease-free survival). Improved efficacy may also be expressed as fold improvement, such as at least about 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold or more, using an appropriate measure (e.g. tumor size reduction, duration of tumor size stability, duration of time free from metastatic events, duration of disease-free survival).

Pharmaceutical Compositions:

A composition of the present disclosure may be formulated in any suitable pharmaceutical formulation. A pharmaceutical composition of the present disclosure typically contains an active ingredient (e.g., a compound of the present disclosure or a pharmaceutically acceptable salt and/or coordination complex thereof), and one or more pharmaceutically acceptable excipients, carriers, including but not limited to, inert solid diluents and fillers, diluents, sterile aqueous solution and various organic solvents, permeation enhancers, solubilizers and adjuvants. A composition of the present disclosure may be formulated in any suitable pharmaceutical formulation. In some embodiments, the pharmaceutical acceptable carriers, excipients are selected from the group consisting of water, alcohol, glycerol, chitosan, alginate, chondroitin, Vitamin E, mineral oil, and dimethyl sulfoxide (DMSO).

Pharmaceutical formulations may be provided in any suitable form, which may depend on the route of administration. In some embodiments, the pharmaceutical composition disclosed herein can be formulated in dosage form for administration to a subject. In some embodiments, the pharmaceutical composition is formulated for oral, intravenous, intraarterial, aerosol, parenteral, buccal, topical, transdermal, rectal, intramuscular, subcutaneous, intraosseous, intranasal, intrapulmonary, transmucosal, inhalation, and/or intraperitoneal administration. In some embodiments, the dosage form is formulated for oral intervention administration. For example, the pharmaceutical composition can be formulated in the form of a pill, a tablet, a capsule, an inhaler, a liquid suspension, a liquid emulsion, a gel, or a powder. In some embodiments, the pharmaceutical composition can be formulated as a unit dosage in liquid, gel, semi-liquid, semi-solid, or solid form.

The amount of each compound administered will be dependent on the mammal being treated, the severity of the disorder or condition, the rate of administration, the disposition of the compound and the discretion of the prescribing physician. However, an effective dosage may be in the range of about 0.001 to about 100 mg per kg body weight per day, in single or divided doses. In some instances, dosage levels below the lower limit of the aforesaid range may be more than adequate, while in other cases still larger doses may be employed without causing any harmful side effect, e.g., by dividing such larger doses into several small doses for administration throughout the day.

In some embodiments, the disclosure provides a pharmaceutical composition comprising an amount of a HIF-2α inhibitor formulated for administration to a subject in need thereof. In some embodiments, the pharmaceutical composition comprises between about 0.0001-500 g, 0.001-250 g, 0.01-100 g, 0.1-50 g, or 1-10 g of HIF-2α inhibitor. In some embodiments, the pharmaceutical composition comprises about or more than about 0.0001 g, 0.001 g, 0.01 g, 0.1, 0.5 g, 1 g, 2 g, 3 g, 4 g, 5 g, 6 g, 7 g, 8 g, 9 g, 10 g, 15 g, 20 g, 25 g, 50 g, 100 g, 200 g, 250 g, 300 g, 350 g, 400 g, 450 g, 500 g, or more of a HIF-2α inhibitor. In some embodiments, the pharmaceutical composition comprises between 0.001-2 g of a HIF-2α inhibitor in a single dose. In some embodiments, the pharmaceutical composition comprises an amount between about 50-150 g of a HIF-2α inhibitor. In some embodiments, the therapeutic amount can be an amount between about 0.001-0.1 g of a HIF-2α inhibitor. In some embodiments, the therapeutic amount can be an amount between about 0.01-30 g of a HIF-2α inhibitor.

In some embodiments, a therapeutically effective amount of HIF-2α inhibitor, which can be a daily amount administered over the course of a period of treatment, can sufficiently provide any one or more of the therapeutic effects described herein. As an example, the therapeutic effective amount can be in the range of about 0.001-1000 mg/kg body weight, 0.01-500 mg/kg body weight, 0.01-100 mg/kg body weight, 0.01-30 mg/kg body weight, 0.1-200 mg/kg body weight, 3-200 mg/kg body weight, 5-500 mg/kg body weight, 10-100 mg/kg body weight, 10-1000 mg/kg body weight, 50-200 mg/kg body weight, 100-1000 mg/kg body weight, 200-500 mg/kg body weight, 250-350 mg/kg body weight, or 300-600 mg/kg body weight of a HIF-2α inhibitor. In some embodiments, the therapeutic amount can be about or more than about 0.001 mg/kg body weight, 0.01 mg/kg body weight, 0.1 mg/kg body weight, 0.5 mg/kg body weight, 1 mg/kg body weight, 2 mg/kg body weight, 3 mg/kg body weight, 4 mg/kg body weight, 5 mg/kg body weight, 6 mg/kg body weight, 7 mg/kg body weight, 8 mg/kg body weight, 9 mg/kg body weight, 10 mg/kg body weight, 15 mg/kg body weight, 20 mg/kg body weight, 25 mg/kg body weight, 50 mg/kg body weight, 100 mg/kg body weight, 200 mg/kg body weight, 250 mg/kg body weight, 300 mg/kg body weight, 350 mg/kg body weight, 400 mg/kg body weight, 450 mg/kg body weight, 500 mg/kg body weight, 600 mg/kg body weight, 800 mg/kg body weight, 1000 mg/kg body weight, or more of a HIF-2α inhibitor. In some embodiments, the effective amount is at least about 0.01 mg/kg body weight of a HIF-2α inhibitor. In some embodiments, the effective amount is an amount between about 0.01-30 mg/kg body weight of a HIF-2α inhibitor. In some embodiments, the therapeutic amount can be an amount between about 50-150 mg/kg body weight of a HIF-2α inhibitor.

In some embodiments, the composition is provided in one or more unit doses. For example, the composition can be administered in 1, 2, 3, 4, 5, 6, 7, 14, 30, 60, or more doses. Such amount can be administered each day, for example in individual doses administered once, twice, or three or more times a day. However, dosages stated herein on a per day basis should not be construed to require administration of the daily dose each and every day. For example, if one of the agents is provided in a suitably slow-release form, two or more daily dosage amounts can be administered at a lower frequency, e.g., as a depot every second day to once a month or even longer. Most typically and conveniently for the subject, a HIF-2α inhibitor can be administered once a day, for example in the morning, in the evening or during the day.

The unit doses can be administered simultaneously or sequentially. The composition can be administered for an extended treatment period. Illustratively, the treatment period can be at least about one month, for example at least about 3 months, at least about 6 months or at least about 1 year. In some cases, administration can continue for substantially the remainder of the life of the subject.

In some embodiments, the HIF-2α inhibitor can be administered as part of a therapeutic regimen that comprises administering one or more second agents (e.g. 1, 2, 3, 4, 5, or more second agents), either simultaneously or sequentially with the HIF-2α inhibitor. When administered sequentially, the HIF-2α inhibitor may be administered before or after the one or more second agents. When administered simultaneously, the HIF-2α inhibitor and the one or more second agents may be administered by the same route (e.g. injections to the same location; tablets taken orally at the same time), by a different route (e.g. a tablet taken orally while receiving an intravenous infusion), or as part of the same combination (e.g. a solution comprising a HIF-2α inhibitor and one or more second agents).

A combination treatment according to the invention may be effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. The exact dosage will depend upon the agent selected, the route of administration, the form in which the compound is administered, the subject to be treated, the body weight of the subject to be treated, and the preference and experience of the attending physician.

Pharmaceutical Composition for Oral Administration.

In some embodiments, the disclosure provides a pharmaceutical composition for oral administration containing at least one compound of the present disclosure and a pharmaceutical excipient suitable for oral administration. The composition may be in the form of a solid, liquid, gel, semi-liquid, or semi-solid. In some embodiments, the composition further comprises a second agent.

In some embodiments, the invention provides a solid pharmaceutical composition for oral administration containing: (i) a HIF-2α inhibitor; and (ii) a pharmaceutical excipient suitable for oral administration. In some embodiments, the composition further contains: (iii) a third agent or even a fourth agent. In some embodiments, each compound or agent is present in a therapeutically effective amount. In other embodiments, one or more compounds or agents is present in a sub-therapeutic amount, and the compounds or agents act synergistically to provide a therapeutically effective pharmaceutical composition.

Pharmaceutical compositions of the disclosure suitable for oral administration can be presented as discrete dosage forms, such as hard or soft capsules, cachets, troches, lozenges, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion, or dispersible powders or granules, or syrups or elixirs. Such dosage forms can be prepared by any of the methods of pharmacy, which typically include the step of bringing the active ingredient(s) into association with the carrier. In general, the composition are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient(s) in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This disclosure further encompasses anhydrous pharmaceutical composition and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the disclosure can be prepared using anhydrous or low moisture containing ingredients and low moisture or low humidity conditions. Pharmaceutical compositions and dosage forms of the disclosure which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the composition for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical composition and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical composition and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the composition of the disclosure to provide tablets that disintegrate when exposed to an aqueous environment. Too much of a disintegrant may produce tablets which may disintegrate in the bottle. Too little may be insufficient for disintegration to occur and may alter the rate and extent of release of the active ingredient(s) from the dosage form. A sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical composition and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical composition and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyllaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical composition and dosage forms of the disclosure include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present disclosure and to minimize precipitation of the compound of the present disclosure. This can be especially important for composition for non-oral use, e.g., composition for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. If present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Composition for Topical (e.g., Transdermal) Delivery.

In some embodiments, the invention provides a pharmaceutical composition for transdermal delivery containing a compound of the present invention and a pharmaceutical excipient suitable for transdermal delivery. The composition may be in the form of a solid, liquid, gel, semi-liquid, or semi-solid. In some embodiments, the composition further comprises a second agent.

Composition of the present disclosure can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical composition also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Formulations for topical administration may include ointments, lotions, creams, gels (e.g., poloxamer gel), drops, suppositories, sprays, liquids and powders. Conventional pharmaceutical carriers, aqueous, powder or oily bases, thickeners and the like may be necessary or desirable. The disclosed compositions can be administered, for example, in a microfiber, polymer (e.g., collagen), nanosphere, aerosol, lotion, cream, fabric, plastic, tissue engineered scaffold, matrix material, tablet, implanted container, powder, oil, resin, wound dressing, bead, microbead, slow release bead, capsule, injectables, intravenous drips, pump device, silicone implants, or any bio-engineered materials.

Another exemplary formulation for use in the methods of the present disclosure employs transdermal delivery devices ("patches"). Such transdermal patches may be used to provide continuous or discontinuous infusion of a compound of the present disclosure in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Composition for Injection.

In some embodiments, the disclosure provides a pharmaceutical composition for injection containing a compound of the present disclosure and a pharmaceutical excipient suitable for injection. Components and amounts of agents in the composition are as described herein.

The forms in which the novel composition of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Composition for Inhalation.

Compositions for inhalation or insufflation include solutions and suspensions in pharmaceutically acceptable, aqueous or organic solvents, or mixtures thereof, and powders. The liquid or solid composition may contain suitable pharmaceutically acceptable excipients as described vide supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Composition.

Pharmaceutical composition may also be prepared from composition described herein and one or more pharmaceutically acceptable excipients suitable for sublingual, buccal, rectal, intraosseous, intraocular, intranasal, epidural, or intraspinal administration. Preparations for such pharmaceutical composition are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., "Methods in Cell Biology", Volume XIV, ISBN: 978-0-12-564114-2, Academic Press, New York, N.W., p. 33 (1976) and Medina, Zhu, and Kairemo, "Targeted liposomal drug delivery in cancer", Current Pharm. Des. 10: 2981-2989, 2004. For additional information regarding drug formulation and administration, see "Remington: The Science and Practice of Pharmacy," Lippincott Williams & Wilkins, Philadelphia, ISBN-10: 0781746736, $21^{st}$ Edition (2005).

The invention also provides kits. The kits may include a HIF-2α inhibitor and one or more additional agents in suitable packaging with written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

Combination Therapies:

The present invention also provides methods for further combination therapies in which, in addition to a HIF-2α inhibitor, one or more second agents known to modulate other pathways, or other components of the same pathway, or even overlapping sets of target proteins is used, or a pharmaceutically acceptable salt, ester, prodrug, solvate, hydrate or derivative thereof. In one aspect, such therapy includes but is not limited to the combination of the composition comprising a HIF-2α inhibitor as described herein with one or more of other HIF-2α inhibitors as described herein, chemotherapeutic agents, therapeutic antibodies, and radiation treatment, to provide, where desired, a synergistic or additive therapeutic effect.

Second agents useful in the methods of the invention include any agent capable of modulating a target molecule, either directly or indirectly. Non-limiting examples of target molecules modulated by second agents include enzymes, enzyme substrates, products of transitions, antibodies, antigens, membrane proteins, nuclear proteins, cytosolic proteins, mitochondrial proteins, lysosomal proteins, scaffold proteins, lipid rafts, phosphoproteins, glycoproteins, membrane receptors, G-protein-coupled receptors, nuclear receptors, protein tyrosine kinases, protein serine/threonine kinases, phosphatases, proteases, hydrolases, lipases, phospholipases, ligases, reductases, oxidases, synthases, transcription factors, ion channels, RNA, DNA, RNAse, DNAse, phospholipids, sphingolipids, nuclear receptors, ion channel proteins, nucleotide-binding proteins, calcium-binding proteins, chaperones, DNA binding proteins, RNA binding proteins, scaffold proteins, tumor suppressors, cell cycle proteins, and histones.

Second agents may target one or more signaling molecules including but not limited to the following: 4EPB-1, 5-lipoxygenase, A1, Abl, Acetyl-CoAa Carboxylase, actin, adaptor/scaffold proteins, adenylyl cyclase receptors, adhesion molecules, AFT, Akt1, Akt2, Akt3, ALK, AMPKs, APC/C, ARaf, Arf-GAPs, Arfs, ASK, ASK1, asparagine hydroxylase FIH transferases, ATF2, ATF-2, ATM, ATP citrate lyase, ATR, Auroras, B cell adaptor for PI3-kinase (BCAP), Bad, Bak, Bax, Bcl-2, Bcl-B, Bcl-w, Bcl-XL, Bid, Bik, Bim, BLNK, Bmf, BMP receptors, Bok, BRAF, Btk, Bub, cadherins, CaMKs, Casein kinases, Caspase 2, Caspase 3, Caspase 6, Caspase 7, Caspase 8, Caspase 9, caspases, catenins, cathepsins, caveolins, Cb1, CBP/P300 family, CD45, CDC25 phosphatases, Cdc42, Cdk 1, Cdk 2, Cdk 4, Cdk 6, Cdk 7, Cdks, CENPs, Chk1, Chk2, CLKs, Cot, cRaf, CREB, Crk, CrkL, Csk, Cyclin A, Cyclin B, Cyclin D, Cyclin E, Db1, deacetylases, DLK, DNA methyl transferases, DNA-PK, Dok, Dual Specificity phosphatases (DUSPs), E2Fs, eg5/KSP, Egr-1, eIF4E-binding protein, Elk, elongation factors, endosomal sorting complex required for transport (ESCRT) proteins, Eph receptors, Erks, esterases, Ets, Eyes absent (EYA) tyrosine phosphatases, FAK, Fas associated death domain (FADD), FGF receptors, Fgr, focal adhesion kinase, fodrin, Fos, FOXO, Fyn, GAD, Grb2, Grb2 associated binder (GAB), GSK3α, GSK3β, H-Ras, H3K27, Hdm, HER receptors, HIFs, histone acetylases, histone deacetylases, Histone H3K4 demethylases, HMGA, Hrk, Hsp27, Hsp70, Hsp90s, hydrolases, hydroxylases, IAPs, IGF receptors, IKKs, IL-2, IL-4, IL-6, IL-8, ILK, Immunoglobulin-like adhesion molecules, initiation factors, inositol phosphatases, Insulin receptor, integrins, interferon α, interferon β, IRAKs, Jak1, Jak2, Jak3, JHDM2A, Jnks, K-Ras, Kit receptor, KSR, LAR phosphatase, LAT, Lck, Lim kinase, LKB-1, Low molecular weight tyrosine phosphatase, Lyn, MAP kinase phosphatases (MKPs), MAPKAPKs, MARKs, Mcl-1, Mek 1, Mek 2, MEKKs, MELK, Met receptor, metabolic enzymes, metalloproteinases, MKK3/6, MKK4/7, MLKs, MNKs, molecular chaperones, Mos, mTOR, multi-drug resistance proteins, muscarinic receptors, Myc, MyD88, myosin, myosin binding proteins, myotubularins, MYST family, Myt 1, N-Ras, Nck, NFAT, NIK, nitric oxide synthase, Non receptor tyrosine phosphatases (NPRTPs), Noxa, nucleoside transporters, p130CAS, p14Arf, p16, p21CIP, p27KIP, p38s, p53, p70S6 Kinase, p90Rsks, PAKs, paxillin, PDGF receptors, PDK1, P-Glycoprotein, phopsholipases, phosphoinositide kinases, PI3-Kinase class 1, Pim1, Pim2, Pim3, Pin1 prolyl isomerase, PKAs, PKCs, PKR, potassium channels, PP1, PP2A, PP2B, PP2C, PP5, PRK, Prks, prolyl-hydroxylases PHD-1, prostaglandin synthases, pS6, PTEN, Puma, RABs, Rac, Ran, Ras-GAP, Rb, Receptor protein tyrosine phosphatases (RPTPs), Rel-A (p65-NFKB), Ret, RHEB, Rho, Rho-GAPs, RIP, RNA polymerase, ROCK 1, ROCK 2, SAPK/JNK1,2,3, SCF ubiquitination ligase complex, selectins, separase, serine phosphatases, SGK1, SGK2, SGK3, Shc, SHIPs, SHPs, sirtuins, SLAP, Slingshot phosphatases (SSH), Smac, SMADs, small molecular weight GTPases, sodium channels, Sos, Sp1, sphingomyelinases, sphingosine kinases, Src, SRFs, STAT1, STAT3, STAT4, STAT5, STAT6, suppressors of cytokine signaling (SOCs), Syk, T-bet, T-Cell leukemia family, TCFs, TGFβ receptors, Tiam, TIE1, TIE2, topoisomerases, Tp1, TRADD, TRAF2, Trk receptors, TSC1,2, tubulin, Tyk2, ubiquitin proteases, urokinase-type plasminogen activator (uPA) and uPA receptor (uPAR) system, UTX, Vav, VEGF receptors, vesicular protein sorting (Vsps), VHL, Wee1, WT-1, WT-1, XIAP, Yes, ZAP70, β-adrenergic receptors and β-catenin.

In one aspect, this invention also relates to methods and pharmaceutical compositions for inhibiting abnormal cell growth in a mammal which comprises an amount of a HIF-2α inhibitor, or a pharmaceutically acceptable salt, ester, prodrug, solvate, hydrate or derivative thereof, in combination with an amount of an anti-cancer agent (e.g., a chemotherapeutic agent). Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, immunotherapeutic agents, proapoptotic agents, and anti-androgens. Non-limiting examples are chemotherapeutic agents, cytotoxic agents, and non-peptide small molecules such as Tykerb/Tyverb (lapatinib), Gleevec (Imatinib Mesylate), Velcade (bortezomib), Casodex (bicalutamide), Iressa (gefitinib), and Adriamycin as well as a host of chemotherapeutic agents. Non-limiting examples of chemotherapeutic agents include 2,2',2"-trichlorotriethylamine; 2-ethylhydrazide; aceglatone; aldophosphamide glycoside; alkyl sulfonates such as busulfan, improsulfan and piposulfan; alkylating agents such as thiotepa and cyclosphosphamide (CYTOXAN™); aminolevulinic acid; amsacrine; anti-adrenals such as aminoglutethimide, mitotane, trilostane; antibiotics such as anthracyclins, actinomycins and bleomycins including aclacinomysins, actinomycin, anthramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); arabinoside ("Ara-C"); aziridines such as benzodopa, carboquone, meturedopa, and uredopa; bestrabucil; bisantrene; capecitabine; cyclophosphamide; dacarbazine; defofamine; demecolcine; diaziquone; edatraxate; elfomithine; elliptinium acetate; esperamicins; ethylenimines and methylamelamines including altretamine, triethylenemelamine, trietylenephosphoramide, triethylenethiophosphaoramide and trimethylolomelamine; etoglucid; folic acid analogues such as denopterin, methotrexate, pteropterin, trimetrexate; folic acid replenisher such as frolinic acid; gacytosine; gallium nitrate; gemcitabine; hydroxyurea; lentinan; lonidamine; mannomustine; mitobronitol; mitoguazone; mitolactol; mitoxantrone; mopidamol; nitracrine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas; nitrosoureas such as carmustine, chlorozotocin, fotemustine, lomustine, nimustine, ranimustine; oxazaphosphorines; pentostatin; phenamet; pipobroman; pirarubicin; podophyllinic acid; procarbazine; PSK®; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; razoxane; retinoic acid; sizofiran; spirogermanium; taxanes, e.g., paclitaxel (TAXOL™, Bristol-Myers Squibb Oncology, Princeton, N.J.) and docetaxel (TAXOTERE™, Rhone-Poulenc Rorer, Antony, France); tenuazonic acid; thiotepa; triazenes; triaziquone; urethan; vindesine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum or platinum analogs and complexes such as cisplatin and carboplatin; anti-microtubule such as diterpenoids, including paclitaxel and docetaxel, or Vinca alkaloids including vinblastine, vincristine, vinflunine, vindesine, and vinorelbine; etoposide (VP-16); ifosfamide; mitomycin C; mitoxantrone; vincristine; vinorelbine; navelbine; novantrone; teniposide; daunomycin; aminopterin; xeloda; ibandronate; topoisomerase I and II inhibitors including camptothecins (e.g., camptothecin-11), topotecan, irinotecan, and epipodophyllotoxins; topoisomerase inhibitor RFS 2000; epothilone A or B; difluoromethylornithine (DMFO); histone deacetylase inhibitors; compounds which induce cell differentiation processes; gonadorelin agonists; methionine aminopeptidase inhibitors; compounds targeting/decreasing a protein or lipid kinase activity; compounds which target, decrease or inhibit the activity of a protein or lipid phosphatase; anti-androgens; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors; temozolomide (TEMODAL®); Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (TEMODAL®); kinesin spindle protein inhibitors, such as SB715992 or SB743921 from GlaxoSmithKline, or pentamidine/chlorpromazine from CombinatoRx; MEK inhibitors such as ARRY 142886 from Array PioPharma, AZD6244 from AstraZeneca, PD181461 or PD0325901 from Pfizer, leucovorin, EDG binders, antileukemia compounds, ribonucleotide reductase inhibitors, S-adenosylmethionine decarboxylase inhibitors, antiproliferative antibodies or other chemotherapeutic compounds. Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, and Velcade®.

This invention further relates to a method for using the compounds or pharmaceutical composition in combination with other tumor treatment approaches, including surgery, ionizing radiation, photodynamic therapy, or implants, e.g., with corticosteroids, hormones, or used as radiosensitizers.

One such approach may be, for example, radiation therapy in inhibiting abnormal cell growth or treating the proliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation, which comprises administering to the mammal an amount of a HIF-2α inhibitor or a pharmaceutically acceptable salt, ester, prodrug, solvate, hydrate or derivative thereof, which is effective in sensitizing abnormal cells to treatment with radiation. The amount of the compound in this method can be determined according to the means for ascertaining effective amounts of such compounds described herein.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

In some embodiments, the compositions and methods further comprise administering, separately or simultaneously one or more additional agents (e.g. 1, 2, 3, 4, 5, or more). Additional agents can include those useful in wound healing. Non-limiting examples of additional agents include antibiotics (e.g. Aminoglycosides, Cephalosporins, Chloramphenicol, Clindamycin, Erythromycins, Fluoroquinolones, Macrolides, Azolides, Metronidazole, Penicillin's, Tetracycline's, Trimethoprim-sulfamethoxazole, Vancomycin), steroids (e.g. Andranes (e.g. Testosterone), Cholestanes (e.g. Cholesterol), Cholic acids (e.g. Cholic acid), Corticosteroids (e.g. Dexamethasone), Estraenes (e.g. Estradiol), Pregnanes (e.g. Progesterone), narcotic and non-narcotic analgesics (e.g. Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, Pentazocine), chemotherapy (e.g. anti-cancer drugs such as but not limited to Altretamine, Asparaginase, Bleomycin, Busulfan, Carboplatin, Carmustine, Chlorambucil, Cisplatin, Cladribine, Cyclophosphamide, Cytarabine, Dacarbazine, Diethylstilbesterol, Ethinyl estradiol, Etoposide, Floxuridine, Fludarabine, Fluorouracil, Flutamide, Goserelin, Hydroxyurea, Idarubicin, Ifosfamide, Leuprolide, Levamisole, Lomustine, Mechlorethamine, Medroxyprogesterone, Megestrol, Melphalan, Mercaptopurine, Methotrexate, Mitomycin, Mitotane, Mitoxantrone, Paclitaxel, pentastatin, Pipobroman, Plicamycin, Prednisone, Procarbazine, Streptozocin, Tamoxifen, Teniposide, Vinblastine, Vincristine), anti-inflammatory agents (e.g. Alclofenac; Alclometasone Dipropionate; Algestone Acetonide; alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Ciclopirofen; Cintazone; Cliprofen; Clobetasol Propionate; Clobetasone Butyrate; Clopirac; Cloticasone Propionate; Cormethasone Acetate; Cortodoxone; Decanoate; Deflazacort; Delatestryl; Depo-Testosterone; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Mesterolone; Methandrostenolone; Methenolone; Methenolone Acetate; Methylprednisolone Suleptanate; Morniflumate; Nabumetone; Nandrolone; Naproxen; Naproxen Sodium; Naproxol; Nimazone; Olsalazine Sodium; Orgotein; Orpanoxin; Oxandrolane; Oxaprozin; Oxyphenbutazone; Oxymetholone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Stanozolol; Sudoxicam; Sulindac; Suprofen; Talmetacin; Talniflumate; Talosalate; Tebufelone; Tenidap; Tenidap Sodium; Tenoxicam; Tesicam; Tesimide; Testosterone; Testosterone Blends; Tetrydamine; Tiopinac; Tixocortol Pivalate; Tolmetin; Tolmetin Sodium; Triclonide; Triflumidate; Zidometacin; Zomepirac Sodium), or anti-histaminic agents (e.g. Ethanolamines (like diphenhydrmine carbinoxamine), Ethylenediamine (like tripelennamine pyrilamine), Alkylamine (like chlorpheniramine, dexchlorpheniramine, brompheniramine, triprolidine), other anti-histamines like astemizole, loratadine, fexofenadine, Bropheniramine, Clemastine, Acetaminophen, Pseudoephedrine, Triprolidine).

EXAMPLES

Example 1: Synthesis of (6R,7S)-4-(3,3-difluorocyclobutoxy)-6-fluoro-1-(trifluoromethyl)-6,7-dihydro-5H-cyclopenta[c]pyridin-7-ol (Compound 1) and (R)-4-(3,3-difluorocyclobutoxy)-1-(trifluoromethyl)-6,7-dihydro-5H-cyclopenta[c]pyridin-7-ol (Compound 2)

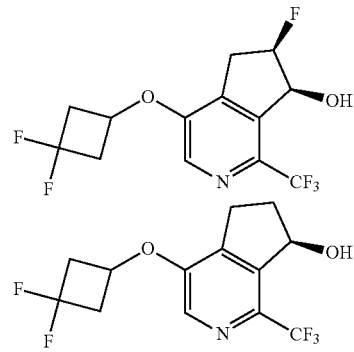

Step A: Preparation of 4-bromo-1-(trifluoromethyl)-5,6-dihydro-7H-cyclopenta[c]pyridin-7-one A suspension of 4-bromo-5,6-dihydrocyclopenta[c]pyridin-7-one (1.0 g, 4.72 mmol) and bis(((trifluoromethyl)sulfinyl)oxy)zinc (4.69 g, 14.15 mmol) in a mixture of dichloromethane (30 mL) and water (15 mL) at 0° C. was treated with tert-butyl hydroperoxide (~70% in water, 2.58 mL, 18.86 mmol, added via pipette using a plastic tip) and stirred overnight. Additional portions of bis(((trifluoromethyl)sulfinyl)oxy)zinc (2.35 g, 7.07 mmol) and tert-butyl hydroperoxide (2.58 mL, 18.86 mmol) were added sequentially to drive the reaction to completion. After stirring for an additional day, the reaction vessel was placed into a water bath and carefully quenched by the addition of saturated NaHCO$_3$. Once effervescence ceased, the reaction mixture filtered through a pad of celite to remove. The pad of celite was rinsed with additional dichloromethane. The filtrate was separated and the aqueous portion extracted further with 2×20 mL CH$_2$Cl$_2$. The combined organics were rinsed with 10 mL of brine, dried with MgSO$_4$, filtered, and concentrated to dryness. Purification was achieved by chromatography on silica using 30-90% CH$_2$Cl$_2$/hexane to afford 4-bromo-1-(trifluoromethyl)-5,6-dihydro-7H-cyclopenta[c]pyridin-7-one as an off-white solid (390 mg, 30%). The desired regioisomer elutes first. LCMS ESI (+) (M+H) m/z 280/282.

Step B: Preparation of 4-bromo-1-(trifluoromethyl)-5,6-dihydrospiro[cyclopenta[c]pyridine-7,2'-[1,3]dioxolane] and 4-bromo-1-(trifluoromethyl)-7-(2-((trimethylsilyl)oxy)ethoxy)-5H-cyclopenta[c]pyridine Trimethylsilyl trifluoromethanesulfonate (75.9 μL, 0.42 mmol) was added to a solution of 4-bromo-1-(trifluoromethyl)-5,6-dihydrocyclopenta[c]pyridin-7-one (389 mg, 1.39 mmol) and trimethyl(2-trimethylsilyloxyethoxy)silane (1.37 mL, 5.56 mmol) in dichloromethane (13.6 mL) cooled in an ice bath. The mixture was allowed to slowly warm to ambient temperature. After 5 h, an additional 1.3 mL of trimethyl(2-trimethylsilyloxyethoxy)silane and 76 µL of trimethylsilyl trifluoromethanesulfonate were added. After another 16 h, the reaction mixture was treated with triethylamine (770 µL, 5.56 mmol), stirred for 10 min, and then concentrated. The residue was treated with 20 mL EtOAc and 20 mL of water and the layers separated. The aqueous portion was extracted further with 2×20 mL of EtOAc. The combined organic extracts were washed with brine, dried over $MgSO_4$, filtered, and evaporated. Purification was achieved by chromatography on silica using 5-20% EtOAc/hexane to afford 4-bromo-1-(trifluoromethyl)-5,6-dihydrospiro[cyclopenta[c]pyridine-7,2'-[1,3]dioxolane] as a shite solid (262 mg, 58%) and 4-bromo-1-(trifluoromethyl)-7-(2-((trimethylsilyl)oxy)ethoxy)-5H-cyclopenta[c]pyridine as a white solid (170 mg, 31%). Data for 4-bromo-1-(trifluoromethyl)-5,6-dihydrospiro[cyclopenta[c]pyridine-7,2'-[1,3]dioxolane]: LCMS ESI (+) (M+H) m/z 324/326. Data for 4-bromo-1-(trifluoromethyl)-7-(2-((trimethylsilyl)oxy)ethoxy)-5H-cyclopenta[c]pyridine: $^1$H NMR (400 MHz, $CDCl_3$): δ 8.56 (s, 1H), 5.59 (t, 1H), 4.10 (t, 2H), 3.96 (t, 2H), 3.36 (d, 2H), 0.15 (s, 9H).

Step C: Preparation of 4-bromo-6-fluoro-1-(trifluoromethyl)-5,6-dihydrospiro[cyclopenta[c]pyridine-7,2'-[1,3]dioxolane]

A solution of 2-[[4-bromo-1-(trifluoromethyl)-5H-cyclopenta[c]pyridin-7-yl]oxy]ethoxy-trimethyl-silane (146.6 mg, 0.37 mmol) and sodium sulfate (262.7 mg, 1.85 mmol) in acetonitrile (3.7 mL) was stirred for 10 min and then treated with Selectfluor® (145.2 mg, 0.41 mmol) and stirred at 25° C. for 1 h. Volatiles were removed by concentration under reduced pressure. The reaction mixture was poured into 30 mL of water and extracted with 3×15 mL EtOAc. The combined organics were rinsed with 10 mL of brine, dried with $MgSO_4$, filtered, and concentrated to dryness. Purification was achieved by chromatography on silica using 5-20% EtOAc/hexane to afford 4-bromo-6-fluoro-1-(trifluoromethyl)-5,6-dihydrospiro[cyclopenta[c]pyridine-7,2'-[1,3]dioxolane] as a white solid (96.2 mg, 76%). LCMS ESI (+) (M+H) m/z 342/344.

Step D: Preparation of 6-fluoro-1-(trifluoromethyl)-5,6-dihydrospiro[cyclopenta[c]pyridine-7,2'-[1,3]dioxolan]-4-ol and 1-(trifluoromethyl)-5,6-dihydrospiro[cyclopenta[c]pyridine-7,2'-[1,3]dioxolan]-4-ol A solution of 4'-bromo-6'-fluoro-1'-(trifluoromethyl)spiro[1,3-dioxolane-2,7'-5,6-dihydrocyclopenta[c]pyridine] (96.2 mg, 0.2800 mmol) and 2-(di-t-butylphosphino)-3,6-dimethoxy-2',4',6'-tri-1-propyl-1,1'-biphenyl (3.4 mg, 0.007 mmol) in 1,4-dioxane (5.0 mL) was sparged with nitrogen for 3 mins. The reaction mixture was then treated sequentially with potassium hydroxide (47.3 mg, 0.84 mmol), water (101 µL, 5.62 mmol) and [2-(2-aminophenyl)phenyl]methylsulfonyloxy-palladium; di-t-butyl-[3,6-dimethoxy-2-(2,4,6-triisopropylphenyl)phenyl]phosphane (6.0 mg, 0.007 mmol) under continuous nitrogen stream. The vessel was sealed and heated to 80 C for 1 h and 30 min. The reaction mixture was quenched by the addition of acetic acid (64.3 µL, 1.13 mmol). The reaction mixture was poured into 75 mL of water and extracted with 4×20 mL EtOAc. The combined organics were dried with $MgSO_4$, filtered, and concentrated to dryness. The product was used without further purification (87 mg). During the reaction, some of the hydrodefluorinated product formed as an impurity. Data for 6-fluoro-1-(trifluoromethyl)-5,6-dihydrospiro[cyclopenta[c]pyridine-7,2'-[1,3]dioxolan]-4-ol: LCMS ESI (+) (M+H) m/z 280. Data for 1-(trifluoromethyl)-5,6-dihydrospiro[cyclopenta[c]pyridine-7,2'-[1,3]dioxolan]-4-ol: LCMS ESI (+) (M+H) m/z 262.

Step E: Preparation of 4-(3,3-difluorocyclobutoxy)-6-fluoro-1-(trifluoromethyl)-5,6-dihydrospiro[cyclopenta[c]pyridine-7,2'-[1,3]dioxolane] and 4-(3,3-difluorocyclobutoxy)-1-(trifluoromethyl)-5,6-dihydrospiro[cyclopenta[c]pyridine-7,2'-[1,3]dioxolane]

A solution of impure 6'-fluoro-1'-(trifluoromethyl)spiro[1,3-dioxolane-2,7'-5,6-dihydrocyclopenta[c]pyridine]-4'-ol (44.0 mg, 0.16 mmol), polymer supported triphenylphosphine (~2.06 mmol/g, 306.2 mg, 0.63 mmol), and 3,3-difluoro-cyclobutanol (68.1 mg, 0.63 mmol) in tetrahydrofuran (3.2 mL) was treated with diisopropyl azodicarboxylate (120 µL, 0.61 mmol) and stirred at 60° C. for 2 h. The reaction mixture was filtered and the filter cake rinsed with 20 mL EtOAc. The filtrate was concentrated and purified by chromatography on silica using 10-30% EtOAc/hexane to afford a clear solid (39.0 mg, 67%) that was a 2:1 mixture of the fluorinated and hydrodefluorinated products. LCMS ESI (+) (M+H) m/z 370. Data for 4-(3,3-difluorocyclobutoxy)-6-fluoro-1-(trifluoromethyl)-5,6-dihydrospiro[cyclopenta[c]pyridine-7,2'-[1,3]dioxolane]: LCMS ESI (+) (M+H) m/z 370. Data for 4-(3,3-difluorocyclobutoxy)-1-(trifluoromethyl)-5,6-dihydrospiro[cyclopenta[c]pyridine-7,2'-[1,3]dioxolane]: LCMS ESI (+) (M+H) m/z 352.

Step F: Preparation of 4-(3,3-difluorocyclobutoxy)-6-fluoro-1-(trifluoromethyl)-5,6-dihydro-7H-cyclopenta[c]pyridin-7-one and 4-(3,3-difluorocyclobutoxy)-1-(trifluoromethyl)-5,6-dihydro-7H-cyclopenta[c]pyridin-7-one A solution of impure 4'-(3,3-difluorocyclobutoxy)-6'-fluoro-1'-(trifluoromethyl)spiro[1,3-dioxolane-2,7'-5,6-dihydrocyclopenta[c]pyridine] (39.0 mg, 0.106 mmol) in dichloromethane (2.0 mL) at 0 C was treated with perchloric acid (70% in water, 200 µL) and stirred at 0 C for 3 h. The reaction mixture was quenched by the addition of 5 mL of saturated aqueous $NaHCO_3$. The resulting mixture was extracted with 3×15 mL $CH_2Cl_2$. The combined organics were rinsed with 10 mL of brine, dried with $MgSO_4$, filtered, and concentrated to dryness. The product was used without further purification as a 2:1 mixture of fluorinated and hydrodefluorinated ketones. LCMS ESI (+) (M+H) m/z 326. Data for 4-(3,3-difluorocyclobutoxy)-6-fluoro-1-(trifluoromethyl)-5,6-dihydro-7H-cyclopenta[c]pyridin-7-one: LCMS ESI (+) (M+H) m/z 326. Data for 4-(3,3-difluorocyclobutoxy)-1-(trifluoromethyl)-5,6-dihydro-7H-cyclopenta[c]pyridin-7-one: LCMS ESI (+) (M+H) m/z 308.

Step G: Preparation of (6R,7S)-4-(3,3-difluorocyclobutoxy)-6-fluoro-1-(trifluoromethyl)-6,7-dihydro-5H-cyclopenta[c]pyridin-7-ol (Compound 1) and (R)-4-(3,3-difluorocyclobutoxy)-1-(trifluoromethyl)-6,7-dihydro-5H-cyclopenta[c]pyridin-7-ol (Compound 2)

A solution of impure 4-(3,3-difluorocyclobutoxy)-6-fluoro-1-(trifluoromethyl)-5,6-dihydrocyclopenta[c]pyridin-7-one (33.8 mg, 0.10 mmol) in dichloromethane (4.0 mL) was cooled to 0° C. and sparged with nitrogen for 5 min. During this time formic acid (11.8 µL, 0.31 mmol) and triethylamine (28.8 µL, 0.21 mmol) were sequentially added. Once sparging was complete, RuCl(p-cymene)[(R,R)-Ts-DPEN] (1.3 mg, 0.002 mmol) was added under a continuous stream of nitrogen. The reaction vessel was sealed and placed into the refrigerator to react overnight. Volatiles were removed by concentration under reduced pressure. The residue was purified by chromatography on silica using 4-18% EtOAc/CH$_2$C$_2$ to afford (6R,7S)-4-(3,3-difluorocyclobutoxy)-6-fluoro-1-(trifluoromethyl)-6,7-dihydro-5H-cyclopenta[c]pyridin-7-ol (Compound 1) as a clear solid (5.4 mg, 16%) and (R)-4-(3,3-difluorocyclobutoxy)-1-(trifluoromethyl)-6,7-dihydro-5H-cyclopenta[c]pyridin-7-ol (Compound 2) as a clear solid (7.4 mg, 23%). Data for (6R,7S)-4-(3,3-difluorocyclobutoxy)-6-fluoro-1-(trifluoromethyl)-6,7-dihydro-5H-cyclopenta[c]pyridin-7-ol (Compound 1): Retention time HPLC (14 min)=3.59 min; LCMS ESI (+) (M+H) m/z 328; $^1$H NMR (400 MHz, CDCl$_3$): δ 8.04 (s, 1H), 5.46-5.26 (m, 2H), 4.89-4.79 (m, 1H), 3.36-3.08 (m, 4H), 2.91-2.74 (m, 2H), 2.60 (dd, 1H). Data for (R)-4-(3,3-difluorocyclobutoxy)-1-(trifluoromethyl)-6,7-dihydro-5H-cyclopenta[c]pyridin-7-ol (Compound 2): Retention time HPLC (14 min)=3.95 min; LCMS ESI (+) (M+H) m/z 310; $^1$H NMR (400 MHz, CDCl$_3$): δ 7.98 (s, 1H), 5.59-5.54 (m, 1H), 4.88-4.79 (m, 1H), 3.24-3.07 (m, 3H), 2.89 (dd, 1H), 2.89-2.74 (m, 2H), 2.44-2.34 (m, 1H), 2.28-2.21 (m, 1H), 2.12-2.09 (m, 1H).

Example 2: Synthesis of 3-fluoro-5-(((6R,7S)-6-fluoro-7-hydroxy-1-(trifluoromethyl)-6,7-dihydro-5H-cyclopenta[c]pyridin-4-yl)oxy)benzonitrile (Compound 3)

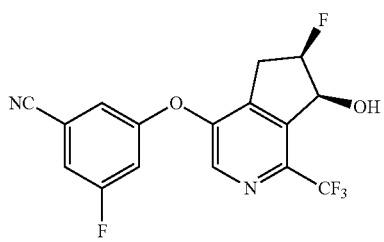

Step A: Preparation of 1-(trifluoromethyl)-5,6-dihydrospiro[cyclopenta[c]pyridine-7,2'-[1,3]dioxolan]-4-ol A solution of 4'-bromo-1'-(trifluoromethyl)spiro[1,3-dioxolane-2,7'-5,6-dihydrocyclopenta[c]pyridine] (226.4 mg, 0.70 mmol) and 2-(di-t-butylphosphino)-3,6-dimethoxy-2',4',6'-tri-1-propyl-1,1'-biphenyl (8.5 mg, 0.017 mmol) in 1,4-dioxane (7.0 mL) was sparged with nitrogen for 3 mins. The reaction mixture was then treated sequentially with potassium hydroxide (117.6 mg, 2.10 mmol), water (252 µL, 13.97 mmol) and [2-(2-aminophenyl)phenyl]-methylsulfonyloxy-palladium; ditert-butyl-[3,6-dimethoxy-2-(2,4,6-triisopropylphenyl)phenyl]phosphane (14.9 mg, 0.017 mmol) under continuous nitrogen stream. The vessel was sealed and heated to 80 C for 1 h and 30 min. The reaction mixture was quenched by the addition of acetic acid (160 µL, 2.79 mmol). The reaction mixture was poured into 75 mL of water and extracted with 4×20 mL EtOAc. The combined organics were dried with MgSO4, filtered, and concentrated to dryness. The brown solid was used without further purification. LCMS ESI (−) (M−H) m/z 260.

Step B: Preparation of 3-fluoro-5-((1-(trifluoromethyl)-5,6-dihydrospiro[cyclopenta[c]pyridine-7,2'-[1,3]dioxolan]-4-yl)oxy)benzonitrile A suspension of potassium tert-butoxide (28.4 mg, 0.25 mmol) in tetrahydrofuran (1.5 mL) at 0 C was treated with 1'-(trifluoromethyl)spiro[1,3-dioxolane-2,7'-5,6-dihydrocyclopenta[c]pyridine]-4'-ol (60.0 mg, 0.23 mmol) and stirred at 0 C for 15 min. The resulting mixture was treated with (3-cyano-5-fluoro-phenyl)-(4-methoxyphenyl)iodonium; 4-methylbenzenesulfonate (144.8 mg, 0.28 mmol) and heated to 40 C. The reaction mixture was filtered through a plastic filter cup using EtOAc to rinse. Volatiles were removed by concentration under reduced pressure. Purification was achieved by chromatography on silica using 10-40% EtOAc/hexane to afford a solid (42 mg, 48%). LCMS ESI (+) (M+H) m/z 381.

Step C: Preparation of 3-fluoro-5-((7-oxo-1-(trifluoromethyl)-6,7-dihydro-5H-cyclopenta[c]pyridin-4-yl)oxy)benzonitrile A solution of 3-fluoro-5-[1'-(trifluoromethyl)spiro[1,3-dioxolane-2,7'-5,6-dihydrocyclopenta[c]pyridine]-4'-yl]oxybenzonitrile (42.0 mg, 0.11 mmol) in dichloromethane (2.0 mL) at 0 C was treated with perchloric acid (70% in water, 240 µL) and stirred at 0 C for 30 min. The reaction mixture was carefully quenched by the addition of 15 mL of saturated NaHCO$_3$ and extracted with 3×15 mL CH$_2$Cl$_2$. The combined organics were rinsed with 10 mL of brine, dried with MgSO$_4$, filtered, and concentrated to dryness. The solid residue was used immediately in the next step without further purification. LCMS ESI (+) (M+H) m/z 337.

Step D: Preparation of 3-((7-((tert-butyldimethylsilyl)oxy)-1-(trifluoromethyl)-5H-cyclopenta[c]pyridin-4-yl)oxy)-5-fluorobenzonitrile A solution of triethylamine (122 µL, 0.88 mmol) and 3-fluoro-5-[[7-oxo-1-(trifluoromethyl)-5,6-dihydrocyclopenta[c]pyridin-4-yl]oxy]benzonitrile (37.0 mg, 0.11 mmol) in dichloromethane (2.2 mL) at 0° C. was treated with tert-butyldimethylsilyl triflate (152 ul, 0.66 mmol). The ice bath was removed and the reaction mixture left to stir for 2 h. The reaction mixture was poured into 30 mL of saturated NaHCO$_3$ and extracted with 3×20 mL CH$_2$Cl$_2$. The combined organics were rinsed with 10 mL of brine, dried with MgSO$_4$, filtered, and concentrated to dryness. The product was used without further purification. LCMS ESI (+) (M+H) m/z 451.

Step E: Preparation of 3-fluoro-5-((6-fluoro-7-oxo-1-(trifluoromethyl)-6,7-dihydro-5H-cyclopenta[c]pyridin-4-yl)oxy)benzonitrile A solution of 3-[[7-[tert-butyl(dimethyl)silyl]oxy-1-(trifluoromethyl)-5H-cyclopenta[c]pyridin-4-yl]oxy]-5-fluorobenzonitrile (49.56 mg, 0.1100 mmol) in acetonitrile (2.2 mL) at 25° C. was treated with Selectfluor® (42.9 mg, 0.12 mmol) and stirred at 25° C. for 1 h. Volatiles were removed by concentration under reduced pressure The reaction mixture was poured into 30 mL of water and extracted with 3×10 mL EtOAc. The combined organics were rinsed with 10 mL of brine, dried with MgSO$_4$, filtered, and concentrated to dryness. Purification was achieved by chromatography on silica using 10-25% EtOAc/hexane to afford a thin film (37.8 mg, 97%). LCMS ESI (+) (M+H) m/z 355.

Step F: Preparation of 3-fluoro-5-(((6R,7S)-6-fluoro-7-hydroxy-1-(trifluoromethyl)-6,7-dihydro-5H-cyclopenta[c]pyridin-4-yl)oxy)benzonitrile (Compound 3)

A solution of 3-fluoro-5-[[6-fluoro-7-oxo-1-(trifluoromethyl)-5,6-dihydrocyclopenta[c]pyridin-4-yl]oxy]benzonitrile (15.3 mg, 0.043 mmol) in dichloromethane (1.5 mL) was cooled to 0° C. and sparged with nitrogen for 5 min. During this time formic acid (4.9 µL, 0.13 mmol) and triethylamine (12.0 µL, 0.086 mmol) were sequentially added. Once the sparging was complete, RuCl(p-cymene)[(R,R)-Ts-DPEN] (0.5 mg, 0.00086 mmol) was added under a continuous stream of nitrogen. The reaction vessel was sealed and placed into the refrigerator to react overnight. Volatiles were removed by concentration under reduced pressure. The residue was purified by chromatography on silica using 10-30% EtOAc/hexane to afford 3-fluoro-5-(((6R,7S)-6-fluoro-7-hydroxy-1-(trifluoromethyl)-6,7-dihydro-5H-cyclopenta[c]pyridin-4-yl)oxy)benzonitrile (Compound 3) as a clear solid (11.8 mg, 77%). Retention time HPLC (14 min)=4.19 min; LCMS ESI (+) (M+H) m/z 357; $^1$H NMR (400 MHz, CDCl$_3$): δ 8.33 (s, 1H), 7.22 (ddd, 1H), 7.10-7.08 (m, 1H), 6.99 (dt, 1H), 5.54-5.46 (m, 1H), 5.46-5.28 (m, 1H), 3.26 (ddd, 1H), 3.11 (ddd, 1H), 2.67 (dd, 1H).

Example 3: Synthesis of 3-fluoro-5-(((6R,7S)-6-fluoro-7-hydroxy-1-(methylsulfonyl)-6,7-dihydro-5H-cyclopenta[c]pyridin-4-yl)oxy)benzonitrile (Compound 4)

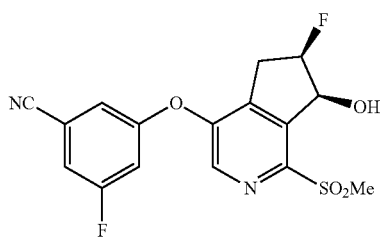 [SMILES: CS(=O)(=O)c1ncc(Oc2cc(F)cc(C#N)c2)c2c1[C@H](O)[C@H](F)C2]

Step A: Preparation of 5-bromo-2-(methylthio)nicotinic Acid

A solution of 5-bromo-2-fluoro-pyridine-3-carboxylic acid (3.50 g, 15.91 mmol) in DMF (62 mL) at 0° C. was treated with potassium carbonate (2.42 g, 17.5 mmol) and vigorously stirred at 0° C. for 7 minutes. During this time, nitrogen was sparged through the solution. Then sodium thiomethoxide (1.23 g, 16.7 mmol) was added in one portion to the reaction vessel under continuous nitrogen stream. The reaction vessel was sealed and the ice bath removed. The solution turned from a tan color to faint yellow. The reaction mixture was left to stir overnight. The reaction mixture was poured onto 10% citric acid solution inducing precipitation of a white solid. The solid was filtered and rinsed exhaustively with water. Finally, the white solid was dried overnight under high vacuum in the presence of solid NaOH and used without further purification (3.63 g, 92%). LCMS ESI (+) (M+H) m/z 248/250.

Step B: Preparation of 5-bromo-4-formyl-2-(methylthio)nicotinic Acid

A solution of 2,2,6,6-tetramethyl-piperidine (3.26 mL, 19.35 mmol) in tetrahydrofuran (40.3 mL) at −50 C was treated with n-butyllithium (~2.5M in hexanes, 7.09 mL, 17.73 mmol) and stirred for 5 min. Then 5-bromo-2-methylsulfanyl-pyridine-3-carboxylic acid (2.00 g, 8.06 mmol) was added via cannula over 30 min as a solution in 60 mL of THF. The resulting mixture stirred for 30 min at −50 C. The reaction mixture was quenched by the addition of N,N-dimethylformamide (0.94 mL, 12.09 mmol). 15 minutes following addition of the DMF, the reaction mixture was quenched by the addition of 40 mL of 10% citric acid solution (aqueous) and the reaction warmed to room temperature. After stirring for 30 min, excess THF removed by concentration under reduced pressure. The leftover mixture was poured into 120 mL of 3% citric acid (aqueous) and extracted with 3×50 mL EtOAc. The combined organics were dried with MgSO$_4$, filtered, and concentrated to dryness. 2.41 g of an orange solid was isolated and used without further purification. The material was contaminated with about 22% citric acid based on proton integration of the unpurified NMR spectra. LCMS ESI (+) (M+H) m/z 276/278.

Step C: Preparation of methyl (E)-5-bromo-4-(3-ethoxy-3-oxoprop-1-en-1-yl)-2-(methylthio)nicotinate A solution of 7-bromo-1-hydroxy-4-methylsulfanyl-1H-furo[3,4-c]pyridin-3-one (2.21 g, 8.00 mmol), lithium chloride (anhydrous, 339.1 mg, 8.00 mmol) and ethyl 2-diethoxyphosphorylacetate (1.60 mL, 8.00 mmol) in acetonitrile (80 mL) at 25 C was treated with 1;8-Diazabicyclo[5.4.0]undec-7-ene (2.87 mL, 19.20 mmol) and stirred at 25 C for 2 h. Initially, the solution is heterogenous with the pyridine being insoluble. Upon addition of the DBU the solution becomes homogeneous and darkens in color. After 1 h, the reaction appears to be mostly complete. In addition a precipitate has formed. Volatiles were removed by concentration under reduced pressure. The product residue was solubilized with 25 mL of DMF and treated with dimethyl sulfate (1.89 mL, 20.00 mmol). After 2 h, the reaction mixture was poured into 300 mL of water and extracted with 4×40 mL Et$_2$O. The combined organics were rinsed with 20 mL of brine, dried with MgSO$_4$, filtered, and concentrated to dryness. Purification was achieved by chromatography on silica using 5-20% EtOAc/hexane to afford methyl (E)-5-bromo-4-(3-ethoxy-3-oxoprop-1-en-1-yl)-2-(methylthio) nicotinate as a white solid (1.90 g, 66%). LCMS ESI (+) (M+H) m/z 360/362.

Step D: Preparation of methyl 5-bromo-4-(3-ethoxy-3-oxopropyl)-2-(methylthio)nicotinate A solution of methyl 5-bromo-4-[(E)-3-ethoxy-3-oxoprop-1-enyl]-2-methylsulfanyl-pyridine-3-carboxylate (1.87 g, 5.19 mmol) and cobalt(ii) chloride hexahydrate (123.5 mg, 0.52 mmol) in methanol (20.8 mL) at 0° C. was sparged with nitrogen for 3 min and treated with sodium borohydride (98.2 mg, 2.60 mmol) under continuous nitrogen stream. The vessel was sealed and the contents stirred at 0° C. for 10 min. LCMS at this time indicated partial consumption of the olefin. An additional portion of sodium borohydride (98.2 mg, 2.60 mmol) was added to drive the reaction to completion. The reaction mixture was quenched by the addition of 30 mL of saturated aqueous $NH_4Cl$. Volatiles were removed by concentration under reduced pressure. The reaction mixture was poured into 30 mL of water and extracted with 3×40 mL EtOAc. The combined organics were rinsed with 10 mL of brine, dried with $MgSO_4$, filtered, and concentrated to dryness. Purification was achieved by chromatography on silica using 5-15% EtOAc/hexane to afford the desired product as a solid (1.08 g, 57%). LCMS ESI (+) (M+H) m/z 362/364.

Step E: Preparation of ethyl 4-bromo-1-(methylthio)-5,6-dihydro-7H-cyclopenta[c]pyridin-7-one A solution of methyl 5-bromo-4-(3-ethoxy-3-oxo-propyl)-2-methylsulfanyl-pyridine-3-carboxylate (1.08 g, 2.98 mmol) in tetrahydrofuran (29.8 mL) at −78° C. was treated with lithium bis(trimethylsilyl)amide (~1.0 M in THF, 7.16 mL, 7.16 mmol) by dropwise addition over 30 minutes. Once the addition was complete, LCMS indicated a small amount of starting material remained so an additional 1 mL of lithium bis(trimethylsilyl)amide was added and the reaction allowed to stir for a further 15 minutes. The reaction mixture was quenched by the addition of 30 mL of saturated aqueous $NH_4Cl$. THF was removed by concentration under reduced pressure. The reaction mixture diluted with 60 mL of EtOAc and an additional 30 mL of water. A thick precipitate formed that could be eliminated by the addition of 10% citric acid solution. The reaction mixture was extracted with 3×30 mL EtOAc. The combined organics were rinsed with 10 mL of brine, dried with $MgSO_4$, filtered, and concentrated to dryness. The intermediate product was transferred into a microwave tube using 9.1 mL of DMSO. The resulting mixture was diluted with 900 µL of water. The vessel was sealed and heated to 150 C by microwave irradiation for 40 min. The reaction mixture was diluted with 120 mL of water to induce precipitation of the product and vigorously stirred for 30 min. The precipitate was collected, dried overnight under high vacuum in the presence of solid NaOH, and used without further purification. Beige solid (705 mg, 92%). LCMS ESI (+) (M+H) m/z 258/260.

Step F: Preparation of 4-bromo-1-(methylsulfonyl)-5,6-dihydro-7H-cyclopenta[c]pyridin-7-one A solution of 4-bromo-1-methylsulfanyl-5,6-dihydrocyclopenta[c]pyridin-7-one (364.5 mg, 1.41 mmol) in methanol (11.3 mL) at 0° C. was treated with a solution of Oxone® (1.91 g, 3.11 mmol) in water (11.3 mL). The reaction was left to stir for 24 h. Volatiles were removed by concentration under reduced pressure. The reaction mixture was poured into 40 mL of water and extracted with 3×20 mL EtOAc. The combined organics were rinsed with 10 mL of brine, dried with $MgSO_4$, filtered, and concentrated to dryness. The off white solid was used without further purification. LCMS ESI (+) (M+H) m/z 290/292.

Step G: Preparation of 4-bromo-1-(methylsulfonyl)-5,6-dihydrospiro[cyclopenta[c]pyridine-7,2'-[1,3]dioxolane]

Trimethylsilyl trifluoromethanesulfonate (331 µL, 1.83 mmol) was added to a solution of 4-bromo-1-methylsulfonyl-5,6-dihydrocyclopenta[c]pyridin-7-one (354 mg, 1.22 mmol) and trimethyl(2-trimethylsilyloxyethoxy)silane (1.20 mL, 4.88 mmol) in dichloromethane (14 mL) cooled in an ice bath. The ice bath was removed. After 3 h, an additional portion of trimethyl(2-trimethylsilyloxyethoxy)silane (1.20 mL, 4.88 mmol) was added. The reaction was left to stir overnight. After stirring, for the rest of the day, the reaction was quenched by the addition of triethylamine (1.02 mL, 7.32 mmol). The reaction mixture stirred for 10 min. Volatiles were removed and the residue suspended into 30 mL of saturated aqueous $NaHCO_3$ and extracted with 3×20 mL EtOAc. The combined organics were rinsed with 10 mL of brine, dried with MgSO4, filtered, and concentrated to dryness. Purification was achieved by chromatography on silica using 15-50% EtOAc/hexane to afford 4-bromo-1-(methylsulfonyl)-5,6-dihydrospiro[cyclopenta[c]pyridine-7,2'-[1,3]dioxolane] as a white solid (74.5 mg, 18%). LCMS ESI (+) (M+H) m/z 334/336. The bulk of the product was isolated as the enol ether (295 mg, 59%).

Step H: Preparation of 1-(methylsulfonyl)-5,6-dihydrospiro[cyclopenta[c]pyridine-7,2'-[1,3]dioxolan]-4-ol A solution of 4'-bromo-1'-methylsulfonyl-spiro[1,3-dioxolane-2,7'-5,6-dihydrocyclopenta[c]pyridine] (74.5 mg, 0.22 mmol) and 2-(di-t-butylphosphino)-3,6-dimethoxy-2',4',6'-tri-1-propyl-1,1'-biphenyl (5.4 mg, 0.011 mmol) in 1,4-dioxane (1.5 mL) was sparged with nitrogen for 3 mins. The reaction mixture was then treated sequentially with potassium hydroxide (37.5 mg, 0.67 mmol), water (80.3 µL, 4.46 mmol) and [2-(2-aminophenyl)phenyl]-methylsulfonyloxy-palladium; ditert-butyl-[3,6-dimethoxy-2-(2,4,6-triisopropylphenyl)phenyl]phosphane (9.5 mg, 0.011 mmol) under continuous nitrogen stream. The vessel was sealed and heated to 80 C for 1 h and 30 min. The reaction mixture was quenched by the addition of acetic acid (51.0 µL, 0.89 mmol). The reaction mixture was poured into 75 mL of water and extracted with 4×20 mL EtOAc. The combined organics were dried with $MgSO_4$, filtered, and concentrated to dryness. The product was used without further purification (77.9 mg). LCMS ESI (+) (M+H) m/z 272.

Step I: Preparation of 3-fluoro-5-((1-(methylsulfonyl)-5,6-dihydrospiro[cyclopenta[c]pyridine-7,2'-[1,3]dioxolan]-4-yl)oxy)benzonitrile A suspension of potassium carbonate (30.6 mg, 0.22 mmol) in acetonitrile (1.5 mL) at 25 C was treated with 1'-methylsulfonylspiro[1,3-dioxolane-2,7'-5,6-dihydrocyclopenta[c]pyridine]-4'-ol (40.0 mg, 0.15 mmol) and stirred at 25 C for 10 min. The resulting mixture was treated with (3-cyano-5-fluoro-phenyl)-(4-methoxyphenyl)iodonium; 4-methylbenzenesulfonate (116.2 mg, 0.22 mmol) and heated to 50 C for 3 h. Volatiles were removed by concentration under reduced pressure. The reaction mixture was poured into 20 mL of water and extracted with 3×15 mL EtOAc. The combined organics were rinsed with 10 mL of brine, dried with $MgSO_4$, filtered, and concentrated to dryness. Purification was achieved by chromatography on silica using 20-50% EtOAc/hexane to afford (3-fluoro-5-((1-(methylsulfonyl)-5,6-dihydrospiro[cyclopenta[c]pyridine-7,2'-[1,3]dioxolan]-4-yl)oxy)benzonitrile as a solid (25.1 mg, 44%). LCMS ESI (+) (M+H) m/z 391.

Step J: Preparation of 3-fluoro-5-((1-(methylsulfonyl)-7-oxo-6,7-dihydro-5H-cyclopenta[c]pyridin-4-yl)oxy)benzonitrile A solution of 4'-(3,3-difluorocyclobutoxy)-6'-fluoro-1'-methylsulfonyl-spiro[1,3-dioxolane-2,7'-5,6-dihydrocyclopenta[c]pyridine] (25.1 mg, 0.064 mmol) in dichloromethane (3.0 mL) at 0 C was treated with perchloric acid (70% in water, 330 μL) and stirred at 0 C for 2 h and then at room temperature for 30 min. The reaction mixture was carefully quenched with 5 mL of saturated NaHCO₃/10 mL of water and extracted with 3×15 mL CH₂Cl₂. The combined organics were rinsed with 10 mL of brine, dried with MgSO₄, filtered, and concentrated to dryness. The product was used without further purification. LCMS ESI (+) (M+H) m/z 347.

Step K: Preparation of 3-((7-((tert-butyldimethylsilyl)oxy)-1-(methylsulfonyl)-5H-cyclopenta[c]pyridin-4-yl)oxy)-5-fluorobenzonitrile A solution of triethylamine (71.4 μL, 0.51 mmol) and 3-fluoro-5-[[7-oxo-1-(trifluoromethyl)-5,6-dihydrocyclopenta[c]pyridin-4-yl]oxy]benzonitrile (22.2 mg, 0.064 mmol) in dichloromethane (3.0 mL) at 0° C. was treated with tert-butyldimethylsilyl trifluoromethanesulfonate (58.2 μL, 0.38 mmol). The ice bath was removed and the reaction mixture stirred for 2 h. The reaction mixture was poured into 30 mL of saturated NaHCO₃ and extracted with 3×20 mL CH₂Cl₂. The combined organics were rinsed with 10 mL of brine, dried with MgSO₄, filtered, and concentrated to dryness. The product was used without further purification. LCMS ESI (+) (M+H) m/z 461.

Step L: Preparation of 3-fluoro-5-((6-fluoro-1-(methylsulfonyl)-7-oxo-6,7-dihydro-5H-cyclopenta[c]pyridin-4-yl)oxy)benzonitrile A solution of 3-[[7-[tert-butyl(dimethyl)silyl]oxy-1-(trifluoromethyl)-5H-cyclopenta[c]pyridin-4-yl]oxy]-5-fluorobenzonitrile (29.5 mg, 0.064 mmol) in acetonitrile (2.6 mL) at 25° C. was treated with Selectfluor® (24.9 mg, 0.070 mmol) and stirred at 25° C. for 1 h. Volatiles were removed by concentration under reduced pressure. The reaction mixture was poured into 30 mL of water and extracted with 3×10 mL EtOAc. The combined organics were rinsed with 10 mL of brine, dried with MgSO₄, filtered, and concentrated to dryness. Purification was achieved by chromatography on silica using 10-25% EtOAc/hexane to afford 3-fluoro-5-((6-fluoro-1-(methylsulfonyl)-7-oxo-6,7-dihydro-5H-cyclopenta[c]pyridin-4-yl)oxy)benzonitrile as a thin film (11.1 mg, 48%). LCMS ESI (+) (M+H) m/z 365.

Step M: Preparation of 3-fluoro-5-((((6R,7S)-6-fluoro-7-hydroxy-1-(methylsulfonyl)-6,7-dihydro-5H-cyclopenta[c]pyridin-4-yl)oxy)benzonitrile (Compound 4)

A solution of 6-fluoro-4-[(5-fluoro-3-pyridyl)oxy]-1-(trifluoromethyl)-5,6-dihydrocyclopenta[c]pyridin-7-one (11.1 mg, 0.031 mmol) in dichloromethane (2.0 mL) was cooled to 0° C. and sparged with nitrogen for 5 min. During this time formic acid (3.4 μL, 0.091 mmol) and triethylamine (8.4 μL, 0.061 mmol) were sequentially added. Once the sparging was complete, RuCl(p-cymene)[(R,R)-Ts-DPEN] (0.4 mg, 0.0006 mmol) was added under a continuous stream of nitrogen. The reaction vessel was sealed and put into the refrigerator to react overnight. Volatiles were removed by concentration under reduced pressure. The residue was purified by chromatography on silica using 20-60% EtOAc/hexane to afford 3-fluoro-5-((((6R,7S)-6-fluoro-7-hydroxy-1-(methylsulfonyl)-6,7-dihydro-5H-cyclopenta[c]pyridin-4-yl)oxy)benzonitrile (Compound 4) as a white solid (7.0 mg, 63%). Retention time HPLC (14 min)=3.16 min; LCMS ESI (+) (M+H) m/z 367; ¹H NMR (400 MHz, CDCl₃): δ 8.27 (s, 1H), 7.25 (ddd, 1H), 7.14 (m, 1H), 7.03 (dt, 1H), 5.69 (dt, 1H), 5.53-5.36 (m, 1H), 4.24 (d, 1H), 3.34 (s, 3H), 3.31-3.24 (m, 1H), 3.09 (ddd, 1H).

Example 4: Synthesis of 4-bromo-1-(3,5-difluorophenoxy)-6,7-dihydro-5H-cyclopenta[c]pyridine (Compound 5) and 4-(difluoromethylsulfonyl)-1-(3, 5-difluorophenoxy)-6,7-dihydro-5H-cyclopenta[c] pyridine (Compound 6)

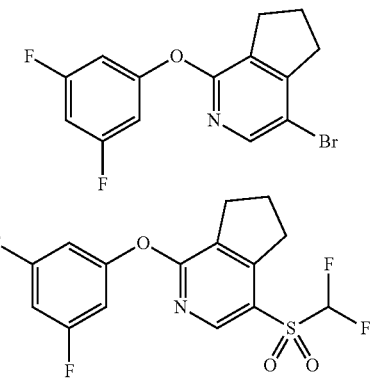

Step A: 4-bromo-1-chloro-6,7-dihydro-5H-cyclopenta[c]pyridine

A mixture of 4-bromo-2,5,6,7-tetrahydrocyclopenta[c]pyridin-1-one (420 mg, 1.96 mmol) and POCl₃ (2.20 mL, 23.6 mmol) was heated at reflux for 40 hours. After cooling, excess POCl₃ was removed under reduced pressure. The residue was taken up in EtOAc, washed with saturated aqueous NaHCO₃ and brine, dried and concentrated. The residue was purified by column chromatography on silica gel (2-10% EtOAc/hexanes) to give 4-bromo-1-chloro-6,7-dihydro-5H-cyclopenta[c]pyridine (207 mg, 45%). LCMS ESI (+) m/z 232/234/236 (M+H)+.

Step B: 4-bromo-1-(3,5-difluorophenoxy)-6,7-dihydro-5H-cyclopenta[c]pyridine (Compound 5)

A mixture of 4-bromo-1-chloro-6,7-dihydro-5H-cyclopenta[c]pyridine (62 mg, 0.27 mmol), 3,5-difluorophenol (38 mg, 0.29 mmol), cesium carbonate (130 mg, 0.400 mmol) and NMP (1.8 mL) was heated at 90° C. overnight under nitrogen. The reaction mixture was heated to 140° C. and stirred overnight again. After cooling, the reaction mixture was partitioned between EtOAc and water. The aqueous layer was extracted with EtOAc. The combined organic layers were washed with brine, dried and concentrated. The residue was purified by Biotage C18 reverse phase flash chromatography (20-95% acetonitrile/water) to give 4-bromo-1-(3,5-difluorophenoxy)-6,7-dihydro-5H-cyclopenta[c]pyridine (Compound 5, 21 mg, 24%) as a pale yellow solid. LCMS ESI (+) m/z 326/328 (M+H)⁺.

Step C: S-[1-(3,5-difluorophenoxy)-6,7-dihydro-5H-cyclopenta[c]pyridin-4-yl]ethanethioate To a vial containing a solution of 4-bromo-1-(3,5-difluorophenoxy)-6,7-dihydro-5H-cyclopenta[c]pyridine (20 mg, 0.060 mmol) in 1,4-dioxane (0.3 mL) were added acetylsulfanylpotassium (8.8 mg, 0.080 mmol) and (5-diphenylphosphanyl-9,9-dimethyl-xanthen-4-yl)-diphenyl-phosphane (4.3 mg, 0.010 mmol). The mixture was sparged with nitrogen. Then tris(dibenzylideneacetone)dipalladium(0) (3.4 mg, 0.004 mmol) was added, and the vial was sealed and heated at 110° C. for 4 hours. After cooling, the reaction mixture was filtered through Celite. The filtrate was concentrated. The residue was purified by Biotage C18 reverse phase flash chromatography (10-80% acetonitrile/water) to give S-[1-(3,5-difluorophenoxy)-6,7-dihydro-5H-cyclopenta[c]pyridin-4-yl] ethanethioate (10 mg, 51%). LCMS ESI (+) m/z 322 (M+H)$^+$.

Step D: 1-(3,5-difluorophenoxy)-6,7-dihydro-5H-cyclopenta[c]pyridine-4-thiol

To a stirred solution of S-[1-(3,5-difluorophenoxy)-6,7-dihydro-5H-cyclopenta[c]pyridin-4-yl]ethanethioate (10 mg, 0.030 mmol) in MeOH (0.3 mL) was added 1 N LiOH solution (0.050 mL, 0.050 mmol). The reaction mixture was stirred at ambient temperature for 30 minutes and then concentrated. To the residue was added water. The pH was added to 2-3 using 0.1 N HCl. The mixture was extracted with EtOAc. The combined organic layers were washed with brine, dried and concentrated. The crude was used in the next step without further purification. LCMS ESI (+) m/z 280 (M+H)$^+$.

Step E: 4-(difluoromethylsulfanyl)-1-(3,5-difluorophenoxy)-6,7-dihydro-5H-cyclopenta[c]pyridine To a stirred solution of crude 1-(3,5-difluorophenoxy)-6,7-dihydro-5H-cyclopenta[c]pyridine-4-thiol (9 mg, 0.03 mmol) in acetonitrile (0.3 mL) was added potassium hydroxide (36 mg, 0.64 mmol) in water (0.3 mL). The reaction mixture was purged with nitrogen and then cooled to −78° C. Bromodifluoromethyl diethylphosphonate (17 mg, 0.060 mmol) was added. The resulting mixture was allowed to warm to ambient temperature and stirred for 3 hours. The reaction mixture was partitioned between EtOAc and water. The aqueous layer was extracted with EtOAc. The combined organics were washed with water and brine, dried over Na$_2$SO4, filtered, and concentrated to dryness. The crude was used in the next step without further purification. LCMS ESI (+) m/z 330 (M+H)$^+$.

Step F: 4-(difluoromethylsulfonyl)-1-(3,5-difluorophenoxy)-6,7-dihydro-5H-cyclopenta[c]pyridine (Compound 6)

Sodium periodate (18 mg, 0.080 mmol) was added all at once to crude 4-(difluoromethylsulfanyl)-1-(3,5-difluorophenoxy)-6,7-dihydro-5H-cyclopenta[c]pyridine (11 mg, 0.030 mmol) and ruthenium(III) chloride (0.2 mg, 0.001 mmol) in acetonitrile (0.2 mL)/CCl$_4$ (0.2 mL)/water (0.4 mL). The reaction mixture was stirred at ambient temperature for 3 hours. Solids were removed by filtration and rinsed with CH$_2$Cl$_2$. The organic layer was separated. The aqueous layer was extracted with CH$_2$Cl$_2$. The combined organics were washed with brine, dried over Na$_2$SO$_4$, filtered and concentrated in vacuo. The crude product was purified by column chromatography on silica gel (4-12% EtOAc/hexanes) affording Compound 6 (3 mg, 25% overall yield for three steps) as a white solid. LCMS ESI (+) m/z 362 (M+H)+. $^1$H NMR (400 MHz, CDCl$_3$): δ 7.49 (s, 1H), 6.80-6.71 (m, 3H), 6.19 (t, 1H), 3.36 (t, 2H), 3.06 (t, 2H), 2.31-2.23 (m, 2H).

Example 5: Synthesis of racemic 3-fluoro-5-((6R,7S)-6-fluoro-7-hydroxy-1-(trifluoromethyl)-6,7-dihydro-5H-cyclopenta[c]pyridin-4-yl)benzonitrile (Compound 7)

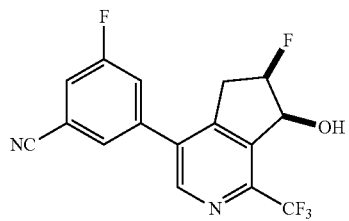 [SMILES: N#Cc1cc(F)cc(-c2cnc(C(F)(F)F)c3c2C[C@@H](F)[C@H]3O)c1]

Step A: Preparation of racemic (6R,7S)-4-bromo-6-fluoro-1-(trifluoromethyl)-6,7-dihydro-5H-cyclopenta[c]pyridin-7-ol A solution of 4-bromo-6-fluoro-1-(trifluoromethyl)-5,6-dihydrocyclopenta[c]pyridin-7-one (6.7 mg, 0.022 mmol) in methanol (0.8 mL) at 0° C. was treated with sodium borohydride (0.9 mg, 0.022 mmol) and stirred at 0° C. for 10 min. The reaction mixture was quenched by the addition of 0.2 mL of saturated NH$_4$Cl. Volatiles were removed by concentration under reduced pressure. The reaction mixture was poured into 20 mL of water and extracted with 3×10 mL EtOAc. The combined organics were rinsed with 10 mL of brine, dried with MgSO$_4$, filtered, and concentrated to dryness. The product was used without further purification. LCMS ESI (+) (M+H) m/z 300/302.

Step B: Preparation of racemic 3-fluoro-5-((6R,7S)-6-fluoro-7-hydroxy-1-(trifluoromethyl)-6,7-dihydro-5H-cyclopenta[c]pyridin-4-yl)benzonitrile (Compound 7)

A suspension of racemic (6R,7S)-4-bromo-6-fluoro-1-(trifluoromethyl)-6,7-dihydro-5H-cyclopenta[c]pyridin-7-ol (6.7 mg, 0.022 mmol), 3-cyano-5-fluorophenylboronic acid (5.5 mg, 0.033 mmol), cesium fluoride (10.5 mg, 0.069 mmol) and bis(di-tert-butyl(4-dimethylaminophenyl)phosphine)dichloropalladium(II) (0.8 mg, 0.0011 mmol) in a mixture 1,4-dioxane (0.8 mL) and water (80 μL) was sparged with nitrogen for 3 mins. The vessel was sealed and heated to 80° C. for 1 h. LCMS indicates product formation. The reaction mixture was poured into 60 mL of water and extracted with 3×20 mL EtOAc. The combined organics were rinsed with 10 mL of brine, dried with MgSO$_4$, filtered, and concentrated to dryness. Purification was achieved by chromatography on silica using 10-30% EtOAc/hexane to afford racemic 3-fluoro-5-((6R,7S)-6-fluoro-7-hydroxy-1-(trifluoromethyl)-6,7-dihydro-5H-cyclopenta[c]pyridin-4-yl)benzonitrile (Compound 7) as an orange solid (1.8 mg, 24%). Retention time HPLC (14 min)=3.80 min; LCMS ESI (+) (M+H) m/z 341; $^1$H NMR (400 MHz, CDCl$_3$): δ 8.65 (s, 1H), 7.53-7.48 (m, 2H), 7.40 (ddd, 1H), 5.56-5.48 (m, 1H), 5.35 (ddt, 1H), 3.41 (ddd, 1H), 3.21 (ddd, 1H), 2.65 (dd, 1H).

Example 6: Synthesis of 3-(((5R,6S,7S)-5,6-difluoro-7-hydroxy-1-(trifluoromethyl)-6,7-dihydro-5H-cyclopenta[c]pyridin-4-yl)oxy)-5-fluorobenzonitrile (Compound 22)

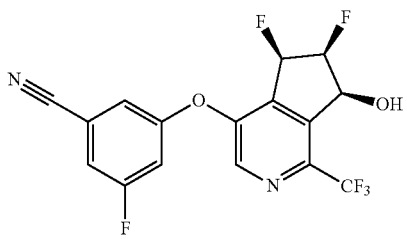 [SMILES: N#Cc1cc(F)cc(Oc2cnc(C(F)(F)F)c3c2[C@@H](F)[C@@H](F)[C@H]3O)c1]

Step A: Preparation of 3-((5-bromo-1-(trifluoromethyl)-5,6-dihydrospiro[cyclopenta[c]pyridine-7,2'-[1,3]dioxolan]-4-yl)oxy)-5-fluorobenzonitrile A suspension of 3-fluoro-5-[1'-(trifluoromethyl)spiro[1,3-dioxolane-2,7'-5,6-dihydrocyclopenta[c]pyridine]-4'-yl]oxy-benzonitrile (1520 mg, 4 mmol), 2,2'-azobisisobutyronitrile (66 mg, 0.4 mmol), magnesium oxide (483 mg, 12 mmol) and N-bromosuccinimide (925 mg, 5.2 mmol) in 1,2-dichloroethane (40 mL) was sparged with nitrogen for 3 minutes. The vessel was sealed and heated to 80° C. for 3 h. Additional 2,2'-azobisisobutyronitrile (66 mg, 0.4 mmol) and N-bromosuccinimide (925 mg, 5.2 mmol) was added to help drive the reaction to completion. Heating was continued for an additional 1.5 h. The reaction mixture was left at room temperature overnight. MgO was removed by filtration through the celite and rinsing of the filter cake with $CH_2Cl_2$. The filtrate was treated with 30 mL of saturated aqueous $NaHCO_3$, stirred for 10 minutes, and extracted with 3×30 mL $CH_2Cl_2$. The combined organics were rinsed with 10 mL of brine, dried with $MgSO_4$, filtered, and concentrated to dryness. Purification was achieved by chromatography on silica using 5-25% EtOAc/hexane to afford 3-((5-bromo-1-(trifluoromethyl)-5,6-dihydrospiro[cyclopenta[c]pyridine-7,2'-[1,3]dioxolan]-4-yl)oxy)-5-fluorobenzonitrile as a yellow foam (931 mg, 51%). LCMS ESI (+) (M+H) m/z 459/461.

Step B: Preparation of 3-fluoro-5-((5-hydroxy-1-(trifluoromethyl)-5,6-dihydrospiro[cyclopenta[c]pyridine-7,2'-[1,3]dioxolan]-4-yl)oxy)benzonitrile A solution of 3-[5'-bromo-1'-(trifluoromethyl)spiro[1,3-dioxolane-2,7'-5,6-dihydrocyclopenta[c]pyridine]-4'-yl]oxy-5-fluoro-benzonitrile (931 mg, 2 mmol) in a mixture of 1,2-dimethoxyethane (15 mL) and water (5 mL) at 25° C. was treated with silver(I) carbonate (1.12 g, 4.1 mmol) and stirred at 85° C. for 8 h. An additional portion of silver(I) carbonate (1.12 g, 4.05 mmol) was added and the reaction mixture left to heat at 85° C. overnight. The reaction mixture was diluted with EtOAc and filtered through celite. The filtrate was washed with water and brine, dried and concentrated. Purification was achieved by chromatography on silica using 20-55% EtOAc/hexane to afford 3-fluoro-5-((5-hydroxy-1-(trifluoromethyl)-5,6-dihydrospiro[cyclopenta[c]pyridine-7,2'-[1,3]dioxolan]-4-yl)oxy)benzonitrile as a yellow solid (295 mg, 37%). LCMS ESI (+) (M+H) m/z 397.

Step C: Preparation of 3-fluoro-5-((5-oxo-1-(trifluoromethyl)-5,6-dihydrospiro[cyclopenta[c]pyridine-7,2'-[1,3]dioxolan]-4-yl)oxy)benzonitrile A solution of 3-fluoro-5-[5'-hydroxy-1'-(trifluoromethyl)spiro[1,3-dioxolane-2,7'-5,6-dihydrocyclopenta[c]pyridine]-4'-yl]oxy-benzonitrile (296 mg, 0.75 mmol) in dichloromethane (15 mL) at 25° C. was treated with Dess-Martin periodinane (396 mg, 0.93 mmol). After 1 h, an additional 20 mg of Dess-Martin periodinane was added. After stirring for another 30 minutes, the reaction was quenched by the addition of 6 mL of saturated $Na_2S_2O_3$ solution and 6 mL of saturated $NaHCO_3$ solution. The resulting biphase was stirred for 10 minutes. The reaction mixture was poured into 10 mL of water and extracted with 3×20 mL $CH_2Cl_2$. The combined organics were rinsed with 10 mL of brine, dried with $MgSO_4$, filtered, and concentrated to dryness. The product, 3-fluoro-5-((5-oxo-1-(trifluoromethyl)-5,6-dihydrospiro[cyclopenta[c]pyridine-7,2'-[1,3]dioxolan]-4-yl)oxy)benzonitrile (264 mg), was used without further purification. LCMS ESI (+) (M+H) m/z 395.

Step D: Preparation of 3-fluoro-5-((6-fluoro-5-oxo-1-(trifluoromethyl)-5,6-dihydrospiro[cyclopenta[c]pyridine-7,2'-[1,3]dioxolan]-4-yl)oxy)benzonitrile A solution of 3-fluoro-5-[5'-oxo-1'-(trifluoromethyl)spiro[1,3-dioxolane-2,7'-6H-cyclopenta[c]pyridine]-4'-yl]oxy-benzonitrile (294 mg, 0.75 mmol) and triethylamine (520 µL, 3.7 mmol) in dichloromethane (15 mL) at 0° C. was treated with tert-butyldimethylsilyl trifluoromethane (690 µL, 2.98 mmol) and stirred at 0° C. for 30 minutes. The reaction mixture was left to stir for 5 h during which it was slowly warmed to room temperature. The reaction mixture was poured into 15 mL of saturated $NaHCO_3$, stirred for 10 minutes, and extracted with 3×15 mL $CH_2Cl_2$. The combined organics were rinsed with 10 mL of brine, dried with $MgSO_4$, filtered, and concentrated to dryness. The crude residue was dissolved in 4 mL of acetonitrile and treated with Selectfluor® (264 mg, 0.75 mmol). The reaction mixture was stirred for 3 h at room temperature. Volatiles were removed by concentration under reduced pressure. The mixture was poured into 30 mL of water and extracted with 3×15 mL EtOAc. The combined organics were rinsed with 10 mL of brine, dried with $MgSO_4$, filtered, and concentrated to dryness. Purification was achieved by chromatography on silica using 5-30% EtOAc/hexane to afford 3-fluoro-5-((6-fluoro-5-oxo-1-(trifluoromethyl)-5,6-dihydrospiro[cyclopenta[c]pyridine-7,2'-[1,3]dioxolan]-4-yl)oxy)benzonitrile as a white solid (206 mg, 67%). $^1$H NMR (400 MHz, $CDCl_3$): δ 8.51 (s, 1H), 7.32-7.28 (m, 1H), 7.21-7.18 (m, 1H), 7.13-7.08 (m, 1H), 5.20 (d, 1H), 4.51-4.31 (m, 4H).

Step E: Preparation of 3-fluoro-5-(((5R,6R)-6-fluoro-5-hydroxy-1-(trifluoromethyl)-5,6-dihydrospiro[cyclopenta[c]pyridine-7,2'-[1.3]dioxolan]-4-yl)oxy)benzonitrile A solution of 3-fluoro-5-[6'-fluoro-5'-oxo-1'-(trifluoromethyl)spiro[1,3-dioxolane-2,7'-6H-cyclopenta[c]pyridine]-4'-yl]oxy-benzonitrile (206 mg, 0.5 mmol) in dichloromethane (10 mL) was cooled to 0° C. and sparged with nitrogen for 5 minutes. During this time, formic acid (57 µL, 1.50 mmol) and triethylamine (104 µL, 0.75 mmol) were sequentially added. Once sparging was complete, RuCl(p-cymene)[(S,S)-Ts-DPEN] (6.4 mg, 0.01 mmol) was added under a continuous stream of nitrogen. The reaction vessel was sealed and put into the refrigerator to react overnight. Volatiles were removed by concentration under reduced pressure. Purification was achieved by chromatography on silica using 20-45% EtOAc/hexane to afford 3-fluoro-5-(((5R,6R)-6-fluoro-5-hydroxy-1-(trifluoromethyl)-5,6-dihydrospiro[cyclopenta[c]pyridine-7,2'-[1,3]dioxolan]-4-yl)oxy)benzonitrile as a clear solid (200 mg, 97%). LCMS ESI (+) (M+H) m/z 415.

Step F: Preparation of (5S,6R)-4-(3-cyano-5-fluorophenoxy)-6-fluoro-1-(trifluoromethyl)-5,6-dihydrospiro[cyclopenta[c]pyridine-7,2'-[1,3]dioxolan]-5-yl 4-nitrobenzoate A solution of 3-fluoro-5-[(5'R,6'R)-6'-fluoro-5'-hydroxy-1'-(trifluoromethyl)spiro[1,3-dioxolane-2,7'-5,6-dihydrocyclopenta[c]pyridine]-4'-yl]oxy-benzonitrile (200 mg, 0.48 mmol), polymer supported triphenylphosphine (~2.06 mmol/g, 938 mg, 1.93 mmol), and 4-nitrobenzoic acid (323 mg, 1.93 mmol) in tetrahydrofuran (9.7 mL) at 25° C. was treated with diisopropyl azodicarboxylate (371 µL, 1.88 mmol) and stirred for 2 h. The reaction mixture was filtered and the filter cake rinsed with EtOAc. The filtrate was concentrated and purified by chromatography on silica using 10-35% EtOAc/hexane to afford (5S,6R)-4-(3-cyano-5-fluorophenoxy)-6-fluoro-1-(trifluoromethyl)-5,6-dihydrospiro[cyclopenta[c]pyridine-7,2'-[1,3]dioxolan]-5-yl 4-nitrobenzoate as a white solid (221 mg, 81%). LCMS ESI (+) (M+H) m/z 564.

Step G: Preparation of 3-fluoro-5-(((5S,6R)-6-fluoro-5-hydroxy-1-(trifluoromethyl)-5,6-dihydrospiro[cyclopenta[c]pyridine-7,2'-[1,3]dioxolan]-4-yl)oxy)benzonitrile A solution of [(5'S,6'R)-4'-(3-cyano-5-fluoro-phenoxy)-6'-fluoro-1'-(trifluoromethyl)spiro[1,3-dioxolane-2,7'-5,6-dihydrocyclopenta[c]pyridine]-5'-yl] 4-nitrobenzoate (238 mg, 0.42 mmol) in tetrahydrofuran (8 mL) at 25° C. was treated with a solution of freshly prepared lithium hydroxide hydrate (19.5 mg, 0.46 mmol) in water (2.4 mL) and stirred at 25° C. for 30 minutes. An additional portion of lithium hydroxide hydrate (10 mg, 0.24 mmol) in water (1.2 mL) was added and the reaction mixture stirred for 30 minutes. 2.0 mL of saturated NH$_4$Cl was added to the reaction mixture and volatiles were removed under reduced pressure. The reaction mixture was poured into 10 mL of saturated NaHCO$_3$ and extracted with 3×15 mL EtOAc. The combined organics were rinsed with 10 mL of brine, dried with MgSO$_4$, filtered, and concentrated to dryness. Purification was achieved by chromatography on silica using 5-10% EtOAc/dichloromethane to afford 3-fluoro-5-(((5S,6R)-6-fluoro-5-hydroxy-1-(trifluoromethyl)-5,6-dihydrospiro[cyclopenta[c]pyridine-7,2'-[1,3]dioxolan]-4-yl)oxy)benzonitrile as a white solid (137 mg, 78%). LCMS ESI (+) (M+H) m/z 415.

Step H: Preparation of 3-(((5R,6S)-5,6-difluoro-1-(trifluoromethyl)-5,6-dihydrospiro[cyclopenta[c]pyridine-7,2'-[1,3]dioxolan]-4-yl)oxy)-5-fluorobenzonitrile A solution of 3-fluoro-5-[(5'S,6'R)-6'-fluoro-5'-hydroxy-1'-(trifluoromethyl)spiro[1,3-dioxolane-2,7'-5,6-dihydrocyclopenta[c]pyridine]-4'-yl]oxy-benzonitrile (137 mg, 0.33 mmol) in dichloromethane (6.6 mL) at 25° C. was treated with diethylaminosulfur trifluoride (87.4 µL, 0.66 mmol). The reaction mixture was allowed to stir for 30 minutes. The reaction mixture was quenched by the careful addition of 2 mL of aqueous saturated NaHCO$_3$. The resulting mixture vigorously stirred for 30 minutes. The reaction mixture was poured into 20 mL of water and extracted with 3×10 mL CH$_2$Cl$_2$. The combined organics were rinsed with 10 mL of brine, dried with MgSO$_4$, filtered, and concentrated to dryness. Purification was achieved by chromatography on silica using 10-30% EtOAc/hexane to afford 3-(((5R,6S)-5,6-difluoro-1-(trifluoromethyl)-5,6-dihydrospiro[cyclopenta[c]pyridine-7,2'-[1,3]dioxolan]-4-yl)oxy)-5-fluorobenzonitrile as a white solid (92.7 mg, 67%). LCMS ESI (+) (M+H) m/z 417.

Step I: Preparation of 3-(((5R,6S,7S)-5,6-difluoro-7-hydroxy-1-(trifluoromethyl)-6,7-dihydro-5H-cyclopenta[c]pyridin-4-yl)oxy)-5-fluorobenzonitrile (Compound 22)

A solution of 3-[(5'R,6'S)-5',6'-difluoro-1'-(trifluoromethyl)spiro[1,3-dioxolane-2,7'-5,6-dihydrocyclopenta[c]pyridine]-4'-yl]oxy-5-fluoro-benzonitrile (93 mg, 0.22 mmol) in dichloromethane (5 mL) at 0 C was treated with 70% aqueous perchloric acid (1.0 mL) and stirred at 44 C for 3 h. The reaction mixture was cooled to 0° C., carefully quenched with a mixture of 10 mL of saturated NaHCO$_3$/10 mL of water and extracted with 3×15 mL CH$_2$Cl$_2$. The combined organics were rinsed with 10 mL of brine, dried with MgSO$_4$, filtered, and concentrated to dryness. The intermediate ketone product was used immediately without further purification by dissolving in 4 mL of MeOH, cooling to 0° C., and treating with sodium borohydride (8.4 mg, 0.22 mmol). The reaction stirred for 15 min and was then quenched by the addition of 1 mL of saturated NH$_4$Cl. Volatiles were removed by concentration under reduced pressure. The reaction mixture was poured into 20 mL of water and extracted with 3×10 mL EtOAc. The combined organics were rinsed with 10 mL of brine, dried with MgSO$_4$, filtered, and concentrated to dryness. Purification was achieved by chromatography on silica using 10-45% EtOAc/hexane to afford 3-(((5R,6S,7S)-5,6-difluoro-7-hydroxy-1-(trifluoromethyl)-6,7-dihydro-5H-cyclopenta[c]pyridin-4-yl)oxy)-5-fluorobenzonitrile as a white solid (60 mg, 72%). Retention time HPLC (14 min)=4.18 minutes; LCMS ESI (+) (M+H) m/z 375; $^1$H NMR (400 MHz, CDCl$_3$): δ 8.42 (s, 1H), 7.28 (ddd, 1H), 7.20-7.18 (m, 1H), 7.09 (dt, 1H), 5.92 (dt, 1H), 5.53-5.46 (m, 1H), 5.19 (ddt, 1H), 2.66 (ddd, 1H).

Example 7: Synthesis of 3-fluoro-5-(((5S,6R)-6-fluoro-5-hydroxy-4-(trifluoromethyl)-6,7-dihydro-5H-cyclopenta[c]pyridin-1-yl)oxy)benzonitrile (Compound 33)

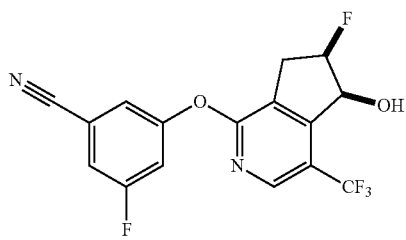 [SMILES: N#Cc1cc(F)cc(Oc2ncc(C(F)(F)F)c3c2C[C@@H](F)[C@H]3O)c1]

Step A: Preparation of ethyl (E)-3-(2-fluoro-4-iodopyridin-3-yl)acrylate

A solution of 2-fluoro-4-iodo-3-pyridinecarboxyaldehyde (1.0 g, 4 mmol), lithium chloride (169 mg, 4 mmol) and ethyl 2-diethoxyphosphorylacetate (800 µL, 4 mmol) in acetonitrile (20 mL) at 25° C. was treated with 1,8-Diazabicyclo[5.4.0]undec-7-ene (630 µL, 4.2 mmol) and stirred at 25° C. for 2 h. Volatiles were removed by concentration under reduced pressure. The reaction mixture was poured into 30 mL of water and extracted with 3×20 mL EtOAc. The combined organics were rinsed with 10 mL of brine, dried with MgSO$_4$, filtered, and concentrated to dryness. Purification was achieved by chromatography on silica using 100% CH$_2$Cl$_2$ to afford ethyl (E)-3-(2-fluoro-4-iodopyridin-3-yl)acrylate as white solid (1.1 g, 86%). LCMS ESI (+) (M+H) m/z 322.

Step B: Preparation of ethyl (E)-3-(4-cyano-2-fluoropyridin-3-yl)acrylate

A solution of ethyl (E)-3-(2-fluoro-4-iodo-3-pyridyl)prop-2-enoate (900 mg, 2.8 mmol) and zinc cyanide (987 mg, 8.4 mmol) in N,N-dimethylacetamide (10 mL) was sparged with nitrogen for 3 minutes. The reaction mixture was then treated sequentially with 1,1'-ferrocenediyl-bis(diphenylphosphine) (61 mg, 0.11 mmol) and tris(dibenzylideneacetone)dipalladium(0) (51 mg, 0.056 mmol) under continuous nitrogen stream. The vessel was sealed and heated to 110° C. for 30 minutes. The reaction mixture was poured into 100 mL of water and extracted with 3×25 mL TBME. The combined organics were rinsed with 10 mL of brine, dried with MgSO$_4$, filtered, and concentrated to dryness. Purification was achieved by chromatography on silica using 5-25% EtOAc/hexane to afford ethyl (E)-3-(4-cyano-2-fluoropyridin-3-yl)acrylate as a solid (594 mg, 97%). LCMS ESI (+) (M+H) m/z 221.

Step C: Preparation of ethyl 3-(4-cyano-2-fluoropyridin-3-yl)propanoate

A suspension of ethyl (E)-3-(4-cyano-2-fluoro-3-pyridyl)prop-2-enoate (560 mg, 2.54 mmol) and palladium on carbon (10 wt. %, 68 mg, 0.064 mmol) in methanol (25 mL) at 25° C. was sparged with nitrogen for 3 minutes. Then the solution was sparged with hydrogen for 1 minute and left under a hydrogen balloon for 3 h. The reaction mixture was carefully sparged with nitrogen for 3 minutes and then filtered through a pad of celite using MeOH as a rinse. The filtrate was concentrated and purification was achieved by chromatography on silica using 5-25% EtOAc/hexane to afford ethyl 3-(4-cyano-2-fluoropyridin-3-yl)propanoate (391 mg, 68%). LCMS ESI (+) (M+H) m/z 223.

Step D: Preparation of 1-hydroxy-6,7-dihydro-5H-cyclopenta[c]pyridin-5-one

A solution of ethyl 3-(4-cyano-2-fluoro-3-pyridyl)propanoate (384 mg, 1.73 mmol) in tetrahydrofuran (10 mL) at −78° C. was treated with lithium bis(trimethylsilyl)amide (1.0 M in THF, 2.25 mL, 2.25 mmol) by slow dropwise addition over 5 minutes. The reaction mixture stirred for 20 minutes at this temperature. The reaction was quenched by the addition of 5 mL of saturated NH$_4$Cl. Organic volatiles were removed by concentration under reduced pressure. The reaction mixture was extracted with 3×20 mL EtOAc. The combined organics were rinsed with 10 mL of brine, dried with MgSO$_4$, filtered, and concentrated to dryness. The intermediate vinylogous carbamate was suspended in 6.6 mL of dioxane and treated with 1.3 mL of water and 2.0 mL of concentrated H$_2$SO$_4$. The resulting mixture was heated to 120° C. by microwave irradiation for 45 min. Volatiles were removed by concentration under reduced pressure. The reaction mixture was poured into 30 mL of water and extracted with 5×15 mL EtOAc. The combined organics were rinsed with 10 mL of brine, dried with MgSO$_4$, filtered, and concentrated to dryness. Purification was achieved by chromatography on silica using 2-8% MeOH/CH$_2$Cl$_2$ to afford 1-hydroxy-6,7-dihydro-5H-cyclopenta[c]pyridin-5-one as a beige solid (167 mg, 65%). LCMS ESI (+) (M+H) m/z 150.

Step E: Preparation of 5-(2-((trimethylsilyl)oxy)ethoxy)-7H-cyclopenta[c]pyridin-1-ol Trimethylsilyl trifluoromethanesulfonate (263 µL, 1.46 mmol) was added to a solution of 1-hydroxy-6,7-dihydrocyclopenta[c]pyridin-5-one (167 mg, 1.12 mmol) and trimethyl(2-trimethylsilyloxyethoxy)silane (1.1 mL, 4.48 mmol) in dichloromethane (11.2 mL) cooled in an ice bath. The ice bath was removed and the reaction stirred at ambient temperature overnight. The next day, an additional portion of trimethylsilyl trifluoromethanesulfonate (263 µL, 1.46 mmol) was added. After 4 h, the reaction mixture was treated with triethylamine (624 µL, 4.48 mmol), stirred for 10 minutes, and then evaporated. The residue was treated with 20 mL of 30% isopropyl alcohol/CHCl$_3$ and 20 mL water and the layers separated. The aqueous layer was further extracted with 3×10 mL of 30% isopropyl alcohol/CHCl$_3$. The combined organic extracts were washed with brine, dried over MgSO$_4$, filtered, and evaporated. Purification was achieved by chromatography on silica using 2-10% MeOH/CH$_2$Cl$_2$ to afford a clear solid (105 mg) that was a ~1:1 mixture of 5-(2-((trimethylsilyl)oxy)ethoxy)-7H-cyclopenta[c]pyridin-1-ol and the ketalized product, 6,7-dihydrospiro[cyclopenta[c]pyridine-5,2'-[1,3]dioxolan]-ol. LCMS ESI (+) (M+H) m/z 194.

Step F: Preparation of 6-fluoro-6,7-dihydrospiro[cyclopenta[c]pyridine-5,2'-[1,3]dioxolan]-1-ol A mixture of impure 5-(2-trimethylsilyloxyethoxy)-7H-cyclopenta[c]pyridin-1-ol (~105 mg) and sodium sulfate (281 mg, 1.98 mmol) in acetonitrile (7.9 mL) was stirred for 10 minutes and then treated with Selectfluor® (154 mg, 0.44 mmol) and stirred at 25° C. for 1 h. Volatiles were removed by concentration under reduced pressure. The reaction mixture was poured into 30 mL of water and extracted with 3×15 mL 30% isopropyl alcohol/CHCl$_3$. The combined organics were rinsed with 10 mL of brine, dried with MgSO$_4$, filtered, and concentrated to dryness. Purification was achieved by chromatography on silica using 2-10% MeOH/CH$_2$Cl$_2$ to afford the desired product with impurities. LCMS ESI (+) (M+H) m/z 212.

Step G: Preparation of 3-fluoro-5-((6-fluoro-4-iodo-6,7-dihydrospiro[cyclopenta[c]pyridine-5,2'-[1,3]dioxolan]-1-yl)oxy)benzonitrile A solution of impure spiro[1,3-dioxolane-2,5'-6,7-dihydrocyclopenta[c]pyridine]-1'-ol (142 mg) in acetonitrile (7.3 mL) was treated with N-iodosuccinimide (182 mg, 0.81 mmol) and heated to 80° C. over 1 h. Volatiles were removed by concentration under reduced pressure. The residue was redissolved in acetonitrile (7.3 mL) and treated with potassium carbonate (305 mg, 2.2 mmol) and (3-cyano-5-fluorophenyl)-(4-methoxyphenyl)iodonium; 4-methylbenzenesulfonate (579 mg, 1.1 mmol). The reaction was heated to 80° C. for 1 h. The reaction mixture was cooled and recharged with potassium carbonate (100 mg) and diaryliodonium salt (385 mg). The reaction mixture was heated to 80° C. for another hour. Volatiles were removed by concentration under reduced pressure. The reaction mixture was poured into 30 mL of water and extracted with 3×20 mL EtOAc. The combined organics were rinsed with 10 mL of brine, dried with MgSO₄, filtered, and concentrated to dryness. Purification was achieved by chromatography on silica using 5-25% EtOAc/hexane to afford the desired product with impurities. LCMS ESI (+) (M+H) m/z 338.

Step H: Preparation of 3-fluoro-5-((6-fluoro-4-iodo-5-oxo-6,7-dihydro-5H-cyclopenta[c]pyridin-1-yl)oxy)benzonitrile A solution of 3-fluoro-5-((6-fluoro-4-iodo-6,7-dihydrospiro[cyclopenta[c]pyridine-5,2'-[1,3]dioxolan]-1-yl)oxy)benzonitrile (22 mg, 0.05 mmol) in dichloromethane (1.0 mL) at 0° C. was treated with 70% aqueous perchloric acid (200 μL) and stirred at 25° C. for 2 h. The reaction mixture was cooled to 0° C., carefully quenched with a mixture of 5 mL of saturated NaHCO₃/10 mL of water and extracted with 3×15 mL CH₂Cl₂. The combined organics were rinsed with 10 mL of brine, dried with MgSO₄, filtered, and concentrated to dryness. Purification was achieved by chromatography on silica using 60-100% CH₂Cl₂/hexane to afford the desired product (6.0 mg) as a thin film. LCMS ESI (+) (M+H) m/z 413.

Step I: Preparation of 3-fluoro-5-((6-fluoro-5-oxo-4-(trifluoromethyl)-6,7-dihydro-5H-cyclopenta[c]pyridin-1-yl)oxy)benzonitrile A solution of 3-fluoro-5-[(6-fluoro-4-iodo-5-oxo-6,7-dihydrocyclopenta[c]pyridin-1-yl)oxy]benzonitrile (6.0 mg, 0.015 mmol) and copper (2.8 mg, 0.044 mmol) in DMF (0.5 mL) was sparged with nitrogen for 3 minutes. The reaction mixture was then with sulfonium diphenyl(trifluoromethyl)-, 1,1,1-trifluoromethanesulfonate (1:1) (12 mg, 0.03 mmol) under continuous nitrogen stream. The vessel was sealed and heated to 60° C. for 6 h. The reaction mixture was poured into 20 mL of water and extracted with 3×15 mL TBME. The combined organics were rinsed with 10 mL of brine, dried with MgSO₄, filtered, and concentrated to dryness. Purification was achieved by chromatography on silica using 5-25% EtOAc/hexane to afford 3-fluoro-5-((6-fluoro-5-oxo-4-(trifluoromethyl)-6,7-dihydro-5H-cyclopenta[c]pyridin-1-yl)oxy)benzonitrile as a thin film (4.3 mg, 83%). LCMS ESI (+) (M+H) m/z 355.

Step J: Preparation of 3-fluoro-5-(((5S,6R)-6-fluoro-5-hydroxy-4-(trifluoromethyl)-6,7-dihydro-5H-cyclopenta[c]pyridin-1-yl)oxy)benzonitrile (Compound 33)

A solution of 3-fluoro-5-[[6-fluoro-5-oxo-4-(trifluoromethyl)-6,7-dihydrocyclopenta[c]pyridin-1-yl]oxy]benzonitrile (4.3 mg, 0.012 mmol) in methanol (1.0 mL) at 0° C. was treated with sodium borohydride (0.5 mg, 0.012 mmol) and stirred at 0 C for 15 minutes. The reaction was then quenched by the addition of 1 mL of saturated NH₄Cl. Volatiles were removed by concentration under reduced pressure. The reaction mixture was poured into 20 mL of water and extracted with 3×10 mL EtOAc. The combined organics were rinsed with 10 mL of brine, dried with MgSO₄, filtered, and concentrated to dryness. Purification was achieved by chromatography on silica using 15-40% EtOAc/hexane to afford 3-fluoro-5-(((5S,6R)-6-fluoro-5-hydroxy-4-(trifluoromethyl)-6,7-dihydro-5H-cyclopenta[c]pyridin-1-yl)oxy)benzonitrile as a thin film (3.6 mg, 83%). Retention time HPLC (14 min)=5.66 minutes; LCMS ESI (+) (M+H) m/z 357; ¹H NMR (400 MHz, CDCl₃): δ 8.36-8.34 (m, 1H), 7.35-7.32 (m, 1H), 7.28 (ddd, 1H), 7.23 (dt, 1H), 5.53-5.35 (m, 2H), 3.40 (ddd, 1H), 3.22 (ddd, 1H), 2.73-2.68 (m, 1H).

Example 8: Synthesis of 5-(((5R,6S,7S)-5,6-difluoro-7-hydroxy-1-(trifluoromethyl)-6,7-dihydro-5H-cyclopenta[c]pyridin-4-yl)oxy)nicotinonitrile (Compound 34)

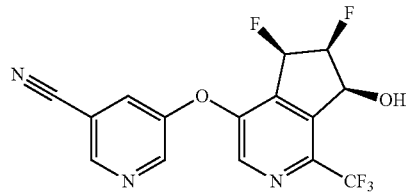 [SMILES: N#Cc1cncc(Oc2cnc(C(F)(F)F)c3c2[C@@H](F)[C@@H](F)[C@H]3O)c1]

Step A: Preparation of 5-(((5R,6S,7S)-5,6-difluoro-7-hydroxy-1-(trifluoromethyl)-6,7-dihydro-5H-cyclopenta[c]pyridin-4-yl)oxy)nicotinonitrile (Compound 34)

A solution of tetrahydrofuran (2.0 mL) and Water (4.0 mL) was sparged with nitrogen for 3 minutes. Sparging was ceased and to the solution were sequentially added under continuous nitrogen stream (5R,6S,7S)-4-[(5-bromo-3-pyridyl)oxy]-5,6-difluoro-1-(trifluoromethyl)-6,7-dihydro-5H-cyclopenta[c]pyridin-7-ol (50 mg, 0.12 mmol), [2-(2-aminophenyl)phenyl]-methylsulfonyloxy-palladium; ditert-butyl-[2-(2,4,6-triisopropylphenyl)phenyl]phosphane (19 mg, 0.024 mmol) and zinc cyanide (20 mg, 0.17 mmol). The vessel was sealed and heated to 40° C. for 3 h. An additional portion of [2-(2-aminophenyl)phenyl]-methylsulfonyloxy-palladium; ditert-butyl-[2-(2,4,6-triisopropylphenyl)phenyl]phosphane (19 mg, 0.024 mmol) and zinc cyanide (20 mg, 0.17 mmol) were added and the reaction mixture was heated to 65° C. for 18 h. The reaction mixture was poured into 10 mL of saturated NaHCO₃ and extracted with 3×10 mL EtOAc. The combined organics were rinsed with 10 mL of brine, dried with MgSO₄, filtered, and concentrated to dryness. Purification was achieved by chromatography on silica using 20-60% EtOAc/hexane to afford 5-(((5R,6S,7S)-5,6-difluoro-7-hydroxy-1-(trifluoromethyl)-6,7-dihydro-5H-cyclopenta[c]pyridin-4-yl)oxy)nicotinonitrile as a white solid (34.3 mg, 80%). Retention time HPLC (14 min)=2.55 minutes; LCMS ESI (+) (M+H) m/z 358; ¹H NMR (400 MHz, CDCl₃): δ 8.79 (dd, 1H), 8.71 (d, 1H), 8.41 (s, 1H), 7.67 (dd, 1H), 5.94 (dt, 1H), 5.53-5.46 (m, 1H), 5.21 (ddt, 1H), 2.73 (ddd, 1H).

Example 9: Synthesis of (5R,6S,7S)-4-(3,3-difluorocyclobutoxy)-5,6-difluoro-1-(trifluoromethyl)-6,7-dihydro-5H-cyclopenta[c]pyridin-7-ol (Compound 37)

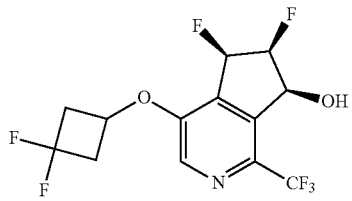 [SMILES: O[C@H]1c2c(C(F)(F)F)ncc(OC3CC(F)(F)C3)c2[C@@H](F)[C@H]1F]

Step A: Preparation of 4-(3,3-difluorocyclobutoxy)-1-(trifluoromethyl)-5,6-dihydrospiro[cyclopenta[c]pyridine-7,2'-[1,3]dioxolane]

A solution of 1'-(trifluoromethyl)spiro[1,3-dioxolane-2,7'-5,6-dihydrocyclopenta[c]pyridine]-4'-ol (1.9 g, 7.27 mmol), (3,3-difluorocyclobutyl) 4-methylbenzenesulfonate (2.86 g, 10.9 mmol), potassium iodide (1.81 g, 10.9 mmol) and potassium carbonate (2.0 g, 14.6 mmol) in acetonitrile (20 mL) was stirred at 100° C. overnight. The reaction mixture was concentrated to dryness, diluted with ethyl acetate (100 mL), washed with water (100 mL) and brine (20 mL). The organic phase was collected, dried over anhydrous $Na_2SO_4$, filtered and the filtrate was concentrated. Purification was achieved by chromatography on silica using 10-20% EtOAc/petroleum ether to afford 4'-(3,3-difluorocyclobutoxy)-1'-(trifluoromethyl)spiro[1,3-dioxolane-2,7'-5,6-dihydrocyclopenta[c]pyridine] as a white solid (1.00 g, 2.85 mmol, 39%). LCMS ESI (+) (M+H) m/z 352. (The Mitsunobu reaction can also be used to derivatize the 1'-(trifluoromethyl)spiro[1,3-dioxolane-2,7'-5,6-dihydrocyclopenta[c]pyridine]-4'-ol.)

Step B: Preparation of 5-bromo-4-(3,3-difluorocyclobutoxy)-1-(trifluoromethyl)-5,6-dihydrospiro[cyclopenta[c]pyridine-7,2'-[1,3]dioxolane]

A solution of 4'-(3,3-difluorocyclobutoxy)-1'-(trifluoromethyl)spiro[1,3-dioxolane-2,7'-5,6-dihydrocyclopenta[c]pyridine] (1.00 g, 2.85 mmol), 2,2'-azobisisobutyronitrile (94 mg, 0.57 mmol), $NaHCO_3$ (420 mg, 5.0 mmol) and 1-bromopyrrolidine-2,5-dione (1.27 g, 7.12 mmol) in 1,2-dichloroethane (20 mL) was sparged with nitrogen for 3 minutes. The vessel was sealed and heated to 80° C. for 1 h. The reaction mixture was poured into 30 mL of saturated aqueous $Na_2SO_3$ and extracted with 3×30 mL $CH_2Cl_2$. The combined organics were rinsed with 20 mL of brine, dried with $MgSO_4$, filtered, and concentrated to dryness. Purification was achieved by chromatography on silica using 5-25% EtOAc/hexane to afford 5'-bromo-4'-(3,3-difluorocyclobutoxy)-1'-(trifluoromethyl)spiro[1,3-dioxolane-2,7'-5,6-dihydrocyclopenta[c]pyridine] as an off-white solid (650 mg, 1.5 mmol, 53%). $^1H$ NMR (400 MHz, $CDCl_3$): δ 8.11 (s, 1H), 5.36-5.31 (m, 1H), 4.98-4.88 (m, 1H), 4.36-4.21 (m, 2H), 4.16-4.07 (m, 2H), 3.26-3.13 (m, 2H), 2.96-2.71 (m, 4H).

Step C: Preparation of 4-(3,3-difluorocyclobutoxy)-1-(trifluoromethyl)-5,6-dihydrospiro[cyclopenta[c]pyridine-7,2'-[1,3]dioxolan]-5-ol A solution of 5'-bromo-4'-(3,3-difluorocyclobutoxy)-1'-(trifluoromethyl)spiro[1,3-dioxolane-2,7'-5,6-dihydrocyclopenta[c]pyridine] (650 mg, 1.5 mmol) in a mixture of 1,2-dimethoxyethane (15 mL) and water (5 mL) was treated with silver carbonate (417 mg, 1.5 mmol) and stirred at 85° C. overnight. The mixture was diluted with EtOAc and filtered through celite. The filtrate was concentrated to remove the dimethoxyethane. The residue was re-suspended in 60 mL of 1:1 EtOAc/$H_2O$ and extracted with 3×15 mL EtOAc. The combined organics were rinsed with 10 mL of brine, dried with $MgSO_4$, filtered, and concentrated to dryness. Purification was achieved by chromatography on silica using 10-30% EtOAc/hexane to afford 4'-(3,3-difluorocyclobutoxy)-1'-(trifluoromethyl)spiro[1,3-dioxolane-2,7'-5,6-dihydrocyclopenta[c]pyridine]-5'-ol as a solid (280 mg, 50%). $^1H$ NMR (400 MHz, $CDCl_3$): δ 8.11 (s, 1H), 5.39-5.32 (m, 1H), 4.97-4.87 (m, 1H), 4.33-4.20 (m, 2H), 4.17-4.04 (m, 2H), 3.27-3.13 (m, 2H), 2.96-2.75 (m, 2H), 2.63 (dd, 1H), 2.53 (d, 1H), 2.28 (dd, 1H).

Step D: Preparation of 4-(3,3-difluorocyclobutoxy)-1-(trifluoromethyl)spiro[cyclopenta[c]pyridine-7,2'-[1,3]dioxolan]-5(6H)-one A solution of 4'-(3,3-difluorocyclobutoxy)-1'-(trifluoromethyl)spiro[1,3-dioxolane-2,7'-5,6-dihydrocyclopenta[c]pyridine]-5'-ol (280 mg, 0.76 mmol) in dichloromethane (10 mL) at 25° C. was treated with Dess-Martin periodinane (500 mg, 1.18 mmol). After 2 h, the reaction was quenched by the addition of 10 mL of saturated $Na_2S_2O_3$ solution and 10 mL of saturated $NaHCO_3$ solution. The resulting biphase stirred for 10 minutes. The reaction mixture was poured into 20 mL of water and extracted with 3×20 mL $CH_2Cl_2$. The combined organics were rinsed with 10 mL of brine, dried with $MgSO_4$, filtered, and concentrated to dryness to afford 4'-(3,3-difluorocyclobutoxy)-1'-(trifluoromethyl)spiro[1,3-dioxolane-2,7'-6H-cyclopenta[c]pyridine]-5'-one as a solid (270 mg, 97%) that was used without further purification. LCMS ESI (+) (M+H) m/z 366.

Step E: Preparation of 4-(3,3-difluorocyclobutoxy)-6-fluoro-1-(trifluoromethyl)spiro[cyclopenta[c]pyridine-7,2'-[1,3]dioxolan]-5(6H)-one A solution of 4'-(3,3-difluorocyclobutoxy)-1'-(trifluoromethyl)spiro[1,3-dioxolane-2,7'-6H-cyclopenta[c]pyridine]-5'-one (270 mg, 0.74 mmol) and triethylamine (410 µL, 3 mmol) in dichloromethane (10 mL) at 0° C. was treated with tert-butyl-dimethyl-(trifluoromethylsulfonyl)silane (480 µL, 2.2 mmol) and stirred at 0° C. for 30 minutes. The reaction mixture was left to stir overnight at room temperature. The reaction mixture was poured into 10 mL of saturated $NaHCO_3$, stirred for 10 minutes, and extracted with 3×15 mL $CH_2Cl_2$. The combined organics were rinsed with 10 mL of brine, dried with $MgSO_4$, filtered, and concentrated to dryness. The unpurified residue was dissolved in acetonitrile (10 mL) and treated with Selectfluor® (322 mg, 0.92 mmol). The reaction stirred for 6 h at room temperature. Volatiles were removed by concentration under reduced pressure. The reaction mixture was poured into 30 mL of water and extracted with 3×15 mL EtOAc. The combined organics were rinsed with 10 mL of brine, dried with $MgSO_4$, filtered, and concentrated to dryness. Purification was achieved by chromatography on silica using 5-20% EtOAc/hexane to afford 4'-(3,3-difluorocyclobutoxy)-6'-fluoro-1'-(trifluoromethyl)spiro[1,3-dioxolane-2,7'-6H-cyclopenta[c]pyridine]-5'-one as a white solid (180 mg, 56%). $^1H$ NMR (400 MHz, CDCl$_3$): δ 8.35 (s, 1H), 5.13 (d, 1H), 5.01-4.91 (m, 1H), 4.47-4.38 (m, 1H), 4.38-4.26 (m, 3H), 3.30-3.14 (m, 2H), 3.04-2.86 (m, 2H).

Step F: Preparation of (5R,6R)-4-(3,3-difluorocyclobutoxy)-6-fluoro-1-(trifluoromethyl)-5,6-dihydrospiro[cyclopenta[c]pyridine-7,2'-[1,3]dioxolan]-5-ol A solution of 4'-(3,3-difluorocyclobutoxy)-6'-fluoro-1'-(trifluoromethyl)spiro[1,3-dioxolane-2,7'-6H-cyclopenta[c]pyridine]-5'-one (180 mg, 0.47 mmol) in dichloromethane (10 mL) was cooled to 0° C. and sparged with nitrogen for 5 minutes. During this time formic acid (53.1 µL, 1.4 mmol) and triethylamine (98.2 τL, 0.70 mmol) were sequentially added. Once sparging was complete, RuCl(p-cymene)[(S,S)-Ts-DPEN] (15 mg, 0.023 mmol) was added under a continuous stream of nitrogen. The reaction vessel was sealed and put into the refrigerator to react overnight. Volatiles were removed by concentration under reduced pressure. Purification was achieved by chromatography on silica using 10-30% EtOAc/hexane to afford (5'R,6'R)-4'-(3,3-difluorocyclobutoxy)-6'-fluoro-1'-(trifluoromethyl)spiro[1,3-dioxolane-2,7'-5,6-dihydrocyclopenta[c]pyridine]-5'-ol as a clear solid (152 mg, 84%). LCMS ESI (+) (M+H) m/z 386.

Step G: Preparation of (5S,6R)-4-(3,3-difluorocyclobutoxy)-6-fluoro-1-(trifluoromethyl)-5,6-dihydrospiro[cyclopenta[c]pyridine-7,2'-[1,3]dioxolan]-5-yl 4-nitrobenzoate A solution of (5'R,6'R)-4'-(3,3-difluorocyclobutoxy)-6'-fluoro-1'-(trifluoromethyl)spiro[1,3-dioxolane-2,7'-5,6-dihydrocyclopenta[c]pyridine]-5'-ol (124 mg, 0.32 mmol), polymer supported triphenylphosphine (~2.06 mmol/g, 627 mg, 1.29 mmol), and 4-nitrobenzoic acid (216 mg, 1.29 mmol) in tetrahydrofuran (3.3 mL) was treated with diisopropyl azodicarboxylate (248 µL, 1.26 mmol) and stirred at 25° C. for 2 h. The reaction mixture was filtered and the filter cake rinsed with 30 mL EtOAc. The filtrate was concentrated and purified by chromatography on silica using 10-25% EtOAc/hexane to afford (5S,6R)-4-(3,3-difluorocyclobutoxy)-6-fluoro-1-(trifluoromethyl)-5,6-dihydrospiro[cyclopenta[c]pyridine-7,2'-[1,3]dioxolan]-5-yl 4-nitrobenzoate as a white solid (160 mg, 93%). LCMS ESI (+) (M+H) m/z 535.

Step H: Preparation of (5S,6R)-4-(3,3-difluorocyclobutoxy)-6-fluoro-1-(trifluoromethyl)-5,6-dihydrospiro[cyclopenta[c]pyridine-7,2'-[1,3]dioxolan]-5-ol A solution of [(5'S,6'R)-4'-(3,3-difluorocyclobutoxy)-6'-fluoro-1'-(trifluoromethyl)spiro[1,3-dioxolane-2,7'-5,6-dihydrocyclopenta[c]pyridine]-5'-yl] 4-nitrobenzoate (194 mg, 0.36 mmol) in tetrahydrofuran (7 mL) at 25° C. was treated with a solution of freshly prepared hydroxylithium hydrate (16.8 mg, 0.4 mmol) in water (2.1 mL) and stirred at 25° C. for 30 minutes. An additional portion of hydroxylithium hydrate (8.4 mg, 0.20 mmol) in water (1.0 mL) was added and the reaction mixture stirred for another 30 minutes. Saturated NH$_4$Cl (0.5 mL) was added and volatiles were removed under reduced pressure. The reaction mixture was poured into 10 mL of saturated NaHCO$_3$ and extracted with 3×15 mL EtOAc. The combined organics were rinsed with 10 mL of brine, dried with MgSO$_4$, filtered, and concentrated to dryness. Purification was achieved by chromatography on silica using 10-35% EtOAc/hexane to afford (5S,6R)-4-(3,3-difluorocyclobutoxy)-6-fluoro-1-(trifluoromethyl)-5,6-dihydrospiro[cyclopenta[c]pyridine-7,2'-[1,3]dioxolan]-5-ol as a white solid (74 mg, 53%). LCMS ESI (+) (M+H) m/z 386.

Step I: Preparation of (5R,6S)-4-(3,3-difluorocyclobutoxy)-5,6-difluoro-1-(trifluoromethyl)-5,6-dihydrospiro[cyclopenta[c]pyridine-7,2'-[1,3]dioxolane]

A solution of (5'S,6'R)-4'-(3,3-difluorocyclobutoxy)-6'-fluoro-1'-(trifluoromethyl)spiro[1,3-dioxolane-2,7'-5,6-dihydrocyclopenta[c]pyridine]-5'-ol (74 mg, 0.19 mmol) in dichloromethane (3.8 mL) at 25° C. was treated with diethylaminosulfur trifluoride (51 µL, 0.38 mmol). The reaction mixture was allowed to stir for 30 minutes. The reaction mixture was quenched by the careful addition of 1 mL of aqueous saturated NaHCO$_3$. The resulting mixture stirred for 30 minutes, poured into 20 mL of water and extracted with 3×15 mL CH$_2$Cl$_2$. The combined organics were rinsed with 10 mL of brine, dried with MgSO$_4$, filtered, and concentrated to dryness. Purification was achieved by chromatography on silica using 5-25% EtOAc/hexane to afford (5R,6S)-4-(3,3-difluorocyclobutoxy)-5,6-difluoro-1-(trifluoromethyl)-5,6-dihydrospiro[cyclopenta[c]pyridine-7,2'-[1,3]dioxolane] as a white solid (72 mg, 97%). LCMS ESI (+) (M+H) m/z 388.

Step J: Preparation of (5R,6S,7S)-4-(3,3-difluorocyclobutoxy)-5,6-difluoro-1-(trifluoromethyl)-6,7-dihydro-5H-cyclopenta[c]pyridin-7-ol (Compound 37)

A solution of (5'R,6'S)-4'-(3,3-difluorocyclobutoxy)-5',6'-difluoro-1'-(trifluoromethyl)spiro[1,3-dioxolane-2,7'-5,6-dihydrocyclopenta[c]pyridine] (72 mg, 0.19 mmol) in dichloromethane (4.0 mL) at 0° C. was treated with 70% aqueous perchloric acid (800 µL). The reaction mixture was heated to 44° C. for 5 h. The reaction mixture was cooled to 0° C., carefully quenched with a mixture of 10 mL of saturated NaHCO$_3$/10 mL of water and extracted with 3×15 mL CH$_2$Cl$_2$. The combined organics were rinsed with 10 mL of brine, dried with MgSO$_4$, filtered, and concentrated to dryness. The product was used immediately without further purification by dissolving in 2 mL of MeOH, cooling to 0° C., and treating with sodium borohydride (7.0 mg, 0.19 mmol). The reaction stirred for 15 min and was then quenched by the addition of 1 mL of saturated NH$_4$Cl. Volatiles were removed by concentration under reduced pressure. The reaction mixture was poured into 20 mL of water and extracted with 3×15 mL EtOAc. The combined organics were rinsed with 10 mL of brine, dried with MgSO$_4$, filtered, and concentrated to dryness. Purification was achieved by chromatography on silica using 10-40% EtOAc/hexane to afford (5R,6S,7S)-4-(3,3-difluorocyclobutoxy)-5,6-difluoro-1-(trifluoromethyl)-6,7-dihydro-5H-cyclopenta[c]pyridin-7-ol as a white solid (53 mg, 83%). Retention time HPLC (14 min)=3.37 minutes; LCMS ESI (+) (M+H) m/z 346; $^1$H NMR (400 MHz, CDCl$_3$): δ 8.24 (s, 1H), 5.95 (ddd, 1H), 5.47-5.41 (m, 1H), 5.07 (ddt, 1H), 4.97-4.88 (m, 1H), 3.30-3.15 (m, 2H), 2.99-2.79 (m, 2H), 2.54-2.49 (m, 1H).

Example 10: Synthesis of 3-fluoro-5-((5-hydroxy-4-(trifluoromethyl)-6,7-dihydro-5H-cyclopenta[d]pyridazin-1-yl)oxy)benzonitrile (Compound 42)

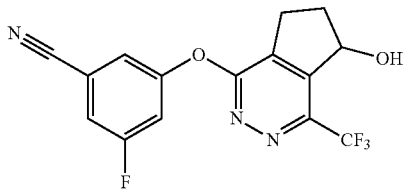 [SMILES: N#Cc1cc(F)cc(Oc2nnc(C(F)(F)F)c3c2CCC3O)c1]

Step A: Preparation of 1,4-dichloro-6,7-dihydro-5H-cyclopenta[d]pyridazine

A solution of 3,6-dichloro-1,2,4,5-tetrazine (2.5 g, 16.6 mmol) in dichloromethane (100 mL) at 0° C. was treated 1-(cyclopenten-1-yl)pyrrolidine (2.42 mL, 16.6 mmol) by dropwise addition over 15 minutes. After 15 minutes following the addition of the enamine, the reaction was quenched by the addition of 30 mL of 10% aqueous citric acid solution and 30 mL of water. The reaction was removed from the ice bath and vigorously stirred for 5 minutes. The reaction mixture extracted with 3×30 mL CH$_2$Cl$_2$. The combined organics were rinsed with 30 mL of brine, dried with MgSO$_4$, filtered, and concentrated to dryness. Purification was achieved by chromatography on silica using 5-20% EtOAc/hexane to afford 1,4-dichloro-6,7-dihydro-5H-cyclopenta[d]pyridazine as a white solid (1.66 g, 53%). LCMS ESI (+) (M+H) m/z 189/191/193.

Step B: Preparation of 5-bromo-1,4-dichloro-6,7-dihydro-5H-cyclopenta[d]pyridazine A solution of 1,4-dichloro-6,7-dihydro-5H-cyclopenta[d]pyridazine (402 mg, 2.1 mmol), 2,2'-azobisisobutyronitrile (35 mg, 0.21 mmol) and N-bromosuccinimide (397 mg, 2.23 mmol) in 1,2-dichloroethane (21.3 mL) was sparged with nitrogen for 3 minutes. The vessel was sealed and heated to 80° C. for 2.5 h. Volatiles were removed by concentration under reduced pressure. The reaction mixture was poured into 20 mL of 0.5 M NaOH and extracted with 3×15 mL CH$_2$Cl$_2$. The combined organics were rinsed with 10 mL of brine, dried with MgSO$_4$, filtered, and concentrated to dryness. The product was used without further purification. LCMS ESI (+) (M+H) m/z 267/269/271.

Step C: Preparation of 1,4-dichloro-6,7-dihydro-5H-cyclopenta[d]pyridazin-5-ol A solution of unpurified 5-bromo-1,4-dichloro-6,7-dihydro-5H-cyclopenta[d]pyridazine (563 mg, 2.1 mmol) in 1,2-dimethoxyethane (11.4 mL) and water (0.6 mL) at 25° C. was treated with silver(I) perchlorate hydrate (713 mg, 3.15 mmol) and stirred at 60° C. for 2.5 h. Volatiles were removed by concentration under reduced pressure. The residue was suspended in 30 mL of EtOAc and filtered through a pad of celite. The filter cake was rinsed with 50 mL of EtOAc. The filtrate was poured into 30 mL of water and extracted with 3×20 mL EtOAc. The combined organics were rinsed with 10 mL of brine, dried with MgSO$_4$, filtered, and concentrated to dryness. Purification was achieved by chromatography on silica using 20-55% EtOAc/hexane to afford 1,4-dichloro-6,7-dihydro-5H-cyclopenta[d]pyridazin-5-ol as a solid (268 mg, 62%). LCMS ESI (+) (M+H) m/z 205/207/209.

Step D: Preparation of 1,4-dichloro-6,7-dihydro-5H-cyclopenta[d]pyridazin-5-one A solution of 1,4-dichloro-6,7-dihydro-5H-cyclopenta[d]pyridazin-5-ol (268.0 mg, 1.31 mmol) in dichloromethane (13 mL) at 25° C. was treated with Dess-Martin periodinane (720.7 mg, 1.70 mmol). After stirring for another 30 min, the reaction was quenched by the addition of 10 mL of saturated Na$_2$S$_2$O$_3$ solution and 10 mL of saturated NaHCO$_3$ solution. The resulting biphase stirred for 10 min. The reaction mixture was poured into 10 mL of water and extracted with 3×20 mL CH$_2$Cl$_2$. The combined organics were rinsed with 10 mL of brine, dried with MgSO$_4$, filtered, and concentrated to dryness. The product was used without further purification. LCMS ESI (+) (M+H) m/z 203/205/207.

Step E: Preparation of 1,4-diiodo-6,7-dihydro-5H-cyclopenta[d]pyridazin-5-one A solution of 1,4-dichloro-6,7-dihydrocyclopenta[d]pyridazin-5-one (31.0 mg, 0.15 mmol) in acetone (1.0 mL) was treated with sodium iodide (57.2 mg, 0.38 mmol) and heated by microwave irradiation to 120° C. over 1.5 h. Volatiles were removed by concentration under reduced pressure. The reaction mixture was poured into 20 mL of water and extracted with 3×10 mL EtOAc. The combined organics were rinsed with 10 mL of brine, dried with MgSO$_4$, filtered, and concentrated to dryness. Purification was achieved by chromatography on silica using 15-45% EtOAc/hexanes to afford 1,4-diiodo-6,7-dihydro-5H-cyclopenta[d]pyridazin-5-one as a yellow solid (32.7 mg, 55%). LCMS ESI (+) (M+H) m/z 387.

Step F: Preparation of 1,4-diiodo-6,7-dihydrospiro[cyclopenta[d]pyridazine-5,2'-[1,3]dioxolane]

Trimethylsilyl trifluoromethanesulfonate (3.7 µL, 0.020 mmol) was added to a solution of 1,4-diiodo-6,7-dihydrocyclopenta[d]pyridazin-5-one (15.6 mg, 0.040 mmol) and trimethyl(2-trimethylsilyloxyethoxy)silane (39.7 µL, 0.16 mmol) in dichloromethane (0.8 mL) cooled in an ice bath. The ice bath was removed and the reaction stirred at ambient temperature overnight. The reaction mixture was quenched by adding triethylamine (22.5 µL, 0.16 mmol), stirring for 10 min, and then concentrating. The residue was dissolved in a mixture of 10 mL of CH$_2$Cl$_2$ and 10 mL water and the layers separated. The aqueous layer was extracted further (2×10 mL of CH$_2$Cl$_2$), the combined organics washed with brine (1×10 mL), dried over MgSO$_4$, filtered, and concentrated to dryness. NMR indicates the desired product in reasonable purity. Used without further purification. LCMS ESI (+) (M+H) m/z 431.

Step G: Preparation of 3-fluoro-5-((4-iodo-6,7-dihydrospiro[cyclopenta[d]pyridazine-5,2'-[1,3]dioxolan]-1-yl)oxy)benzonitrile A solution of 1',4'-diiodospiro[1,3-dioxolane-2,5'-6,7-dihydrocyclopenta[d]pyridazine] (11.0 mg, 0.026 mmol) and 3-fluoro-5-hydroxy-benzonitrile (3.5 mg, 0.026 mmol) in DMF (0.5 mL) was treated with cesium bicarbonate (7.4 mg, 0.038 mmol) and stirred at 90° C. overnight. The reaction mixture was poured into 20 mL of water and extracted with 3×10 mL TBME. The combined organics were rinsed with 10 mL of brine, dried with MgSO$_4$, filtered, and concentrated to dryness. Purification was achieved by chromatography on silica using 15-40% EtOAc/hexane to afford 3-fluoro-5-((4-iodo-6,7-dihydrospiro[cyclopenta[d]pyridazine-5,2'-[1,3]dioxolan]-1-yl)oxy)benzonitrile as a white solid (6.0 mg, 53%). LCMS ESI (+) (M+H) m/z 440.

Step H: Preparation of 3-fluoro-5-((4-(trifluoromethyl)-6,7-dihydrospiro[cyclopenta[d]pyridazine-5, 2'-[1,3]dioxolan]-1-yl)oxy)benzonitrile A solution of 3-fluoro-5-(4'-iodospiro[1,3-dioxolane-2,5'-6,7-dihydrocyclopenta[d]pyridazine]-1'-yl)oxy-benzonitrile (6.0 mg, 0.014 mmol) in DMF (0.6 mL) was sparged with nitrogen for 3 minutes. The reaction mixture was treated sequentially with copper (2.6 mg, 0.041 mmol) and sulfonium diphenyl(trifluoromethyl)-, 1,1,1-trifluoromethanesulfonate (1:1) (11 mg, 0.027 mmol) under continuous nitrogen stream. The vessel was sealed and heated to 60° C. overnight. The reaction mixture was poured into 20 mL of water and extracted with 3×10 mL TBME. The combined organics were rinsed with 10 mL of brine, dried with MgSO$_4$, filtered, and concentrated to dryness. Purification was achieved by chromatography on silica using 15-45% EtOAc/hexane to afford 3-fluoro-5-((4-(trifluoromethyl)-6,7-dihydrospiro[cyclopenta[d]pyridazine-5,2'-[1,3]dioxolan]-1-yl)oxy)benzonitrile as a thin film (4.9 mg, 94%). LCMS ESI (+) (M+H) m/z 382.

Step I: Preparation of 3-fluoro-5-((5-hydroxy-4-(trifluoromethyl)-6,7-dihydro-5H-cyclopenta[d]pyridazin-1-yl)oxy)benzonitrile (Compound 42)

A solution of 3-fluoro-5-[1'-(trifluoromethyl)spiro[1,3-dioxolane-2,7'-5,6-dihydrocyclopenta[d]pyridazine]-4'-yl]oxy-benzonitrile (4.9 mg, 0.013 mmol) in dichloromethane (1.0 mL) at 0° C. was treated with 70% aqueous perchloric acid (200 µL) and stirred at 25° C. for 2 h. The reaction mixture was cooled to 0° C., carefully quenched with a mixture of 2 mL of saturated NaHCO$_3$/4 mL of water, and extracted with 3×10 mL CH$_2$Cl$_2$. The combined organics were rinsed with 10 mL of brine, dried with MgSO$_4$, filtered, and concentrated to dryness. The product was used immediately without further purification by dissolving in 1 mL of MeOH, cooling to 0° C., and treating with sodium borohydride (0.5 mg, 0.013 mmol). The reaction stirred for 15 minutes and was then quenched by the addition of 0.5 mL of saturated NH$_4$Cl. Volatiles were removed by concentration under reduced pressure. The reaction mixture was poured into 20 mL of water and extracted with 3×10 mL EtOAc. The combined organics were rinsed with 10 mL of brine, dried with MgSO$_4$, filtered, and concentrated to dryness. Purification was achieved by chromatography on silica using 20-50% EtOAc/hexane to afford 3-fluoro-5-((5-hydroxy-4-(trifluoromethyl)-6,7-dihydro-5H-cyclopenta[d]pyridazin-1-yl)oxy)benzonitrile as a thin film (3.3 mg, 76%). Retention time HPLC (14 min)=4.76 minutes; LCMS ESI (+) (M+H) m/z 340; $^1$H NMR (400 MHz, CDCl$_3$): δ 7.43-7.41 (m, 1H), 7.33 (dt, 1H), 7.33-7.29 (m, 1H), 5.67-5.62 (m, 1H), 3.36-3.26 (m, 1H), 3.05 (ddd, 1H), 2.63-2.53 (m, 1H), 2.40-2.30 (m, 2H).

Example 11: Synthesis of N-(3-Chlorophenyl-4,6-t2)-4-nitrobenzo[c][1,2,5]oxadiazol-5-amine

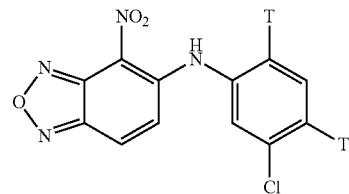

Step A: Synthesis of 3-chlorobenzene-4,6-t$_2$-amine

3-Chloro-4,6-diiodoaniline (100 mg) was dissolved in methanol (3 mL) and added with triethylamine (0.1 mL) and submitted for overnight tritiation using 50 Ci of tritium gas, at room temperature. Labile tritium was removed by dissolving the crude reaction mixture in methanol (3 mL) and bringing to dryness under vacuum. Labile removal was done in duplicate. The crude tritiated material was purified by preparative TLC (Silica gel, 1000µ) using hexane:ethyl acetate:AcOH (85:14:1). The product band was eluted with ethyl acetate to give 3-chlorobenzen-4,6-t$_2$-amine (yield=600 mCi, radiochemical purity was >98%).

Step B: Synthesis of N-(3-Chlorophenyl-4,6-t2)-4-nitrobenzo[c][1,2,5]oxadiazol-5-amine A stirred mixture of 5-chloro-4-nitro-2,1,3-benzoxadiazole (20 mg, 0.1 mmol), 3-chlorobenzen-4,6-t$_2$-amine (600 mCi) and Cs$_2$CO$_3$ (65 mg, 0.20 mmol) in DMF (1 mL) was heated at 60° C. for 1 h. After cooling, the reaction mixture was partitioned between EtOAc and water. The aqueous layer was extracted with EtOAc. The combined organic layers were washed with water and brine, dried and concentrated. The residue was purified by preparative HPLC on an ACE-5 C18 Semi-prep column, 250×10 mm, 100 Å. Elution was carried out isocratically using 0.1% TFA in water/Acetonitrile (35:65) to give the title compound (478 mCi, 80%).

Example 12: HIF-2α Scintillation Proximity Assay (SPA)

The total assay volume was about 100 µL in the following configuration: 2 µL compound in 100% DMSO, 88 µL buffer with protein and probe and 10 µL of SPA beads. The compound was diluted in a master plate consisting of a 10-point dose response with a 3-fold compound dilution from 100 µM to 5 nM. Assays were run on a 96-well plate in which one column, designated as the high signal control, contained DMSO with no compound and another column, designated as the low signal control, contained no protein. Prior to plating out of compound, a buffer solution, consisting of 25 mM TRIS pH 7.5 (Sigma), 150 mM NaCl (Sigma), 15% Glycerol (Sigma), 0.15% BSA (Sigma), 0.001% Tween-20 (Sigma), 150 nM N-(3-Chlorophenyl-4,6-t$_2$)-4-nitrobenzo[c][1,2,5]oxadiazol-5-amine and 100 nM HIF-2α HIS TAG-PASB Domain, was made and allowed to equilibrate for 30 minutes. Compounds that were to be tested were then plated in to a 96-well white clear bottom Isoplate-96 SPA plate (Perkin Elmer). To the compounds was added 88 µL of the buffer solution, then the plate covered with a plastic cover and aluminum foil, placed onto a shaker and equilibrated for 1 hour. After equilibration, 10 μL of a 2 mg/mL solution of YSi Cu His tagged SPA beads (Perkin Elmer) were then added to each well of the plate, covered and equilibrated for another 2 hours. The plates were then removed from the shaker, placed into a 1450 LSC and luminescence counter MicroBeta Trilux (Perkin Elmer) to measure the extent of probe displacement. The percent inhibition was determined and $IC_{50}$ values were calculated using the Dotmatics system based on the following equation: % inhibition=[(high control−sample)/(high control−low control)]×100.

Example 13: VEGF ELISA Assay

Figure 3:
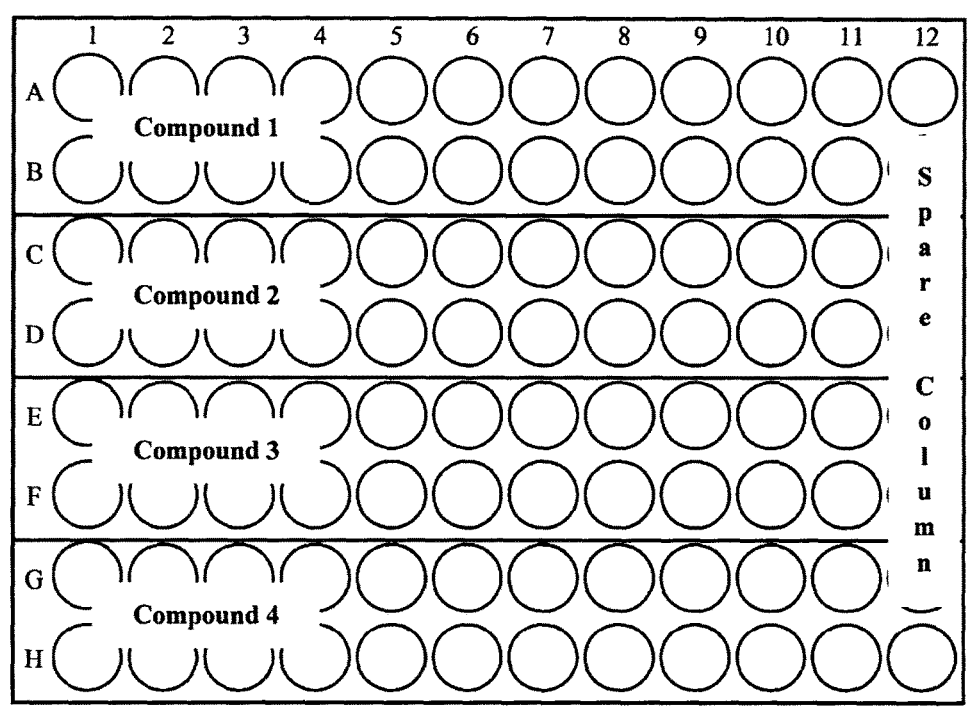
FIG. 3 depicts a 96-well plate layout of an ELISA assay.

About 7500 786-O cells in 180 μL of growth medium were seeded into each well of a 96-well, white, clear bottom plate (07-200-566, Fisher Scientific) on day one in the layout presented in FIG. 3. Four hours later, serial dilutions of 10× compound stocks were made in growth medium from 500× DMSO stocks, and 20 μL of those 10× stocks were added to each well to make final concentrations as follows (μM): 20, 6.67, 2.22, 0.74, 0.25, 0.082, 0.027, 0.009, 0.003, 0.001, and 0. Each concentration was plated in duplicate. About 20 hours later, medium was removed by suction and each well was supplied with 180 μL of growth medium. About 20 μl freshly-made 10× compound stocks were added to each well. About 24 hours later, cell culture medium was removed and the VEGF concentration determined using an ELISA kit purchased from R&D systems, following the manufacturer's suggested method. The $EC_{50}$ was calculated by GraphPad Prism using the dose-response-inhibition (four parameter) equation. The cell-seeded plate was then subjected to Cell-Titer-Glo luminescence cell viability assay (Promega) by adding 50 μL of Celltiter Glo reagent into each well and shaking the plate for 8 minutes at 550 rpm (Thermomixer R, Eppendorf) then the luminescence signal immediately read in a plate reader (3 second delay, 0.5 second/well integration time, Synergy 2 multi Detection Microplate reader).

Example 14: Luciferase Assay

Figure 4:
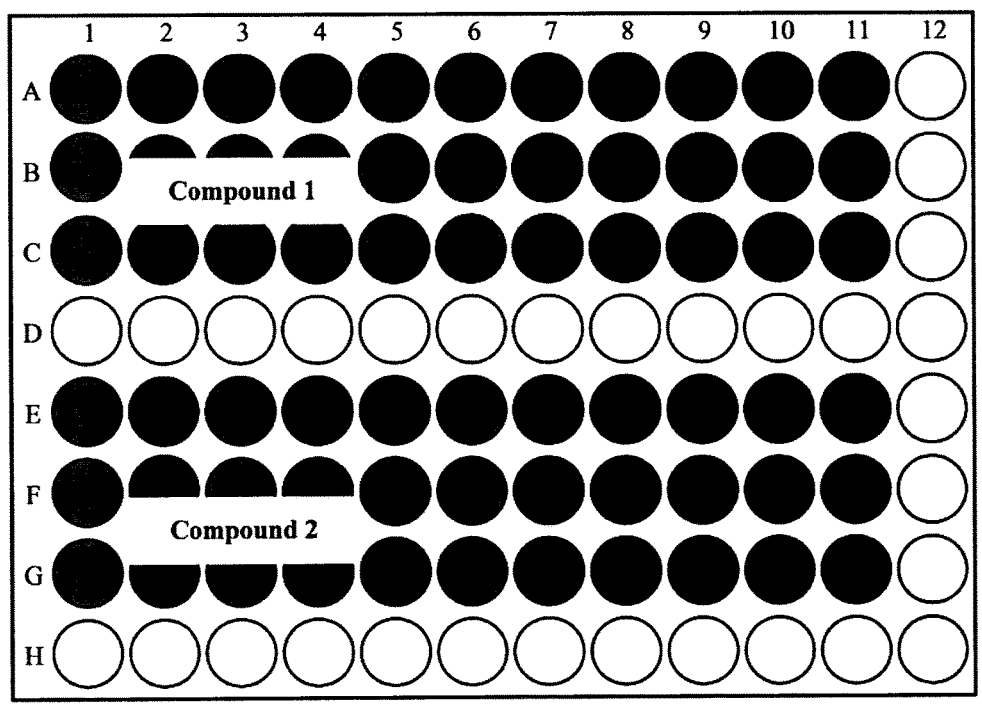
FIG. 4 depicts a 96-well plate layout of a luciferase assay.

786-O-Hif-Luc single clone cells were obtained by infecting 786-O cells (ATCC® CRL-1932™) with commercial lentivirus that delivers a luciferase gene driven by multiple HIF responsive elements (Cignal Lenti HIF Reporter (luc): CLS-007L, Qiagen) at Multiplicity of Infection (MOI) of 25 for 24 hours. The cells were replenished with fresh medium (Dulbecco's Modified Eagle's Medium (DMEM, D5796, Sigma) supplemented with 10% FBS (F6178, Sigma), 100 units penicillin and 100 μg streptomycin/mL (P4333, Sigma)) for another 24 hours. A pool of infected cells were then selected against 2 μg/mL of puromycin (P8833, Sigma) for 10 days followed by limited dilution to select single clones. The clones were tested for their response to HIF-2 inhibitors and the ones that showed the biggest dynamic range (786-O-Hif-Luc) were expanded and used for the luciferase assay. For the luciferase assay, about 7500 786-O-Hif-Luc cells in 90 μL growth medium were seeded into each well of a 96-well white opaque plate (08-771-26, Fisher scientific) a day before treatment with the layout presented in FIG. 4. On treatment day, serial dilutions of 10× compound stocks were made in growth medium from 500× DMSO stocks, and 10 μL of the 10× stocks were added to each well to make final concentrations as follows (μM): 20, 6.67, 2.22, 0.74, 0.25, 0.08, 0.027, 0.009, 0.003, 0.001, and 0. Each concentration was tested in triplicate. After about 24 hours, luciferase activity was determined using ONE-Glo Luciferase Assay Reagent (E6110, Promega) following the manufacturer's recommended procedure. $EC_{50}$ were calculated using Dotmatics software.

Table 2 shows biological activities of selected compounds in Luciferase, VEGF ELISA and Scintillation Proximity assays. Compound numbers correspond to the numbers and structures provided in Table 1 and Examples 1-10.

TABLE 2

|  | Less than 50 nM (++++) | 50 nM to 249 nM (+++) | 250 nM to 1000 nM (++) | Greater than 1000 nM (+) |
| --- | --- | --- | --- | --- |
| Scintillation Proximity Assay $IC_{50}$ (nM) | 1, 2, 3, 8, 9, 14, 20, 22, 23, 34, 37, 40 | 4, 13, 17, 24, 27 | 7, 12, 21, 25, 36 | 5, 6, 10, 11, 16, 18, 19, 26, 28, 29, 30, 31, 32, 33, 35, 38, 39, 42 |
| Mean VEGF ELISA $EC_{50}$ (nM) | 1, 14, 22, 37 | 3, 34 | 9 |  |
| Mean Luciferase $EC_{50}$ (nM) | 1, 3, 14, 22, 37, 40 | 9, 13, 23, 27, 34 | 2, 4, 7, 8 | 6, 10, 12, 17, 20, 21, 42 |

Example 15: In Vivo Efficacy Studies

Figure 2:
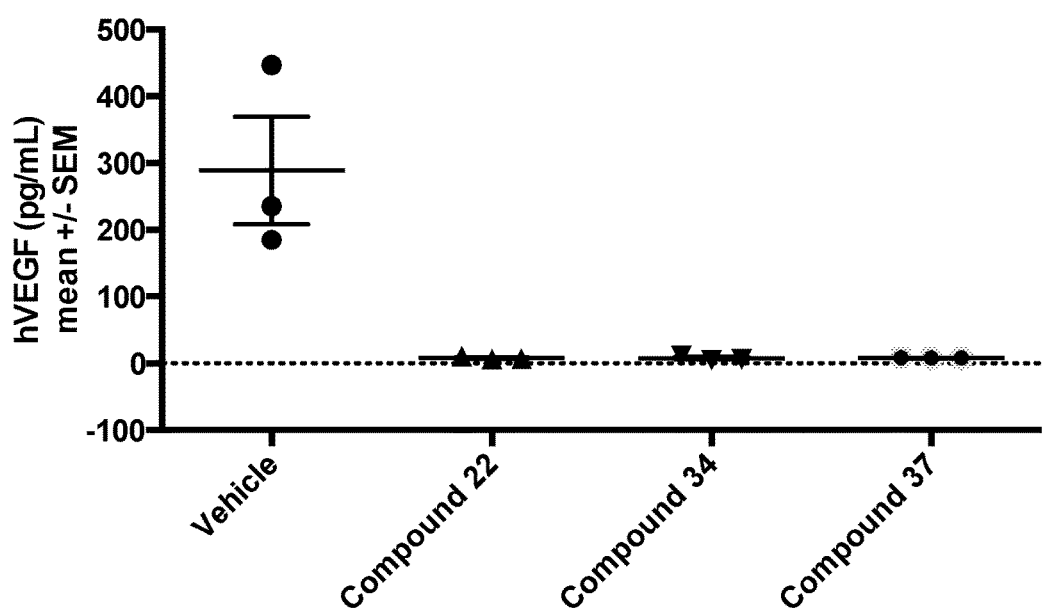
FIG. 2 shows decreased levels of human VEGF in the plasma of 786-0 xenograft bearing mice treated with compound 22, 34, or 37.

PK/PD studies for Compounds 22, 34 and 37: All compounds were formulated with 10% absolute ethanol, 30% PEG400, 60% water containing 0.5% methylcellulose and 0.5% Tween80®. About 5×10⁶ 786-0 renal cell carcinoma cells (ATCC® CRL-1932™) in PBS and Matrigel (1:1 in volume) were inoculated subcutaneously in the right flanks of 16 SCID/Biege mice at 6-7 weeks of age for tumor xenograft development. When the xenografts reached about 750 mm³ in size, the tumor bearing mice were randomly grouped into four groups (n=3). The animals were treated with either vehicle or test compound (Compound 22, Compound 34 or Compound 37) as a single agent at 10 mg/kg by oral gavage for six doses in total at a 12 hour dosing interval. All animals were sacrificed at 12 hours post last dose. Tumors and plasma were collected from each animal. Total RNA was extracted from the tumors, and the expression levels of putative HIF-2α regulated genes were determined by qRT-PCR. HIF-2α target genes VEGF, PAI-1 and CCND1 displayed a significant reduction in response to compound treatment as depicted in FIG. 1. The level of human VEGFA was assessed using an ELISA assay. As shown in FIG. 2, compound treatment led to a significant reduction in human VEGFA in the plasma, reflecting the inhibition of HIF-2α in the 786-O tumor xenografts.

What is claimed is:
1. A compound of Formula I-C:

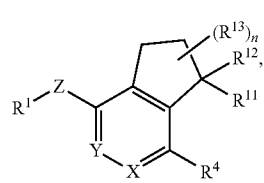

Formula I-C or a pharmaceutically acceptable salt or prodrug thereof, wherein:
X is $CR^5$ or N;
Y is $CR^6$ or N, wherein at least one of X and Y is N;

Z is —O—, —S—, —S(O)—, —S(O)₂—, —C(HR⁷)—, —N(R⁸)—, or C₁-C₃ alkenylene;

R¹ is alkyl, heteroalkyl, cycloalkyl, heterocycloalkyl, aryl or heteroaryl;

R⁴ is nitro, halo, cyano, alkyl, cycloalkyl, heteroaryl, carboxyl, sulfinyl, sulfonamidyl, sulfonyl, sulfoximinyl or fluoroalkylsulfonyl;

R⁵, R⁶, R⁷ and R⁸ are independently hydrogen, halo, hydroxy, cyano, alkyl or alkoxy;

R¹¹ is halo, hydroxy, alkoxy or amino;

R¹² is hydrogen, alkyl, alkenyl or alkynyl; or R¹¹ and R¹² in combination form =O, =CH₂ or =N(OH);

each of R¹³ is independently selected from the group consisting of hydrogen, fluoro, chloro, hydroxy, alkyl and heteroalkyl; and two R¹³s and the carbon atom(s) to which they are attached may form a 3- to 8-membered cycloalkyl or heterocycloalkyl moiety; and n is 0, 1, 2, 3 or 4.

2. The compound of claim 1, wherein R¹² is hydrogen, R¹³ is fluoro and n is 1, 2, or 3.

3. The compound of claim 1, represented by a formula selected from:

Formula I-H

Formula I-I

Formula I-J

Formula I-K

4. The compound of claim 1, wherein R¹ is monocyclic cycloalkyl, monocyclic aryl, monocyclic heteroaryl or bicyclic heteroaryl.

5. The compound of claim 4, wherein R¹ is cyclobutyl, phenyl or pyridyl.

6. The compound of claim 1, wherein R¹ is substituted with at least one substituent selected from the group consisting of halo, hydroxy, C₁-C₄ alkyl, C₁-C₄ alkoxy and cyano.

7. The compound of claim 6, wherein R¹ is substituted with one to six fluorines.

8. The compound of claim 5, wherein R¹ is selected from:

9. The compound of claim 1, wherein R⁴ is cyano, fluoroalkyl, sulfinyl, sulfonamidyl, sulfonyl, sulfoximinyl or fluoroalkylsulfonyl.

10. The compound of claim 1, wherein R¹¹ is hydroxy or amino.

11. The compound of claim 1, wherein Z is —O—.

12. The compound of claim 1, wherein:

R⁴ is fluoroalkyl or sulfonyl;

n is 0, 1, 2 or 3;

Z is —O—;

R¹¹ is hydroxy; and

R¹² is hydrogen.

13. The compound of claim 12, wherein R¹ is monocyclic aryl, monocyclic heteroaryl, bicyclic heteroaryl, monocyclic cycloalkyl, or heterocycloalkyl.

14. The compound of claim 13, wherein R¹ is substituted with at least one substituent selected from the group consisting of halo, hydroxy, C₁-C₄ alkyl, C₁-C₄ alkoxy and cyano.

15. The compound of claim 1, wherein X is N and Y is CR⁶.

16. The compound of claim 1, wherein the compound is selected from the group consisting of:

-continued

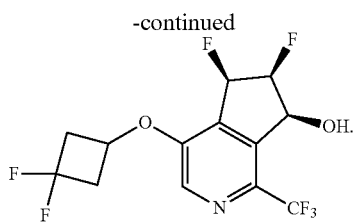

17. A pharmaceutical composition comprising the compound of claim 1 and a pharmaceutically acceptable carrier.

18. A method of inhibiting HIF-2α signaling output, comprising contacting HIF-2α with an effective amount of the compound of claim 1.

19. A method of inhibiting HIF-2α, comprising contacting HIF-2α with an effective amount of the compound of claim 1.

20. A method of treating von Hippel-Lindau (VHL) disease, comprising administering to a subject in need thereof an effective amount of the compound of claim 1.

21. A method of treating renal cell carcinoma, comprising administering to a subject in need thereof a therapeutically effective amount of the compound of claim 1.

22. The method of claim 21, wherein said renal cell carcinoma is clear cell renal cell carcinoma (ccRCC).

23. A compound of Formula I-C:

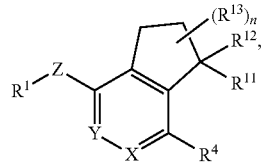

Formula I-C or a pharmaceutically acceptable salt or prodrug thereof, wherein:

X is $CR^5$ or N;
Y is $CR^6$ or N, wherein at least one of X and Y is N;
Z is —O—, —S—, —S(O)—, —S(O)$_2$—, —C(O)—, —C(HR$^7$)—, —N(R$^8$)—, C$_1$-C$_3$ alkylene, C$_1$-C$_3$ heteroalkylene, C$_1$-C$_3$ alkenylene or absent;

$R^1$ is alkyl, heteroalkyl, cycloalkyl, heterocycloalkyl, aryl or heteroaryl;
$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;
$R^5$, $R^6$, $R^7$ and $R^8$ are independently hydrogen, halo, hydroxy, cyano, alkyl or alkoxy;
$R^{11}$ is hydrogen, halo, hydroxy, alkoxy or amino;
$R^{12}$ is hydrogen;
$R^{13}$ is fluoro; and
n is 1, 2 or 3.

24. A compound of Formula I-C:

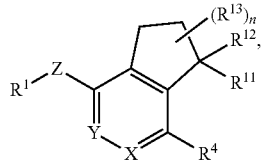

Formula I-C or a pharmaceutically acceptable salt or prodrug thereof, wherein:

X is $CR^5$ or N;
Y is $CR^6$ or N, wherein at least one of X and Y is N;
Z is —O—;
$R^1$ is alkyl, heteroalkyl, cycloalkyl, heterocycloalkyl, aryl or heteroaryl;
$R^4$ is nitro, halo, cyano, alkyl, cycloalkyl, heteroaryl, carboxyl, sulfinyl, sulfonamidyl, sulfonyl, sulfoximinyl or fluoroalkylsulfonyl;
$R^5$, $R^6$, $R^7$ and $R^8$ are independently hydrogen, halo, hydroxy, cyano, alkyl or alkoxy;
$R^{11}$ is hydrogen, halo, hydroxy, alkoxy or amino;
$R^{12}$ is hydrogen, alkyl, alkenyl or alkynyl; or $R^{11}$ and $R^{12}$ in combination form =O, =CH$_2$ or =N(OH);
each of $R^{13}$ is independently selected from the group consisting of hydrogen, fluoro, chloro, hydroxy, alkyl and heteroalkyl; and two $R^{13}$s and the carbon atom(s) to which they are attached may form a 3- to 8-membered cycloalkyl or heterocycloalkyl moiety; and
n is 0, 1, 2, 3 or 4.

* * * * *